United States Patent
Thakur et al.

(10) Patent No.: US 11,952,370 B2
(45) Date of Patent: Apr. 9, 2024

(54) SELECTIVE LIGANDS FOR MODULATION OF GIRK CHANNELS

(71) Applicants: Northeastern University, Boston, MA (US); Indiana University Research and Technology Corporation, Indianapolis, IN (US)

(72) Inventors: Ganeshsingh A. Thakur, Cambridge, MA (US); Diomedes E. Logothetis, Brookline, MA (US); Lucas Cantwell, Plymouth, MA (US); Yu Xu, Malden, MA (US); Anantha Shekhar, Indianapolis, IN (US)

(73) Assignees: Northeastern University, Boston, MA (US); Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 17/053,458

(22) PCT Filed: Jun. 11, 2019

(86) PCT No.: PCT/US2019/036639
§ 371 (c)(1),
(2) Date: Nov. 6, 2020

(87) PCT Pub. No.: WO2019/241311
PCT Pub. Date: Dec. 19, 2019

(65) Prior Publication Data
US 2021/0253561 A1    Aug. 19, 2021

Related U.S. Application Data

(60) Provisional application No. 62/683,424, filed on Jun. 11, 2018.

(51) Int. Cl.
*A61K 31/415* (2006.01)
*A61P 25/22* (2006.01)
(Continued)

(52) U.S. Cl.
CPC .......... *C07D 409/12* (2013.01); *A61K 31/415* (2013.01); *A61P 25/22* (2018.01);
(Continued)

(58) Field of Classification Search
CPC .. C07D 409/12; C07D 231/40; C07D 401/12; C07D 403/12; C07D 405/12;
(Continued)

(56) References Cited

U.S. PATENT DOCUMENTS 7,750,160 B2   7/2010   Milanov et al.
8,163,756 B2   4/2012   Flynn et al.
(Continued)

FOREIGN PATENT DOCUMENTS

WO   2000/026203 A1   5/2000
WO   2004/089929 A1   10/2004
(Continued)

OTHER PUBLICATIONS

Viventini et al , Pyrazolo[3,4-d][1,2,3]triazole-1-carboxamides and 5-alkylaminopyrazolo[3,4-d]oxazoles: synthesis and evaluation of the in vitro antifungal activity, Farmaco, 1992, 47(7-8), 1021-1034 (Year: 1992).*

(Continued)

*Primary Examiner* — Taylor V Oh
(74) *Attorney, Agent, or Firm* — Verrill Dana, LLP

(57) ABSTRACT

Selective small molecule regulators of GIRK potassium channels are provided, which are effective in treatment of post-traumatic stress disorder and other medical conditions.

13 Claims, 70 Drawing Sheets

(51) Int. Cl.
| | |
|---|---|
| *C07D 231/40* | (2006.01) |
| *C07D 401/12* | (2006.01) |
| *C07D 403/12* | (2006.01) |
| *C07D 405/12* | (2006.01) |
| *C07D 409/12* | (2006.01) |
| *C07D 413/12* | (2006.01) |
| *C07D 417/12* | (2006.01) |

(52) U.S. Cl.
CPC ......... *C07D 231/40* (2013.01); *C07D 401/12* (2013.01); *C07D 403/12* (2013.01); *C07D 405/12* (2013.01); *C07D 413/12* (2013.01); *C07D 417/12* (2013.01)

(58) Field of Classification Search
CPC .. C07D 413/12; C07D 417/12; C07D 231/38; A61P 25/22; A61P 25/00; A61K 31/415; A61K 31/422; A61K 31/427; A61K 31/4439; A61K 31/506
USPC .................................................. 514/256, 403
See application file for complete search history.

(56) References Cited

U.S. PATENT DOCUMENTS

| 9,067,894 B1 | 6/2015 | Weaver |
| 2009/0312349 A1 | 12/2009 | Flynn et al. |
| 2012/0302581 A1* | 11/2012 | Ratner .................... A61P 31/10 514/369 |
| 2016/0229850 A1 | 8/2016 | Cooke et al. |

FOREIGN PATENT DOCUMENTS

| WO | 2005/023818 A3 | | 3/2005 |
| WO | 2006/040569 A1 | | 4/2006 |
| WO | 2015/039333 A1 | | 3/2015 |
| WO | WO2015039333 | * | 3/2015 |

OTHER PUBLICATIONS

Viventini et al , Synthesis of N-alkyl-N'-(4-diazo-5-pyrazolyl)ureas and their conversion to pyrazolo[3,4-d][1,2,3]triazole and pyrazolo [3,4-d]oxazole derivatives, Heterocvcles, 1991, 32(4), p. 727-734 (Year: 1991).*

Vicentini et al , Synthesis of N-alkyl-N'-(4-diazo-5-pyrazolyl)ureas and their conversion to pyrazolo[3,4-d][1,2,3]triazole and pyrazolo [3,4-d]oxazole derivatives, Heterocycles (1991), 32(4), 727-734 , abstract pages (p. 1-2) (Year: 1991).*

Yow, T. T. et al., "Naringin directly activates inwardly rectifying potassium channels at an overlapping binding site to tertispin-Q.", Br. J. Pharmacol., 163, (2011), pp. 1017-1033.

Chan, K. W. et al., "D. E. Specific regions of heteromeric subunits involved in enhancement of G protein-gated K+ channel activity", J. Biol. Chem. 272, (1997), pp. 6548-6555.

Mase, Y. et al., "Structural basis for modulation of gating property of G protein-gated inwardly rectifying potassiun ion channel (GIRK) by i/o-family G protein α subunit (Gαi/o)", J. Biol. Chem., 287, (2012), pp. 19537-19549.

Kaufmann, K. et al., "ML297 (VU0456810), the first potent and selective activator of the GIRK potassium channel, displays antiepileptic properties in mice", ACS Chem. Neurosci., 4, (2013), pp. 1278-1286.

Wen, W. et al., "Discovery of potent and selective GIRK1/2 modulators via 'molecular switches' within a series of 1-(3-cyclopropyl-1-phenyl-1H-pyrazol-5-yl)ureas", Bioorg. Med. Chem. Lett., 24, (2014), pp. 5102-5106.

Weiting, J. M. et al., "Discovery and Characterization oh 1H-Pyrazol-5-yl-2-phenylacetamides as Novel, Non-Urea-Containing GIRK1/2 Potassium Channel Activators", ACS Chem. Neurosci., 8, (2017), pp. 1873-1879.

Takemoto, Y. et al., "Structural basis for the antiarrhythmic bloackade of a potassium channel with a small molecule", FASEB J., 32, (2018), pp. 1778-1793.

Wydeven N. et al., "Mechanisms underlying the activation of G-protein-gated inwardly rectifying K+ (GIRK) channels by the novel anxiolytic drug, ML297", PNAS, Jul. 22, 2014, vol. 111, No. 29, pp. 10755-10760.

Wen W. et al., "Discovery of 'molecular switches' within a GIRK activator scaffold that afford selective GIRK inhibitors", Bioorganic & Medicinal Chemistry Letters, (2013), vol. 23, pp. 4562-4566.

Kobayashi et al., "G Protein-Activated Inwardly Rectifying Potassium Channels as Potential Therapeutic Targets", Current Pharmaceutical Design, 2006, 12, pp. 4513-4523.

Ha et al., "Hydrogen sulfide inhibits Kir2 and Kir3 channels by decreasing sensitivity to the phospholipid phosphatidylinositol 4,5-bisphosphate (PIP2)", J Biol Chem., (2018), 293(10): pp. 3546-3561.

* cited by examiner

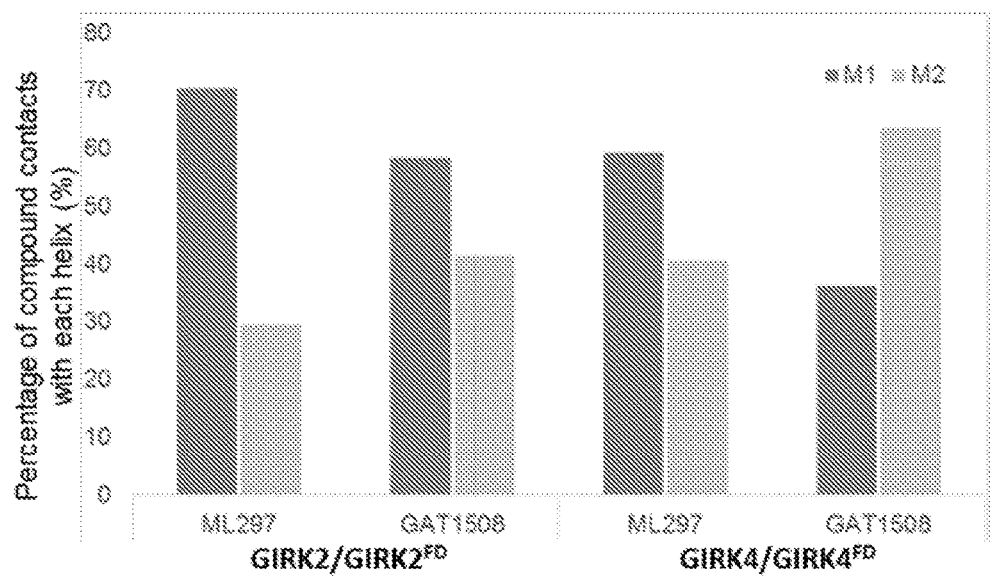
*Fig. 6*
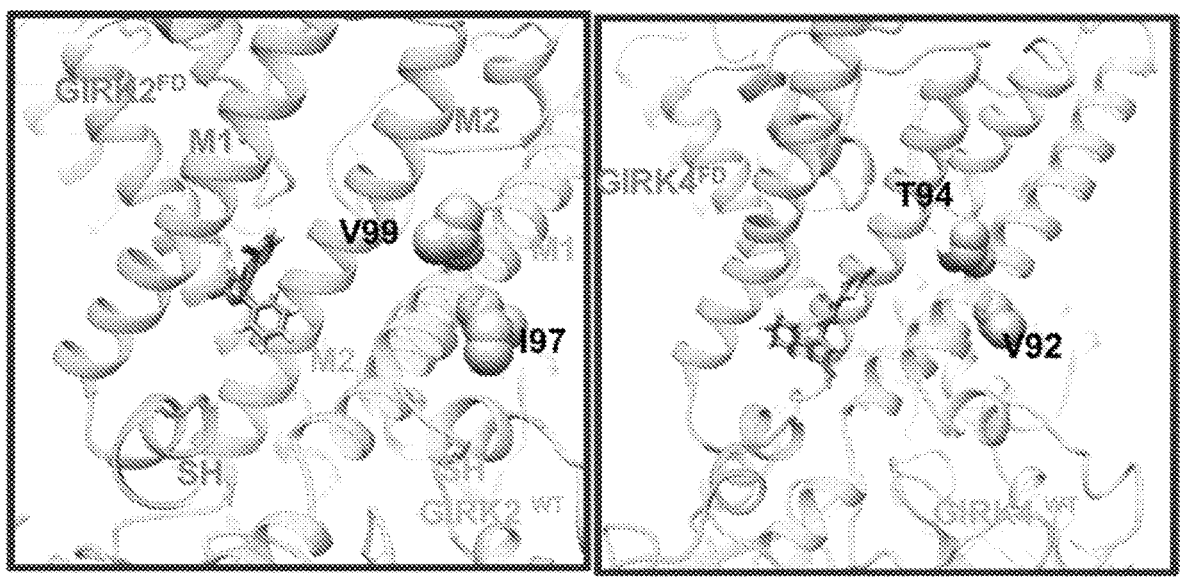
*Fig. 7A*  *Fig. 7B*

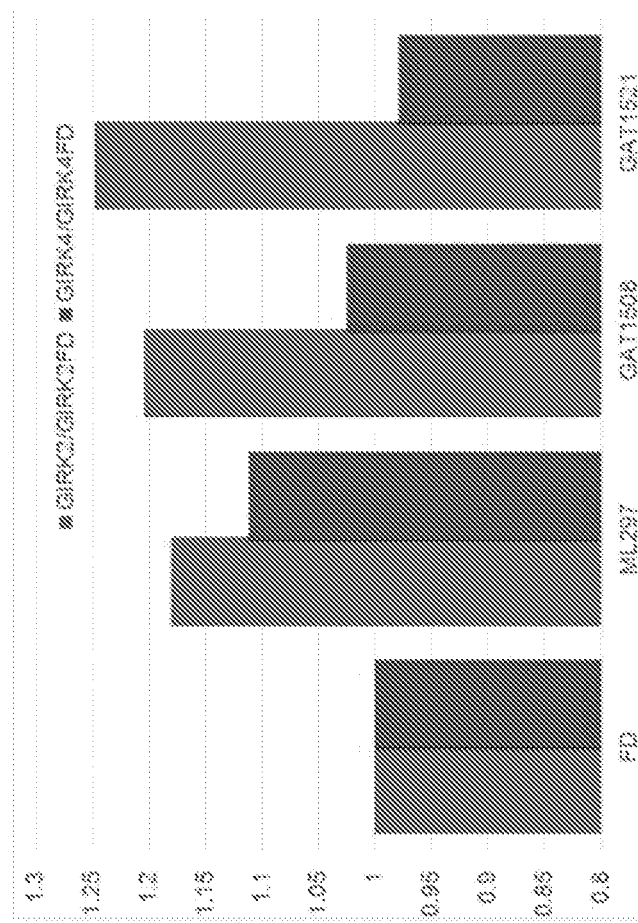
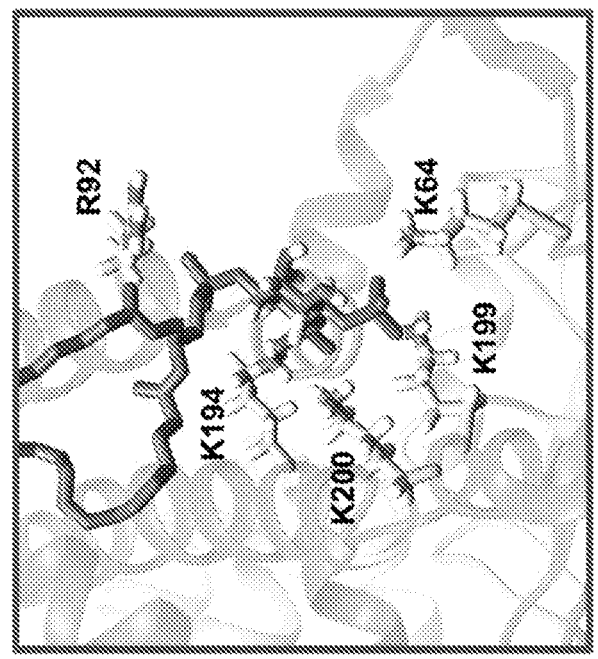
Fig. 13A
Fig. 13B

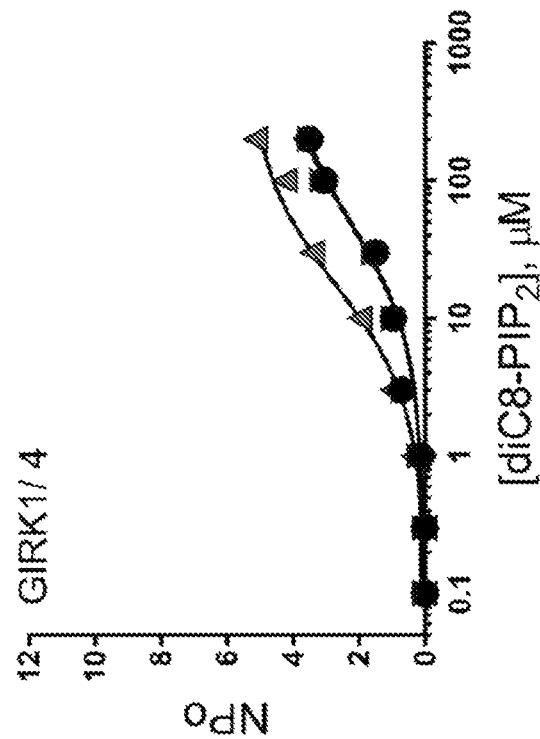
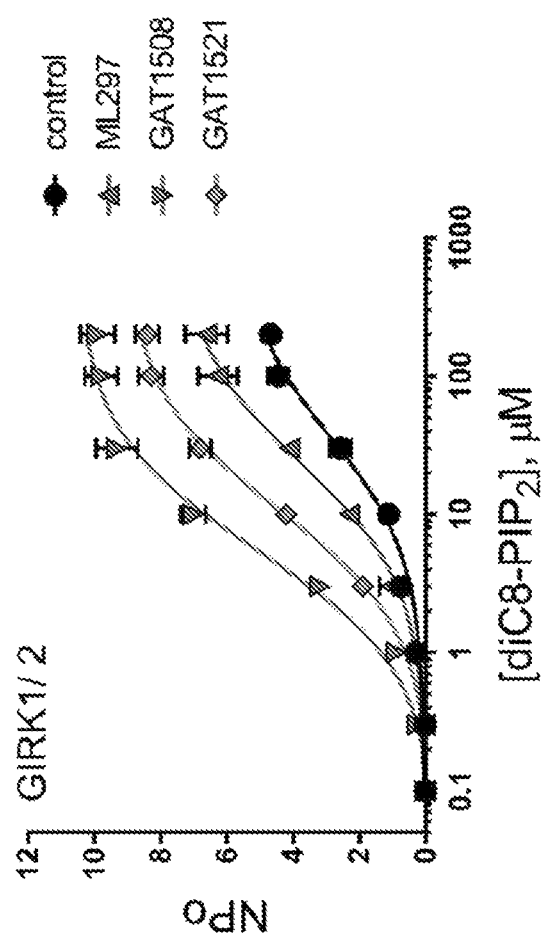
Fig. 14A
Fig. 14B

| Channel | ML297 | | GAT1508 | | GAT1521 | |
|---|---|---|---|---|---|---|
| | No ptase | + ptase | No ptase | + ptase | No ptase | + ptase |
| GIRK1-2 EC$_{50}$, nM | 109 ± 13 | 317 ± 16 | 76 ± 10 | 148 ± 21 | 349 ± 58 | 1284 ± 92 |
| Emax | 5.1 ± 0.1 | 3.8 ± 0.2 | 8.4 ± 0.2 | 3.9 ± 0.2 | 4.15 ± 0.13 | 3.65 ± 0.2 |
| GIRK1-4 EC50, nM | 1203 ± 47 | NA | NA | NA | | |
| Emax | 2.28 ± 0.2 | 1.07 ± 0.04 | 1.04 ± 0.02 | 1.04 ± 0.02 | | |

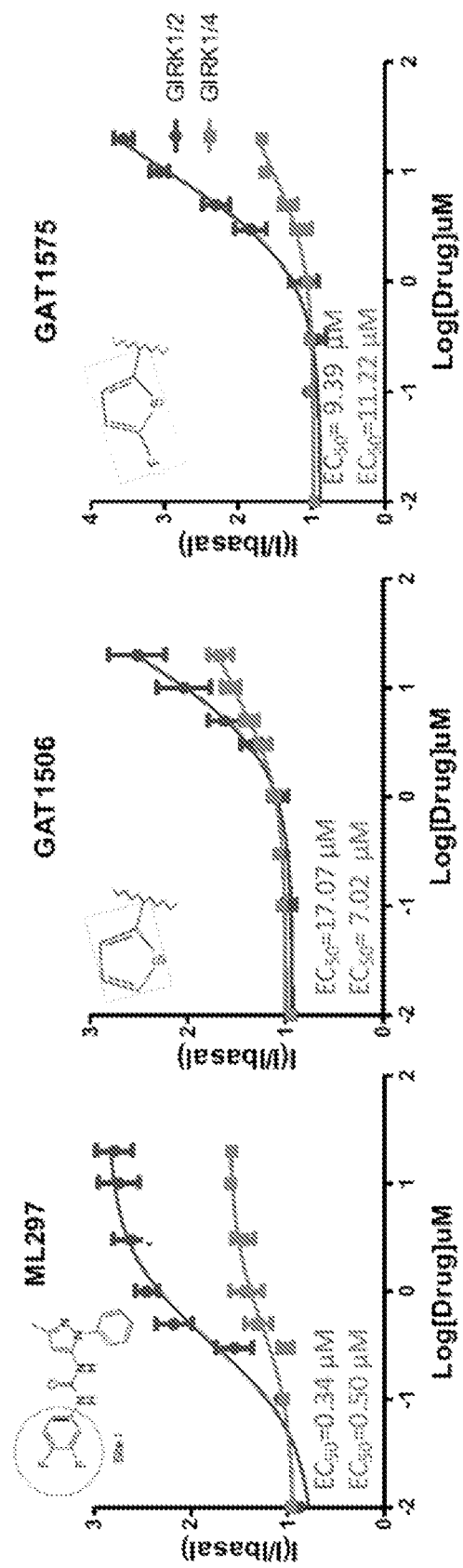
*Fig. 34A*  *Fig. 34B*  *Fig. 34C*

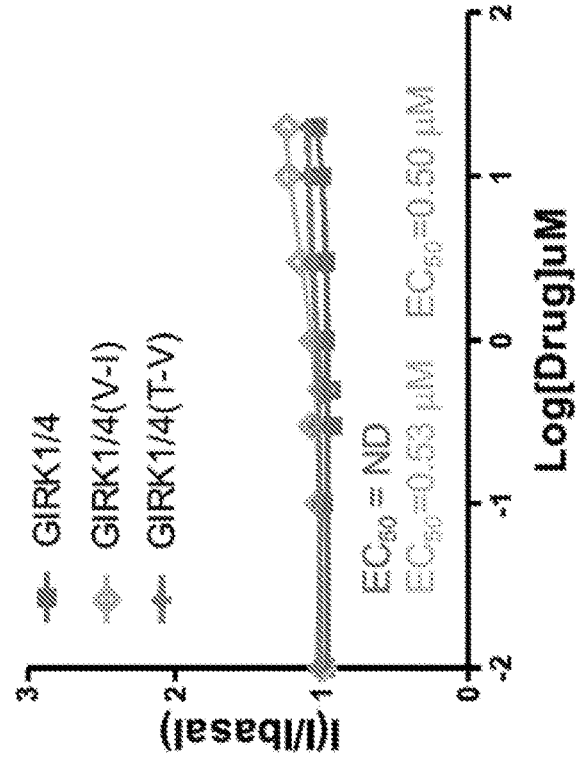
Fig. 35
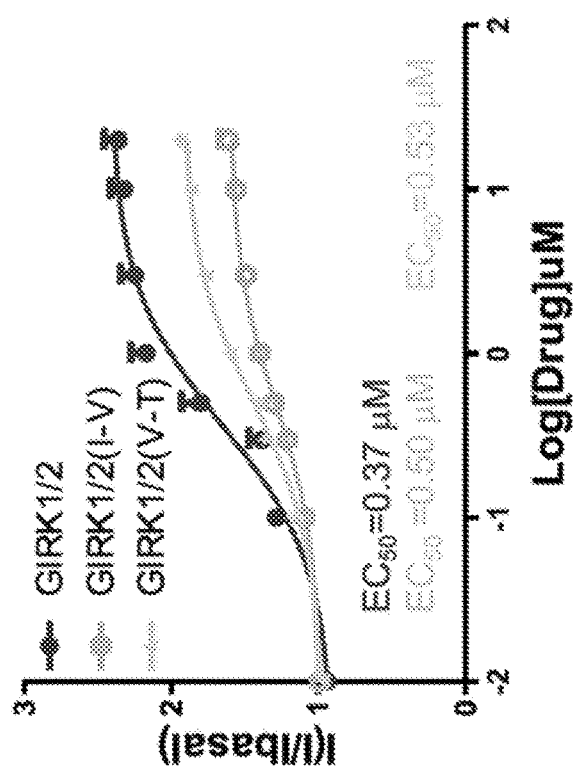
Fig. 36A
Fig. 36B

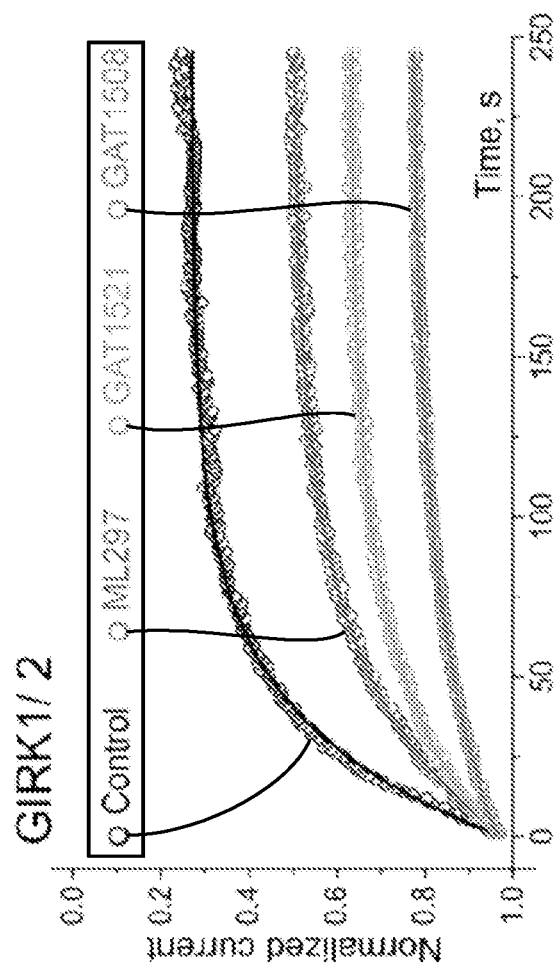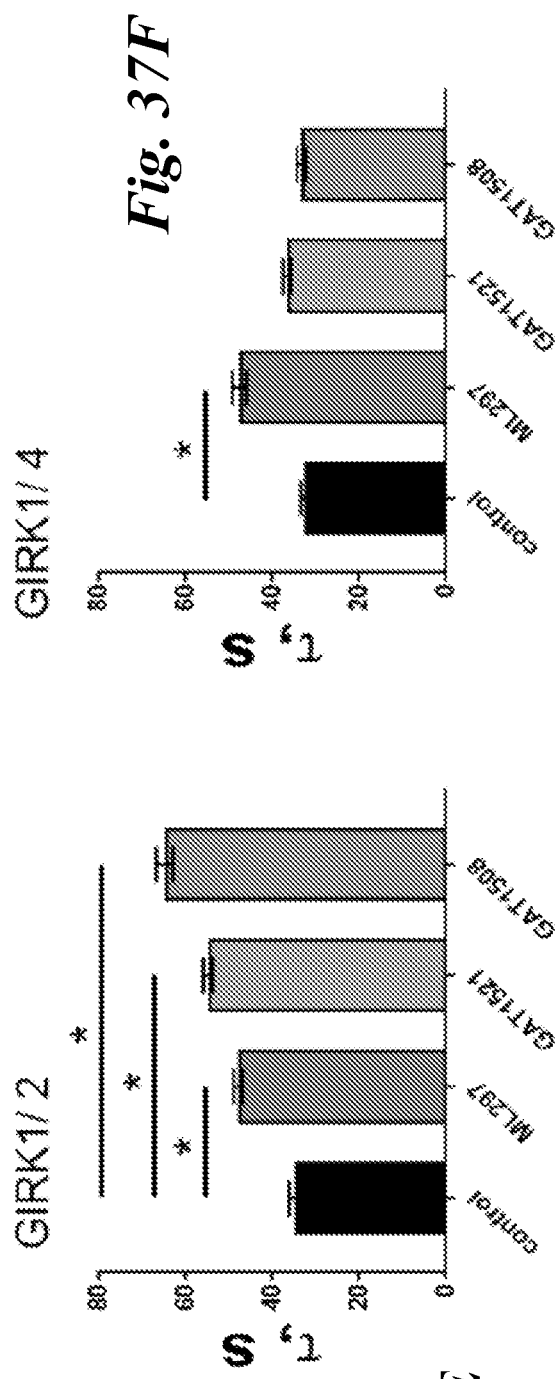
Fig. 37D
Fig. 37E
Fig. 37F

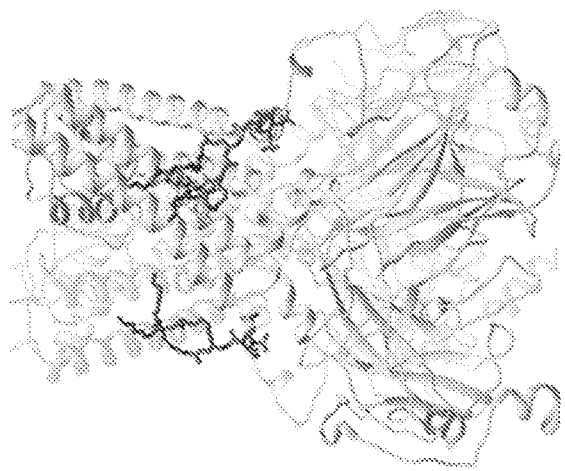
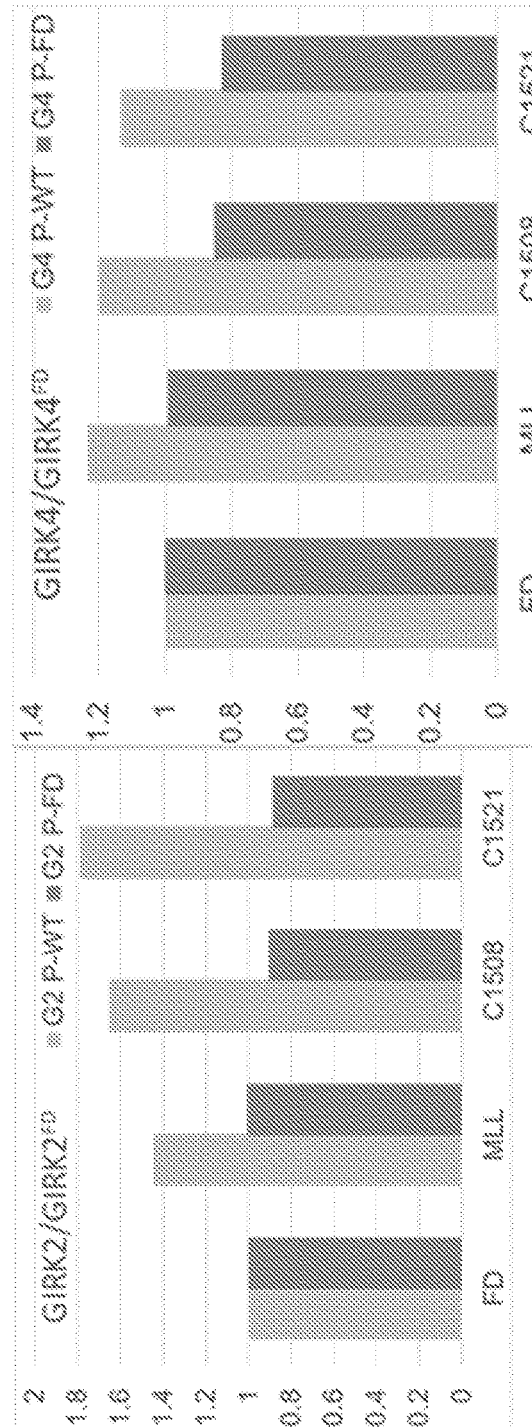
Fig. 38A
Fig. 38B
Fig. 38C

| | | |
|---|---|---|
| GIRK1 | KKRQRFVDKNGRCNVQHGNLGSETSRYLSDLFTTLVDLKWRWNLFIFILTYTVAWLFMAS | 100 |
| GIRK2 | RKIQRYVRKDGKCNVHHGNVRETYRYLTDIFTTLVDLKWRFNLLIFVMVYTVTWLFFGM | 111 |
| GIRK4 | KPRQRYMEKSGKCNVHHGNVQETYRYLSDLFTTLVDLKWRFNLLVFTMVYTVTWLFFGF | 106 |

*Fig. 41*

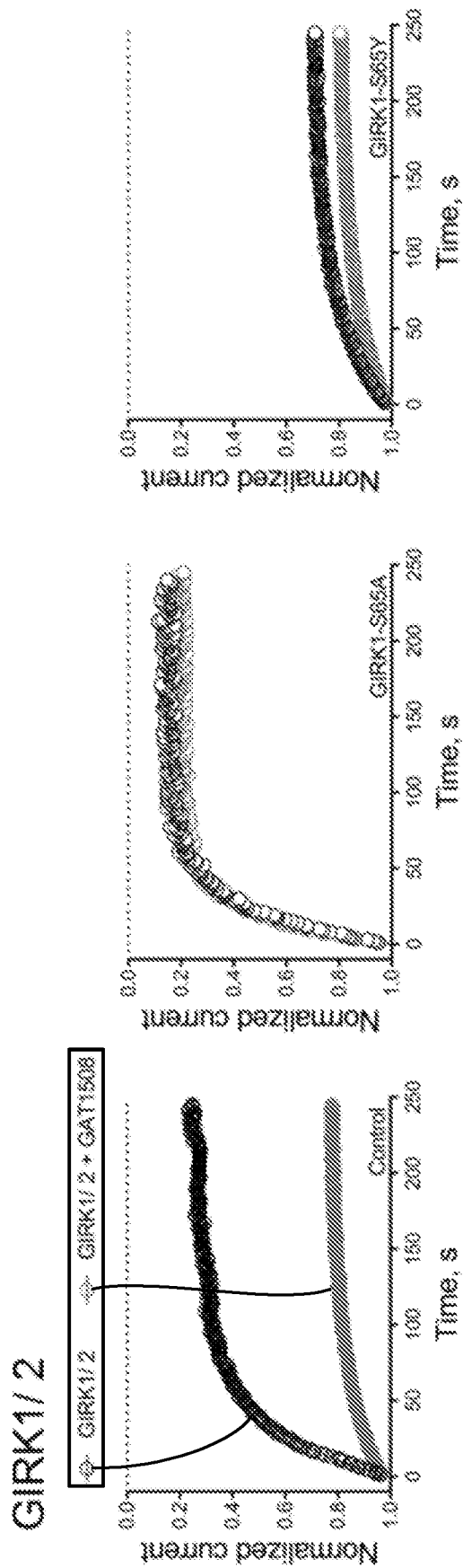
*Fig. 42A*  *Fig. 42B*  *Fig. 42C*

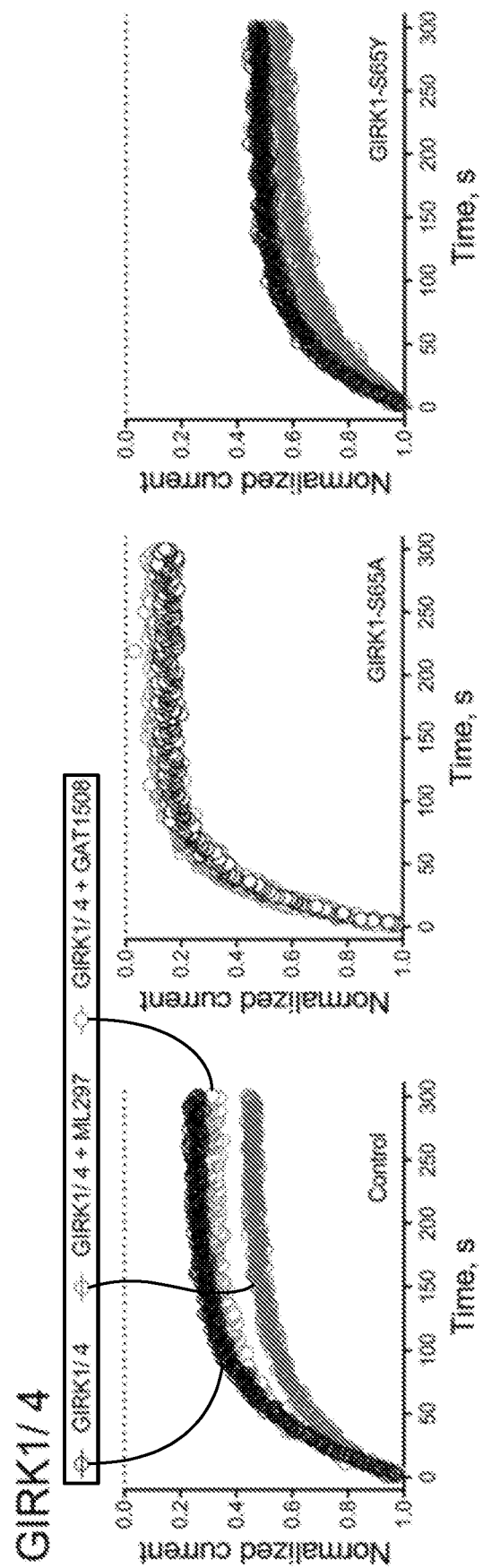
*Fig. 44A*  *Fig. 44B*  *Fig. 44C*

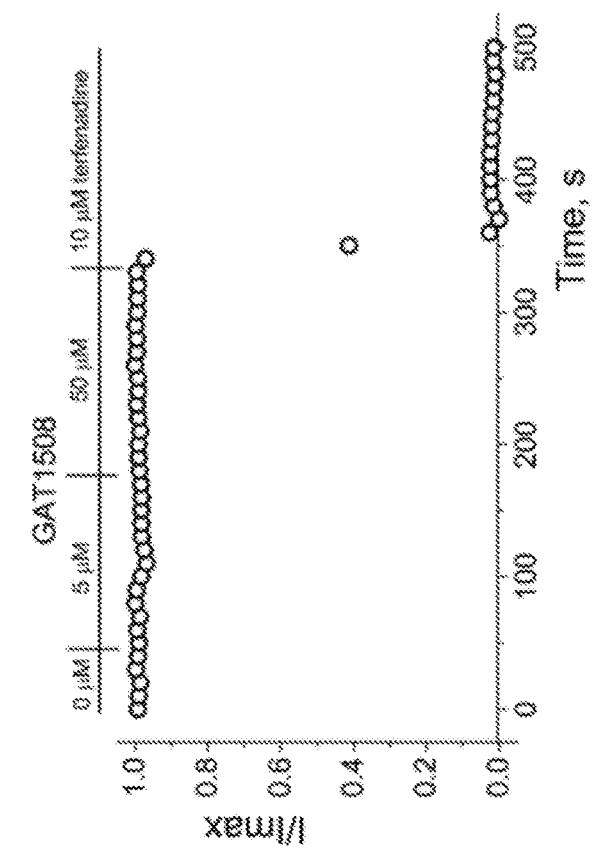
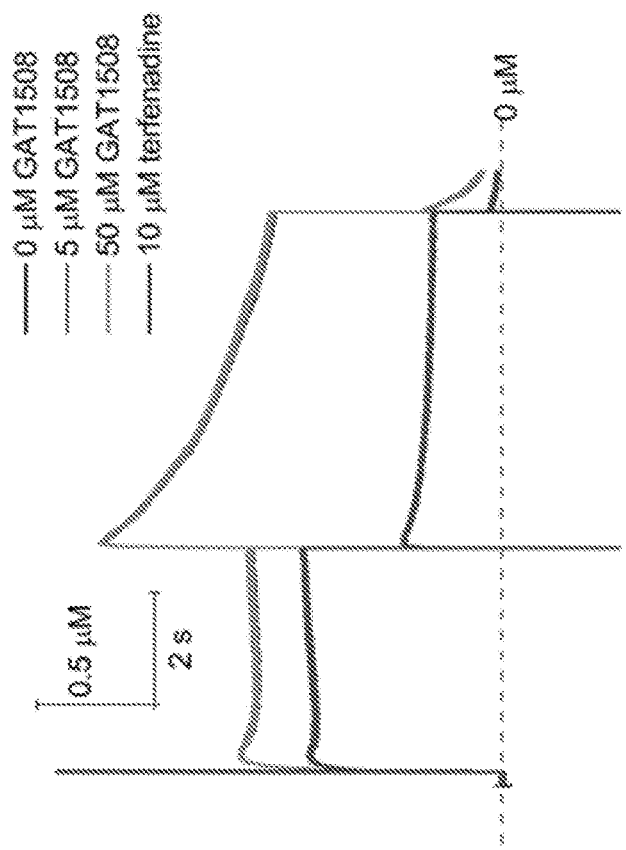
Fig. 52A
Fig. 52B

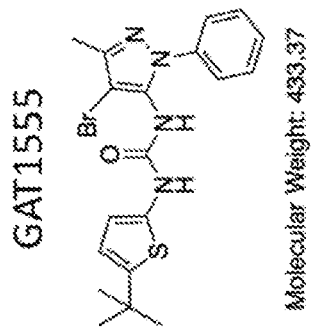
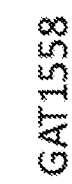
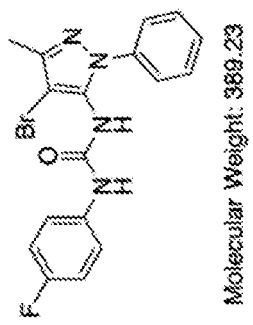
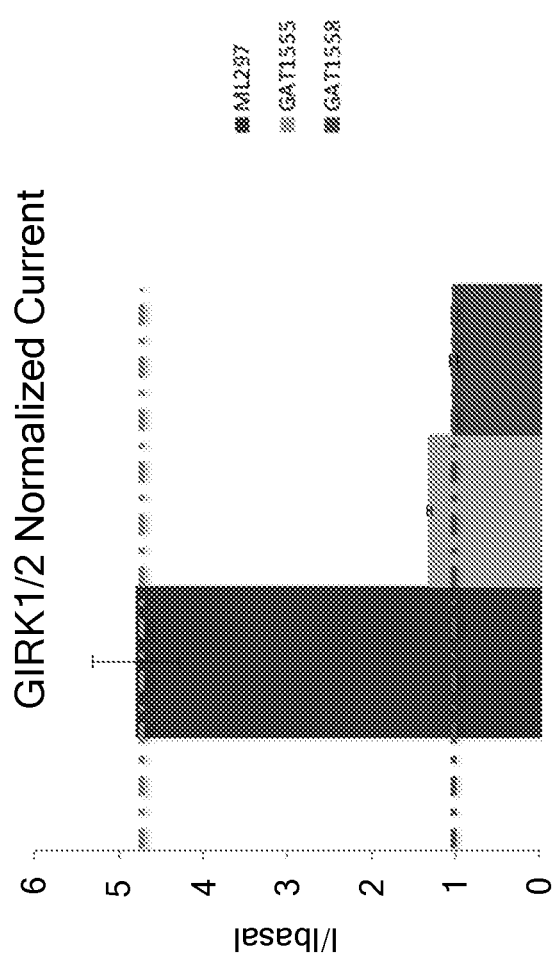
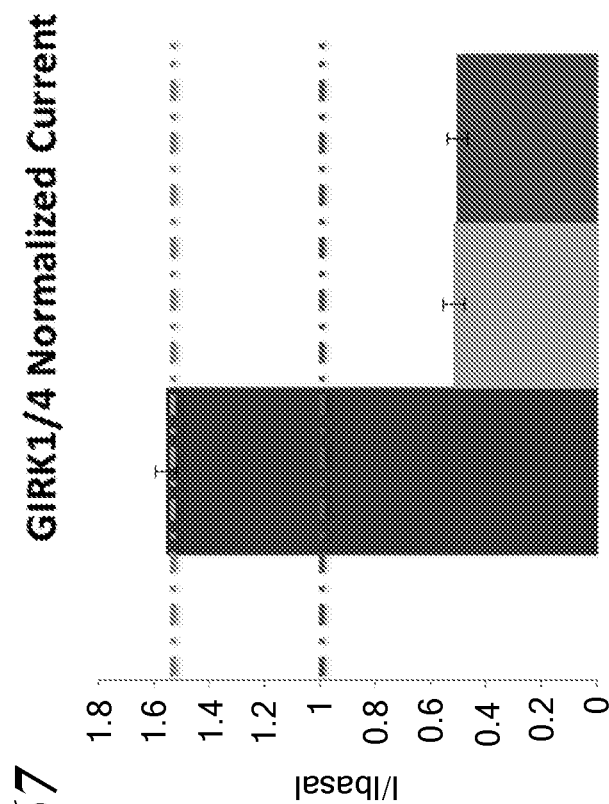
Fig. 67

SELECTIVE LIGANDS FOR MODULATION OF GIRK CHANNELS

CROSS-REFERENCE TO RELATED APPLICATIONS

This application claims priority to U.S. Provisional Appl. No. 62/683,424, filed 11 Jun. 2018, the entire technology of which is incorporated herein by reference.

STATEMENT REGARDING FEDERALLY SPONSORED RESEARCH OR DEVELOPMENT

The invention was developed with government support from Grant No. R01-HL059949-21 from the National Institutes of Health. The government has certain rights in the invention.

BACKGROUND

G protein-gated inwardly rectifying $K^+$ channels (GIRKs) are members of a family of inwardly rectifying potassium channels. GIRK channels regulate neuronal excitability. Nerve cell hyperpolarization can have different effects depending on function and location of the affected nerve cells. Mammals express four GIRK subunits (GIRK1-4), whose distribution varies by tissue. GIRK4 expression is low in brain but high in heart, while GIRK subunits 1-3 are broadly distributed throughout the nervous system and can affect excitability in different areas of the brain, resulting in modulation of brain functions including reward and addiction. GIRK channels can be formed from various homotetrameric or heterotetrameric combinations in native cells and in heterologous expression systems such as *Xenopus* oocytes. The GIRK2 subunit can form homotetramers or can combine with the GIRK1 subunit to form heterotetramers of GIRK1/2 channels. GIRK2 can also form heterotetrmers with the GIRK3 subunit (GIRK2/3 channels). GIRK1/4 channels represent a heterotetrameric combination of GIRK1 subunit and GIRK4 subunit.

GIRK channels can be activated by $G_{i/o}$-dependent (pertussis toxin-sensitive) signaling pathways in the heart and nervous system. Their activation can inhibit excitability, slowing the rate of pacemaker and atrial cell firing in the heart, inhibiting transmitter release by pre-synaptic neurons, or opposing excitation of post-synaptic neurons. Polymorphisms and mutations in human GIRK channels have been linked to arrhythmias, hyperaldosteronism (and associated hypertension), sensitivity to analgesics, addiction, alcohol dependence, anxiety, and schizophrenia. Although GIRK channels have been implicated in multiple conditions, the lack of selective drugs that discriminate among GIRK channel subtypes has hampered investigation into their precise physiological relevance and therapeutic potential.

GIRK channels are activated by binding of the G protein βγ (Gβγ) subunits. Gβγ binding strengthens channel affinity for phosphatidylinositol-4,5-bisphosphate ($PIP_2$), a necessary cofactor for channel gating. Structural studies, using crystallography or computational modeling, have produced three-dimensional models of the interactions of GIRK channels with $PIP_2$ and the Gβγ subunits. GIRK channels can also be activated in a G-protein-independent manner by intracellular $Na^+$, ethanol, volatile anesthetics, and naringin, again in a $PIP_2$-dependent manner. Many psychoactive and clinically relevant compounds with other primary molecular targets inhibit GIRK channels, albeit at relatively high doses.

Although it cannot form functional homotetramers, GIRK1 is an integral subunit of the cardiac GIRK channel and most neuronal GIRK channels. GIRK1 confers basal and receptor-dependent activity to GIRK heteromers, attributable in part to unique residues in the pore and second transmembrane domain. The intracellular C-terminal domain also contributes to the potentiating influence of GIRK1 on channel activity, likely due to the presence of unique structures that modify the interaction between the channel and Gβγ, Gα, and $PIP_2$.

ML297 activates GIRK1-containing channels, requiring only two amino acids specific to GIRK1, F137 and D173 (FD). Although ML297 has been shown to be more biased towards GIRK1/2 activation than GIRK1/4 heteromers, the significant activation of GIRK1/4 by ML297, which is highly expressed in supraventricular cardiac tissues, limits its utility as a potential drug targeting GIRK1 heteromers expressed in the brain. Based on detailed in vivo studies of the pharmacological properties of the non-selective GIRK activators, it is believed that compounds that are truly selective for GIRK1/2 activation would represent a novel class of anxiolytic compounds with limited sedative and addictive liabilities.

SUMMARY

The present technology is directed to highly specific, potent, and efficacious activators of brain GIRK1/2 channels and inhibitors of cardiac GIRK1/4 channels and their use in treatment of various medical conditions including PTSD, pain, epilepsy, traumatic brain injury, neurodegenerative diseases (GIRK1/2 activators), as well as atrial fibrillation and other forms of cardiac arrhythmia (GIRK1/4 inhibitors). The action of the GIRK1/2 activators is specific for GIRK1/2 over cardiac GIRK1/4 channels, and their function as allosteric modulators of channel interactions with phosphatidylinositol-4,5-bisphosphate ($PIP_2$) is elucidated herein. Direct stimulation of GIRK currents in the basolateral amygdala (BLA) by the activators and potentiation of baclofen-induced currents when used in subthreshold concentrations is shown. The GIRK 1/2 activators are shown to be effective in facilitating extinction of conditioned fear in rodents, while lacking cardiac and behavioral side effects, making the GIRK1/2 activators a specific new pharmacotherapeutic tool for PTSD and other neuropsychiatric disorders.

A bromo-thiophene substituted version of compound ML297 was selected from among ~80 variants for its specificity, potency and efficacy of activation of brain GIRK1/2 channels over cardiac GIRK1/4 channels. See FIGS. 1-2. The resulting compound was named GAT1508 and is shown below.

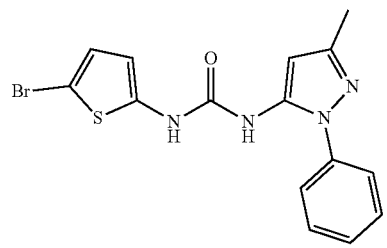

1-(5-bromothiophen-2-yl)-3-(3-methyl-1-phenyl-1H-pyrazol-5-yl) urea GAT1508, Molecular Weight: 377.26

The molecular mechanism of action of GAT1508 (and another slightly less effective variant, GAT1521, see below) was tested in rodent models of PTSD using fear extinction paradigms. GAT1508 was found to be one of the most selective GIRK1/2 activators known to the inventors for extinguishing fear, and therefore GAT1508 is the most effective small molecule drug known from testing in rodent models of PTSD. The brain specificity of GAT1508, along with its efficacy and potency, make it a lead compound for neuronal indications involving GIRK1/2 channels.

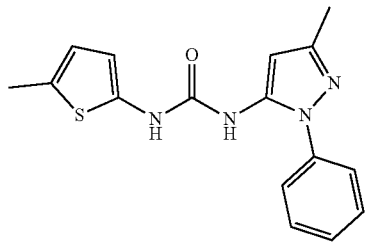

1-(3-methyl-1-phenyl-1H-pyrazol-5-yl)-3-(5-methylthiophen-2-yl)urea
GAT1521, Molecular Weight: 312.39

A novel pharmacophore was identified within this scaffold (see, e.g., GAT1537 below) which imparts high selectivity for activation of GIRK1/2 over GIRK1/4. The GIRK1/2-selective compounds disclosed herein are effective in treating epilepsy as well as general anxiety disorder, panic disorder, social anxiety disorder, obsessive-compulsive disorder, and pain, including chronic pain, neuropathic pain, inflammatory pain, and pain resulting from traumatic brain injury.

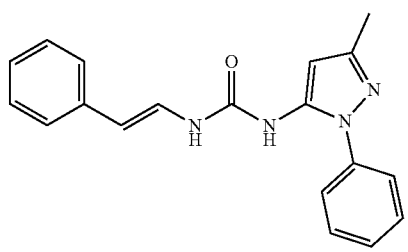

(E)-1-(3-methyl-1-phenyl-1H-pyrazol-5-yl)-3-styrylurea
GAT1537, Molecular Weight: 318.38

Further compounds from this series, such as GAT1528 shown below, are expected to act as inhibitors of GIRK1/4 channels and to be potentially useful in treating cardiac arrhythmia.

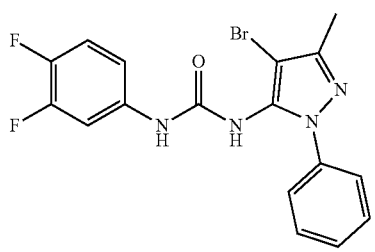

GAT1528

Examples of synthetic products are provided herein. The urea-containing compounds can be synthesized using a microwave method, and a flask method is also presented.

The present technology includes compounds containing any possible combination of Site 1 substituents, Site 2 substituents, Site 3, and Site 4 substituents as illustrated in FIG. 1 and pharmaceutically-acceptable salts thereof. The technology further includes compositions, including pharmaceutical compositions, containing one or more of these compounds. According to some aspects, the technology is directed to the use of any of these compounds, compositions, and pharmaceutical compositions in treating, or to prepare a medicament for use in treating, PTSD, epilepsy, general anxiety disorder, panic disorder, social anxiety disorder, cardiac arrhythmias, obsessive-compulsive disorder, and pain, including chronic pain, neuropathic pain, and inflammatory pain.

The technology includes compounds having structures according to any of Formulas I-IV below:

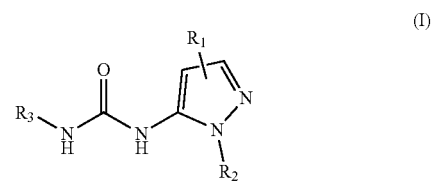

(I)

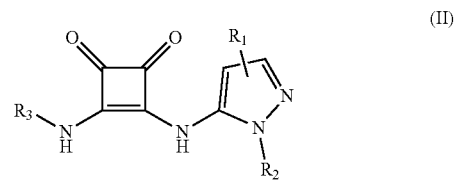

(II)

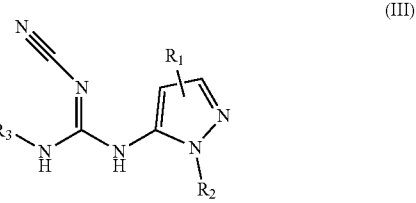

(III)

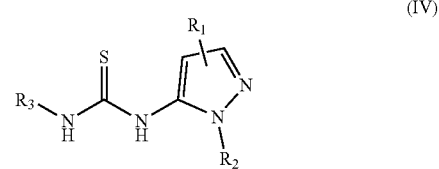

(IV)

wherein $R_1$ is chosen from hydrogen, halo, methyl, halomethyl, deuteromethyl, cyclopropyl, and cyclopropylmethyl;

wherein $R_2$ is —(CH$_2$)—$R_C$ or —$R_C$; $R_C$ can be piperidine, thiane, tetrahydropyran, cyclohexyl, or phenyl, optionally substituted with one $R_D$; the phenyl can optionally include one N, S, and O in place of one carbon atom; $R_D$ can be C1-C6 alkyl, halogen, or CF$_3$;

wherein $R_3$ is chosen from —$R_E$—$R_G$, —$R_F$—$R_G$, —$R_H$, and —$R_I$; $R_E$ is C2 alkene with trans configuration; $R_F$ is cyclopropyl, oxirane, alkyl, or connecting group; $R_G$ is a 5 or 6 membered aromatic ring optionally comprising one or two N, S, or O in place of one or two carbon atoms, the 5 or 6 membered aromatic ring can be optionally substituted with $R_H$; $R_H$ can be C1-C6 alkyl, halogen, CF$_3$, or CD$_3$; and $R_I$ is a substituted or unsubstituted ring or ring system chosen from thiophene, benzo[b]thiophene, 4,5,6,7-tetrahydrobenzo[b]thiophene, pyridine, pyrimidine, isoxazole, thiazole, adamantane, benzo[d][1,3]dioxole, naphthalene, and isoquinoline; wherein $R_1$ is optionally substituted with one or more functional groups chosen from halo, phenyl, and C1-C6 branched or unbranched alkyl optionally substituted with one or more halogens.

According to certain aspects, the compound has a structure according to Formula V, wherein $R_1$ is methyl and $R_2$ is substituted phenyl.

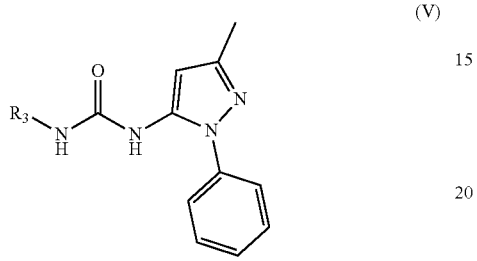

(V)

$R_3$ is chosen from —$R_E$—$R_G$, —$R_F$—$R_G$, —$R_H$, and —$R_I$; $R_E$ is C2 alkene with trans configuration; $R_F$ is cyclopropyl, oxirane, alkyl, or connecting group; $R_G$ is a 5 or 6 membered aromatic ring optionally comprising one or two N, S, or O in place of one or two carbon atoms, the 5 or 6 membered aromatic ring can be optionally substituted with $R_H$; $R_H$ can be C1-C6 alkyl, halogen, $CF_3$, or $CD_3$; $R_I$ is a substituted or unsubstituted ring or ring system chosen from thiophene, benzo[b]thiophene, 4,5,6,7-tetrahydrobenzo[b]thiophene, pyridine, pyrimidine, isoxazole, thiazole, adamantane, benzo[d][1,3]dioxole, naphthalene, and isoquinoline; and wherein $R_I$ is optionally substituted with one or more functional groups chosen from halo, phenyl, and C1-C6 branched or unbranched alkyl optionally substituted with one or more halogens; or a pharmaceutically-acceptable salt thereof.

According to some aspects, the compound is selected from the group consisting of the compounds shown below:

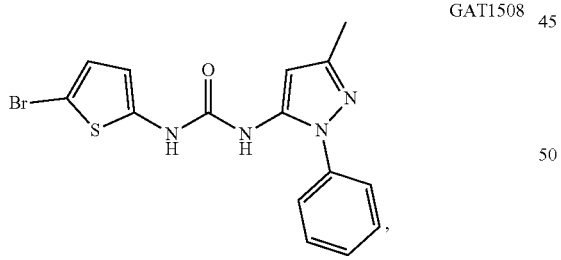

GAT1508

Molecular Weight: 377.26

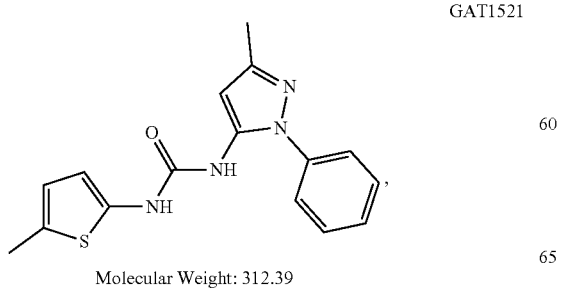

GAT1521

Molecular Weight: 312.39

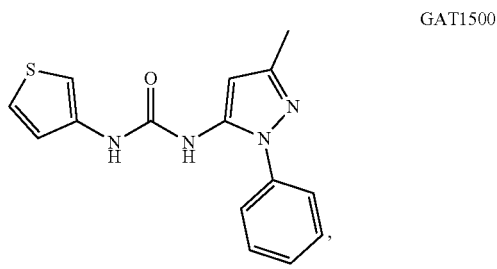

GAT1500

Molecular Weight: 298.36

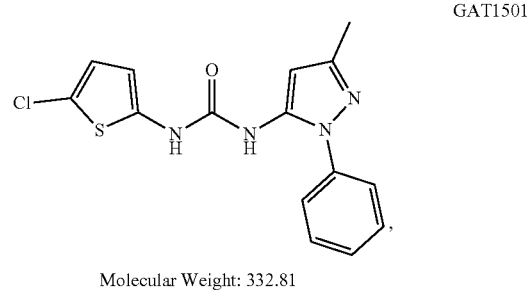

GAT1501

Molecular Weight: 332.81

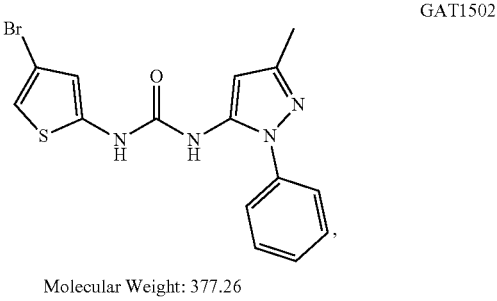

GAT1502

Molecular Weight: 377.26

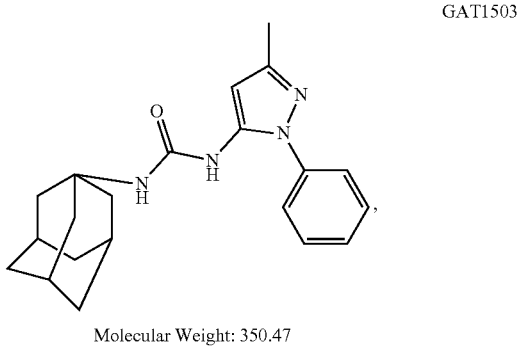

GAT1503

Molecular Weight: 350.47

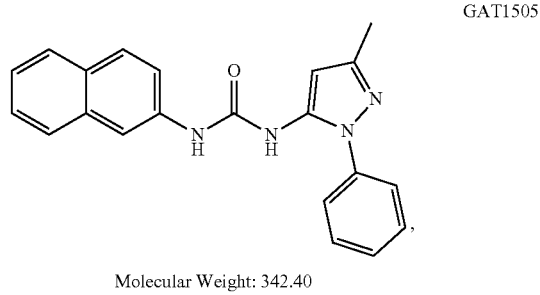

GAT1505

Molecular Weight: 342.40

GAT1506
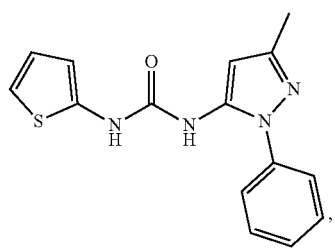
Molecular Weight: 298.36
GAT1507
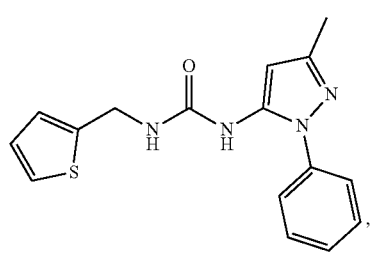
Molecular Weight: 312.39
GAT1509
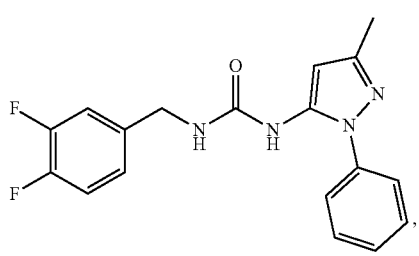
Molecular Weight: 342.35
GAT1510
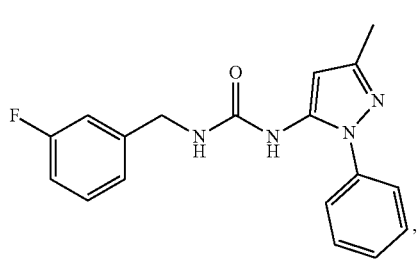
Molecular Weight: 324.36
GAT1512
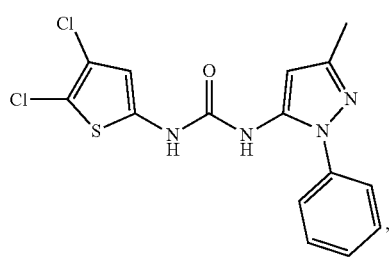
Molecular Weight: 367.25
GAT1513
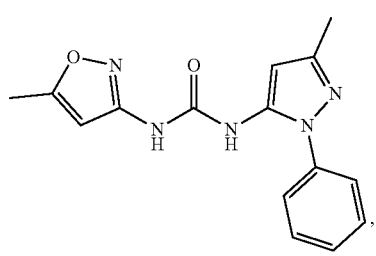
Molecular Weight: 297.32
GAT1514
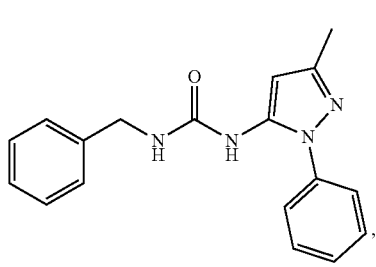
Molecular Weight: 356.38
GAT1515
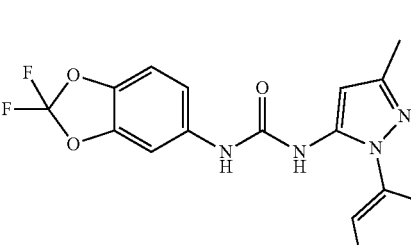
Molecular Weight: 306.37
GAT1516
Molecular Weight: 372.33
GAT1518
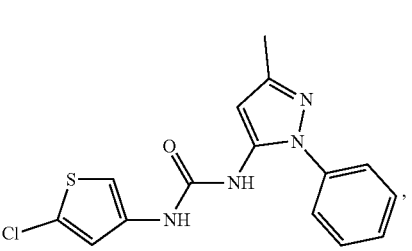
Molecular Weight: 332.81

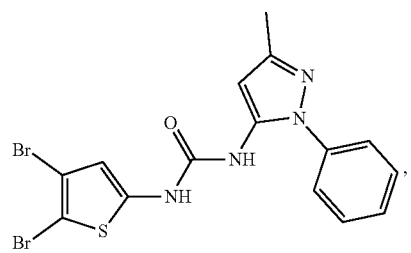
GAT1519
Molecular Weight: 456.15
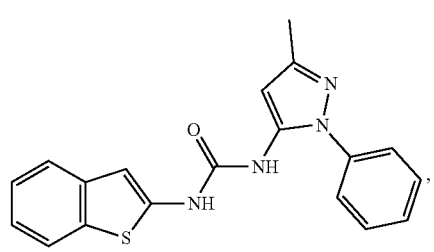
GAT1522
Molecular Weight: 348.42
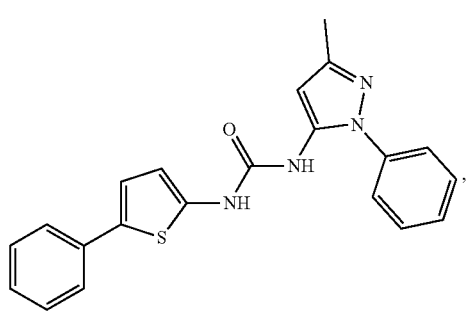
GAT1523
Molecular Weight: 374.46
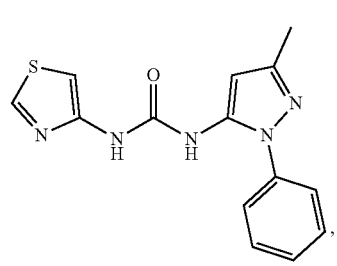
GAT1529
Molecular Weight: 299.35
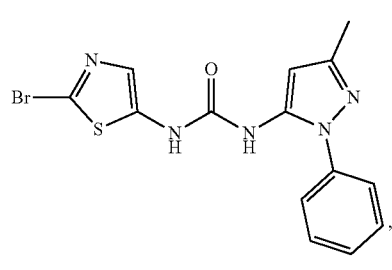
GAT1530
Molecular Weight: 378.25
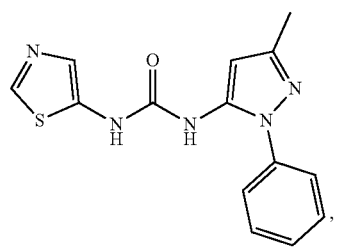
GAT1531
Molecular Weight: 299.35
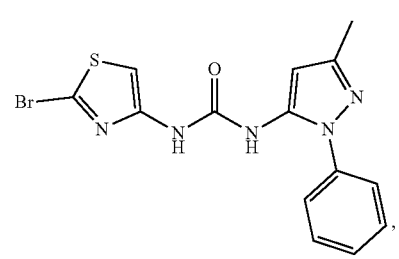
GAT1532
Molecular Weight: 378.25
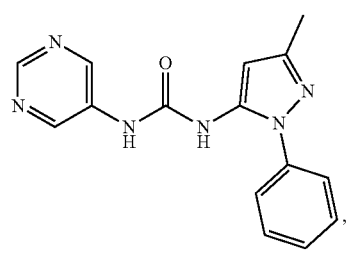
GAT1535
Molecular Weight: 294.32
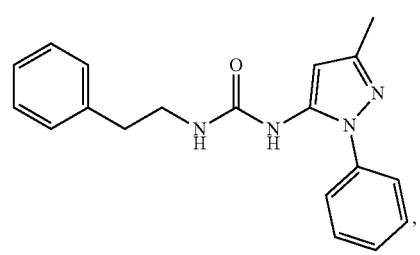
GAT1536
Molecular Weight: 320.40
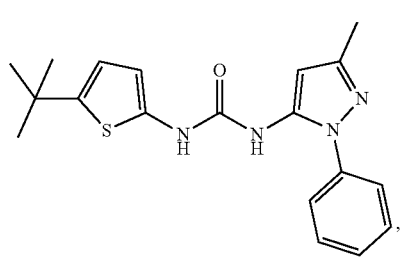
GAT1551
Molecular Weight: 354.47

GAT1552
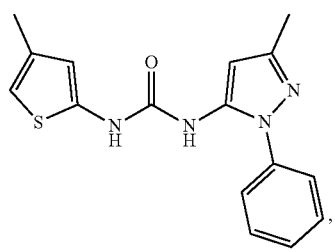
Molecular Weight: 312.39
GAT1553
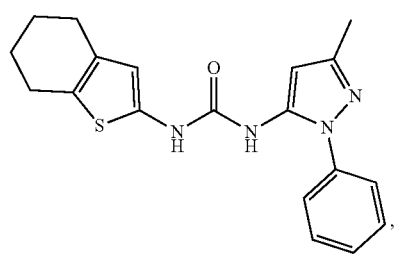
Molecular Weight: 352.46
GAT1561
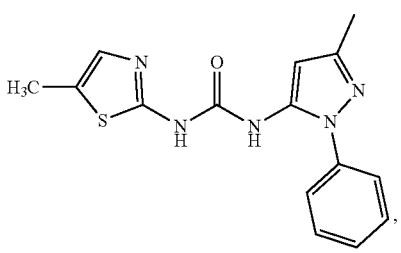
Molecular Weight: 313.38
GAT1564
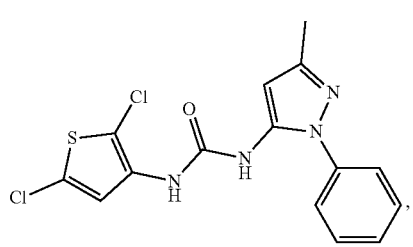
Molecular Weight: 367.25
GAT1565
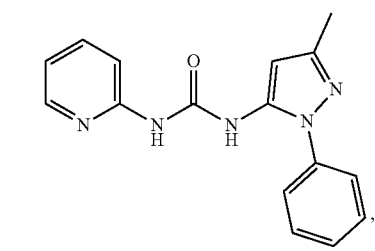
Molecular Weight: 293.33
GAT1566
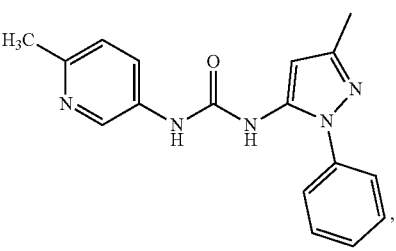
Molecular Weight: 307.36
GAT1568
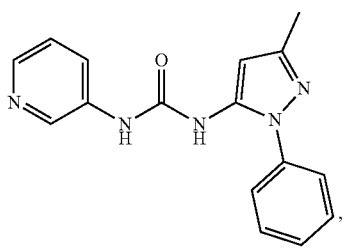
Molecular Weight: 293.33
GAT1569
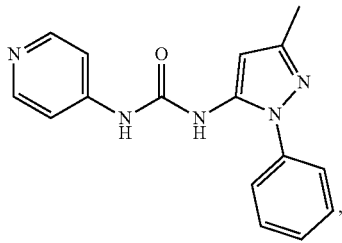
Molecular Weight: 293.33
GAT1570
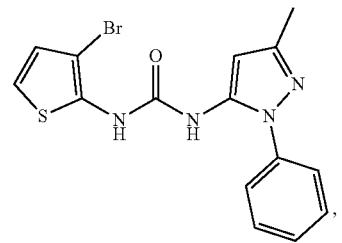
Molecular Weight: 377.26
GAT1574
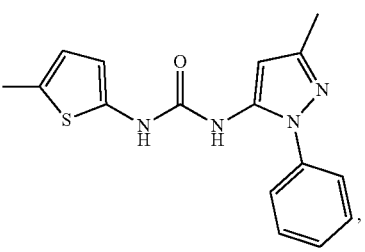
Molecular Weight: 424.26

-continued

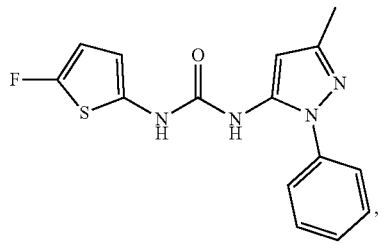

GAT1575

Molecular Weight: 316.35 or a pharmaceutically-acceptable salt thereof.

Hydrates, solvates, and pharmaceutically acceptable salts can readily be produced from any of the compounds disclosed herein, and such forms of the compounds are encompassed by the presently disclosed compounds. According to some aspects, specific polymorphs, crystal forms, amorphous forms, co-crystals, and formulations provide physiological delivery or stability of the compounds disclosed herein, and these forms, combinations, and variations are encompassed by the present technology as it is known in the art that, for example, co-crystals can sometimes provide a formulation suitable for one route of delivery without expanding the inventive concepts described herein. Another non-limiting example is wherein an amorphous form of one of the compounds is provided for bioavailability, stability, or other reasons. It should be understood that as used herein, the term "excipient" can include co-crystals, lipids, active delivery mixtures, solubility enhancers, or inactive blending agents.

As used herein, the term "connecting group" can mean any number of carbon atoms (C), sulfur (S), nitrogen (N), oxygen atoms (O), used so as to connect one molecular piece to another. For example, alkyl/alkenyl/alkynyl with or without heteroatoms with lengths from C1-C6, or optionally from C1-C5, or optionally from C1-C4, or optionally from C1-C3, or optionally from C1-C2, or optionally C1, aromatic or non-aromatic rings can form connecting groups. As used herein, the terms from C1-C6, from C1-C5, etc. can optionally denote a heteroatom in place of one or more carbons in the chain.

According to some aspects, the presently disclosed technology can include a compound having a structure according to Formula VI:

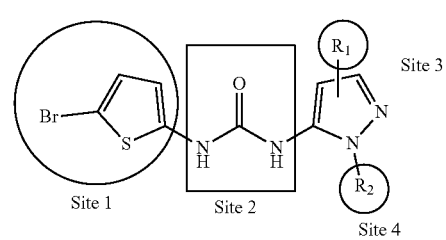

(VI)

wherein Site 1 is as depicted as in Formula VI or is selected from:

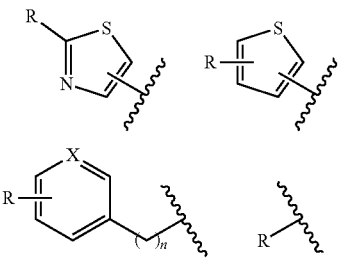

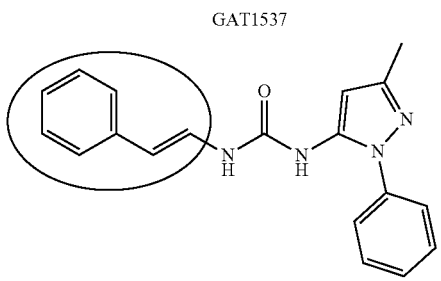

GAT1537

Novel trans geometry
activating pharmacophore

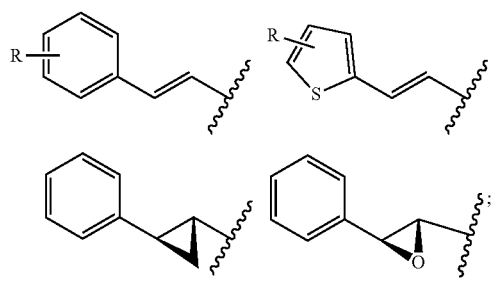

R: alkyl, halogen, CD$_3$, CF$_3$
X: C, N, S O and wherein Site 2 is as depicted in Formula VI or is selected from cyclobutene dione, cyanoguanidine, and thiourea; and wherein Site 3 (R$_1$) is as depicted in Formula VI or is selected from:

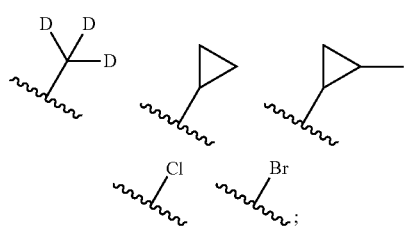

and wherein Site 4 ($R_2$) is as depicted in Formula VI or is selected from:

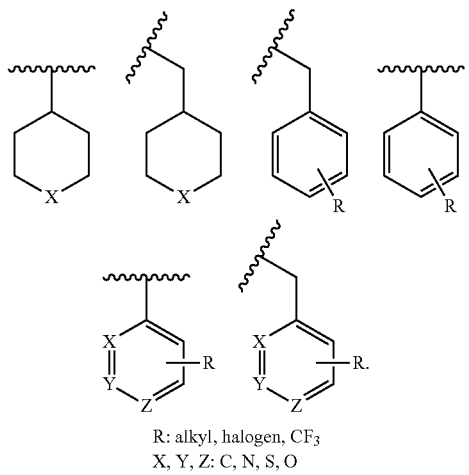

R: alkyl, halogen, $CF_3$
X, Y, Z: C, N, S, O

According to some aspects, the technology can include a compound having a structure according to Formula VII:

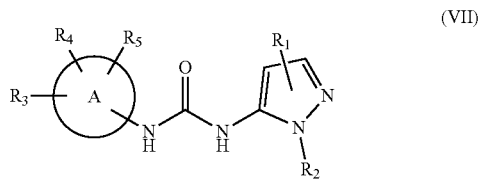

(VII)

wherein ring A is a 3-12 membered ring or ring system comprising aromatic or non-aromatic bonds and optionally comprising heteroatoms N, S, or O and an optional connecting group to NH. Ring A can optionally be substituted with one or more groups, for example, alkyl, halo, alkenyl, alkynyl, and aromatic or non-aromatic rings.

wherein $R_1$ is chosen from hydrogen, halo, alkyl, haloalkyl, deuteroalkyl, cyclopropyl, alkenyl, alkynyl, cyclopropylmethyl, phenyl, other aromatic rings and non-aromatic rings;

wherein $R_2$ is —$(CH_2)$—$R_C$ or —$R_C$; $R_C$ can be piperidine, thiane, tetrahydropyran, cyclohexyl, or phenyl optionally substituted with one $R_D$; the phenyl can optionally include one N, S, and O in place of one carbon atom; $R_D$ can be C1-C6 alkyl, halogen, or $CF_3$;

wherein $R_3$, $R_4$, and $R_5$ are independently chosen from —$R_E$—$R_G$, —$R_F$—$R_G$, —$R_H$, and —$R_I$; $R_E$ is C2 alkene with trans configuration; $R_F$ is cyclopropyl, oxirane, or an alkyl connecting group; $R_G$ is a 5 or 6 membered aromatic ring optionally comprising one or two N, S, or O in place of one or two carbon atoms, the 5 or 6 membered aromatic ring can be optionally substituted with $R_H$; $R_H$ can be C1-C6 alkyl, halogen, $CF_3$, or $CD_3$; $R_I$ is a substituted or unsubstituted ring or ring system chosen from thiophene, benzo[b]thiophene, 4,5,6,7-tetrahydrobenzo[b]thiophene, pyridine, pyrimidine, isoxazole, thiazole, adamantane, benzo[d][1,3]dioxole, naphthalene, and isoquinoline; and wherein $R_1$ is optionally substituted with one or more functional groups chosen from halo, phenyl, and C1-C6 branched or unbranched alkyl optionally substituted with one or more halogens.

The compounds disclosed herein can include wherein $R_D$ is C1-C2 alkyl, or C1-C3 alkyl, or C1-C4 alkyl, or C1-C5 alkyl; wherein $R_H$ is C1-C2 alkyl, or C1-C3 alkyl, or C1-C4 alkyl, or C1-C5 alkyl; and wherein $R_1$ is substituted with C1-C2 alkyl, or C1-C3 alkyl, or C1-C4 alkyl, or C1-C5 alkyl. The compounds disclosed herein can include one or more of $^{18}F$, $^{19}F$, $^{75}Br$, $^{76}Br$, $^{123}I$, $^{124}I$, $^{125}I$, $^{131}I$, $^{11}C$, $^{13}C$, $^{13}N$, $^{15}O$, or $^3H$. According to some aspects, a radiolabeled compound is provided by the aforementioned example or a pharmaceutically acceptable salt, hydrate, or solvate thereof, and an excipient. In some embodiments, the radiolabeled compound can be utilized for diagnosis, prevention, or treatment of one or more medical conditions as the usefulness of binding a radiolabeled compound selectively to one or more GIRK channels in diagnosis, prevention, or treatment is encompassed by the present technology.

According to some aspects, the compounds are direct agonists or antagonists of one or more forms of GIRK channels. Preferably, the compounds are selective so as to activate or inhibit one GIRK channel form while not activating or inhibiting one or more other GIRK channel forms at physiologically relevant levels. According to some aspects, the compounds are a positive allosteric modulator of a GIRK channel, an allosteric agonist of a GIRK channel, a negative allosteric modulator of a GIRK channel, an allosteric antagonist of a GIRK channel. According to some aspects, the activities exemplified above can include partial antagonism, partial agonism, partial allosteric effects, and combinations of the aforementioned activities on one or more GIRK channels.

In some embodiments, the compound can treat PTSD or reduce the symptoms of PTSD in a mammalian subject, such as a human subject who has PTSD or symptoms of PTSD. The compound also can be administered in a prophylactic fashion, so as to prevent or reduce the likelihood of developing PTSD in a subject likely to develop PTSD. According to some aspects, the compound can provide an effective treatment for a disease or disorder. Some non-limiting examples of neurological or neuropsychiatric diseases or disorders include PTSD, epilepsy, stroke, general anxiety disorder, panic disorder, social anxiety disorder, obsessive-compulsive disorder, cardiac arrhythmia including atrial fibrillation, neurodegenerative disease, including Alzheimer's disease, Parkinson's disease, Huntington's disease, addiction, and pain, including chronic pain, neuropathic pain, inflammatory pain, cancer-related pain, headache, and pain resulting from traumatic brain injury (TBI).

Another aspect of the technology is a composition comprising one or more of the above compounds. Another aspect of the technology is a pharmaceutical composition comprising one or more of the above compounds and one or more excipients. Another aspect of the technology is a pharmaceutical composition, comprising a therapeutically effective amount of a modulator of one or more GIRK channels, the modulator having the structure of the compounds disclosed herein, or a pharmaceutically acceptable salt, hydrate, or solvate thereof, and an excipient. In some embodiments, the pharmaceutical composition can activate GIRK1/2 channels; further with some embodiments not activating GIRK1/4 channels at physiologically relevant levels. In some embodiments, the pharmaceutical composition can activate GIRK1/4 channels. According to some aspects, the pharmaceutical composition selectively activates GIRK channels.

According to some aspects, the therapeutically effective amount is less than about 1000 mg, or less than about 900 mg, or less than about 800 mg, or less than about 700 mg, or less than about 600 mg, or less than about 500 mg, or less than about 400 mg, or less than about 300 mg, or less than about 200 mg, or less than about 100 mg. According to some aspects, the pharmaceutical composition includes a therapeutically effective amount of a disclosed compound of about 10 to about 100 mg, or about 10 to about 90 mg, or about 10 to about 80 mg, or about 10 to about 70 mg, or about 10 to about 60 mg, or about 10 to about 50 mg. According to some aspects, the pharmaceutical composition includes a therapeutically effective amount about 1 mg, about 2 mg, about 3 mg, or about 5 mg, or about 7.5 mg, or about 10 mg, or about 12.5 mg, or about 15 mg, or about 17.5 mg, or about 20 mg, or about 22.5 mg, or about 25 mg, or about 30 mg, or about 40 mg, or about 50 mg.

In some embodiments, the pharmaceutical composition can be formulated for long-action or sustained-release. In some embodiments, the pharmaceutical composition is suitable for oral delivery and can be, by way of non-limiting examples, in the form of a capsule, tablet, or lozenge. In some embodiments, the pharmaceutical composition is a patch.

According to some aspects, the pharmaceutical composition is formulated for immediate-release. Non-limiting examples of immediate-release formulations can be applied to transmucosal delivery, transdermal delivery, intra-arterial, or intra-venous delivery.

Another aspect of the technology is a method of treating a medical condition comprising post-traumatic stress disorder, epilepsy, general anxiety disorder, panic disorder, social anxiety disorder, obsessive-compulsive disorder, cardiac arrhythmia, pain, chronic pain, neuropathic pain, and inflammatory pain, the method comprising administering the compounds disclosed herein, the compositions, or the pharmaceutical compositions disclosed herein to a subject in need thereof.

According to some aspects, the compounds and pharmaceutical compositions disclosed herein provide a means or method for prevention or diagnosis of medical conditions comprising post-traumatic stress disorder, epilepsy, general anxiety disorder, panic disorder, social anxiety disorder, cardiac arrhythmia, obsessive-compulsive disorder, pain, chronic pain, neuropathic pain, and inflammatory pain. For example, administration of a compound or pharmaceutical composition disclosed herein can alter the acquisition or progression of a medical condition. Another example is wherein a disclosed compound is used for diagnosis of a medical condition by noting a change in one or more symptoms of a subject after administering one of the disclosed compounds. According to some aspects, the compounds and pharmaceutical compositions disclosed herein provide methods for diagnosis and imaging of GIRK-channel related medical conditions. For example, binding of a selective GIRK-channel modulator disclosed herein comprising an acceptable radiolabel can enable imaging of the GIRK-channel. Another example is administration of a compound or pharmaceutical composition disclosed herein followed by changes in symptoms of a medical condition, wherein symptom changes provide diagnosis information comprising effects on GIRK channel modulation.

According to some aspects, methods of manufacturing, treatments comprising the compounds disclosed herein, methods of treatment, prevention, and diagnosis comprising the compounds disclosed herein, and methods of selectively regulating GIRK channels are provided herein.

As used herein, the terms "about" and "approximately" refer to a range of values within 10%, preferably within 5%, more preferably within 1% or within 0.5% of a stated value.

BRIEF DESCRIPTION OF THE DRAWINGS

FIG. 6 shows percentage of ML297 or GAT1508 contacts with the M1 (darker gray bars) and M2 (lighter gray bars) helices of the GIRK2/2$^{FD}$ and GIRK4/4$^{FD}$ channels during Molecular Dynamics (MD) trajectories. 'Contact' was defined as compound (ligand)-Cα distance ≤7 angstroms. ML297 showed greater contacts with the M1 than the M2 helix in both GIRK2 and GIRK4 heteromeric channels. GAT1508 showed a similar contact pattern as ML297 in the GIRK2 heteromeric channel, while switching to greater contacts with the M2 helix in the GIRK4 heteromeric channel.

FIGS. 7A-7B show snapshots of GAT1508 binding in GIRK2/2$^{FD}$ (FIG. 7A) and GIRK4/4$^{FD}$ (FIG. 7B). GAT1508 shows overall flipping in the GIRK4/4$^{FD}$ system (FIG. 7B), with the bromine atom attached to the thiophene ring forming hydrogen bonds with T94 of the M1 helix of the wild-type GIRK4 subunit.

FIGS. 13A-13B illustrate how specific activation by GAT compounds increases brain GIRK2 but not cardiac GIRK4 channel-PIP$_2$ interactions. FIG. 13A shows normalized salt-bridge formation between the head group phosphatidylinositol-4,5-bisphosphate (PIP$_2$) and positively charged channel residues, calculated during Molecular Dynamics (MD) simulations in the absence of ligand or with ML297, GAT1508 or GAT1521 bound in the GIRK2/2$^{FD}$ (lighter gray) and GIRK4/4$^{FD}$ (darker gray) systems. The interactions between the channel and PIP$_2$ increase in the presence of all three compounds in the GIRK2 heteromeric channel. In the case of GIRK4 heteromer, only ML297 increases channel-PIP$_2$ interactions. GAT1508 and GAT1521 fail to enhance channel-PIP$_2$ interactions in the GIRK4/4$^{FD}$ system (Also see FIGS. 14A-14B). FIG. 13B shows a snapshot of predicted interactions.

FIG. 14A shows that ML297, GAT1508 and GAT1521 increase the PIP$_2$-dependence of GIRK1/2 channels open probability (NPo). GIRK1/2 channel NPo was assessed by diC8-PIP$_2$ concentration-response curves using inside-out macropatches from *Xenopus* oocytes in the presence and absence of 10 μM ML297, GAT1508 or GAT1521; data are means±s.e.m. for 5-6 patches per condition. When studied under control conditions (●), GIRK1/2 channels showed an apparent affinity to diC8-PIP$_2$ of 36±7 μM and an E$_{MAX}$ of 5.7±0.3 (100%). ML297 (▲) increased the apparent affinity to 23±5 μM and the E$_{MAX}$ to 7.5±0.4 (100%). GAT1521 (♦) raised the apparent affinity to 11±2 μM and E$_{MAX}$ to 9.1±0.2 (160%) while GAT1508 (▼) increased the apparent affinity and E$_{MAX}$ further to 5.5±7 μM and 10.5±0.3 (184%), respectively.

FIG. 14B shows that ML297 (▲) but not GAT1508 (▼) or GAT1521 (♦) increases the diC8-PIP$_2$ sensitivity of GIRK1/4 channels. Under control conditions (●), GIRK1/4 channels had an apparent affinity for diC8-PIP$_2$ of 48.4±8 μM and an E$_{MAX}$ of 4.4±0.2 (100%). ML297 increased the apparent affinity to 17.4±2 μM and raised the E$_{MAX}$ to 5.4±0.2 (123% of the control). In contrast, treatment with GAT1508 or GAT1521 did not change the apparent affinity for diC8-PIP$_2$ from control (46±7.4 μM and 51±6.5 μM, respectively) or the efficacy (98.6% and 103%, respectively). Thus, the plots for GAT1508 and GAT1521 are overlayed with the control plot (●).

FIG. 23A shows quantification of APD 70% repolarization (APD$_{70}$) where ML297 at 2×IC$_{50}$ significantly shortened the duration from 23.93 ms±2.28 to 16.53 ms±2.36, N=3, p<0.01 (paired t-test). FIG. 23B shows that in contrast, GAT1508, at concentrations several-fold higher than its IC$_{50}$ for activation of GIRK1/2, did not affect the atrial APD, where the duration was 23.1 ms±1.21 in control, and 23.57 ms±1.96 in the presence of the ligand, p is N.S, (paired t-test).

FIG. 24A shows representative current responses from BLA neurons in response to 30 sec GAT1508 perfusion from −50 mV holding potential at baseline, 10 μM, and 30 μM. FIG. 24B shows summary data depicting significant current response following 30 μM GAT1508, shown on the right, with 10 μM GAT1508 shown in the center, and the baseline shown on the left. Symbols denote statistical significance by one-way ANOVA and Tukey's post-hoc, *p<0.05 versus all other conditions.

FIGS. 34A-34I show concentration-response curves for ML297 and GAT compounds. Recordings were conducted in Xenopus oocytes expressing GIRK1/2 wild-type (●) and GIRK1/4 wild-type (■).

FIG. 35 shows sequence alignment of the M1 helical region of the GIRK channel. For GIRK2 and GIRK4, the two key residues identified by the computational modeling for selective binding are highlighted in gray. Mutations that were performed on each or both of the two M1 key wild-type GIRK4 subunit residues to the corresponding GIRK2 residues (GIRK4-V92I, GIRK4-T94V, GIRK4-V92I/T94V or GIRK4-dm) and vice-versa the GIRK2 residues to the corresponding GIRK4 ones (GIRK2-I97V, GIRK2-V99T, GIRK2-I97V/V99T or GIRK2-dm). These mutations were performed to test computational predictions (also see FIGS. 8-11, 15-18).

FIGS. 36A-36B show single mutants between brain and cardiac channels switch GAT1508 sensitivity. FIGS. 36A-36B show concentration-response curves of GAT1508 in GIRK1/2 (●) and GIRK1/4 (■) wild-type or single mutant channels between unique M1 residues in GIRK2 and GIRK4: GIRK1/2(I-V) (o), GIRK1/2(V-T) (★), GIRK1/4 (V-I) (◇) and GIRK1/4(T-V) (+). Each of the mutants of the predicted GIRK4 binding residues decreased GAT1508 sensitivity of GIRK1/2 (presumably by inducing binding) while they increased the sensitivity of GIRK1/4 (presumably by reducing binding). Data are mean±s.e.m for 8 cells (4 oocytes×2 frogs) per concentration.

FIGS. 37A-37F show ML297, GAT1521, and GAT1508 increasingly protect channel activity from inhibition by phosphatidylinositol-4,5-bisphosphate ($PIP_2$) dephosphorylating light-activated phosphatase. On the left (FIGS. 37A, 37D), representative plots of normalized current magnitude against time show that GIRK1/2 channel current decreases in response to light-activated metabolism of $PIP_2$ by the phosphatase 5-ptase$_{OCRL}$ (control, black 'o'). The decrease in current is reduced when GIRK1/2 channels are studied in the presence of 10 μM GAT1508 (gray 'o'). The 5-ptase$_{OCRL}$-mediated decrease in GIRK1/2 current is characterized by mono-exponential fits in the presence and absence of 10 μM ML297 (o), GAT1521 (o) or GAT1508 (o). ML297, GAT1521 and GAT1508 increase the percentage of GIRK1/2 channel current remaining following activation of 5-ptase$_{OCRL}$ and increase the τ of current-inhibition. ML297, but not GAT1508 or 1521, increases the percentage of residual GIRK1/4 channel current and the τ of the current-decrease following activation of 5-ptase$_{OCRL}$. Data are currents recorded from HEK293 cells using patch-clamp in whole-cell mode and are shown as means±s.e.m. for 6-8 cells per group. Statistical significance was calculated using unpaired t-tests, *p<0.01.

FIGS. 38A-38C show GAT1508 induces a smaller increase in the adjacent (nonligand-binding) subunit in GIRK4 than in GIRK2 possibly by failing to position the phosphatidylinositol-4,5-bisphosphate (PIP$_2$) headgroup via a specific polar interaction. In FIG. 38A, based on the PIP$_2$ binding area, the inventors classified PIP$_2$ into two kinds, P-WT (light gray) represents the two PIP$_2$ molecules interacting with wild-type (non-ligand binding) subunits around the area that ligands bind when present. P-FD (dark gray) represents the two PIP$_2$ interacting molecules with the FD-mutated ligand-binding subunits (analogous to GIRK1) in the absence of ligands bound. In FIG. 38B, the percentage of salt-bridge formation between each type of PIP$_2$ (P-WT and P-FD) and positive charged channel residues in GIRK2/$2^{FD}$ are shown, and in FIG. 38C for GIRK4/$4^{FD}$. The binding of ML297 or GAT1508 shift the PIP$_2$ binding site and increase P-WT interactions with the GIRK2 more so than GIRK4 wild-type subunits.

FIG. 41 shows sequence alignment of the GIRK channel Slide Helix (SH) region. The key residue interactions proposed by the simulations for the GAT1508-induced changes in GIRK activation are highlighted with a rectangle. As polar residues, both Ser and Tyr could form H-bond interactions with PIP$_2$.

FIGS. 42A-42C show representative plots of normalized current magnitude against time. On the left (control), the GIRK1/2 channel current decreases in response to light-activated metabolism of phosphatidylinositol-4,5-bisphosphate (PIP$_2$) by the phosphatase 5-ptase$_{OCRL}$ (control, black 'o'). The decrease in current is reduced when GIRK1/2 channels are studied in the presence of 10 μM GAT1508 (control, gray 'o'). In the center (GIRK1-S65A), channels containing GIRK1-S65A subunits currents are more sensitive to 5-ptase$_{OCRL}$ (light gray 'o') and are not protected by GAT1508 (gray 'o'). On the right (GIRK1-S65Y), in contrast, channels with GIRK1-S65Y subunits (black 'o') are more protected than the wild-type and GAT1508 no additional effect (gray 'o'). Data are currents recorded from HEK293 cells using patch-clamp in whole-cell mode and are shown as means±s.e.m. for 5-6 cells per group. Statistical significance was calculated using unpaired t-tests, *p<0.01.

FIGS. 44A-44C show representative plots of normalized current magnitude against time. In FIG. 44A, the GIRK1/4 channel current decreases in response to light-activated metabolism of PIP$_2$ by the phosphatase 5-ptase$_{OCRL}$ (control, black 'o'). The decrease in current is reduced when GIRK1/4 channels are studied in the presence of ML297 (gray 'o') but not with GAT1508 (light gray 'o'). In FIG. 44B (GIRK1-S65A), channels containing GIRK1-S65A subunits currents are more sensitive to 5-ptase$_{OCRL}$ and are not protected by either compound (ML297 and GAT1508). In FIG. 44C, channels with GIRK1-S65Y subunits are more protected than wild-type.

FIGS. 42-45 show the increase in current mediated by GAT1508 in GIRK1/2 and by ML297 in GIRK1/4 requires Ser 65 in the GIRK1 subunit.

FIGS. 52A-52B show human ERG currents are modulated by ML297 but not by GAT1508. In FIG. 52A, human ERG (hERG) channels were expressed in *Xenopus* oocytes and studied by two-electrode voltage clamp (TEVC). In FIG. 52A, hERG tail-current magnitude was assessed at −50 mV, following a 4 second test step to 20 mV from a holding voltage of −100 mV. The test pulse was repeated every 10-seconds. Currents were not inhibited by 5 µM (dark gray) or 50 µM GAT1508 (black) but were inhibited by 10 µM terfenadine (light gray, bottom trace). In FIG. 52B, a representative time-course showing inhibition of hERG tail currents by terfenadine but not by GAT1508 in the same oocyte is shown.

FIG. 53A is a bar chart showing that terfenadine, but not GAT1508, decreases hERG tail-currents. FIG. 53B is a bar chart showing that 5 µM ML297 inhibits ~40% of the hERG tail current (center bar), *p<0.01 unpaired t-test, consistent with a published $IC_{50}$ value of ~10 µM; the residual current is inhibited by 10 µM terfenadine. Data are mean±s.e.m. for 6 oocytes per group.

FIG. 54A is a bar graph demonstrating total distance travelled. FIG. 54B is a bar graph indicating mean speed. Both bar charts are for rats (n=8 animals per group) in an open field arena following intraperitoneal (i.p.) injection of either vehicle or ML297 (30 mg/kg).

FIG. 55A shows time spent on the open arm in the elevated plus maze (EPM) test. FIG. 55B shows time spent in the light compartment in light dark box (LD) test. FIG. 56A shows total distance travelled in the open field (OF) test. FIG. 56B shows mean speed in the OF test. FIG. 57A shows duration of social interaction in the social interaction (SI) test. FIG. 57B shows latency to fall in the rotorod test. FIG. 58A shows total exploration time of familiar (Fam) and novel arms. FIG. 58B shows the discrimination index in the novel object recognition (NOR) test. For FIGS. 55A to 58B, *p<0.05, ANOVA with Sidak's posthoc test, vehicle ●, GAT1508 (10 mg/kg) ■, GAT1508 (30 mg/kg) ▲.

In FIG. 61B, the inventors compared the 10 µM GAT1508-induced thallium and potassium currents in oocytes expressing GIRK1/2 and GIRK1/4 by TEVC recording. Based on the solubility of TlCl, instead of using 96 mM potassium, the inventors used potassium and thallium at 10 mM concentration. In an effort to enhance the current, the TEVC recording was performed at a holding potential of −100 mV. Interestingly, GAT1508 only showed a selective activation effect in 10 mM K+, which significantly increased currents in oocytes coexpressing GIRK1/2 but not GIRK1/4. For thallium ions, consistent with our modeling predictions, GAT1508 induced current increases in both GIRK1/2 and GIRK1/4 expressing cells.

FIG. 67 shows a different representation of the data for GAT1555 and GAT1558 from FIG. 66 (boxes). ML297 results are represented by the bar on the left, GAT1555 by the bar in the middle, and GAT1558 by the baron the right.

DETAILED DESCRIPTION

Figure 1:
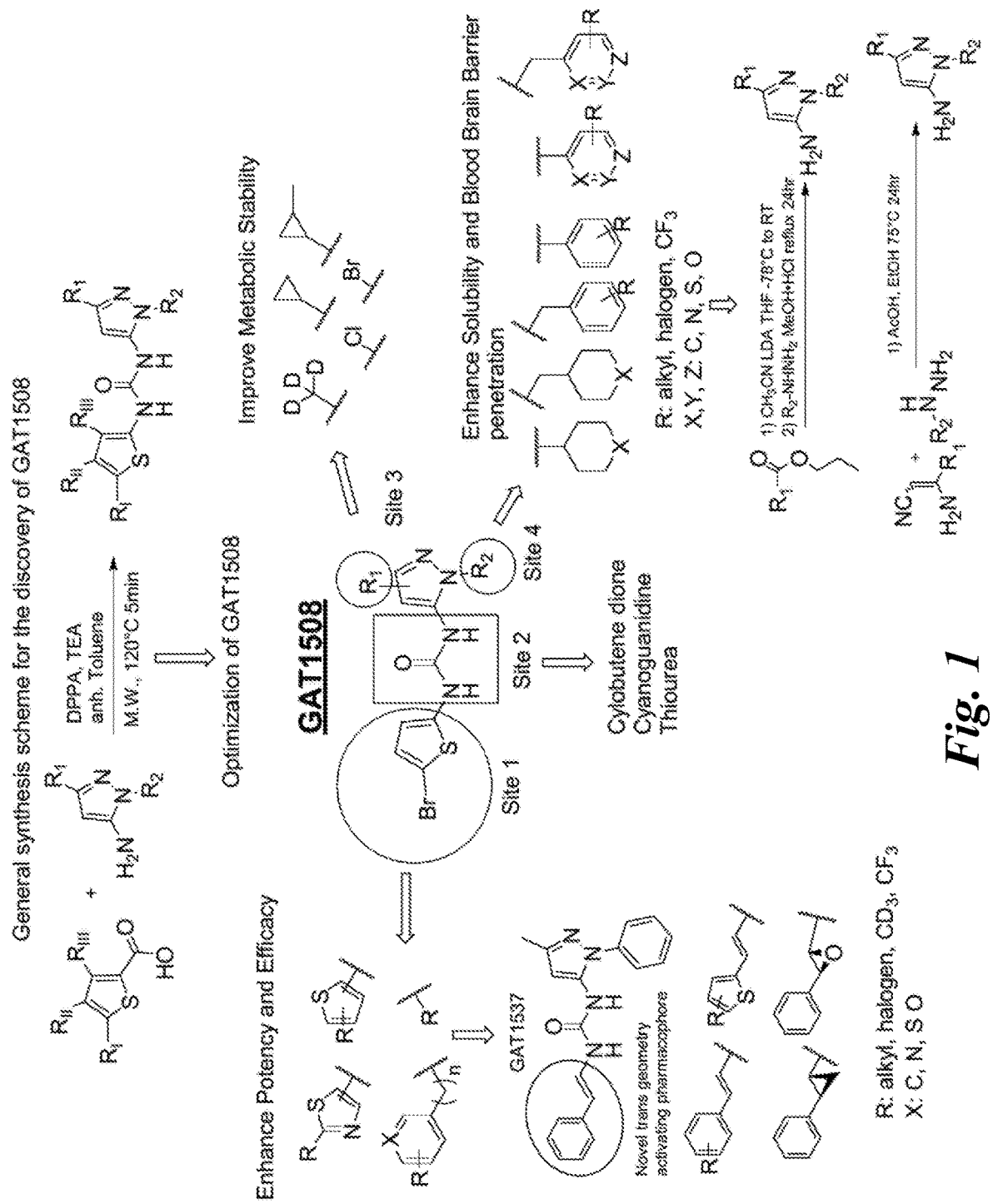
FIG. 1 shows a general synthetic scheme for the discovery of GAT1508.
Figure 2:
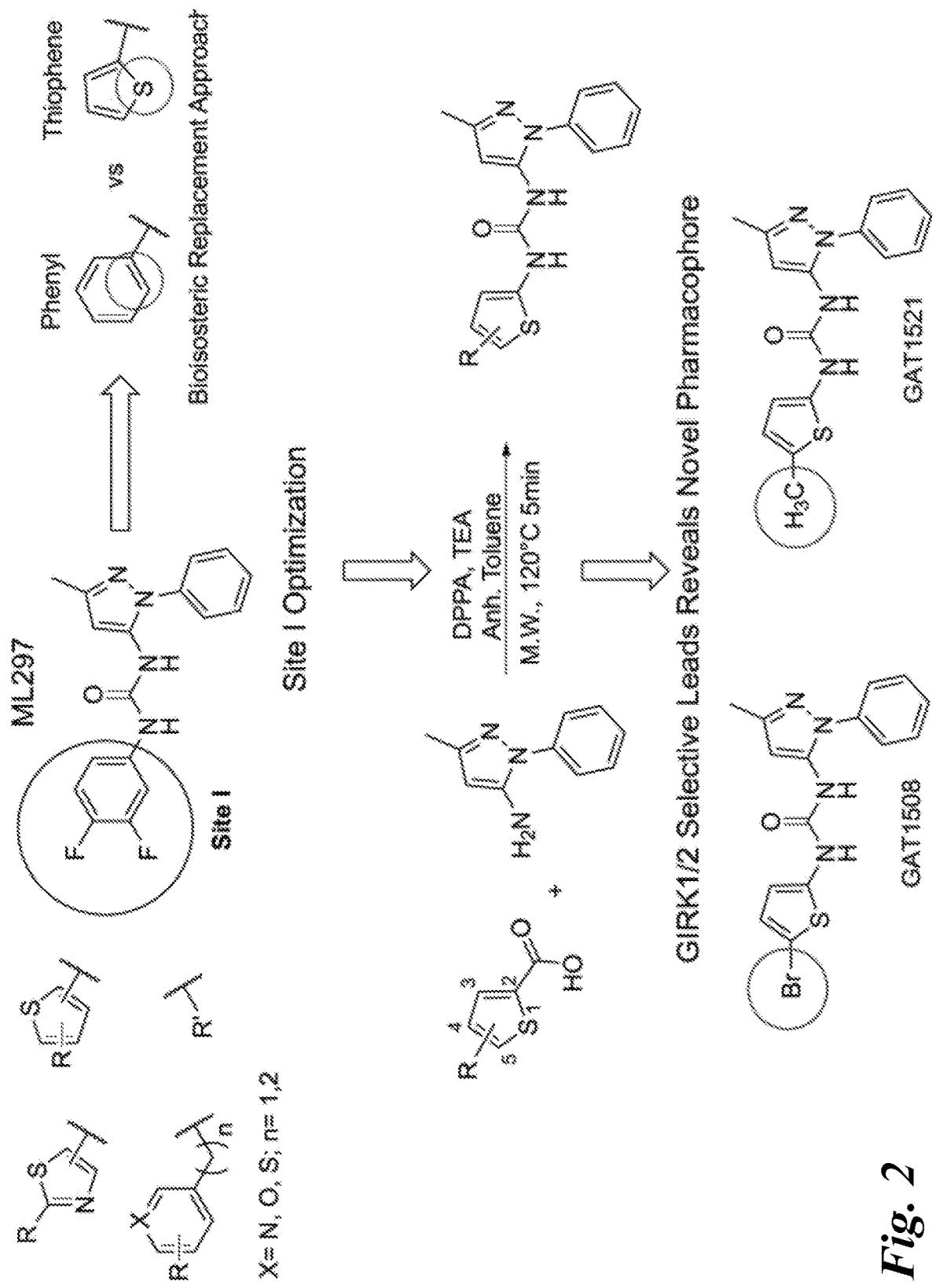
FIG. 2 shows the rational design and systematic focused approach to a preliminary SAR study on ML297 leading to GAT1508 and GAT1521.
Figure 12:
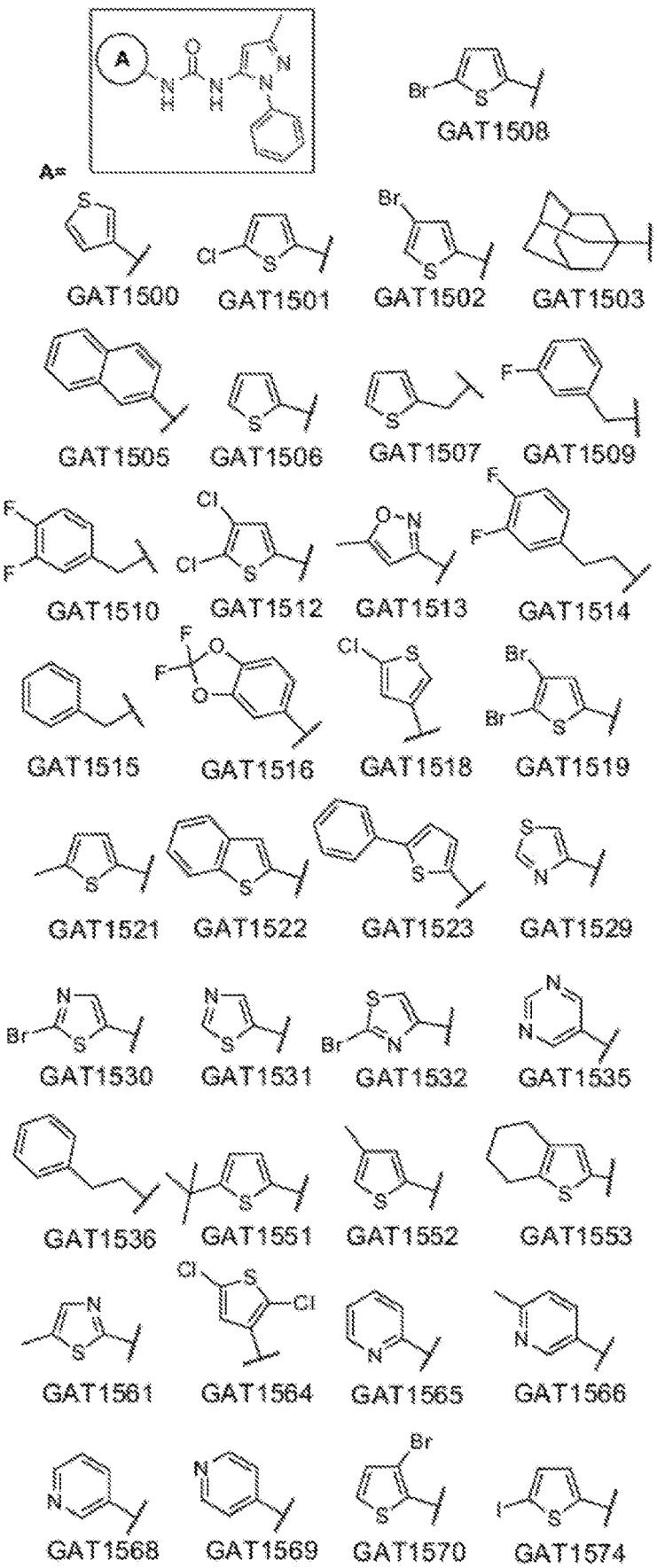
FIG. 12 shows a series of 37 new analogs that were produced by a number of structure-activity relationship (SAR) strategies, such as spacer addition, heteroatom introduction, and bioisosteric replacement.

The inventors have developed novel molecules that are selective modulators of GIRK1/2 over GIRK1/4 channels. Initial chemical optimization focusing on Site I (R or difluorinated phenyl ring in ML297) resulted in nearly 40 new analogs that were produced by a number of structure-activity relationship (SAR) strategies, such as spacer addition, heteroatom introduction, and bioisosteric replacement (FIGS. 1, 2, 12).

Figure 5A:
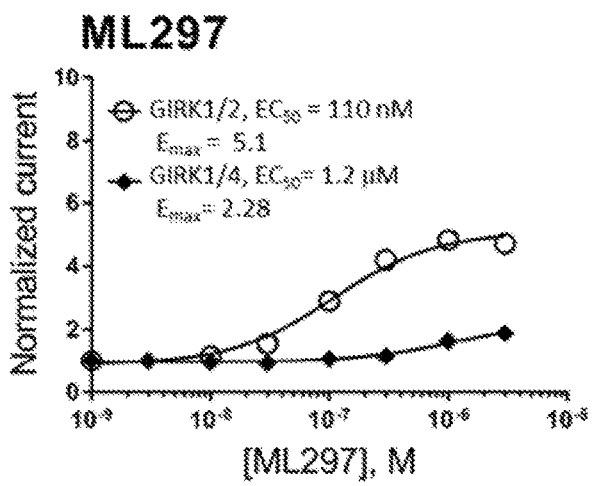
FIGS. 5A-5C show concentration-response curves for ML297 (FIG. 5A) and the selective compounds GAT1508 (FIG. 5B) and GAT1521 (FIG. 5C). The response curves were assessed in HEK293 cells expressing GIRK1/2 wild-type (o) and GIRK1/4 wild-type (♦) using whole-cell patch-clamp recording. Data are mean±standard error of the mean for 7-12 cells per condition.
Figure 5B:
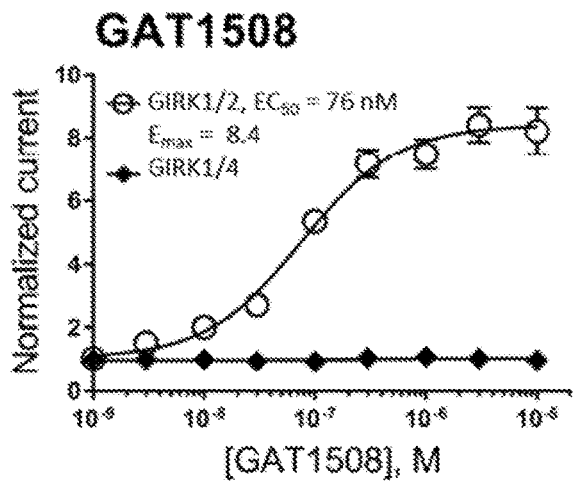
Figure 5C:
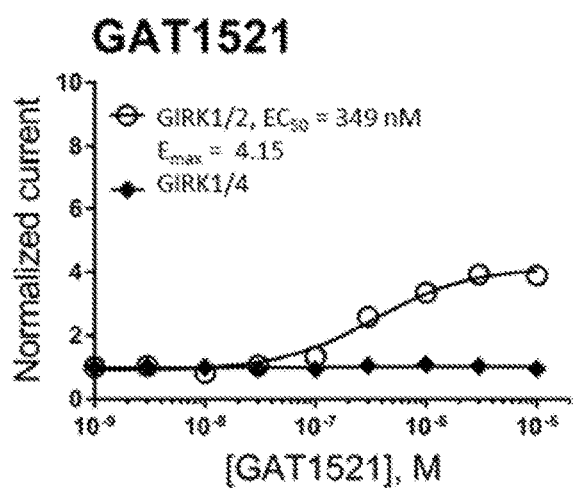
Figure 8:
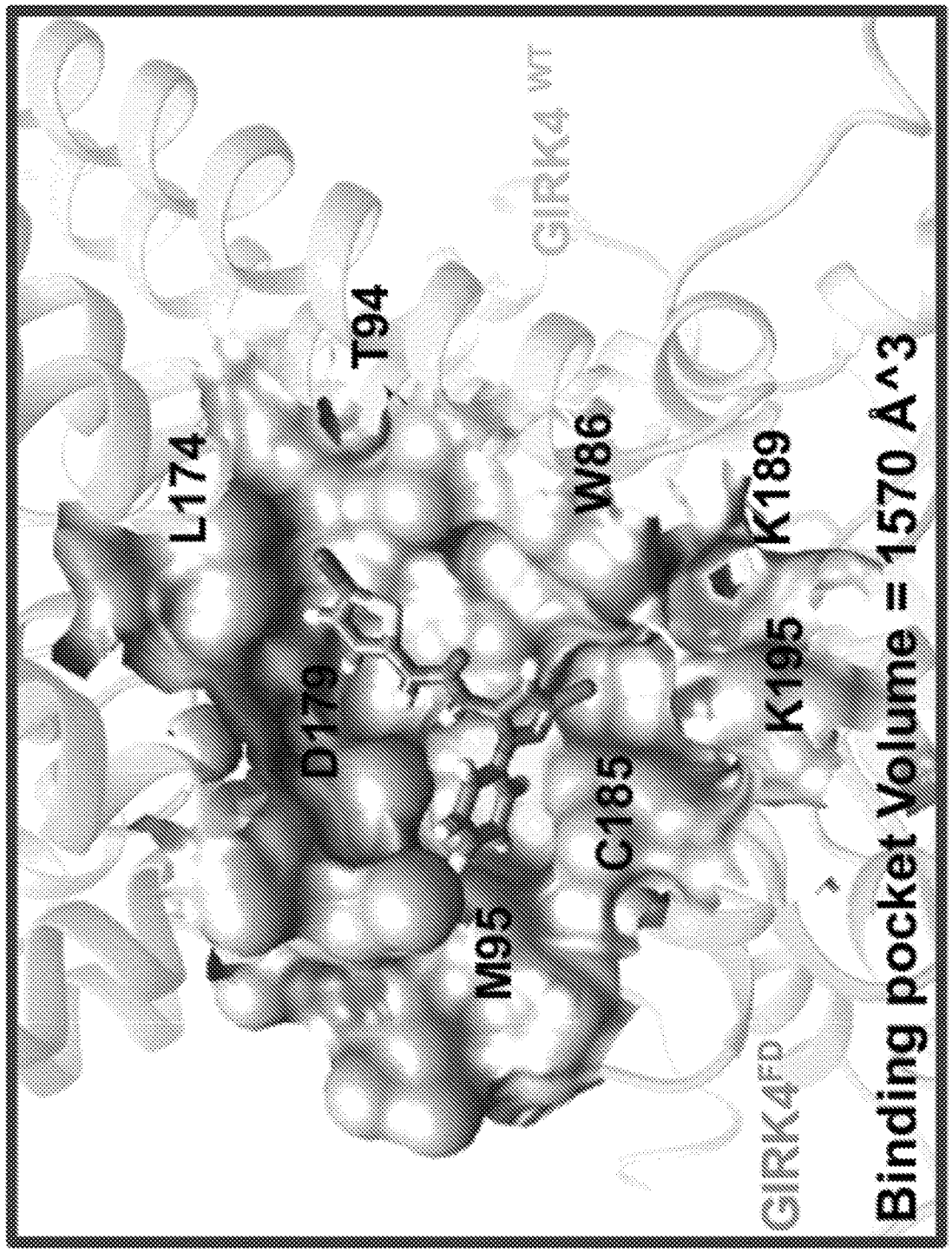
FIG. 8 shows the binding site surface with GAT1508 between the M1 and M2 helical regions in GIRK4/4$^{FD}$. The binding pocket volume=1570 cubic angstroms.
Figure 9:
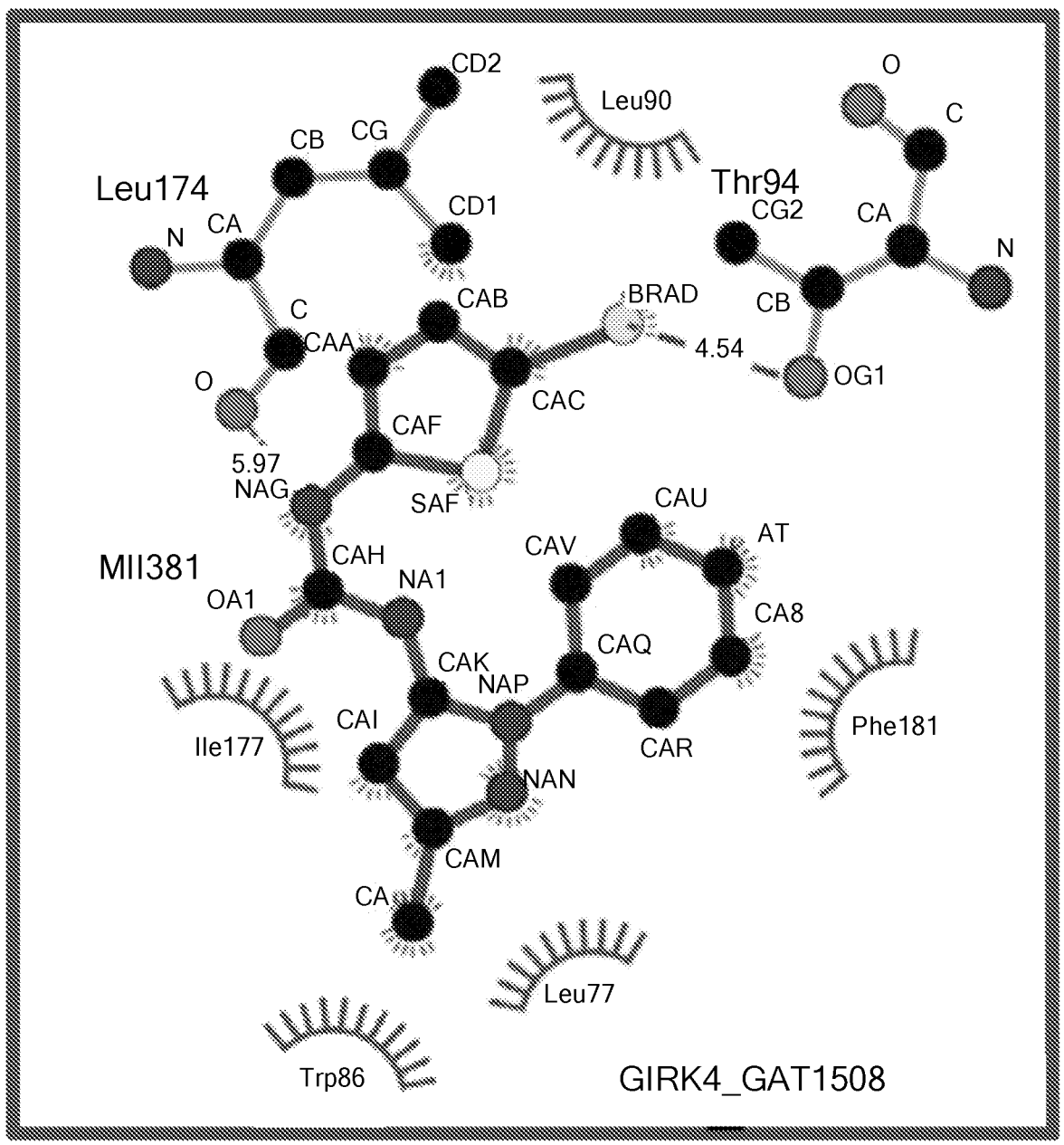
FIG. 9 shows a LIGPLOT diagram of GAT1508 interactions with its immediate environment in GIRK4/4$^{FD}$. LIGPLOT is a software program for generating schematic diagrams of protein-ligand interactions. Hydrogen bonds are dashed lines with indicated distances in angstroms. Residues in hydrophobic contact with GAT1508 are represented by semicircles with radiating spokes.
Figure 31:
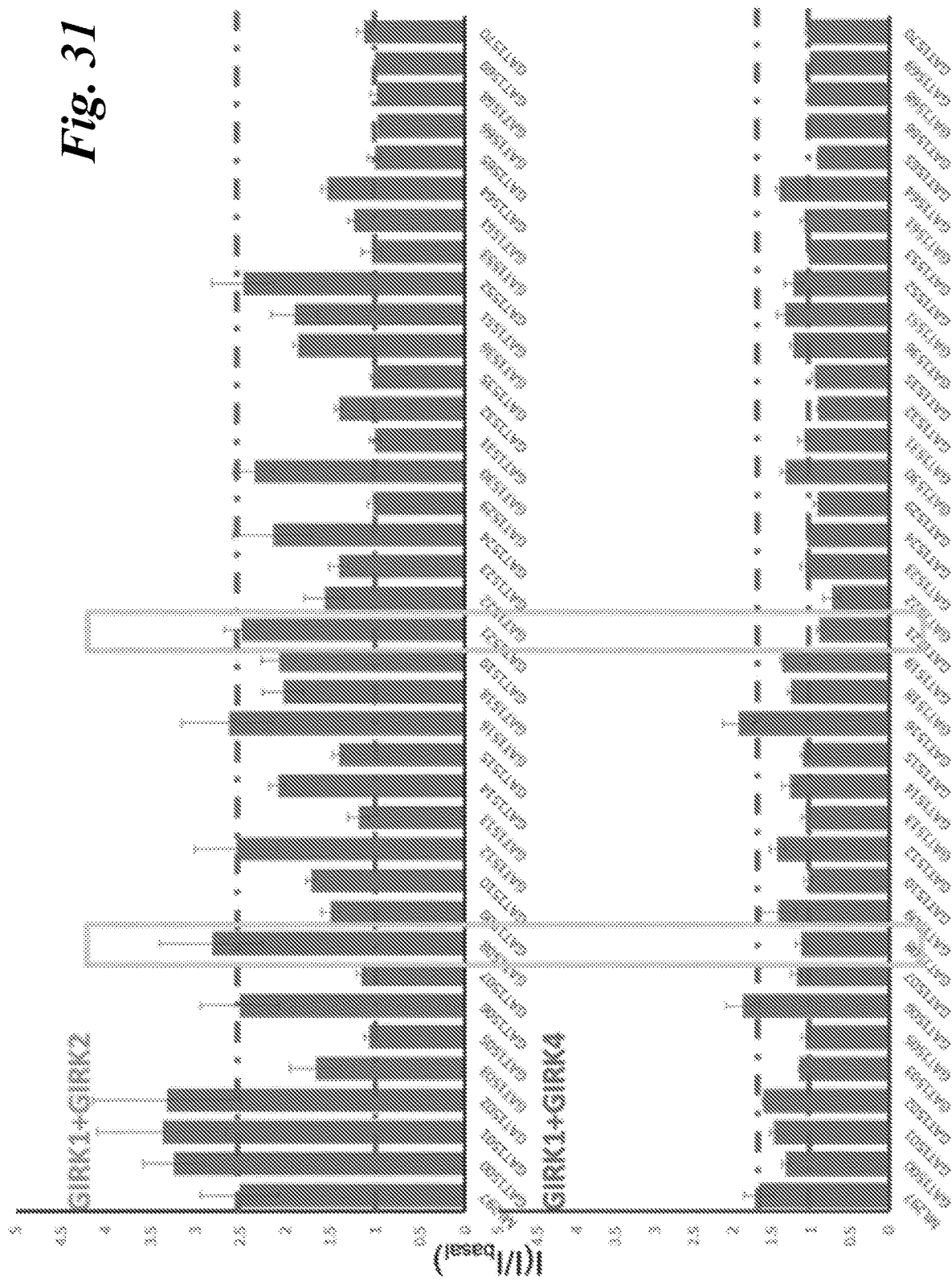
FIG. 31 shows effects of GAT compounds compared to effects of ML297. The compounds were characterized by two-electrode voltage clamp (TEVC) recording in Xenopus oocytes expressing GIRK1/2 (upper) and GIRK1/4 (lower). The dashed line at "1" on the Y-axis shows normalized basal channel activity (value of "1"), while the dot and dashed line shows the ML297-induced current normalized to the basal activity. The two most selective activators are highlighted by narrow vertical rectangles. Data are mean current±s.e.m for 8-16 oocytes (4 cells per frog from 2-4 frogs) in response to 10 μM of each compound shown.

To explore the selectivity of these compounds, the inventors evaluated their effects using two-electrode voltage-clamp of *Xenopus laevis* oocytes expressing either brain or cardiac heteromeric GIRK channel subunits (brain=GIRK1/2 versus cardiac=GIRK1/4). Current responses to perfusion of 10 µM of each compound were assessed (FIG. 31). FIG. 31 summarizes current increases normalized to the basal current level in High Potassium (HK) solution (dashed lines shown at 1 on the Y-axes) versus current level in compound tested relative to that of the ML297 compound (dashed line at ~1.75 on Y-axis of GIRK1+GIRK4 plot and dashed line at ~2.5 on Y-axis of GIRK1+GIRK2 plot, FIG. 31). Similar to ML297, most compounds elicited greater current increases in GIRK1/2 compared to GIRK1/4 channels. Among them, two thiophene ring derivatives, one with a bromine and the other with a methyl at the 5' position, named GAT1508 and GAT1521 respectively, were the most selective GIRK1/2 activators relative to GIRK1/4. GAT1508 and GAT1521 are highlighted with rectangles in FIG. 31. Concentration-response curves of these two compounds compared to ML297, using whole-cell patch clamp electrophysiology in HEK-293 cells expressing GIRK1/2 or GIRK1/4 channels (FIGS. 5A-5C), further confirmed the selectivity for activation of the brain-expressing subunits and determined that GAT1508 possessed the highest potency and efficacy compared to ML297 or GAT1521.

Altered Binding of GAT1508 to GIRK Channels Underlies its Specificity.

To understand why GAT1508 has the highest potency and efficacy, docking studies and molecular dynamics (MD) simulations using the experimentally determined X-ray structure (Whorton and MacKinnon, 2013) were initiated and compared to simulations using mutated GIRK2 (GIRK2$^{FD}$) and GIRK4 (GIRK4$^{FD}$) subunits ("FD"=mimics the contribution of GIRK1 residues F137 and D173, see Example 2). MD simulations demonstrate GAT1508 showed a contact pattern similar to ML297 in the GIRK2/2$^{FD}$ heteromeric channel (FIG. 6, FIG. 7A). In the GIRK4/4$^{FD}$ heteromeric channel, where GAT1508 lost its stimulatory effect, it made greater contacts with the M2 helix (FIG. 6, FIG. 7B).

Activation Effects of Selective GAT Compounds Relate to Channel-PIP$_2$ Interactions.

Figures 33A, 33B:
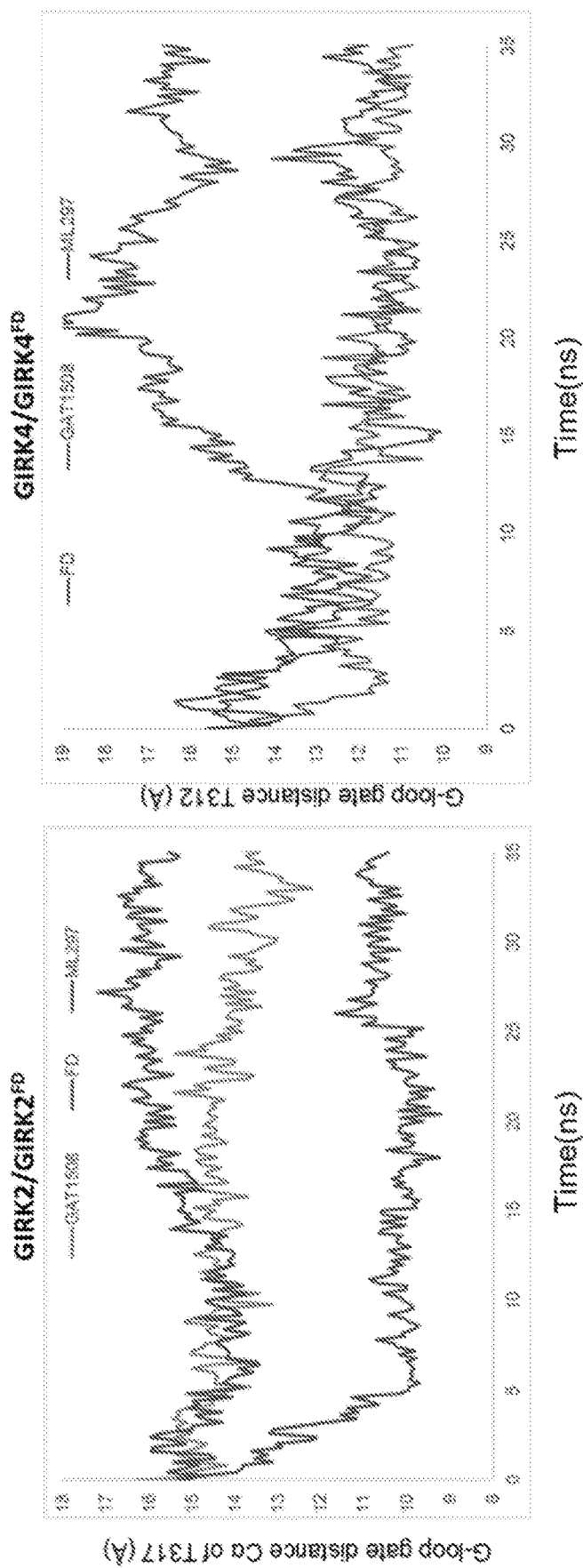
FIGS. 33A-33B show calculations of the distance between the G-loop gates during the Molecular Dynamics (MD) simulation between T317 in $GIRK2/2^{FD}$ (33A) and between T312 in $GIRK4/4^{FD}$ (33B) in the absence of compound (black) or with bound ML297 (medium gray) and GAT1508 (light gray). All systems became stable after 15 ns in the MD simulation. The MD trajectories from 25 ns-35 ns were used for interaction analysis (also see FIG. 32) and RMSF calculations (FIGS. 42-45). Both ML297 and GAT1508 could induce the opening of the G-loop gate in the $GIRK2/2^{FD}$ system. Opening of the $GIRK4/4^{FD}$ G-loop gate only took place in the presence of ML297 but not GAT1508.

As was previously shown, the ML297 activation was dependent on intact PIP$_2$ levels (Wydeven et al., 2014). Our results have shown that the GAT1508 binding site lies 10-16 angstroms away from the PIP$_2$ headgroup interacting with the adjacent subunit (FIGS. 33A-33B). To gain structural insights as to whether the GAT1508 compound's specific binding (FIGS. 6-9, FIG. 15) opened the channel gates by strengthening channel-PIP$_2$ interactions, the inventors conducted Molecular Dynamics (MD) simulations to further investigate possible differences between brain and cardiac channels in the PIP$_2$ binding area. The movement of compounds and PIP$_2$ relative to the channel were monitored to explore the binding stability in each heteromeric system during the simulation. Compared to the channels without ligand, binding of PIP$_2$ did not introduce major structural changes around the binding pocket of the activators. In contrast, binding of the activating compounds showed significant changes in channel-PIP$_2$ interactions. To quantify these interactions, the normalized salt-bridge formation between the head group of PIP$_2$ and positively charged channel residues were generated during the MD simulation without any ligand or in the presence of ML297, GAT1508 or GAT1521 for each of the GIRK2/2$^{FD}$ and GIRK4/4$^{FD}$ systems (FIGS. 13A-13B). The interaction between channel and PIP$_2$ increased by 18-25% in the presence of each of the three compounds in the GIRK2/2$^{FD}$ heteromeric channel. In the case of the GIRK4/4$^{FD}$ heteromeric channel simulation, however, only ML297 increased channel-PIP$_2$ interactions, while GAT1508 and GAT1521 did not show significant increases in channel-PIP$_2$ interactions (FIG. 13A). The inventors proceeded to test experimentally these model predictions.

Figure 20A:
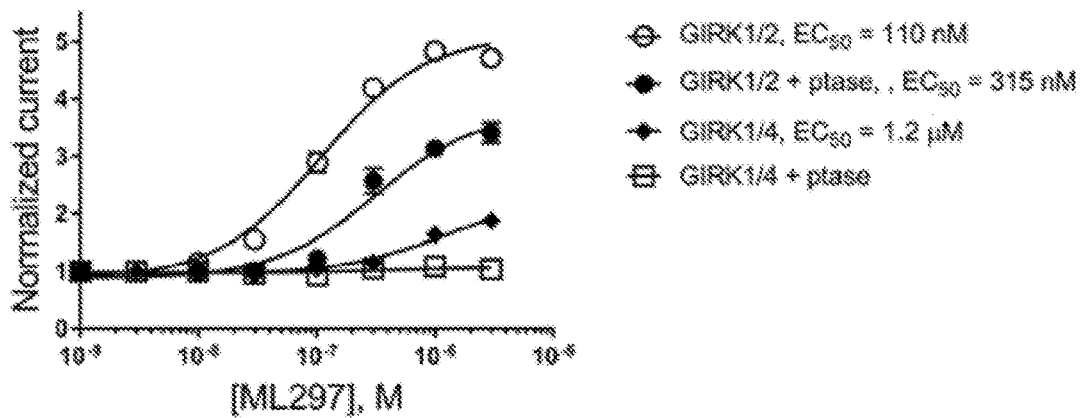
FIGS. 20A-20C show experimental validation of GAT compound activation through phosphatidylinositol-4,5-bisphosphate (PIP$_2$). The Molecular Dynamics (MD) simulations indicated a PIP$_2$-dependent activation effect by ML297 (FIG. 20A), GAT1508 (FIG. 20B), and GAT1521 (FIG. 20C) compounds in GIRK heteromers leading to channel gating. To experimentally test the role of PIP$_2$ in channel activation by ML297 and the GAT compounds, the inventors proceeded to first manipulate PIP$_2$ levels by inducing a light-sensitive phosphatase in whole-cell patch-clamp experiments in mammalian cells and to examine the effects of the activating compounds. Like ML297, both GAT selective compounds showed decreased potency and efficacy effects following hydrolysis of PIP$_2$ by stimulation of light-sensitive phosphatase. Interestingly, the most potent and efficacious compound (GAT1508) showed the least decrease in potency (~2-fold) compared to ML297 (3-fold) and GAT1521 (~3.7-fold).
Figure 20B:
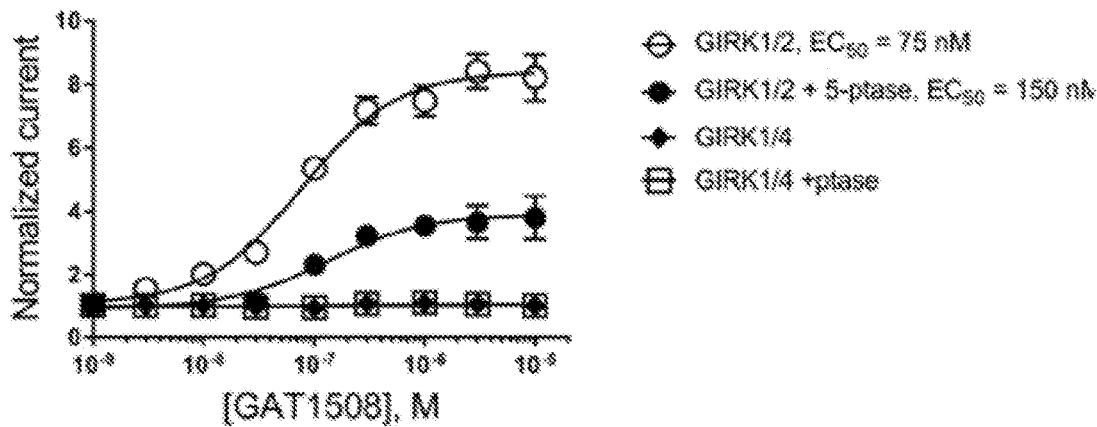
Figure 20C:
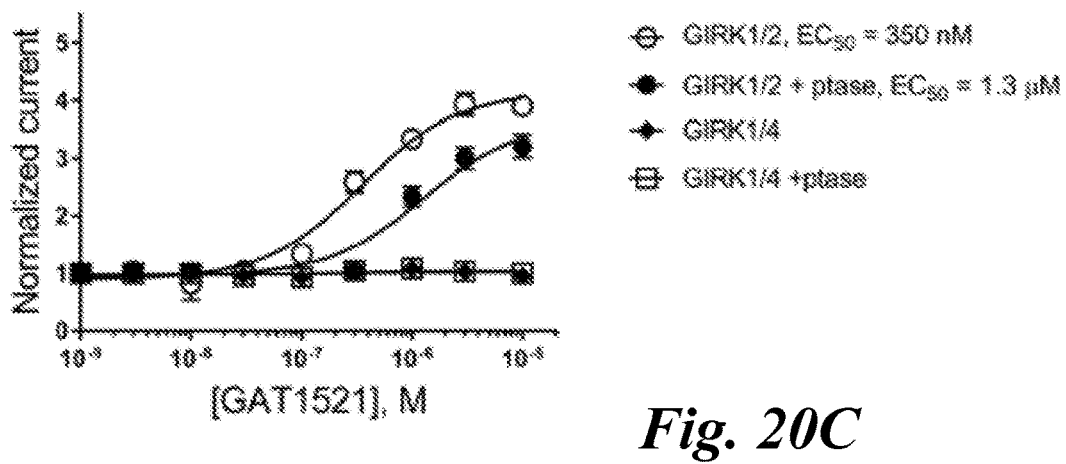

The MD simulations indicated a PIP$_2$-dependent activation effect by ML297 and the GAT compounds in GIRK heteromers leading to channel gating. To experimentally test the role of PIP$_2$ in channel activation by ML297 and the GAT compounds, the inventors proceeded to first manipulate PIP$_2$ levels by inducing a light-sensitive phosphatase in whole-cell patch-clamp experiments in mammalian cells and to examine the effects of the activating compounds (FIGS. 20A-20C).

The inventors next turned to inside-out macropatches from *Xenopus* oocytes to compare changes in the PIP$_2$ sensitivity by examining diC8 concentration-responses in the absence and presence of saturating concentrations of each of the activating compounds. FIG. 14A shows results from inside-out macropatches of GIRK1/2 expressed in *Xenopus* oocytes, where diC8-PIP$_2$ dose-dependent activity (NPo) from control patches in the absence of any compound was compared to those from patches exposed to 10 µM of ligand (ML297, GAT1508, or GAT1521). GAT1508 was most potent and efficacious in sensitizing the channel to PIP$_2$ activation, with GAT1521 next, and ML297 following. FIG. 14B shows results from the analogous experiments with GIRK1/4. In FIG. 14B, the control plot overlays the GAT1508 and GAT1521 plots; only ML297 was able to left-shift the sensitivity of GIRK1/4 heteromers to PIP$_2$, while both GAT1508 and GAT1521 were ineffective in changing the sensitivity of these heteromers to PIP$_2$.

Figure 19:
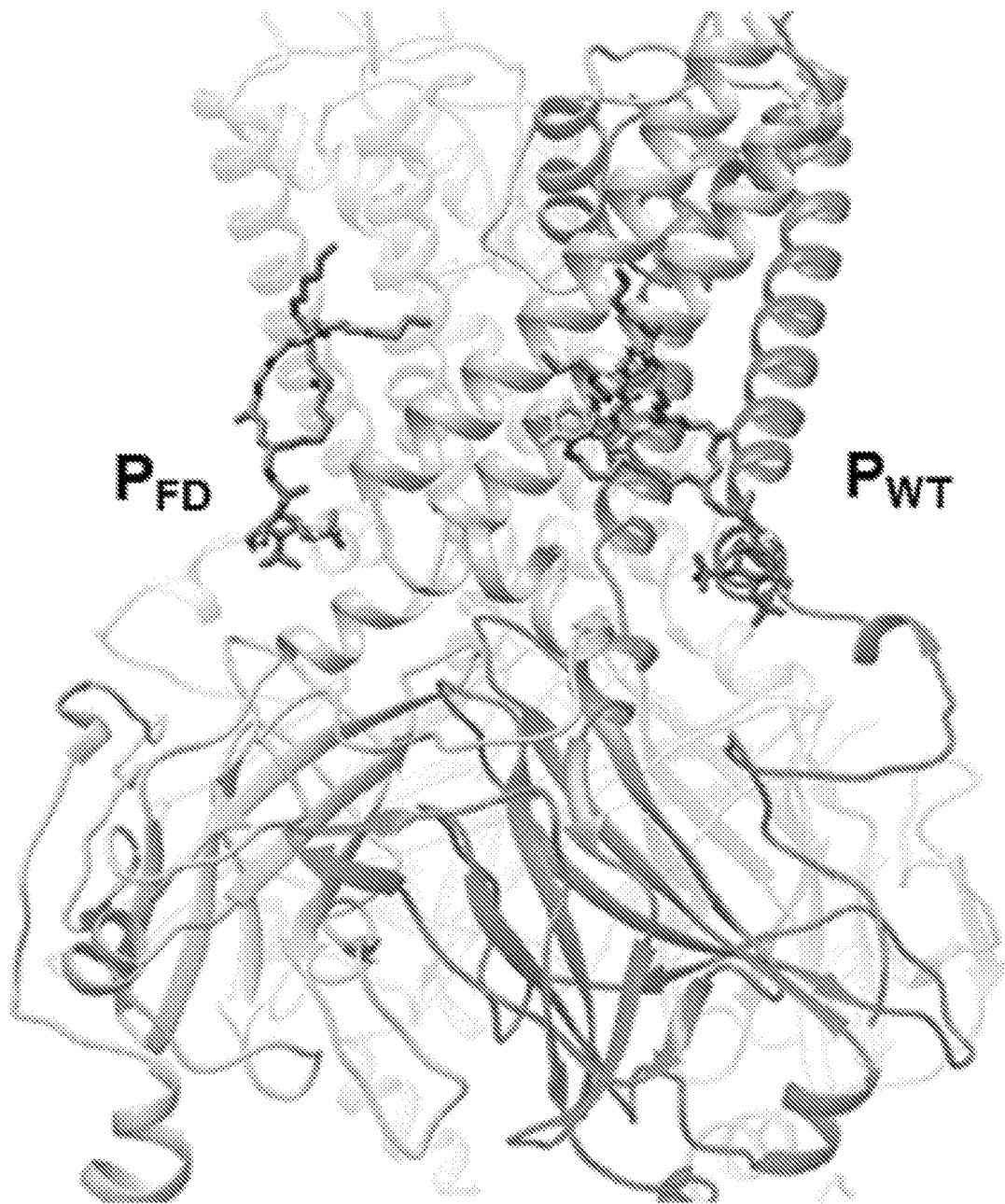
FIG. 19 shows how, based on the phosphatidylinositol-4,5-bisphosphate (PIP$_2$) binding area, the inventors classified PIP$_2$ into two kinds, P-WT (darker gray) represents the two PIP$_2$ molecules interacting with wild-type (non-ligand binding) subunits around the area that ligands bind when present. P-FD (lighter gray) represents the two PIP$_2$ interacting molecules with the FD-mutated ligand-binding subunits (analogous to GIRK1) in the absence of ligands bound (see FIG. 38A).

The inventors next pursued whole-cell patch-clamp experiments to further validate the model predictions and excised-patch results. Expression of a light-activated phosphatase that upon exposure to blue light dephosphorylates PI(4,5)P$_2$ to PI(4)P and inhibits GIRK currents allowed recording of macroscopic currents in the absence and presence of ML297 and the two brain-specific GAT compounds. Indeed, time courses of current inhibition upon stimulation of light-activated phosphatase showed increasing protection from current inhibition with GAT1508>GAT1521>ML297>Control for GIRK1/2 expressing HEK-293 cells both for current levels and kinetics of inhibition (FIGS. 37A-37F). These results were in marked contrast to GIRK1/4 currents, where only ML297 but not GAT1508 or GAT1521 were able to provide some protection of currents from inhibition by the light-activated phosphatase (FIGS. 37A-37F). Since GAT1508 and ML297 only bind GIRK1 or GIRK1-like (i.e. "FD-containing", "FD"=mimics the contribution of GIRK1 residues F137 and D173, see Example 2) subunits resulting in corresponding changes in channel-PIP$_2$ interactions and channel activity, the inventors next sought to compare channel subunit specific interactions with PIP$_2$ for subunits bound to the ligand (P-FD) versus those not bound to the ligand (P-WT) (FIGS. 19, 38A).

The inventors calculated the normalized salt-bridge formation between P-FD and P-WT subunits in the GIRK2/2$^{FD}$ and GIRK4/4$^{FD}$ systems and found that the binding of ML297 or GAT1508 in the "FD-containing" subunits shifted the neighboring subunit PIP$_2$ binding and increased P-WT interactions with the GIRK2 or GIRK4 wild-type subunits (FIGS. 38B-38C). The MD simulations allowed us to examine specifically interactions of the FD-containing subunits with PIP$_2$ (P-FD, shown in light gray) versus the non-FD-containing subunits with PIP$_2$ (P-WT, shown in dark gray) in the absence or presence of ML297 or GAT compound binding (FIGS. 19, 38A-38C). In fact, the probability of salt bridges between channel and PIP$_2$ increased more in the GIRK2 than GIRK4 subunits. In contrast, the compounds decreased the channel P-FD interactions in the FD-containing subunits for both heteromeric channels and perhaps somewhat more for GIRK4/4$^{FD}$ than GIRK2/2$^{FD}$ heteromers. Thus, the overall changes (P$_{WT}$-P$_{FD}$) in channel-PIP$_2$ interactions by GAT1508 showed increases only in GIRK2/2$^{FD}$ heteromers, consistent with the changes in overall interactions shown in FIG. 13A.

The greater reduction in the GIRK4/4$^{FD}$ heteromers of P-FD (FIG. 13A) by GAT1508 (and GAT1521) counteracted any strengthening effects in the P-WT interactions thus showing no overall changes in channel-PIP$_2$ interactions, consistent with the failure of these GAT compounds to activate the cardiac channels. Concurrent with the above changes, the probability of interaction between PIP$_2$ and channel show overall strengthening in GIRK2/2$^{FD}$ heteromeric channel by the two GAT compounds, consistent with the stimulatory effects of these GAT compounds on brain channels.

Figure 39:
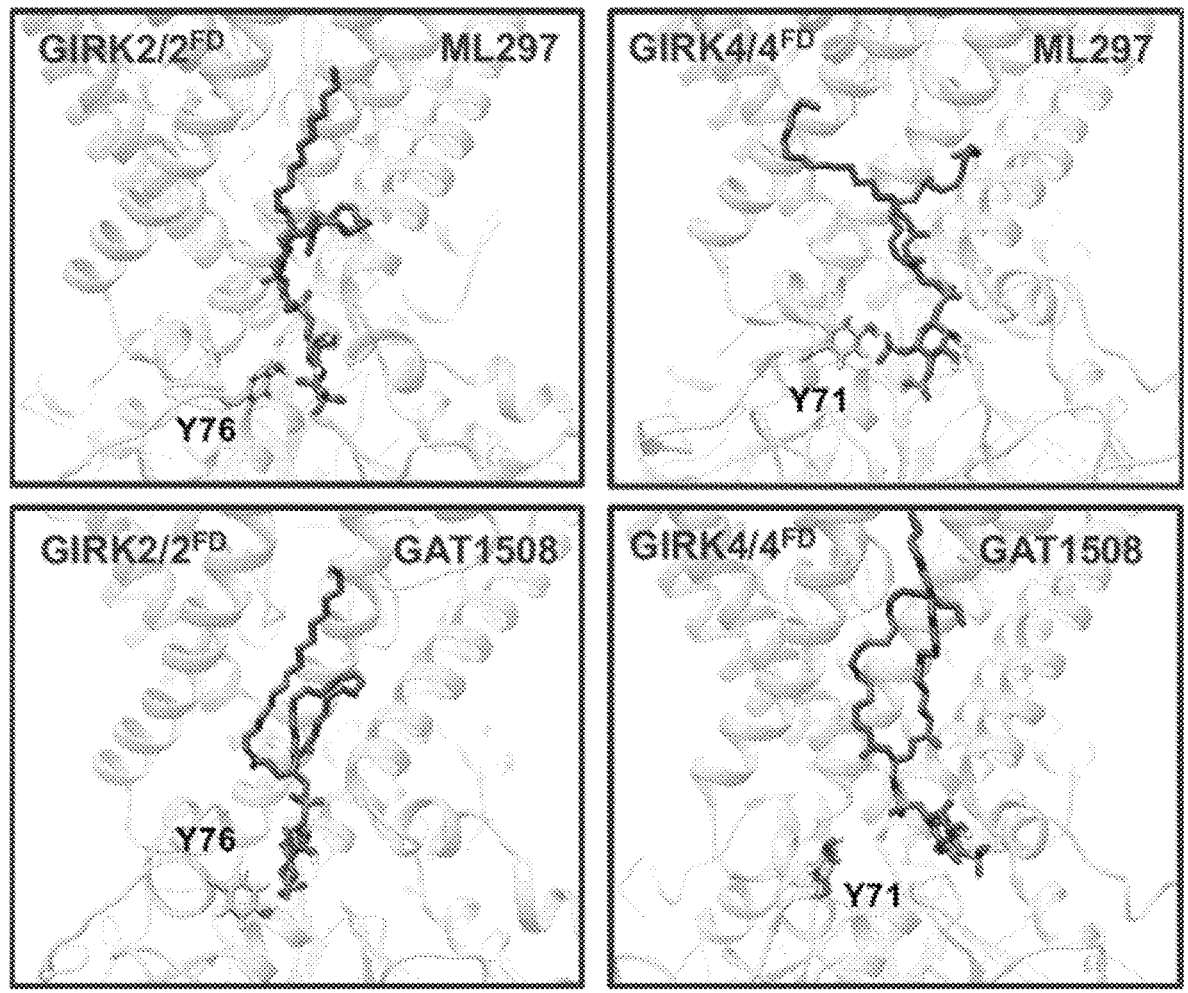
FIG. 39 shows average snapshots of phosphatidylinositol-4,5-bisphosphate (PIP$_2$) interacting with GIRK2/GIRK4 Y76/71 residues in the channel slide helix region with ML297 (top) and GAT1508 (bottom) binding in GIRK2/$2^{FD}$ and GIRK4/$4^{FD}$. Principal component analysis (PCA) suggests large conformational changes induced by GAT1508 binding in GIRK2$^{FD}$ or ML297 binding in GIRK2$^{FD}$ and GIRK4$^{FD}$.
Figure 40:
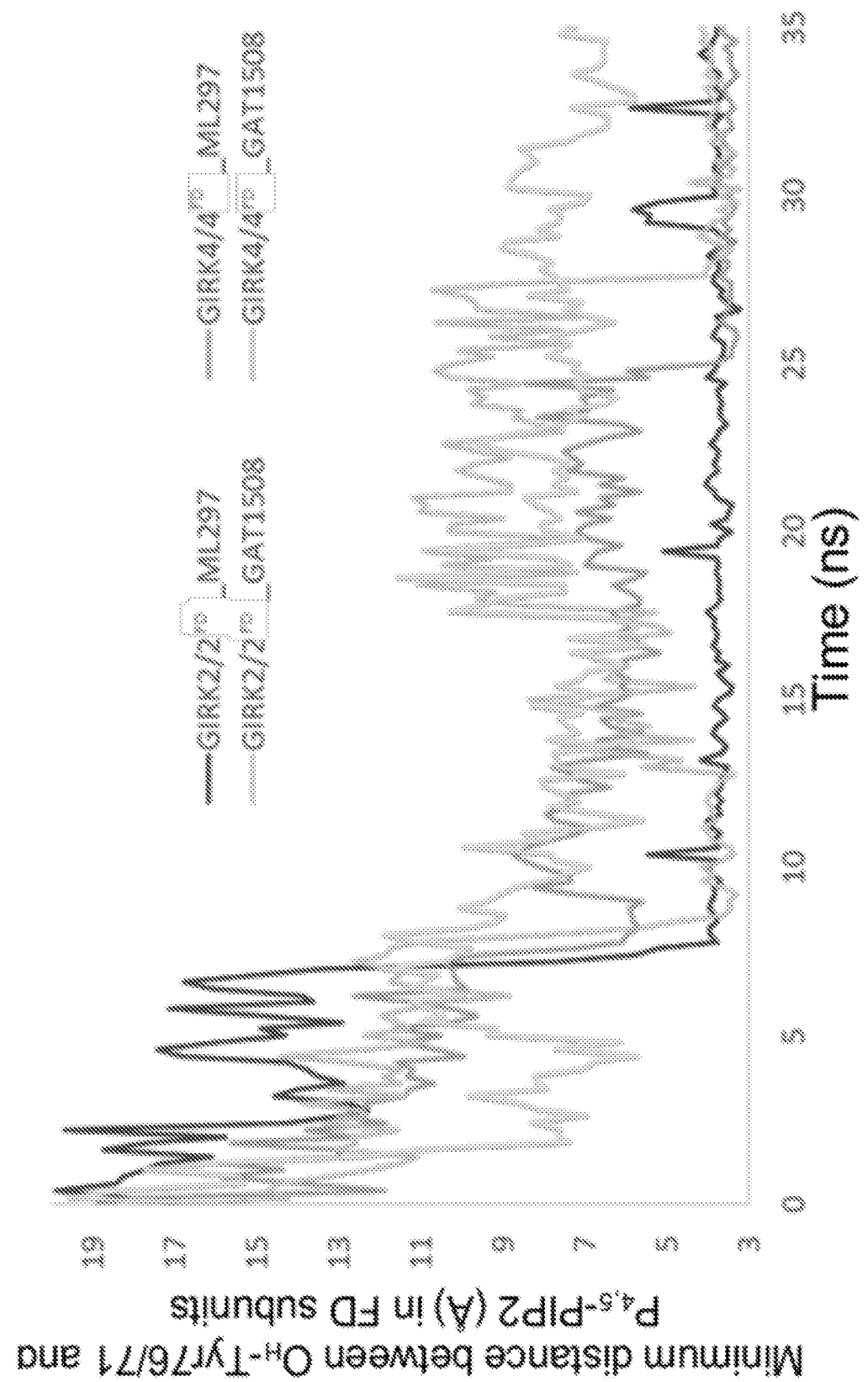
FIG. 40 shows the minimum distance between the O atom of Tyr76/71 in the FD-mutated subunits and P4,5-PIP$_2$ in Principal Component Analysis. To identify changes in specific channel residue interactions with PIP$_2$ upon ligand binding, the inventors carried out Principal Component Analysis (PCA) in the presence and absence of ML297 and GAT1508. The PCA analysis implicated changes in the slide (or interfacial) helix interactions with PIP$_2$ upon ligand binding. Polar interactions could be formed between GIRK2FD(Y76) and GIRK4FD(Y71) with the P(4,5) of PIP$_2$ when ML297 was bound to the same subunit. In contrast, when GAT1508 was bound this interaction was retained by GIRK2FD but not GIRK4FD.

FIGS. 38A-38C show that the interaction between GAT1508 and the FD-mutated subunits decrease the channel P-FD interaction in both GIRK2 and GIRK4 heteromeric channels. FIG. 39 shows average snapshots of PIP$_2$ interacting with GIRK2/GIRK4 Y76/71 residues in the channel slide helix region with ML297 (top) and GAT1508 (bottom) binding in GIRK2/2$^{FD}$ (left panels) and GIRK4/4$^{FD}$ (right panels). Principal component analysis (PCA) suggests large conformational changes induced by GAT1508 binding in GIRK2$^{FD}$ or ML297 binding in GIRK2$^{FD}$ and GIRK4$^{FD}$ (FIGS. 39-40). A strong H-bond interaction is formed between the Tyr residue in the slide helix of FD-mutated subunit and P4/5 of PIP$_2$, which can position the PIP$_2$ headgroup towards the junction of the M2 and TM-CTD (CTD: cytoplasmic domain) linker and induce the increase in channel P-WT interactions. However, GAT1508 binding around the M2 helix of GIRK4/4$^{FD}$ results in loss of the H-bond interaction between GIRK4$^{FD}$(Y71) and PIP$_2$ and failure to position the headgroup for optimal interactions. FIG. 40 shows the minimum distance between the O atom of Tyr76/71 in the FD-mutated subunits and P4,5-PIP$_2$. FIG. 41 shows sequence alignment of the GIRK channel Slide Helix (SH) region, and the key residue interactions proposed by the simulations for the GAT1508-induced changes in GIRK activation are highlighted with a vertical rectangle. As polar residues, both Ser and Tyr could form H-bond interactions with PIP$_2$.

Ligand-Induced Changes in Specific Channel-PIP$_2$ Interactions

Figure 43B:
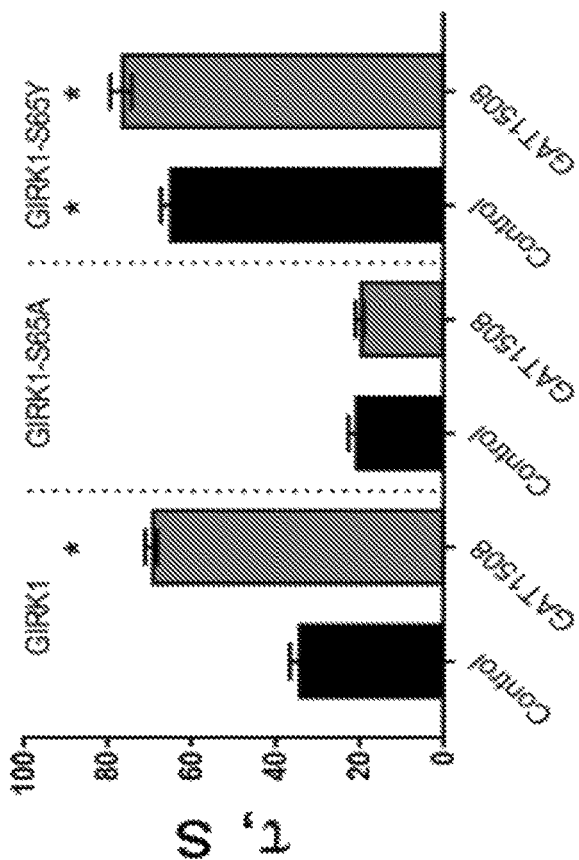
FIGS. 43A-43B show a bar graph (43A) representing the mean increase in the percentage of GIRK1/2 channel current remaining following activation of 5-ptase$_{OCRL}$ in the presence and absence of GAT1508. The 5-ptase$_{OCRL}$-mediated decrease in GIRK1/2 current is characterized by mono-exponential fits in the presence and absence of 10 μM GAT1508. The bar graph (43B) shows the mean T of current-inhibition is increased when wild-type channels are studied with GAT1508, is decreased when GIRK1-S65A subunits are expressed and is increased when GIRK-S65Y containing channels are studied.
Figure 43A:
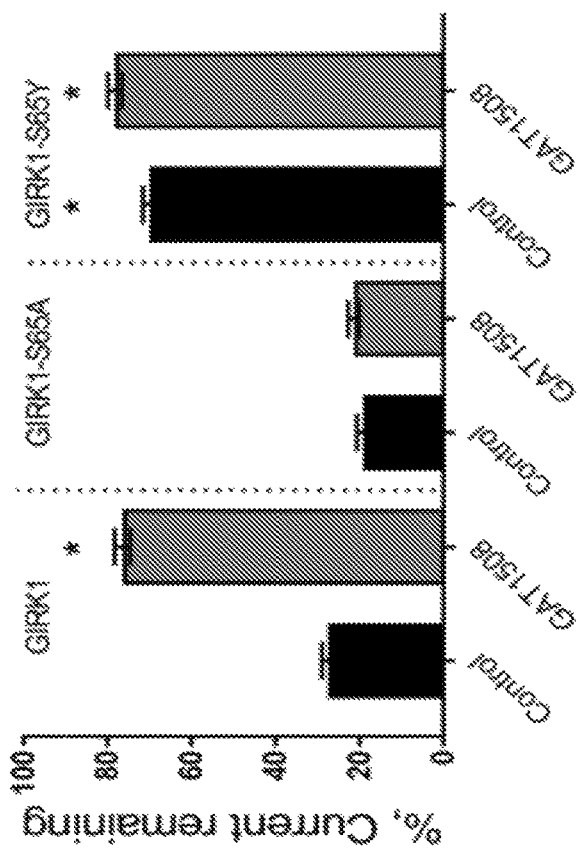
Figure 45B:
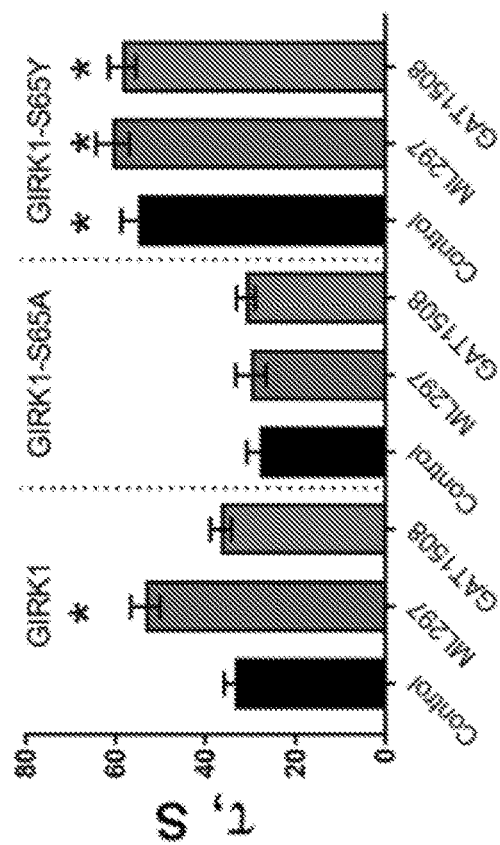
FIGS. 45A-45B show a bar graph (45A) representing the mean increase in the percentage of GIRK1/4 channel current remaining following activation of 5-ptase$_{OCRL}$ in the absence (control) or presence of ML297 or GAT1508. The 5-ptase$_{OCRL}$-mediated decrease in GIRK1/4 current is characterized by mono-exponential fits in the presence and absence of the compound indicated. The bar graph (FIG. 45B) shows the mean τ of current-inhibition is increased when wild-type channels are studied with ML297 but not GAT1508. This effect is decreased when GIRK1-S65A subunits are expressed. Channels with GIRK1-S65Y subunits have an increased τ of current-inhibition that is not statistically increased with ML297 or GAT1508.
Figure 45A:
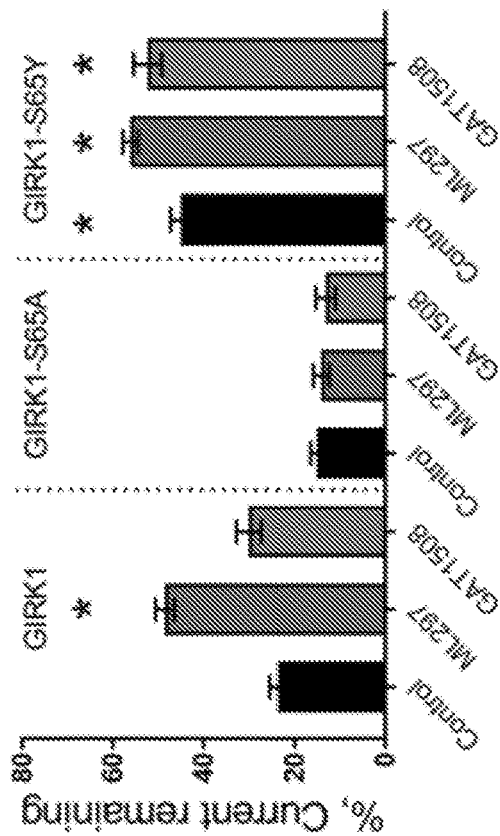

To identify changes in specific channel residue interactions with PIP$_2$ upon ligand binding, the inventors carried out Principal Component Analysis (PCA) in the presence and absence of ML297 and GAT1508. The PCA analysis implicated changes in the slide (or interfacial) helix interactions with PIP$_2$ upon ligand binding. Polar interactions could be formed between GIRK2$^{FD}$(Y76) and GIRK4$^{FD}$(Y71) with the P(4,5) of PIP$_2$ when ML297 was bound to the same subunit (FIG. 39 top, FIG. 40). In contrast, when GAT1508 was bound this interaction was retained by GIRK2$^{FD}$ but not GIRK4$^{FD}$ (FIG. 39 bottom, FIG. 40). The corresponding GIRK1(S65) residue (FIG. 41, highlighted with vertical rectangle) could be serving the same role in stabilizing the phosphoinositol headgroup for interactions with non-ligand binding subunits. As polar residues, both Ser and Tyr could form H-bond interactions with PIP$_2$. To test the prediction of the model that GIRK1(S65) may be a residue in the ligand-binding subunit that critically affects channel-PIP$_2$ interactions, the inventors produced two mutants at this position, an Ala mutation that would be predicted to abolish the ability to strengthen channel-PIP$_2$ interactions or a Tyr residue (like in the GIRK2$^{FD}$ and GIRK4$^{FD}$ simulations) that should enable channel-PIP$_2$ interactions. The inventors tested each of these mutants and compared them to the wild-type GIRK1 as part of heteromeric channels with GIRK2 and GIRK4 in the presence and absence of GAT1508 (GIRK1/2 and GIRK1/4) or ML297 (GIRK1/4). The GIRK1(S67A) decreased while the GIRK1(S67Y) increased channel-PIP$_2$ interactions in the GIRK1/2 heteromer (FIGS. 42-43) as well as in the GIRK1/4 heteromer (FIGS. 44-45).

FIG. 39 shows that principal component analysis (PCA) suggests large conformational changes induced by GAT1508 binding in GIRK2$^{FD}$ or ML297 binding in GIRK2$^{FD}$ and GIRK4$^{FD}$. A strong H-bond interaction is formed between the Tyr residue in the slide helix of FD-mutated subunit and P4/5 of PIP$_2$, which can position the PIP$_2$ headgroup towards the junction of the M2 and TM-CTD (CTD: cytoplasmic domain) linker and induce the increase in channel P-WT interactions. However, GAT1508 binding around the M2 helix of GIRK4/4$^{FD}$, results in loss of the H-bond interaction between GIRK4$^{FD}$(Y71) and PIP$_2$ and failure to position the headgroup for optimal interactions.

The activators showed no effect in the GIRK1(S67A) mutant heteromers, failing to strengthen channel-PIP$_2$ interactions, while no significant effect by the activators could be obtained in the already enhanced channel-PIP$_2$ interactions of the GIRK1(S67Y) mutant heteromers. These results support the model predictions for the importance of GIRK1 (S65) in its ability to form polar interactions with the PIP$_2$ phosphates and position the PIP$_2$ headgroup for interactions with the GIRK2 or GIRK4 subunits.

Figures 46A, 46B:
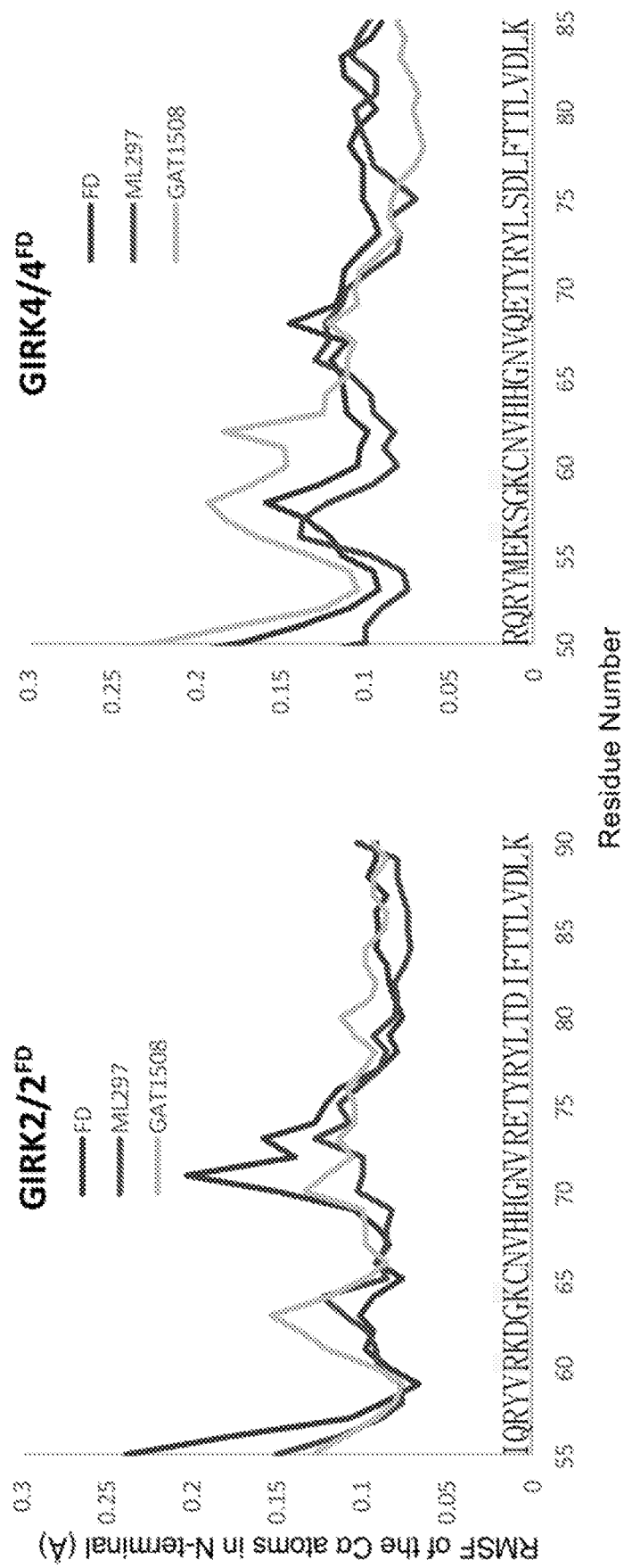
FIGS. 46A-46B shows N-terminal cardiac GIRK4 channel interaction with PIP$_2$ disrupted by brain-specific GAT compounds. The Cα RMSF of the channel N-terminus were calculated during the Molecular Dynamics (MD) simulation in the absence of ligand (black) or with ML297 (dark gray), GAT1508(light gray) in GIRK2/$2^{FD}$ (FIG. 46A) and GIRK4/$4^{FD}$ (FIG. 46B) systems. The sequence of the N-termini highlighting the two key positively charged residues that interact with PIP$_2$ are shown in the x-axes (highlighted in gray) for the two heteromeric channel systems. Binding of selective compound GAT1508 increased the flexibility of the N-terminus of the GIRK4$^{FD}$ subunits the most.
Figure 47:
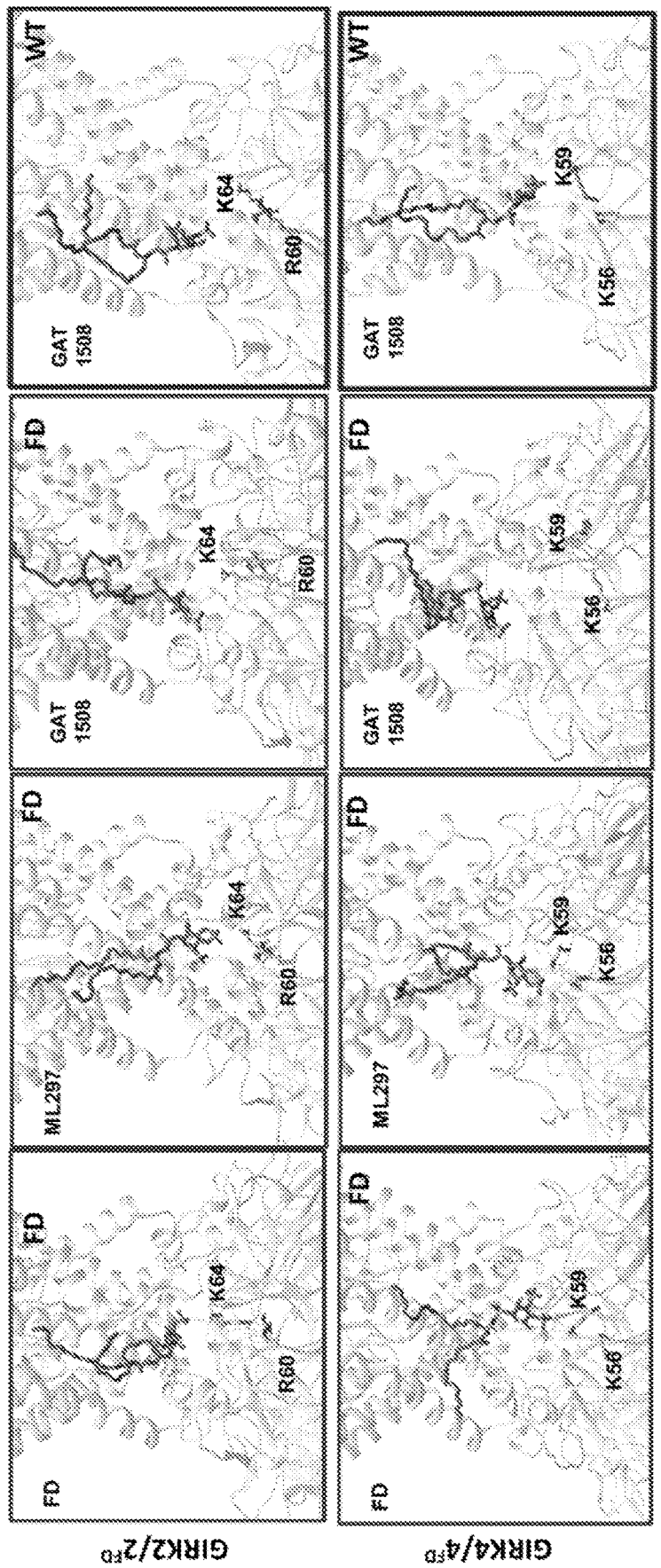
FIG. 47 shows average snapshots of PIP$_2$ interacting with two positive residues in the channel N-terminus. GIRK2/$2^{FD}$ (top panels) and GIRK4/$4^{FD}$ (bottom panels) in the absence of bound compounds (FD, left), with ML297, or with GAT1508. In the GIRK2 heteromeric channel, the N-terminal residue K64 interacted with PIP$_2$ in the absence of compound (also see FIG. 32, right). Binding of ML297 that increased channel-PIP$_2$ interactions, caused not only K64 but also R60 to interact with PIP$_2$. In the GIRK4 heteromeric channel, in the absence of ligand or with ML297 bound a similar pattern as in the GIRK2 heteromeric channel was seen.
Figure 48:
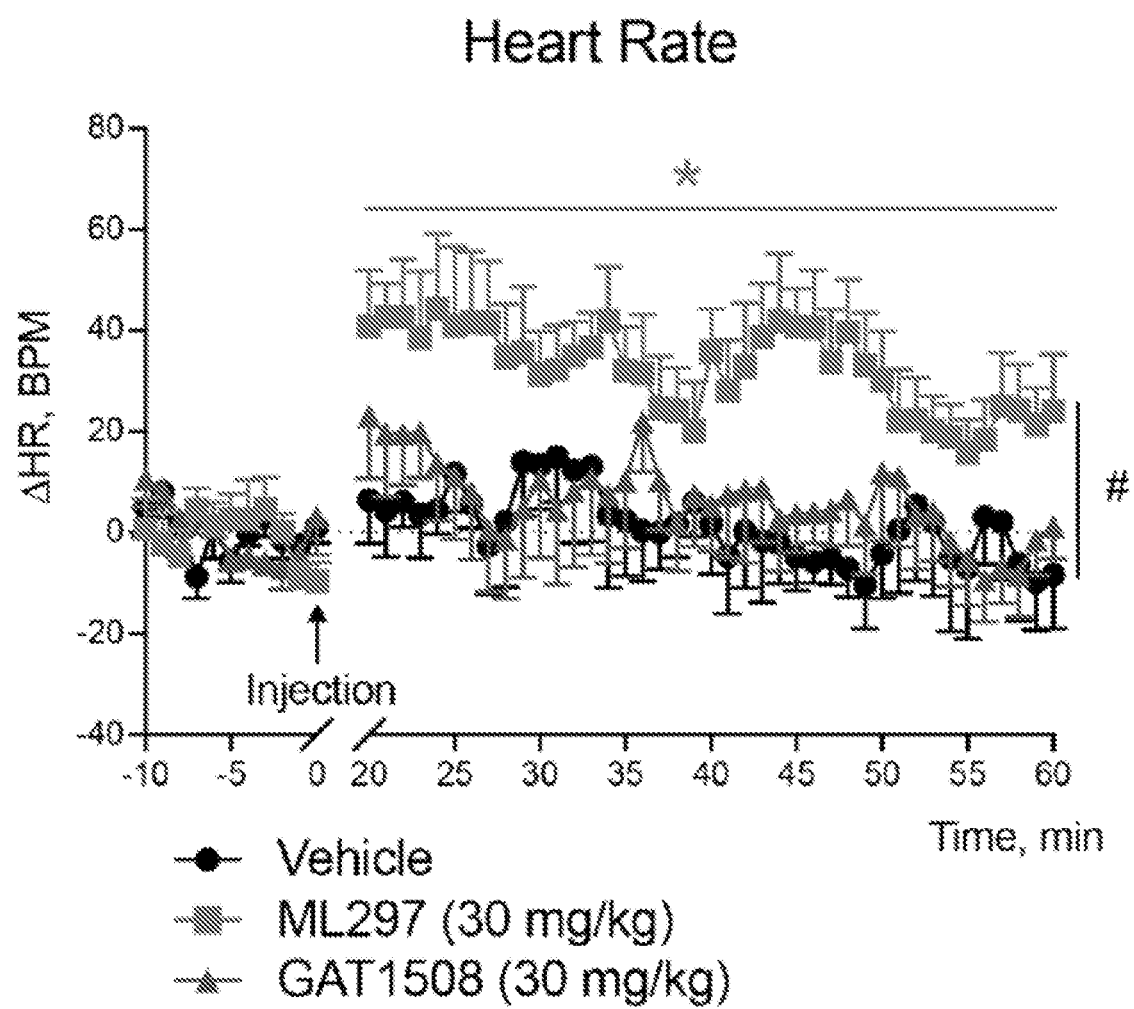
FIG. 48 shows mean±SE changes from baseline heart rate (HR) in rats injected with Vehicle ●, ML297 (30 mg/kg) ■, GAT1508 (30 mg/kg) ▲. Unlike ML297, treatment with GAT1508 doesn't show cardiovascular side effects. The plot is over time following systemic treatment with GAT1508 (30 mg/kg, n=7 animals), ML397 (30 mg/kg, n=6 animals) or vehicle (n=6 animals) of freely moving rats surgically implanted with radiotelemetry probes. The asterix * indicates within subject and # between subjects' differences using a Fisher's LSD post hoc test, p<0.05, two-way ANOVA.
Figure 49:
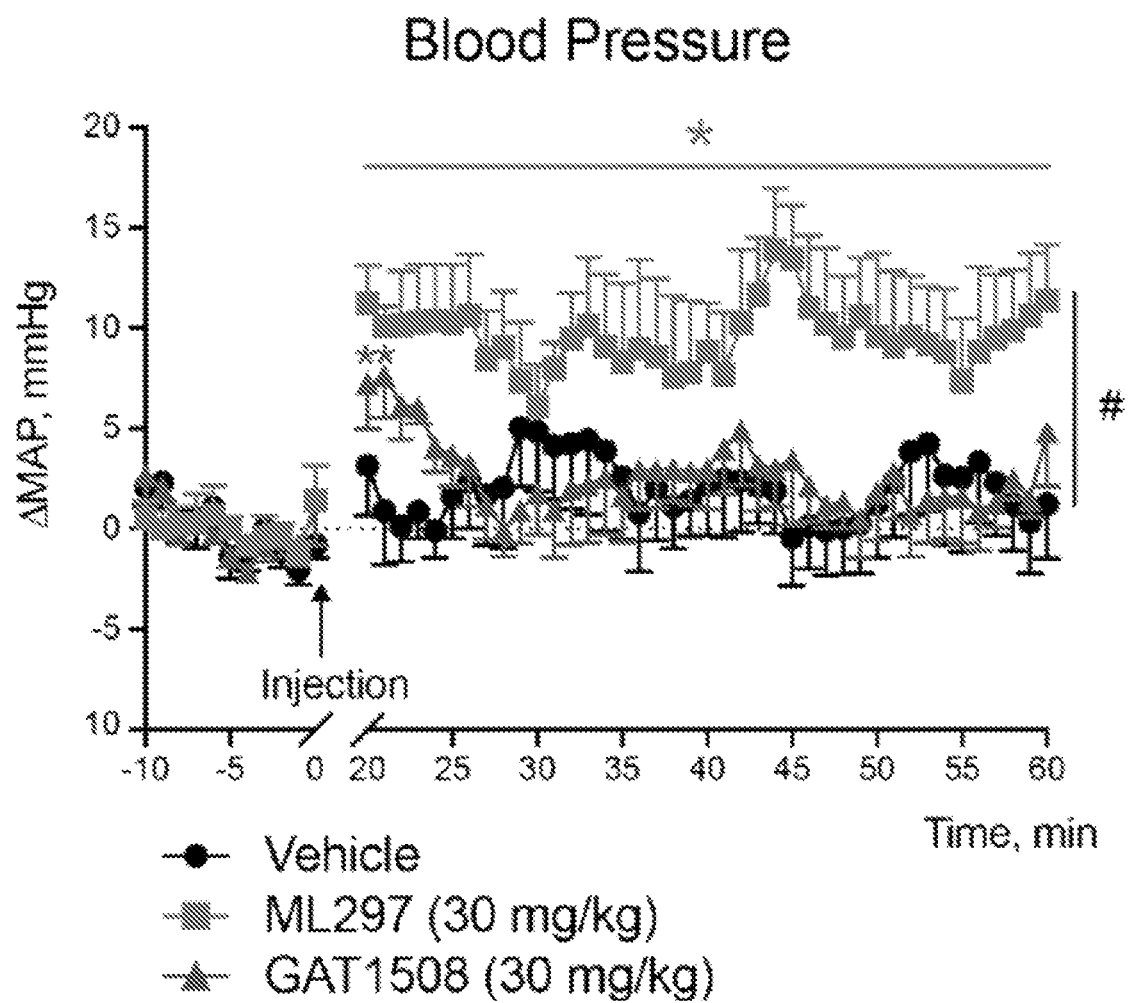
FIG. 49 shows mean±SE changes from baseline blood pressure (BP) in rats injected with Vehicle ●, ML297 (30 mg/kg) ■, GAT1508 (30 mg/kg) ▲. The plot is over time following systemic treatment with GAT1508 (30 mg/kg, n=7 animals), ML397 (30 mg/kg, n=6 animals) or vehicle (n=6 animals) of freely moving rats surgically implanted with radiotelemetry probes. An asterisk * indicates within subject and # between subjects' differences using a Fisher's LSD post hoc test, p<0.05, two-way ANOVA.
Figure 50:
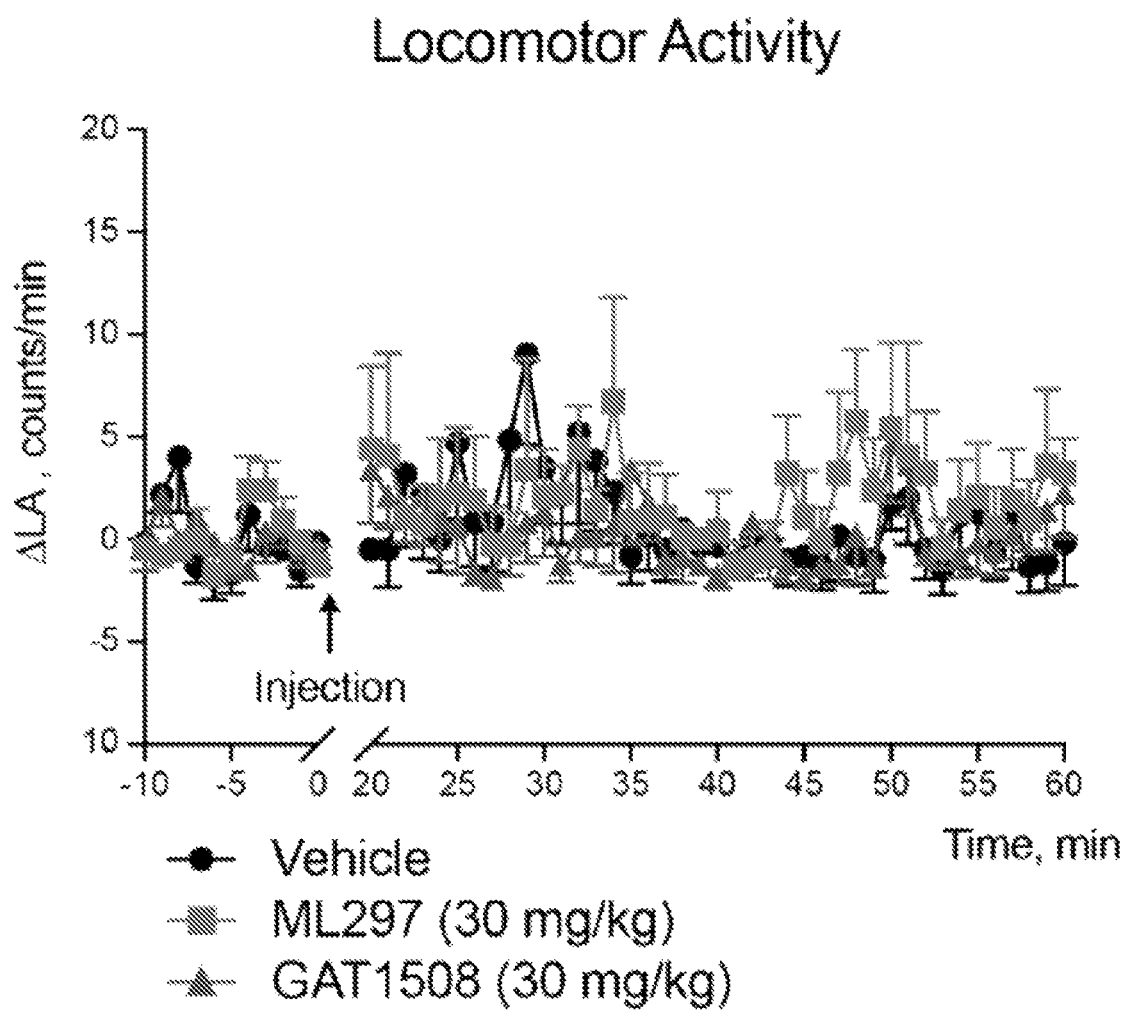
FIG. 50 shows mean±SE changes from baseline locomotor activity (LA) in rats injected with Vehicle ●, ML297 (30 mg/kg) ■, GAT1508 (30 mg/kg) ▲. The plot is over time following systemic treatment with GAT1508 (30 mg/kg, n=7 animals), ML397 (30 mg/kg, n=6 animals) or vehicle (n=6 animals) of freely moving rats surgically implanted with radiotelemetry probes. An asterisk * indicates within subject and # between subjects' differences using a Fisher's LSD post hoc test, p<0.05, two-way ANOVA.
Figure 51:
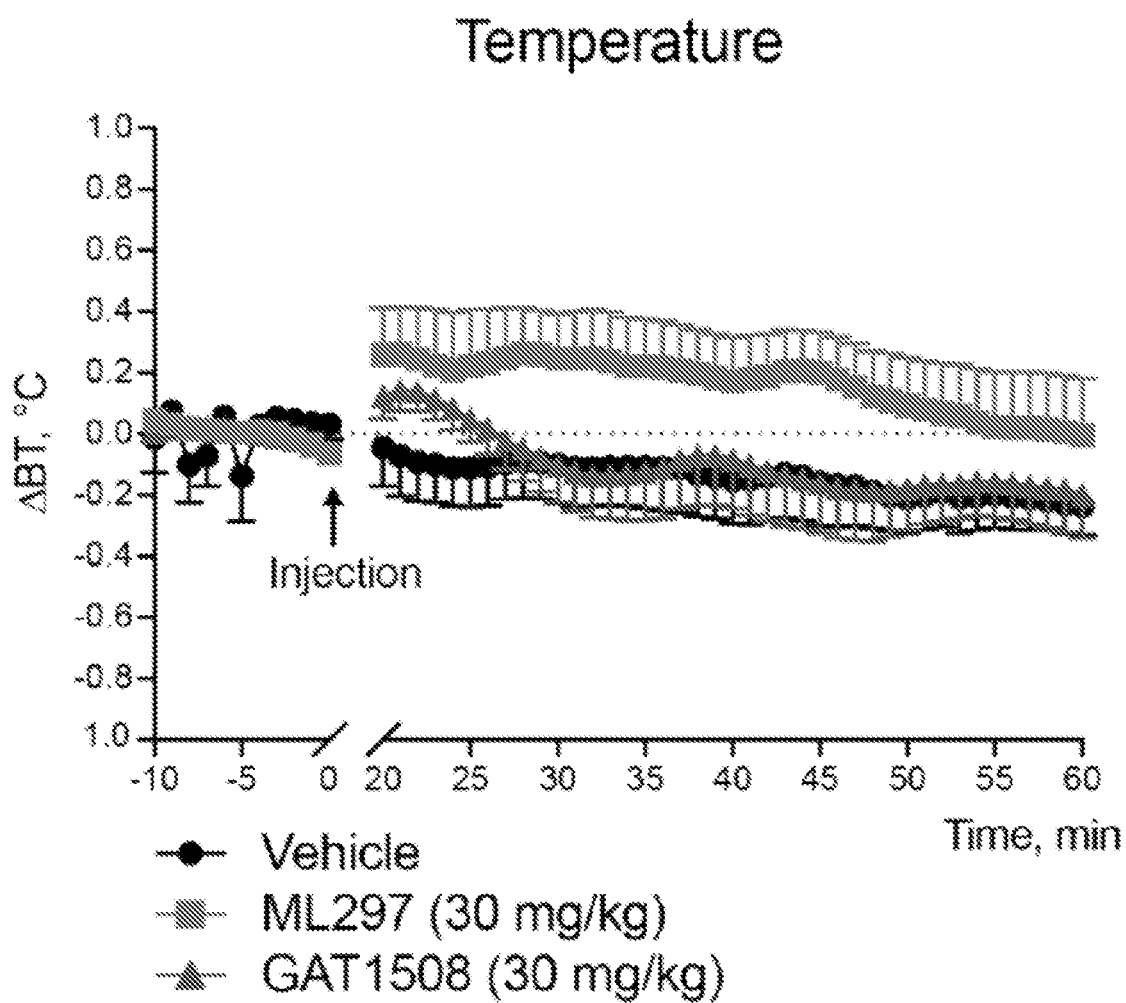
FIG. 51 shows mean±SE changes from baseline core body temperature (BD) in rats injected with Vehicle ●, ML297 (30 mg/kg) ■, GAT1508 (30 mg/kg) ▲. The plot is over time following systemic treatment with GAT1508 (30 mg/kg, n=7 animals), ML397 (30 mg/kg, n=6 animals) or vehicle (n=6 animals) of freely moving rats surgically implanted with radiotelemetry probes. An asterisk * indicates within subject and # between subjects' differences using a Fisher's LSD post hoc test, p<0.05, two-way ANOVA.
Figure 53B:
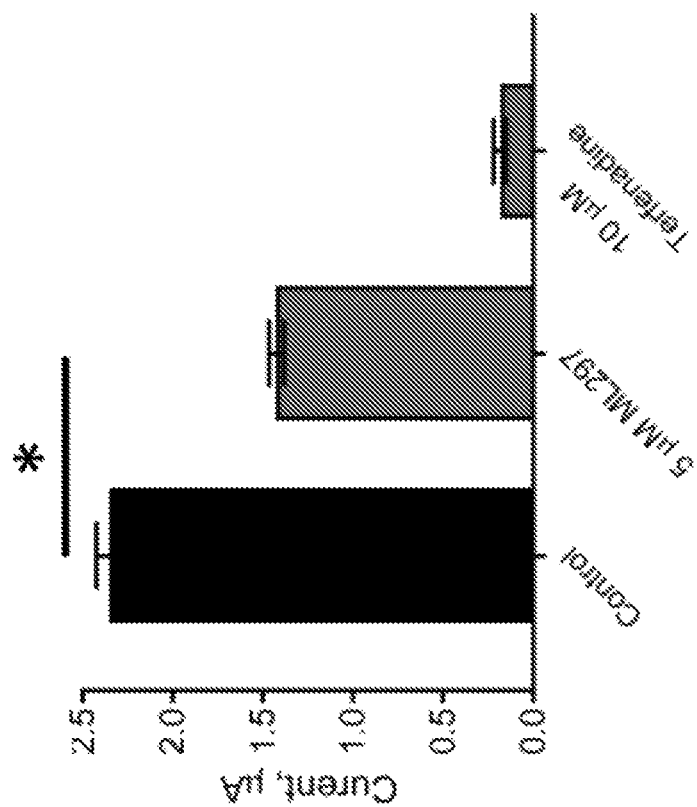
FIGS. 53A-53B show bar charts indicating terfenadine and ML297 decrease hERG tail-currents.
Figure 53A:
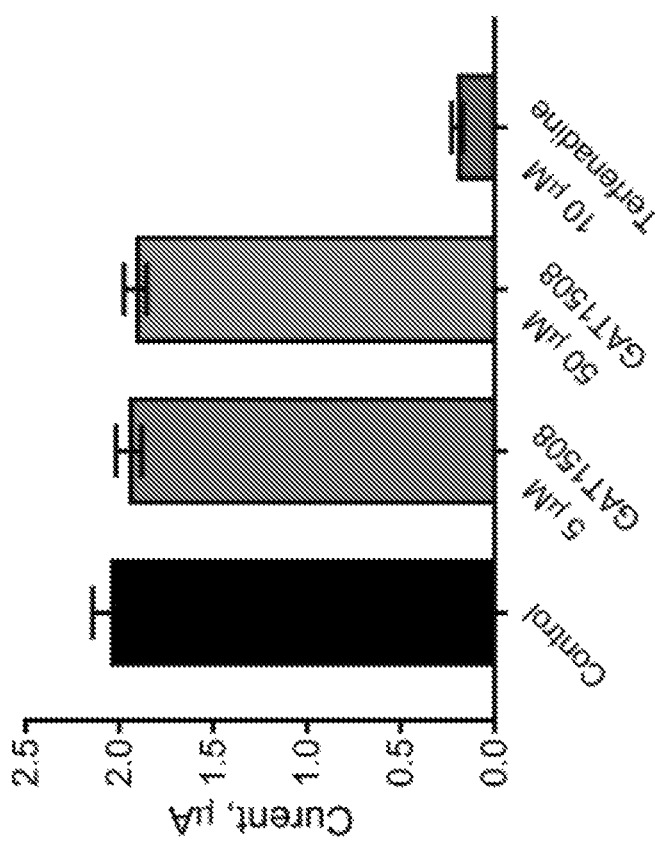

Root Mean Square Fluctuation—CαRMSF—analysis was also carried out as a measure of flexibility induced by each of ML297 and GAT1508 during the MD simulations. Compared to ligand-free or the bound ML297, binding of GAT1508 increased the flexibility of the N-terminus of the GIRK4 FD-containing subunits (FIG. 46, right) more than the corresponding GIRK2 subunits (FIG. 46, left). The crystal structure of GIRK2 in complex with PIP$_2$ has revealed that K64 is part of the PIP$_2$ binding site for this channel (see FIG. 32, right) (Whorton and MacKinnon, 2013). During the MD simulation of both GIRK2 and GIRK4 heteromeric channels in the absence of ligands (labeled FD, left, FIG. 47) the sidechain of K64/K59 in the N-terminus of GIRK2/GIRK4 adopted an upward orientation and formed interactions with the phosphate group of PIP$_2$, similar to those seen in the GIRK2-PIP$_2$ co-crystal structure (FIG. 47). In the presence of ML297, the N-terminus of GIRK2 and GIRK4 FD-containing subunit appeared to be more stable. Thus, in addition to the K64/K59, the R60/K56 residue also moved upward forming a new salt-bridge with PIP$_2$ in both heteromeric channels (FIG. 47, ML297 panels). GAT1508, binding in GIRK2 heteromeric channels also increased channel-PIP$_2$ interactions, and PIP$_2$ now interacted with K64 and R60 simultaneously in both the FD and WT subunits (FIG. 47, top, GAT1508, FD and WT). In contrast, in the GIRK4 heteromeric channel, the binding site of GAT1508 was shifted, partially losing its ability to regulate the M1 helix. Coincident with this change, the N-terminus showed an increase in its flexibility moving downward, forcing PIP$_2$ to lose its interaction with both K56 and K59 in the FD-containing subunits (FIG. 47, bottom, GAT1508, FD) but not with the corresponding residues in the wild-type subunits (FIG. 47, bottom, GAT1508, WT).

Figures 59A, 59B:
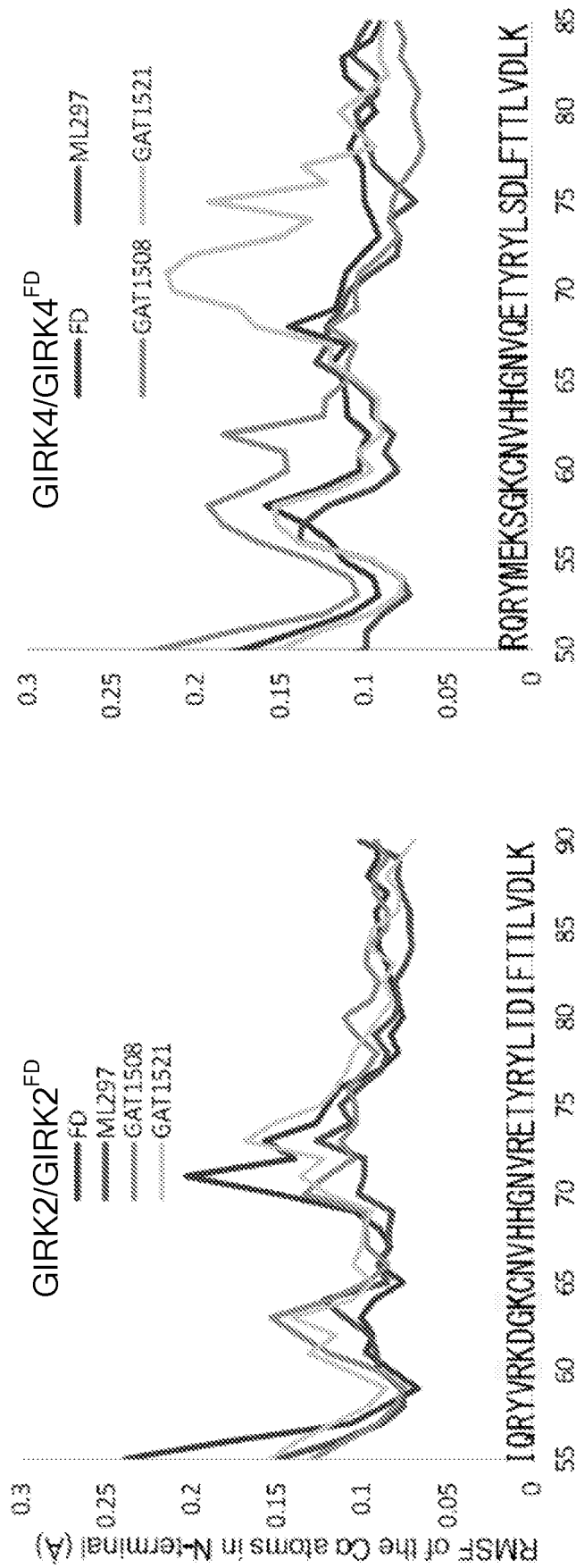
FIGS. 59A-59B show calculated channel Ca Root Mean Square Fluctuation (RMSF) during the MD simulations in the absence or presence of ML297 and GAT compounds in the GIRK2/2FD (FIG. 59A) and GIRK4/4FD (FIG. 59B) systems. Compared to ligand free or the bound ML297, binding of the selective compounds GAT1508 and GAT1521 dramatically increased the flexibility of the N-terminus of the GIRK4 FD-containing subunits but not of the corresponding GIRK2 subunits, (also see FIG. 47).

Changes in the CαRMSF of the N-terminus were also notable for GAT1521 (FIGS. 59A-59B). Compared to ligand free or the bound ML297, binding of the selective compounds GAT1508 and GAT1521 dramatically increased the flexibility of the N-terminus of the GIRK4 FD-containing subunits but not of the corresponding GIRK2 subunits. During the MD simulation of both GIRK2 and GIRK4 heteromeric channels in the absence of ligands (labeled FD) the sidechain of K64/K59 in the N-terminus of GIRK2/GIRK4 adopted an upward orientation and formed interactions with the phosphate group of PIP$_2$, similar to the crystal structure (FIG. 47, left). In the presence of ML297, the N-terminus of GIRK2 and GIRK4 FD-containing subunit appeared to be more stable. Thus, in addition to the K64/K59, the R60/K56 residue also moved upward forming a new salt-bridge with PIP$_2$ in both heteromeric channels (FIG. 47, center). GAT1508, binding in GIRK2 heteromeric channels also increased channel-PIP$_2$ interactions, and PIP$_2$ now interacted with K64 and R60 simultaneously. In the simulation of the GIRK4 heteromeric channel, however, the binding site of GAT1508 was shifted, partially losing its ability to regulate the M1 helix. Coincident with this change, the N-terminus showed an increase in its flexibility moving downward, forcing PIP$_2$ to lose its interaction with both K56 and K59 in the FD-containing subunits (FIG. 47, right) but not in the wild-type subunits (FIG. 47, right). GAT1521 also showed similar effects to the GIRK2 and GIRK4 heteromeric channels (FIGS. 59A-59B). Thus, both the selective compounds GAT1508 and GAT1521 shifted their binding region in the GIRK4/4$^{FD}$ channel and could not induce channel opening, indicating that the interactions of the channel N-terminus with PIP$_2$ play an important role in the selective activation by these compounds.

FIG. 46 shows that binding of selective compound GAT1508 increased the flexibility of the N-terminus of the GIRK4$^{FD}$ subunits the most. Average snapshots of PIP$_2$ interacting with two positive residues in the channel N-terminus in the absence of bound compounds (FD), with ML297, or with GAT1508 in the GIRK2/2$^{FD}$ and GIRK4/4$^{FD}$ are shown in FIG. 47. In the GIRK2 heteromeric channel, the N-terminal residue K64 interacted with PIP$_2$ in the absence of compound. Binding of ML297 that increased channel-PIP$_2$ interactions, caused not only K64 but also R60 to interact with PIP$_2$. In the GIRK4 heteromeric channel, in the absence of ligand or with ML297 bound a similar pattern as in the GIRK2 heteromeric channel was seen.

Selective GAT Compounds Change Channel Selectivity to TV but not K$^+$

Figures 60A, 60B:
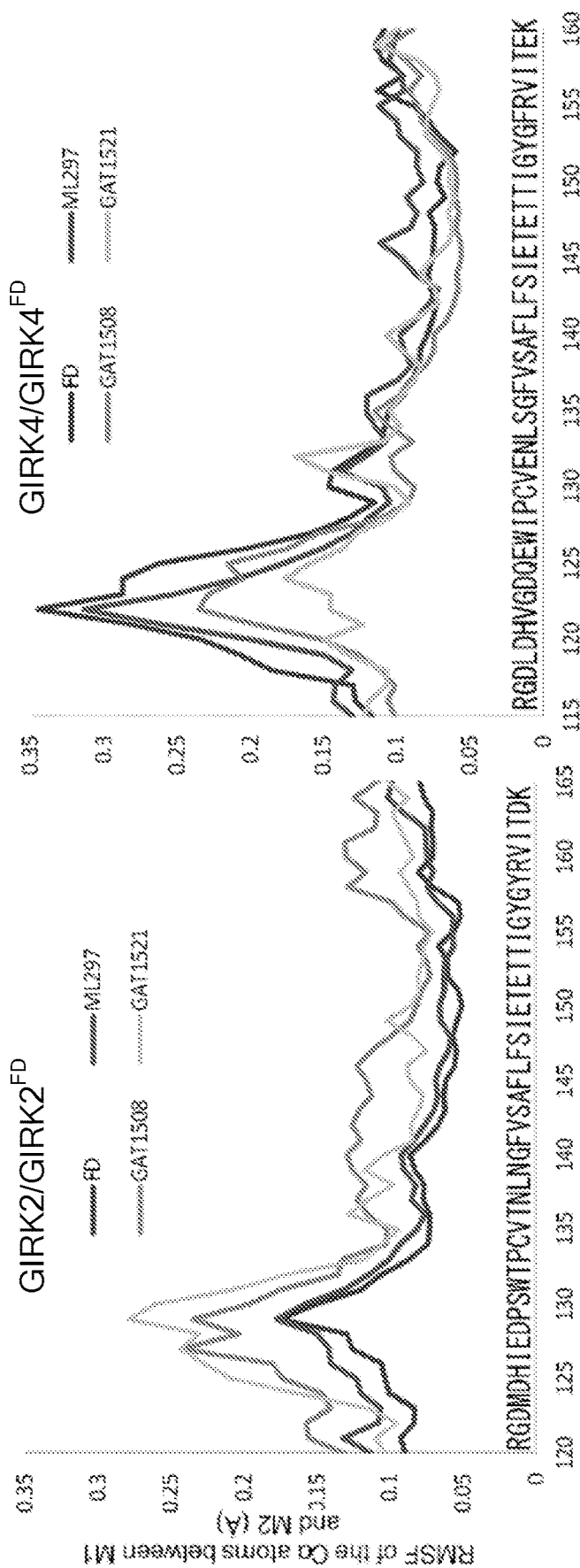
FIGS. 60A-60B show calculations of the Ca Root Mean Square Fluctuation (RMSF) of the region between the M1 and M2 helices of the channel during the MD simulation with or without ML297 and the selective GAT compounds in the GIRK2/2$^{FD}$ (FIG. 60A) and GIRK4/4$^{FD}$ (FIG. 60B) systems.
Figures 61A, 61B:
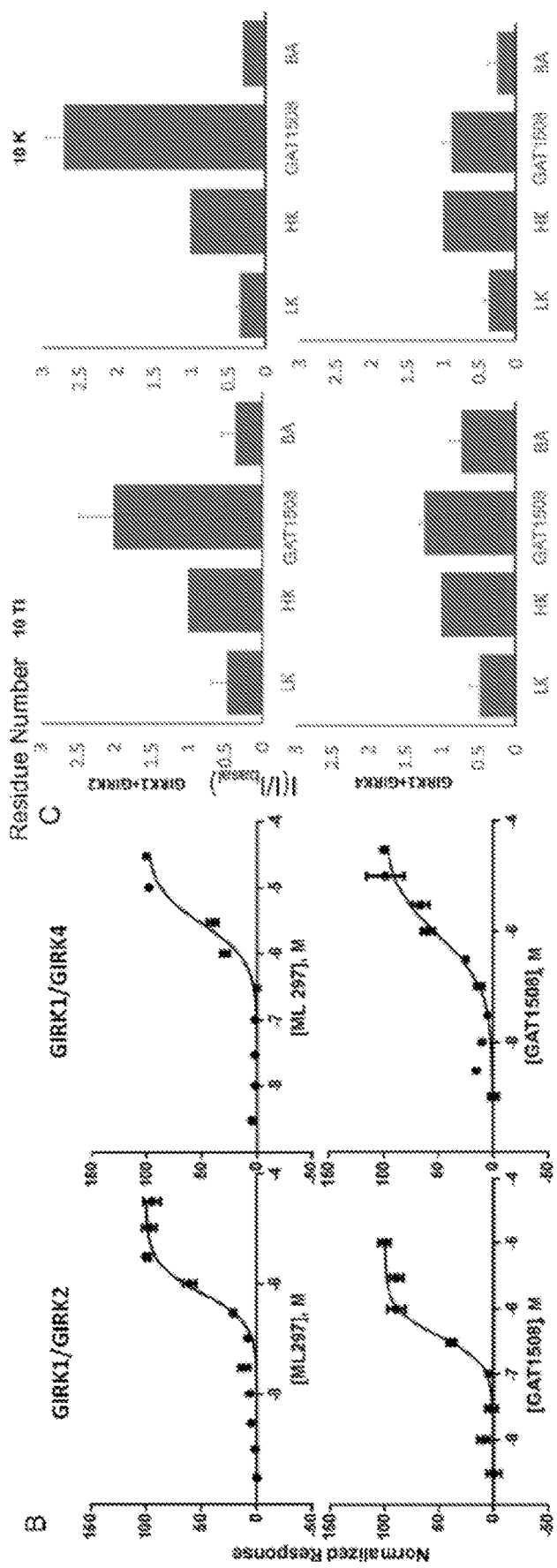
FIGS. 61A-61B show the thallium flux Assay to test the effects of ML297 and related compounds in cells co-expressing GIRK1/2 and GIRK1/4. In the thallium flux assay, ML297 showed dose-dependent activation effects on cells expressing GIRK1/2 and GIRK1/4 with a higher potency difference compared to the TEVC assay for the brain versus cardiac channels (GIRK1/2 $EC_{50}$~0.689 µM and GIRK1/4 $EC_{50}$~2.893 µM). However, concentration-response curves of GAT1508 for both GIRK1/2 and GIRK1/4 activation showed that this compound also activated the cardiac heteromer (FIG. 61A).

Previous studies have utilized the thallium flux Assay to test the effects of ML297 and related compounds in cells coexpressing GIRK1/2 and GIRK1/4. In order to fully investigate the selective activation of GAT compounds, the inventors also utilized this assay. In our hands using the thallium flux assay, ML297 showed dose-dependent activation effects on cells expressing GIRK1/2 and GIRK1/4 with a higher potency difference compared to the two-electrode voltage clamp (TEVC) assay for the brain versus cardiac channels (GIRK1/2 EC$_{50}$~0.689 μM and GIRK1/4 EC$_{50}$~2.893 μM). However, concentration-response curves of GAT1508 for both GIRK1/2 and GIRK1/4 activation showed that this compound also activated the cardiac heteromer. In other words, GAT1508 displayed a loss of selective activation of brain over cardiac channels in the thallium flux assay (FIG. 61A). To determine the differences between the thallium flux and TEVC assays, the inventors computationally tested whether the binding of selective compounds could affect the selectivity of the pore area. The CαRMSF of the region between the M1 and M2 helices of the channel were calculated during the MD simulation with or without ML297 and the selective GAT compounds in the GIRK2/2$^{FD}$ and GIRK4/4$^{FD}$ systems (FIGS. 60A-60B). It seems that binding of GAT1508 and GAT1521 did affect the flexibility of the selectivity filter pore turrets in terms of increasing the flexibility in GIRK2/2$^{FD}$ channel but decreasing it in GIRK4/4$^{FD}$ channels, suggesting that ion selective permeation may be changed by GAT1508 and GAT1521. To further test this idea, the inventors compared the 10 μM GAT1508-induced thallium and potassium currents in oocytes expressing GIRK1/2 and GIRK1/4 by TEVC recording (FIG. 61B). Based on the solubility of thallium (I) chloride (TICl), instead of using 96 mM potassium, the inventors used potassium and thallium at 10 mM concentration. In an effort to enhance the current, the TEVC recording was performed at a holding potential of −100 mV. Interestingly, GAT1508 only showed a selective activation effect in 10 mM K$^+$, which significantly increased currents in oocytes coexpressing GIRK1/2 but not GIRK1/4. For thallium ions, consistent with our modeling predictions, GAT1508 induced current increases in both GIRK1/2 and GIRK1/4 expressing cells.

Figures 21, 22:
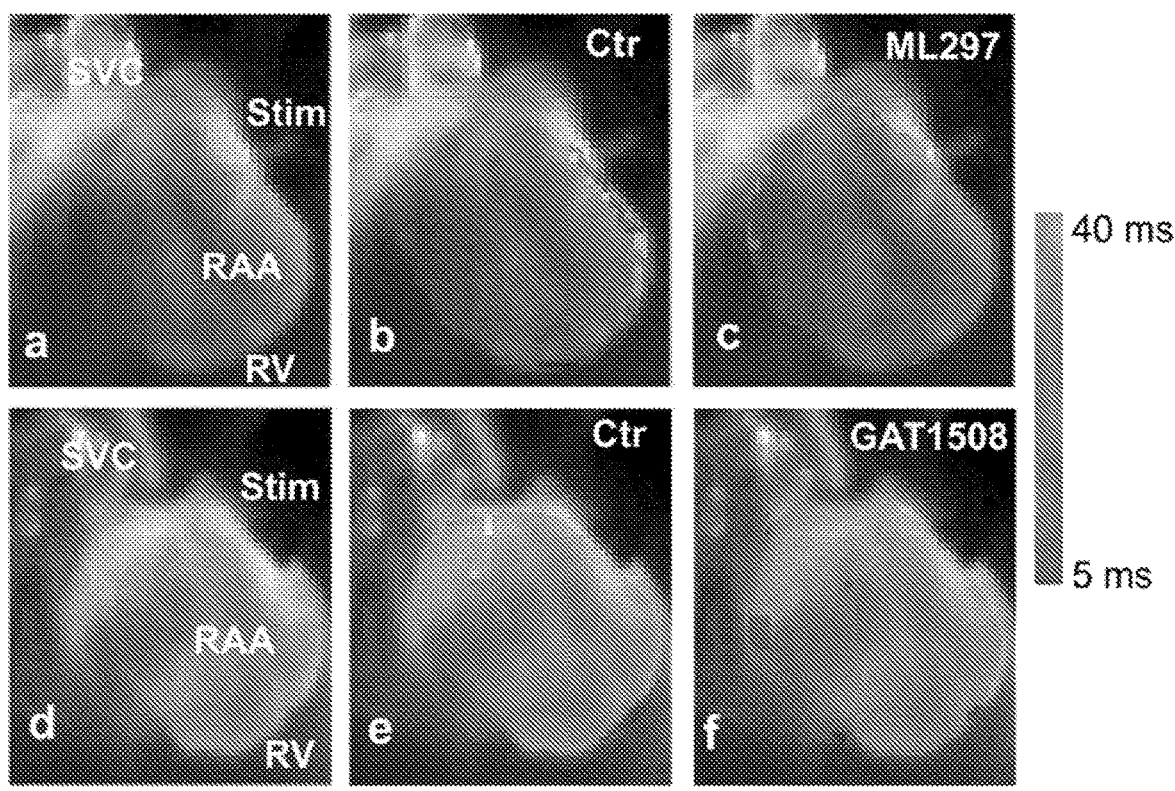
FIG. 21 shows tabulated results from FIGS. 20A-20C.
FIG. 22 shows a series of optical fluorescence mapping images of atrial electrical propagation in the isolated Langendorff-perfused mouse heart. On the left, fluorescence images showing the mapped fields; SVC, superior vena cava; RAA, right atrial appendage; RV, right ventricle; Stim, bipolar stimulation electrode; are labeled. In the center, atrial optical action potential duration 70% repolarization (APD$_{70}$) maps at 10 Hz stimulation in the control hearts. On the right, APD$_{70}$ maps at 10 Hz stimulation 10 minutes after perfusion with 2.4 μM ML297 and GAT1508, respectively.
Figure 23A:
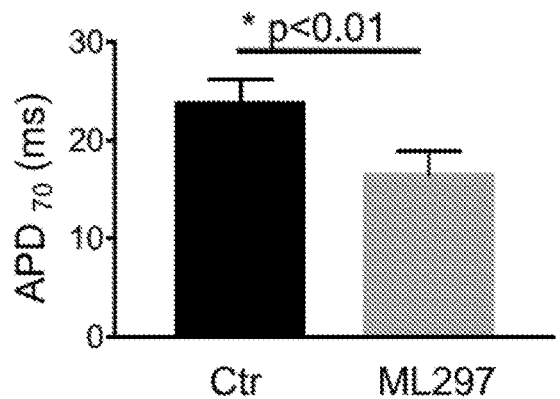
FIGS. 23A-23B compare atrial optical action potential duration 70% repolarization (APD$_{70}$) between ML297 and GAT1508.
Figure 23B:
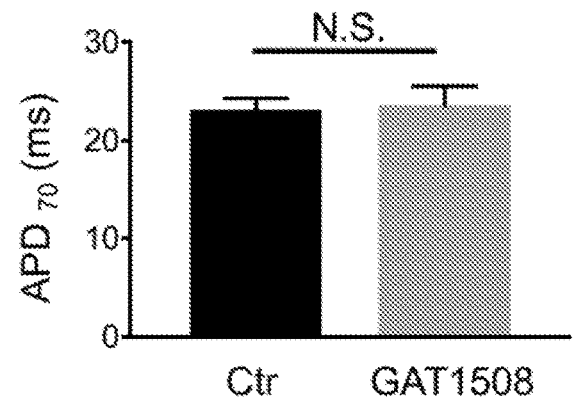

GIRK1/2 Selective GAT1508 Shows No Cardiac or Cardiovascular Effects Ex Vivo or In Vivo GIRK channels are widely expressed in the brain and in the heart; however, the distribution of the GIRK1/4 is predominantly in the heart, while GIRK1/2 channels are more restricted to the CNS. As our SAR and in vitro studies suggest that GAT1508 is more selective for GIRK1/2 channels, the inventors investigated the cardiovascular effects of GAT1508 versus the less selective ML297 in freely moving animals implanted with radiotelemetry probes. Rats injected with ML297 (30 mg/kg) demonstrated paradoxical long-lasting increases in heart rate (HR, treatment effect $F_{2,16}=5.6$, $p=0.014$, time effect $F_{51,816}=2.66$, $p<0.0001$, RM ANOVA, FIG. 48) and mean arterial pressure ($\Delta$MAP, treatment×time interaction $F_{102,816}=1.4$, $p=0.01$, RM ANOVA, FIG. 49) without affecting significantly locomotor activity ($\Delta$LA, treatment effect $p=0.7$, FIG. 50) or body temperature ($\Delta$BT, treatment effect $p=0.2$, FIG. 51). In contrast, animals treated with GAT1508 (30 mg/kg) showed no significant changes in cardiovascular parameters or motor activity (FIGS. 48-51). The persistent paradoxical increases in the in vivo heart rate by ML297 prompted us to compare the effects of GAT1508 and ML297 on the atrial optical action potential duration (APD) in an isolated Langendorff mouse heart preparation. FIG. 22, top left and top center, shows fluorescence pictures of the right atria showing the superior vena cava, the right atrial appendage, and the stimulation electrode. In FIG. 22, top center, under control conditions, the APD 70% repolarization ($APD_{70}$) map of the stimulated right atrium had an average duration of 23.9 ms. Ten minutes after 2.4 µM ML297 was introduced through the perfusate (FIG. 22, top right), the $APD_{70}$ shortened dramatically, to an average of 16 ms, secondary to the activation of GIRK1/4 by ML297. FIG. 22, bottom center panel, shows under control conditions that the average $APD_{70}$ was 21.8 ms, and 10 minutes after 2.4 µM GAT1508 was introduced through the perfusate (FIG. 22, bottom right panel), the average $APD_{70}$ was 20.3 ms. Summary bar graphs show the significant decrease in APD by ML297, unlike GAT1508 that did not shorten the APD (FIGS. 23A-23B). The inventors next compared the effects of the two compounds on the cardiac hERG channel expressed in Xenopus oocytes, a common target that many ligands are screened against to assess cardiac toxicity. Concentrations of GAT1508 up to 50 µM did not affect hERG channel currents, while 5 µM ML297 caused a significant block and 10 µM terfenadine produced a complete block of these currents (FIGS. 52A, 52B, 53A, 53B).

The discovery of GAT1508, the first GIRK channel single subtype-specific activator for GIRK1/2 heteromers, overcomes the cardiac side effects of non-selective GIRK activators, as evidenced by the lack of a decrease in the atrial action potential duration in an isolated heart preparation, the lack of effect on hERG currents, or the lack of effects in heart rate and blood pressure in freely moving animals. Since GIRK2 subunit expression is restricted to the nervous system and GAT1508 fails to strengthen channel-$PIP_2$ interactions and activate peripheral GIRK1/4 channels, its effects would be expected to also be restricted to neuronal tissues. Detailed studies in adult rodent brains have suggested co-expression of the GIRK1/2 subunits in multiple brain regions, including the olfactory bulb, neocortex, hippocampus, cerebellum, thalamus, hypothalamus and amygdala. Given this widespread pattern of expression, the inventors explored the effects of GAT1508 in the amygdala and in fear conditioning paradigms, where the role of the physiological relevance and therapeutic potential of GIRK1/2 has not been studied in depth.

The effectiveness of baclofen in activating GIRK currents in brain slices of the basolateral amygdala. Indeed, not only could baclofen induce $Ba^{2+}$-sensitive currents but so could sufficient concentrations of GAT1508. Interestingly, at lower concentrations of GAT1508, insufficient to produce significant GIRK activation, the baclofen responses were significantly potentiated, suggesting synergism in the allosteric effects of GAT1508 and Gβγ in strengthening channel-$PIP_2$ interactions. The inventors further examined the effectiveness of GAT1508 in fear extinction paradigms that serve as models of posttraumatic stress disorder (Examples 3-4).

The positive results offer validation for both the physiological relevance and the therapeutic potential of GIRK1/2 as a drug target for posttraumatic stress disorder. The wide expression of GIRK1/2 in the brain begged the question of whether side effects could become limiting if GAT1508 were to be pursued as a candidate drug. The general positive results expected from GIRK channel activation in the brain without cardiac side effects, as well as negative results in rat behavioral tests modeling anxiety, memory and social interaction with no additional obvious sedative or other overt behaviors, suggest that GAT1508 is suitable for treating PTSD and other fear related neuropsychiatric disorders.

Descriptions of Experimental Conditions;

Chemicals for electrophysiology were acquired from sources known in the art, for example, DiC8-$PIP_2$ was purchased from Echelon and terfenadine was from Sigma. ML297 and all GAT compounds were synthesized in-house as described herein. As applicable, other chemical sources are discussed herein.

Molecular biology: For Xenopus oocyte expression, human GIRK1 and human GIRK4 cDNAs were subcloned into pGEMHE. For mammalian expression, human GIRK1 and human GIRK4 cDNAs were subcloned into pcDNA3 and pcDNA3.1/V5-His B, respectively (Invitrogen). Mouse GIRK2 cDNA was subcloned in the dual-function vector, pXoom. Point mutations were introduced using a standard Pfu-based mutagenesis technique according to the QuikChange protocol (Agilent). Mutations were verified by sequencing.

Xenopus laevis oocyte expression: Plasmid DNAs of GIRK channel subunits were linearized prior to in vitro transcription. Capped RNAs were transcribed using mMESSAGE mMACHINE T7 Transcription Kit (Thermo Fisher Scientific). Xenopus oocytes were surgically extracted, dissociated and defolliculated by collagenase treatment, and microinjected with 50 nl of a water solution containing 1 ng of each GIRK subunit RNA. For TEVC experiments, oocytes were kept 2 days at 17° C. before recording, while for NPo experiments oocytes were incubated for up to 4 days at 17° C.

Two-electrode voltage-clamp and data analysis: Whole-oocyte currents were measured by two-electrode voltage clamp (TEVC) with GeneClamp 500 (Molecular Devices), or TEC-03X (NPI) amplifiers. Electrodes were pulled using a Flaming-Brown micropipette puller (Sutter Instruments) and were filled with 3 M KCl in 1.5% (w/v) agarose to give resistances between 0.5 and 1.0 MΩs. The oocytes were bathed in ND96 recording solution comprising, in mM: KCl 2, NaCl 96, $MgCl_2$ 1 and HEPES 5, buffered to pH 7.4 with KOH. Where indicated, GIRK channel currents were assessed in a high $K^+$ recording solution comprising, in mM: KCl 96, NaCl 2, $MgCl_2$ 1 and HEPES 5, buffered to pH 7.4 with KOH. Currents were digitized using a USB interface (National Instruments) and recorded using WinWCP software (University of Strathclyde). To study GIRK channels, oocytes were held at 0 mV, and currents were assessed by 100 ms ramps from −80 to +80 mV that were repeated every second. The effect of the reagents was determined at −80 mV, then the channels were blocked by 5 mM $BaCl_2$. Block was expressed as the percent-current block normalized to the maximum current. Between 8-12 oocytes from different Xenopus frogs were studied per experiment.

Oocyte macropatch studies: Macropatch GIRK channel activity was recorded from devitellinized oocytes under the inside-out mode of standard patch clamp methods using an AM2400 patch clamp amplifier (A-M systems). Currents were digitized using a USB-interface (National Instruments) and WinEDR (University of Strathclyde) data acquisition software. Electrodes were fabricated using Kimax glass (WPI) and had a resistance of 0.5-1 MΩ when filled with an electrode solution containing (in mM): 96 KCl, 1 $MgCl_2$, and 5 HEPES (pH 7.4). Oocytes were bathed with a solution comprising (in mM): 96 KCl, 5 EGTA, 1 MgATP and 10 HEPES (pH 7.4). Current amplitudes were measured at −80 mV with a sampling rate of 10 kHz. Data were analyzed using WinEDR and Clampfit software (Molecular Devices).

Culture of HEK293 cells: HEK293-T cells were obtained from ATCC and maintained in DMEM medium supplemented with 10% FBS and 1% penicillin and streptomycin (Hyclone). For patch-clamp studies, cells were seeded on glass coverslips and transfected 24-hours later using a polyethylenimine solution (1 mg/ml) at a ratio of 8 µl per µg of DNA. To study GIRK-currents, cells were transfected with 0.75 µg each of plasmids encoding GIRK1, GIRK2 or GIRK4 as indicated. In the optogenetic experiments, cells were co-transfected with plasmids encoding 5-ptase$_{OCRL}$ and CIBN-CAAX, as previously described. 5-ptase$_{OCRL}$ and CIBN-CAAX were a kind gift from the DeCamilli lab, Yale CT. All experiments were performed at room temperature 24-36 hours post transfection.

Patch-clamp recording: Whole-cell currents were recorded with an Axopatch 200B amplifier (Molecular Devices) controlled via a USB-interface (National Instruments) using WinWCP software (University of Strathclyde). Currents were acquired through a lowpass Bessel filter at 2 kHz and were digitized at 10 kHz. Patch-pipettes were fabricated from borosilicate glass (Clark), using a vertical puller (Narishige) and had a resistance of 2.5-4 MΩ when filled with an intracellular buffer comprising: 140 mM KCl, 2 mM $MgCl_2$, 1 mM EGTA, 5 mM $Na_2ATP$, 0.1 mM $Na_2GTP$, and 5 mM HEPES; pH 7.2. Cells for study were selected based on GFP expression using an epifluorescence microscope (Nikon). To study the activity of GIRK channels, cells were held at 0 mV, and currents were assessed by ramps from −80 to +80 mV that were repeated at 1 Hz. Cells were perfused via a multi-channel gravity-driven perfusion manifold with a physiological buffer comprising: 135 mM NaCl, 5 mM KCl, 1.2 mM $MgCl_2$, 1.5 mM $CaCl_2$, 8 mM Glucose, and 10 mM HEPES; pH 7.4, then quickly transitioning to a high-$K^+$ buffer comprising 5 mM NaCl, 135 mM KCl, 1.2 mM $MgCl_2$, 1.5 mM $CaCl_2$, 8 mM Glucose, and 10 mM HEPES; pH 7.4. The barium-sensitive component of the current, observed when cells were perfused with the high-$K^+$ buffer, was analyzed and was determined by perfusing 5 mM $BaCl_2$ in the high-$K^+$ buffer at the end of each experiment. HEK293 cells had a mean whole-cell capacitance of 10±1 pF; series resistance was typically <10 MΩ, and the voltage-error of <3 mV was not adjusted for.

Light-activated phosphatase system: The inventors used a light-activated phosphatase system to dephosphorylate $PIP_2$ that is comprised of two fusion proteins: CRY2-5-ptase$_{OCRL}$ contains the photolyase domain of cryptochrome 2 (CRY2) and the inositol 5-phosphatase domain of the Lothe inventors oculocerebrorenal syndrome protein (OCRL), while CIBN-CAAX contains the CRY2 binding domain (CIBN) and a C-terminal CAAX box for plasma membrane targeting. When CRY2-5-ptase$_{OCRL}$ and CIBN-CAAX fusion proteins are co-expressed and exposed to blue light between 458-488 nm, the 5-ptase is localized to the plasma membrane, where it dephosphorylates $PIP_2$. The utility of this system to study the $PIP_2$ dependence of ion channel activity was demonstrated by the Hille and De Camilli labs. The 5-ptase$_{OCRL}$ system was activated using a 460 nm LED (Luminus) that was focused on the cells through the objective lens of an inverted microscope (Nikon).

Electrophysiological recordings from brain slices containing basolateral amygdala (BLA) neurons: Electrophysiology was performed using 150-200 g male Sprague-Dawley rats (Harlan/Envigo, Indianapolis, Ind.). Rats were group housed in plastic cages in standard housing conditions with ad libitum access to food and water with 12:12 light/dark cycle (lights on at 07:00 h). All experiments were conducted in accordance with the Guide for the Care and Use of Laboratory Animals (Institute for Laboratory Animal Research, The National Academies Press) and the guidelines of the IUPUI Institutional Animal Care and Use Committee. Rats were anesthetized with isoflurane and immediately decapitated. Brains were then rapidly removed, placed in ice-cold oxygenated artificial cerebrospinal fluid solution (ACSF) and coronal slices (350 µM) were prepared containing the amygdala. Slices were incubated at 31° C. for 30 min and then returned to room temperature until recording. [ACSF solution in mM: 130 NaCl; 3.5 KCl; 1.1 KH2P04; 1.3 MgCl2; 2.5 CaCl$_2$; 30 NaHCO$_3$; 10 glucose, 315 mOsm, 7.4 pH], Cells were identified for recording at 40× magnification using Scientifica Slicescope microscope under DIC illumination (Scientifica, Uckfield, UK). ACSF was warmed to 30° C. and perfused at a rate of 2-3 ml/min during recordings. Compounds were added to ACSF at desired concentrations. Whole-cell patch-clamp recordings were obtained using standard techniques. Borosilicate glass electrodes (WPI, Sarasota, Fla.) (resistance 3-6 MΩ) were prepared and used for both recording and baclofen application. [Recording internal solution in mM: 140 K-gluconate; 2 KCl; 3 $MgCl_2$; 10 HEPES; 5 Phosphocreatinine; 2 K-ATP; 0.2 Na-GTP, 290 mOsm, 7.4 pH], In voltage-clamp mode, the cell was adjusted to −50 mV at the beginning of all experiments and 5 min stable baseline was established before treatment. Picospritzer II (Parker Hannifin, Hollis, N.H.) was utilized for local application of 100 µM GABA-B agonist baclofen in ACSF to activate GIRKs. Baseline and baclofen-induced currents were averaged from three responses per cell and analyzed using ClampFit software (Molecular Devices, San Jose, Calif.). $Ba^{2+}$ depolarized resting potential suggesting that BLA GIRK channels contribute to resting membrane potential. Several control cells were subjected to baclofen at 2 min intervals for 30 min and consistent responses were observed, thus ruling out time-dependent effects.

Optical mapping studies in isolated hearts: Isolated hearts of C57BL/6 mice, four to six months of age, were retrogradely perfused with Tyrode's solution in the Langendorff mode. The preparations were maintained at 37° C., and stained with a bolus of a voltage sensitive dye (0.25 ml, 10 µM Di-4-ANEPPS, Molecular Probes) and imaged with a CCD camera (RedShirt Imaging), 80×80 pixels, 85 µm per pixel, and 1000 frames per second. Excitation contraction uncoupling was achieved with 7 µM Blebbistatin (Tocris Bioscience). A bipolar, silver tip stimulation electrode was used to pace the right atrium (2.5 5 ms pulses, 2× diastolic threshold) at 10 Hz using an AD Instrument stimulation platform. ML297 or GAT1508 at 2.4 µM were introduced into the perfusate. The action potential duration at 70% repolarization ($APD_{70}$), was quantified as the inventors have done extensively.

Computational modeling, Molecular docking: To accurately reproduce the geometry of ML297 and the GAT molecules, the inventors optimized their structures by Gaussian 03. The inventors then used AutoDock 4.2 to dock ML297 and the GAT compounds to the GIRK2/GIRK2$^{FD}$ (from the crystal structure, PDB ID: 3YSA) and GIRK4/GIRK4$^{FD}$ heteromers a homology model of which was constructed based on the GIRK2 crystal structure (PDB: 3YSA) by the MODELLER program. Although both the S148F and N184D mutations are required for ML297 activation, residue 148 is in the pore helix and is unlikely to directly interact with ML297. Thus, the docking box (size: 22.5×22.5×30 angstroms) was set around D184 of each of the two FD subunits. By empirical free energy scoring, the inventors selected 100 top docking configurations.

Computational modeling, Molecular dynamics (MD) simulation experiments: The GIRK2/GIRK2$^{FD}$ and GIRK4/GIRK4$^{FD}$ channel in the presence or absence of ML297, GAT1508 and GAT1521 in the FD containing subunits were subjected to MD simulations with four $PIP_2$ molecules. GROMACS version 4.5 was used to conduct simulations, applying the GROMOS96 53a6 force field. Topology files and charges for the atoms of $PIP_2$ and the compounds were calculated using the PRODRG web server, as described in previous work. The channel-ligand-$PIP_2$ structures were immersed in an explicit POPC bilayer using the VMD membrane package and solvated with SPC water molecules in a 150 mM KCl. To mimic the activated state, the inventors applied a constant depolarizing electric field of $-0.128$ V·nm$^{-1}$. Energy minimization was performed, followed by a 800-ps position-restrained (1000 kJ/mol/nm$^2$) MD run. Subsequently, the eight systems (GIRK2/2$^{FD}$, GIRK4/4$^{FD}$, alone and each of ML297, GAT1508, and GAT1521) the inventors ran subjected to 35-ns MD simulations. For analysis, the SIMULAID program was used to analyze/cluster structures and to calculate interaction networks, including hydrogen bonds, salt bridges, and hydrophobic contacts.

Xenopus laevis oocyte expression: All cDNA constructs in the pGEMHE vector were linearized using the NheI restriction enzyme, whereas those in the pXoom vector were linearized using the XhoI restriction enzyme. Linearized cDNAs were in vitro-transcribed using the mMessage mMachine® kit (Ambion) kit. Complementary RNA (cRNA) concentrations were quantified by optical density. Xenopus oocytes were surgically extracted, dissociated, and defolliculated by collagenase treatment and microinjected with 50 nl of the desired cRNAs diluted in RNAase-free water. The use of Xenopus laevis frogs for this study was approved by the Institutional Animal Care and Use Committee (IACUC) at Northeastern University. All constructs used in this study were injected to achieve between 1-2 ng per oocyte depending on the channel. Oocytes were incubated for 2 days at 18° C.

Electrophysiology of oocytes: Whole-oocyte currents were measured by conventional two-electrode voltage clamp (TEVC) with a GeneClamp 500 amplifier (Axon Instruments). Agarose cushion microelectrodes were filled with 1.5% (w/v) agarose in 3 M KCl and were used with resistances between 0.1 and 1.5 megaohms. Oocytes were held at 0 mV, and currents were assessed by 800-ms ramps from $-80$ to $+80$ mV. Barium-sensitive basal currents from both groups, 1) Vehicle, 2) single concentration at 10 µM and 3) multiple concentrations of ML297 or GAT compounds in the presence of HK solution, were assessed at $-80$ mV using TEVC. Barium-sensitive currents were normalized to average basal current in the vehicle solutions. The HK solution contained the following: 96 mM KCl, 1 mM NaCl, 1 mM $MgCl_2$, 5 mM KOH/HEPES, pH 7.4. The barium solution consisted of HK+10 mM $BaCl_2$. Five to ten oocytes from the same batch (same frog) were recorded for each group, and the experiments were repeated in at least four batches. Data acquisition and analysis were carried out using pClamp9 (Molecular Devices) and OriginPro (Microcal) software.

Patch clamp studies of mammalian cells: Description of culture of HEK293 cells: HEK293-T cells were maintained in DMEM medium supplemented with 10% FBS and 1% penicillin and streptomycin (Hyclone). For patch-clamp studies, cells were seeded on glass coverslips and transfected 24-hours later using a polyethylenimine solution (1 mg/ml) at a ratio of 8 µl per µg of DNA. To study GIRK-currents, cells were transfected with 0.75 µg each of plasmids encoding Kir3.1, Kir3.2 or Kir3.4 as indicated. In the optogenetic experiments, cells were co-transfected with plasmids encoding 5-ptase$_{OCRL}$ and CIBN-CAAX, as described by Idevall-Hagren et al., PNAS 2012 that were a kind gift from the DeCamilli lab, Yale CT). All experiments were performed at room temperature 24-36 hours post transfection.

Patch-clamp recording: Whole-cell currents were recorded with an Axopatch 200B amplifier (Molecular Devices) controlled via a USB-interface (National Instruments) using WinWCP software (University of Strathclyde). Currents were acquired through a lowpass Bessel filter at 2 kHz and were digitized at 10 kHz. Patch-pipettes were fabricated from borosilicate glass (Clark), using a vertical puller (Narishige) and had a resistance of 2.5-4 MΩ when filled with an intracellular buffer comprising: 140 mM KCl, 2 mM $MgCl_2$, 1 mM EGTA, 5 mM $Na_2ATP$, 0.1 mM $Na_2GTP$, and 5 mM HEPES; pH 7.2. Cells for study were selected based on GFP expression using an epifluorescence microscope (Nikon). To study the activity of Kir channels, cells were held at 0 mV, and currents were assessed by ramps from $-80$ to $+80$ mV that were repeated at 1 Hz. Cells were perfused via a multi-channel gravity-driven perfusion manifold with a physiological buffer comprising: 135 mM NaCl, 5 mM KCl, 1.2 mM $MgCl_2$, 1.5 mM $CaCl_2$, 8 mM Glucose, and 10 mM HEPES; pH 7.4, then quickly transitioning to a high-K$^+$ buffer comprising 5 mM NaCl, 135 mM KCl, 1.2 mM $MgCl_2$, 1.5 mM $CaCl_2$, 8 mM Glucose, and 10 mM HEPES; pH 7.4. The barium-sensitive component of the current, observed when cells were perfused with the high-K$^+$ buffer, was analyzed and was determined by perfusing 5 mM $BaCl_2$ in the high-K$^+$ buffer at the end of each experiment. The 5-ptase$_{OCRL}$ system was activated using a 460 nm LED (Luminus) that was focused on the cells through the objective lens of an inverted microscope (Nikon). HEK293 cells had a mean whole-cell capacitance of 10±1 pF; series resistance was typically <10 MΩ, and the voltage-error of <3 mV was not adjusted for. ML297, GAT1508 or GAT1521 were maintained as 10 mM stock solutions in DMSO and were diluted to concentrations between 10 µM and 1 nM using the high K$^+$ buffer for patch-clamp experiments.

Behavioral Studies

Cued fear conditioning test: On day 1, animals were habituated to the sound attenuating fear conditioning chamber (Kinder Scientific, Poway, Calif.) for 10 min. Between each animal, the chamber was cleaned with 70% ethanol. On day 2, acquisition of fear was achieved by placing rats back into the chamber for a 120 s acclimation period and then five pairings (120 s inter-trial interval) of the conditioned stimulus (CS; 20 s, 80 dB) followed immediately by the unconditioned shock stimulus (US; 500 ms, 0.8 mA foot shock). On day 3, CS consolidation was assessed by placing the rats back into the chamber with a 120 s acclimation period followed by five presentations of the CS only (20 s, 80 dB) with 120 s inter-trial-intervals. On day 4, extinction was assessed by presenting a 120 s acclimation period followed by 20 trials of the CS (20 s, 80 dB) with 120 s inter-trial-intervals. The same experimenter (SDF) handled the rats during all sessions and was blinded to the treatment. All trials were digitally video-recorded. For this behavioral test and all others, blind scoring was aided by modification of video file names by AIM. Freezing behavior (no visible signs of movement) was scored by SDF during the sound presentation and converted to percentage of total time.

Open-field (OF) test: The OF apparatus is a plexiglass open-topped chamber (91.5×91.5×30.5 cm), filmed by a ceiling-mounted CCD camera and illuminated by a 25 W red light bulb placed 2 meters above the center of the chamber. One hour after vehicle or ligand treatment, rats were gently placed in the center and allowed to freely move 5 minutes. The automated tracking system ANY-MAZE (ANY-MAZE, Stoelting Co., Wood Dale, Ill., USA) was utilized to measure total distance traveled and mean speed.

Social interaction (SI) test: Social interaction (SI) test was performed 5 min after OF test in the same apparatus. The protocol used for the SI test has been described previously. In brief, the "experimental" rat and the "partner" rat were simultaneously placed into the chamber for a 5 min test. The "partner" rat was age-, sex- and weight-matched to the "experimental" rat. All tests were video recorded then manually scored using ODlog for Mac OS X version 2.6.1. Time spent by the "experimental" rat engaging in non-aggressive physical investigation of the "partner" rat is reported as social interaction time (in s). Investigation of the "partner" includes sniffing, climbing over and crawling under, mutual grooming, genital investigation, or following and walking around the partner.

Novel object recognition test (NORT): Novel object recognition test was performed in an open-field box measuring 100×100×20 cm as previously described. Prior to testing, the rats were allowed to explore the box for 5 min per day for 3 consecutive days with no objects present. Testing consisted of two 2 min trials. During a familiarization trial, two identical objects (plastic cylinders 6 cm in diameter and 12 cm tall in white and red) were placed in two adjacent corners. The animal was then released against the center of the opposite wall with its back to the objects. This was done to prevent coercion to explore the objects. The animals were regarded to be exploring when they were facing, sniffing, or biting the object with nose and/or forepaws. Immediately after familiarization, the rats received intraperitoneal (i.p.) injections of vehicle or ligands and were returned to its home cage. After a waiting period of 3 h (ITI=3 h), the rat was placed in the box again and test trial was performed. During this trial, a new object (plastic building block in yellow or green, 7×3.5×9 cm) replaced one of the familiar objects used in the familiarization trial. The times spent in exploring each object during both trials were recorded manually by using a stopwatch. The box and the objects were cleaned with 70% of ethanol between trials. Discrimination index (DI) was used to measure object recognition and is calculated as the difference in time exploring the novel (TN) versus familiar object (TF), then dividing this value by the total time spent exploring the two objects in the test trial. DI=TN−TF/TN+TF.

Light-dark box: Light-Dark Box test was preformed using a cage 52×100×39 cm divided into two equal sections by an opening. One section is brightly illuminated whereas the other section is dark. Animals were injected 30 min prior to testing with vehicle or ligand and then placed into the light side with immediate access to explore the entire cage. Time spent in the illuminated section was analyzed. The chamber was cleaned between each experiment.

Rotorod tests: Animals were habituated to the rotarod test for 5 concecutive days and tested on day 6. On test day, animals were injected with vehicle or GAT1508 30 min prior to testing. Each day consisted of three trials separated by 1 min. A trial constituted animals being placed on an immobile rotarod that was then accelerated from 0-40 rotations/min. Trails lasted 120 seconds during which the rotatod accelerated at a rate of 0.33 rotations/second. Mechanical detection of latency to fall was registered by Panlab RotaRod RS (Harvard Apparatus, Holliston, Mass.).

Elevated plus maze (EPM): The EPM, as described previously was performed in a black Plexiglas apparatus (Hamilton Kinder, San Diego, Calif.) that consists of two open arms and two closed arms each 50.17 cm long and 10.8 cm wide. The closed arms have walls that are 40.01 cm high. The entire apparatus is elevated 100 cm above the ground on a square aluminum base. For a testing period of 5 min, anxiety is estimated by the amount of time rats spend in the closed versus open arms. Test sessions were video recorded by ceiling mounted cameras.

Cardiovascular experiments: Radiotelemetry probes [Cat. no. HD-S11, Data Sciences International, St. Paul, Minn., United States] were surgically implanted into the peritoneal cavity and sutured to the muscle wall in order to assess general motor activity and temperature. A pressure transducer was implanted into the femoral artery to assess cardiovascular responses [i.e., mean arterial blood pressure (MAP) and heart rate (HR)]. Animals were injected with selected compounds following a 10 min baseline period and data points were analayzed between 20 min and 60 min after injection. This allowed us to investigate ligand effects without confounding effects of animal handling or the injection itself and to allow the ligand to cross the blood-brain barrier.

EXAMPLES

Example 1. Production of GAT1508 and Related Compounds

All commercial chemicals and solvents were purchased from standard commercial sources as reagent grade and, unless otherwise specified, were used without further purification. A Biotage Initiator microwave system was used for the synthesis. Reaction progress was monitored by thin-layer chromatography (TLC) using commercially prepared silica gel 60 F254 glass plates. Compounds were visualized under ultraviolet (UV) light or by staining with iodine. Flash column chromoatography was carried out on an autoflash purification unit using prepacked columns from Reveleris, Biotage and Lunknova. Solvents used include hexanes and ethyl acetate. Characterization of compounds and their purity was established by a combination of HPLC, TLC, mass spectrometry, and NMR analyses. NMR spectra were recorded in DMSO-$d_6$, on a NMR spectrometer (1H NMR at 500 MHz). Chemical shifts were recorded in parts per million (δ) relative to tetramethylsilane (TMS; 0.00 ppm) or solvent peaks as the internal reference. Multiplicities are indicated as br (broadened), s (singlet), d (doublet), t (triplet), q (quartet), quin (quintet), and m (multiplet). Coupling constants (J) are reported in hertz (Hz). All test compounds were greater than 95% pure, as determined by LC-MS analysis performed with a dual-wavelength UV-visible detector and quadrupole mass spectrometer. Refer to individual compounds for detail and for the synthetic scheme followed. The synthesis schemes discussed below were followed for production of GAT1508 and the other compounds.

An example synthetic route for synthesizing asymmetric urea ligands is shown below.

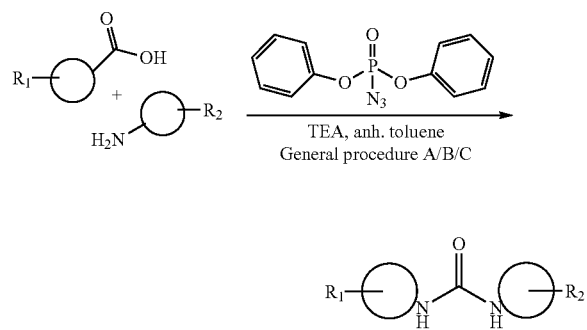

General Procedure A: In a microwave vial was placed a suspension of the carboxylic acid, the amine, diphenyl phosphorylazide (DPPA), and triethylamine (TEA) in anhydrous toluene, and the reaction mixture was irradiated in a Biotage Microwave synthesizer for 1-5 min at 120° C. (surface sensor). The reaction mixture was poured into water and extracted with ethyl acetate (3×50 mL). The combined organic layers were washed with water (20 mL) and brine (20 mL), dried over $Na_2SO_4$ and evaporated under vacuum. The crude residue was purified by silica gel column chromatography (EtOAc/hexane) to yield the desired urea. An example of the reaction procedure is shown below.

Scheme I

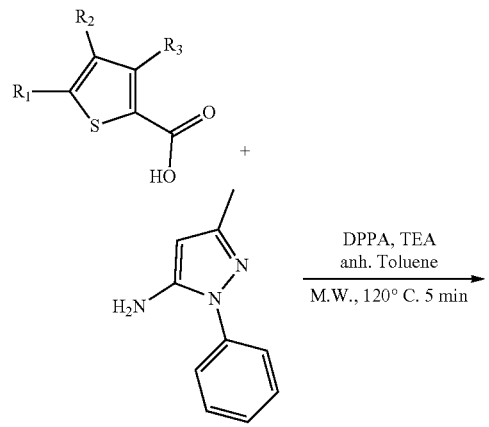

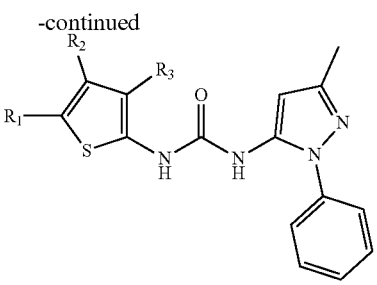

General Procedure B: A suspension of the carboxylic acid, diphenyl phosphorylazide (DPPA), and triethylamine (TEA) in anhydrous toluene was placed in a microwave vial and the reaction mixture was irradiated in a Biotage Microwave synthesizer for 2 min at 100° C. (surface sensor). The amine in anhydrous toluene was directly injected into the microwave vial then further irradiated under microwave condition for 2 min at 120° C. The reaction mixture was cooled and poured into water and extracted with ethyl acetate (3×50 mL). The combined organic layers were washed with water (20 mL) and brine (20 mL), dried over $Na_2SO_4$ and evaporated under vacuum. The crude residue was purified by silica gel column chromatography (EtOAc/hexane) to yield the desired urea.

General Procedure C: A suspension of the carboxylic acid, the amine, diphenyl phosphorylazide (DPPA), and triethylamine (TEA) in anhydrous toluene was placed in a round bottom flask and the reaction mixture was refluxed at 120° C. and monitored by TLC until completion. The reaction mixture was poured into water and extracted with ethyl acetate (3×50 mL). The combined organic layers were washed with water (20 mL) and brine (20 mL), dried over $Na_2SO_4$ and evaporated under vacuum. The crude residue was purified by silica gel column chromatography (EtOAc/hexane) to yield the desired urea.

Figure 3:
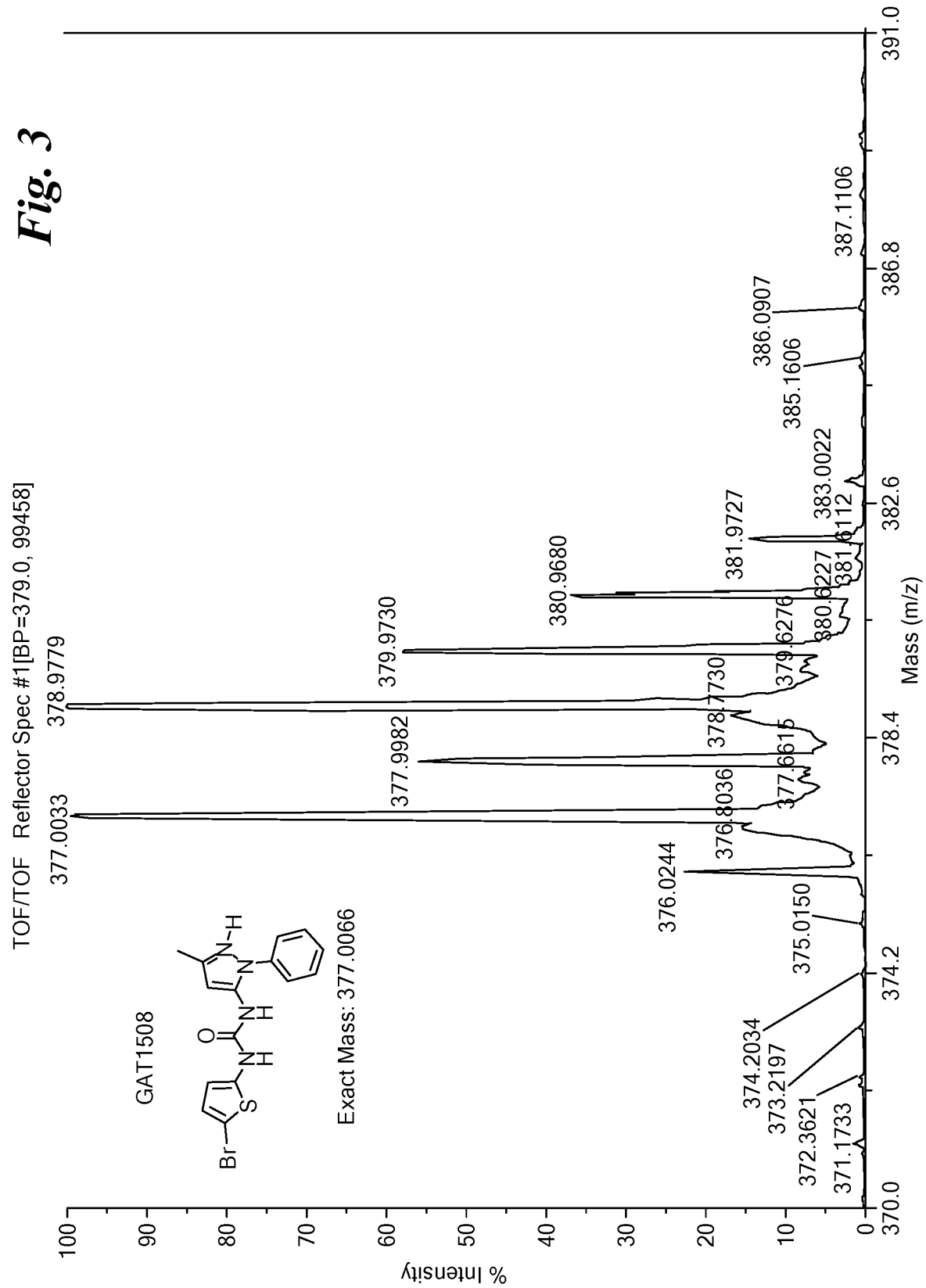
FIG. 3 shows a high-resolution mass spectrum of GAT1508 from Matrix Assisted Laser Desorption Ionization Time of Flight (MALDI-TOF) using 39468 SIGMA-ALDRICH, α-Cyano-4-hydroxycinnamic acid, matrix substance for MALDI-MS, Ultrapure.
Figure 4:
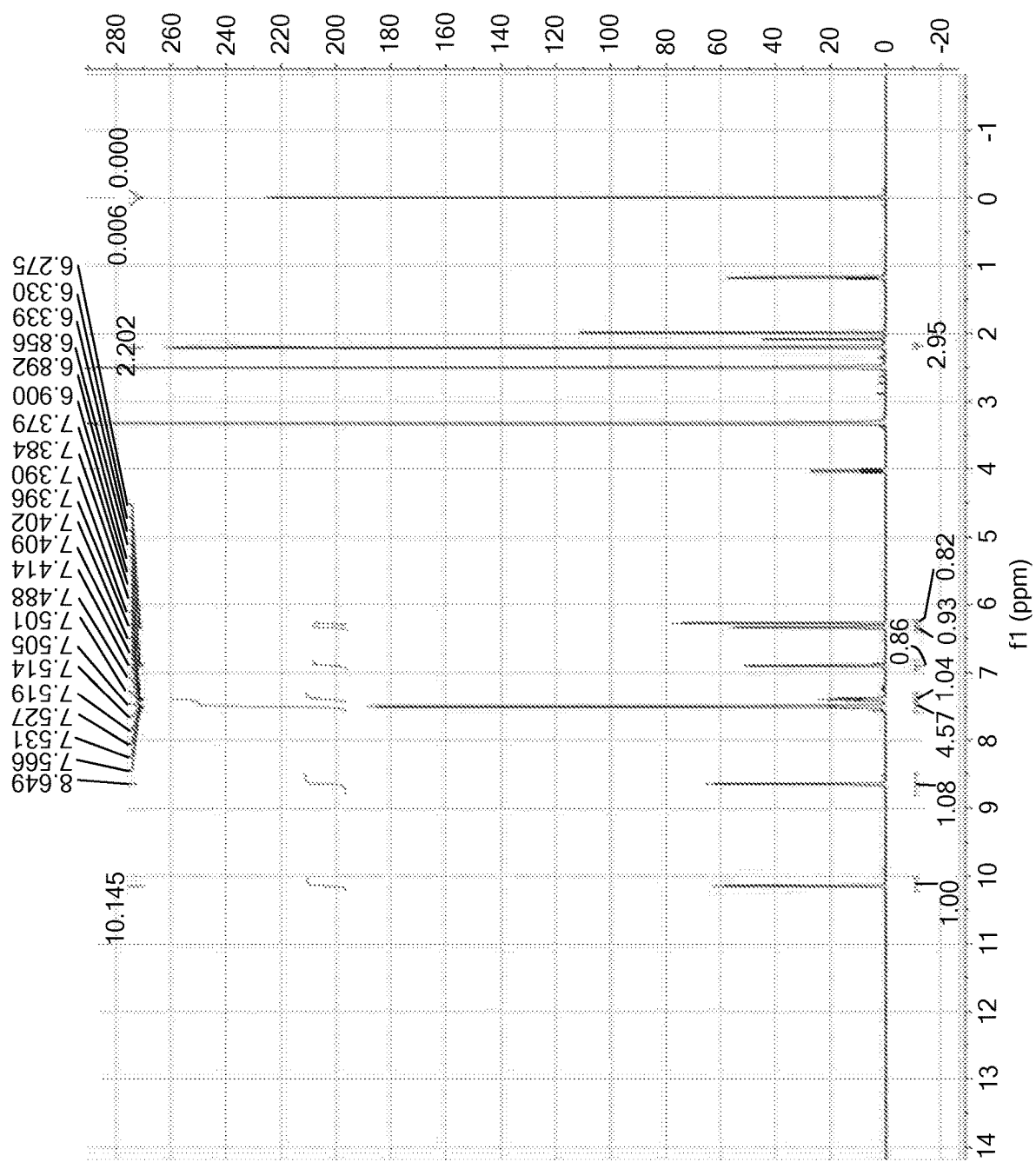
FIG. 4 shows a $^1$H NMR (500 MHz, DMSO-$d_6$) spectrum of GAT1508.

Examples of compounds synthesized using General Procedures A, B, and C are described below:

1-(5-bromothiophen-2-yl)-3-(3-methyl-1-phenyl-1H-pyrazol-5-yl)urea (GAT1508): The compound was synthesized according to the general procedure A using 5-bromothiophene-2-carboxylic acid (358 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 196 mg, 45% yield, of a pale amber solid: $^1$H NMR (500 MHz, DMSO-$d_6$): δ 10.14 (s, 1H), 8.65 (s, 1H), 7.54-7.47 (m, 4H), 7.42-7.37 (m, 1H), 6.90 (d, J=4.0 Hz, 1H), 6.34 (d, J=4.0 Hz, 1H), 6.27 (s, 1H), 2.20 (s, 3H); HRMS (ESI): m/z calcd for $C_{15}H_{13}BrN_4OS$ [M+H]$^+$, 377.0066; found, 377.0033. NMR data is shown in FIG. 4 and HRMS data is shown in FIG. 3.

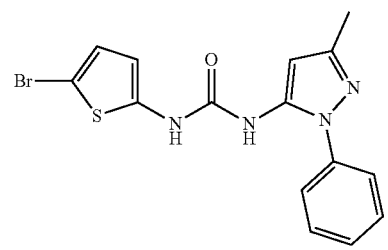

Molecular Weight: 377.26

1-(3-methyl-1-phenyl-1H-pyrazol-5-yl)-3-(5-methylthiophen-2-yl)urea (GAT1521): The compound was synthesized according to the general procedure A using 5-methylthiophene-2-carboxylic acid (246 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield, 175 mg, 48% yield, of a light tan solid: $^1$H NMR (500 MHz DMSO-d$_6$): δ 9.69 (s, 1H), 8.45 (s, 1H), 7.56-7.47 (m, 4H), 7.44-7.37 (m, 1H), 6.48-6.42 (m, 1H), 6.29 (d, J=3.5 Hz, 1H), 6.26 (s, 1H), 2.31 (s, 3H), 2.19 (s, 3H); HRMS (ESI): m/z calcd for $C_{16}H_{16}N_4OS$ [M+H]$^+$, 313.1118; found, 313.1089.

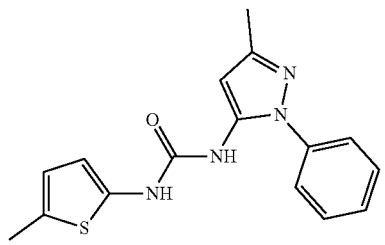

Molecular Weight: 312.39

1-(3-methyl-1-phenyl-1H-pyrazol-5-yl)-3-(thiophen-3-yl)urea (GAT1500): The compound was synthesized according to the general procedure A using thiophene 3-carboxylic acid (222 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to give 211 mg, 62% yield, of a white solid: $^1$H NMR (500 MHz, DMSO-d$_6$): δ 9.23 (s, 1H), 8.38 (s, 1H), 7.55-7.48 (m, 4H), 7.44-7.38 (m, 2H), 7.24 (dd, J=3.0, 1.0 Hz, 1H), 6.99 (dd, J=5.0, 1.0 Hz, 1H), 6.27 (s, 1H), 2.19 (s, 3H); HRMS (ESI): m/z calcd for $C_{15}H_{14}N_4OS$ [M+H]+, 299.0961; found, 299.0962.

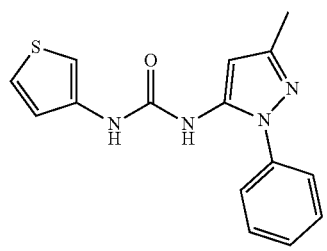

Molecular Weight: 298.36

1-(5-chlorothiophen-2-yl)-3-(3-methyl-1-phenyl-1H-pyrazol-5-yl)urea (GAT1501): The compound was synthesized according to the general procedure A using 5-chlorothiophene-2-carboxylic acid (282 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to give 318 mg, 83% yield, of a pale amber solid: $^1$H NMR (500 MHz, DMSO-d$_6$): δ 10.11 (s, 1H), 8.65 (s, 1H), 7.54-7.48 (m, 4H), 7.42-7.37 (m, 1H), 6.79 (d, J=4.0, 1H), 6.34 (d, J=4.0 Hz, 1H), 6.28 (s, 1H), 2.20 (s, 3H); HRMS (ESI): m/z calcd for $C_{15}H_{13}ClN_4OS$ [M+H]$^+$, 333.0571; found, 333.0500.

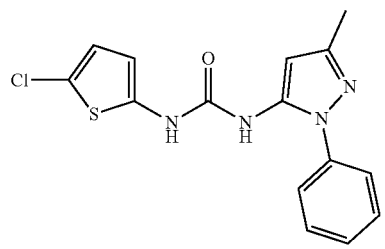

Molecular Weight: 332.81

1-(4-bromothiophen-2-yl)-3-(3-methyl-1-phenyl-1H-pyrazol-5-yl)urea (GA T1502): The compound was synthesized according to the general procedure A using 4-bromothiophene-2-carboxylic acid (358 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 205 mg, 47% yield, of a white solid: $^1$H NMR (500 MHz, DMSO-d$_6$): δ 10.10 (s, 1H), 8.70 (s, 1H), 7.55-7.48 (m, 4H), 7.43-7.37 (m, 1H), 6.96 (d, J=1.0 Hz, 1H), 6.51 (d, J=1.5 Hz, 1H), 6.28 (s, 1H), 2.20 (s, 3H); HRMS (ESI): m/z calcd for $C_{15}H_{13}BrN_4OS$ [M+H]+, 377.0066; found, 377.0084.

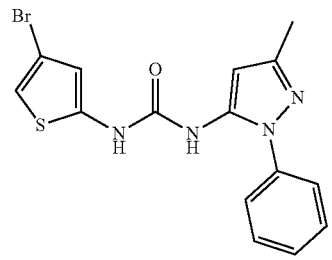

Molecular Weight: 377.26

1-(-adamantan-1-yl)-3-(3-methyl-1-phenyl-1H-pyrazol-5-yl)urea (GAT1503): The compound was synthesized according to the general procedure B using adamantane-1-carboxylic acid (312 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 100 mg, 25% yield, of a white solid: $^1$H NMR (500 MHz, DMSO-d$_6$): δ 7.96 (s, 1H), 7.51 (dd, J=8.5, 7.0 Hz, 2H), 7.46-7.36 (m, 3H), 6.31 (s, 1H), 6.17 (s, 1H), 2.14 (s, 3H), 2.00 (brs, 3H), 1.87 (brs, 6H), 1.61 (brs, 6H); HRMS (ESI): m/z calcd for $C_{21}H_{26}N_4O$ [M+H]$^+$, 351.2179; found, 351.2094.

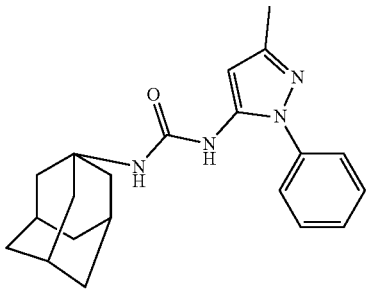

Molecular Weight: 350.47

1-(3-methyl-1-phenyl-1H-pyrazol-5-yl)-3-(naphthalen-2-yl)urea (GAT1505): The compound was synthesized according to the general procedure A using 2-napthoic acid (300 mg, 1.37 mmol), 3-methyl-1 phenyl-1H-pyrazol-5-amine (200 mg, 1.15 mmol), DPPA (476 mg, 1.73 mmol), TEA (349 mg, 3.45 mmol) to yield 200 mg, 50% yield, of a white solid: $^1$H NMR (500 MHz, DMSO-d$_6$): δ 9.20 (s, 1H), 8.52 (s, 1H), 8.05 (s, 1H), 7.81 (dd, J=8.5, 6.0 Hz, 2H), 7.77 (d, J=8.0 Hz, 1H), 7.58-7.50 (m, 4H), 7.48-7.39 (m, 3H), 7.35 (dd as t, J=8.0, 7.0 Hz, 1H), 6.33 (s, 1H), 2.21 (s, 3H); HRMS (ESI): m/z calcd for C$_{21}$H$_{18}$N$_4$O [M+H]$^+$, 343.1553; found, 343.1577.

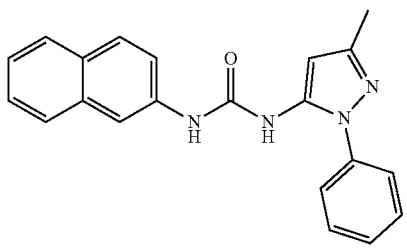

Molecular Weight: 342.40

1-(3-methyl-1-phenyl-1H-pyrazol-5-yl)-3-(thiophen-2-yl)urea (GAT1506): The compound was synthesized according to the general procedure A using thiophene-2-carboxylic acid (222 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 270 mg, 78% yield, of a white solid: $^1$H NMR (500 MHz, DMSO-d$_6$): δ 9.90 (s, 1H), 8.51 (s, 1H), 7.55-7.48 (m, 4H), 7.44-7.37 (m, 1H), 6.86 (dd, J=5.5 Hz, 1.5 Hz, 1H), 6.79 (dd, J=5.5, 4.0 Hz, 1H) 6.52 (dd, J=3.5, 1.5 Hz, 1H), 6.28 (s, 1H) 2.20 (s, 3H); HRMS (ESI): m/z calcd for C$_{15}$H$_{14}$N$_4$OS [M+H]$^+$, 299.0961; found, 299.0950.

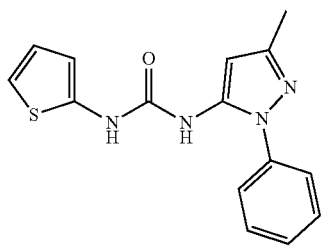

Molecular Weight: 298.36

1-(3-methyl-1-phenyl-1H-pyrazol-5-yl)-3-(thiophen-2-ylmethyl)urea (GAT1507): The compound was synthesized according to the general procedure B using 2-thiophene acetic acid (123 mg, 0.87 mmol), 3-methyl-1 phenyl-1H-pyrazol-5-amine (100 mg, 0.58 mmol), DPPA (239 mg, 0.87 mmol), TEA (175 mg, 1.74 mmol) to yield 48 mg, 26% yield, of a white solid: $^1$H NMR (500 MHz, DMSO-d$_6$): δ 8.25 (s, 1H), 7.51-7.43 (m, 4H), 7.41-7.34 (m, 2H), 7.02 (br t, J=5.5 Hz, 1H), 6.97-6.91 (m, 2H), 6.18 (s, 1H), 4.40 (d, J=5.5 Hz, 2H), 2.17 (s, 3H); HRMS (ESI): m/z calcd for C$_{16}$H$_{16}$N$_4$OS [M+H]$^+$, 313.1118; found, 313.1097.

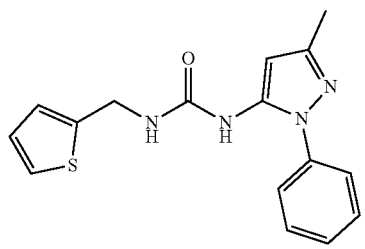

Molecular Weight: 312.39

1-(3,4-difluorobenzyl)-3-(3-methyl-1-phenyl-1H-pyrazol-5-yl)urea (GAT1509): The compound was synthesized according to the general procedure B using (3,4-difluorophenyl)methanamine (200 mg, 1.39 mmol), 3-methyl-1 phenyl-1H-pyrazol-5-carboxylic acid, (423 mg, 2.09 mmol), DPPA (576 mg, 2.09 mmol), TEA (636 mg, 6.28 mmol) to yield 211 mg, 54% yield, of a white solid: $^1$H NMR (500 MHz, DMSO-d$_6$): δ 8.32 (s, 1H), 7.50-7.42 (m, 4H), 7.40-7.31 (m, 2H), 7.267.16 (m, 1H), 7.07-7.00 (m, 1H), 6.99 (t, J=6.0 Hz, 1H), 6.17 (s, 1H), 4.20 (d, J=6.0 Hz, 2H), 2.17 (s, 3H); HRMS (ESI): m/z calcd for C$_{18}$H$_{16}$F$_2$N$_4$O [M+H]$^+$, 343.1365; found, 343.1343.

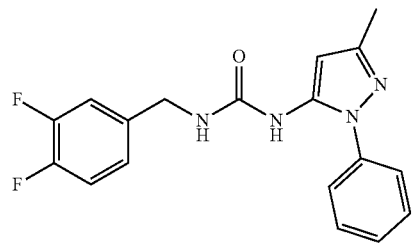

Molecular Weight: 342.35

1-(3-fluorobenzyl)-3-(3-methyl-1-phenyl-1H-pyrazol-5-yl)urea (GAT1510): The compound was synthesized according to the general procedure B using (3-fluorophenyl)methanamine (100 mg, 0.79 mmol), 3-methyl-1 phenyl-1H-pyrazol-5-carboxylic acid, (242 mg, 1.19 mmol), DPPA (330 mg, 1.19 mmol), TEA (242 mg, 2.39 mmol) to yield 30 mg, 12% yield, of a white solid: $^1$H NMR (500 MHz, DMSO-d$_6$): δ 8.30 (s, 1H), 7.52-7.42 (m, 4H), 7.42-7.30 (m, 2H), 7.10-6.94 (m, 4H), 6.17 (s, 1H), 4.24 (d, J=5.5 Hz, 2H), 2.17 (s, 3H); HRMS (ESI): m/z calcd for C$_{18}$H$_{17}$FN$_4$O [M+H]$^+$, 325.1459; found, 325.1457.

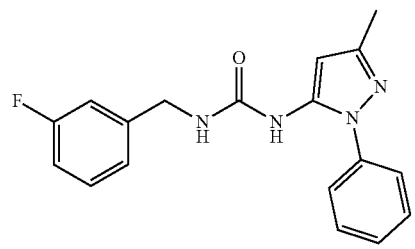

Molecular Weight: 324.36

1-(4,5-dichlorothiophen-2-yl)-3-(3-methyl-1-phenyl-1H-pyrazol-5-yl)urea (GAT1512): The compound was synthesized according to the general procedure A using 4-5- dichlorothiophene-2-carboxylic acid (170 mg, 0.87 mmol), 3-methyl-1 phenyl-1H-pyrazol-5-amine (100 mg, 0.57 mmol), DPPA (238 mg, 0.87 mmol), TEA (175 mg, 1.73 mmol) to yield, 60 mg, 28% yield, of a white solid: $^1$H NMR (500 MHz, DMSO-d$_6$): δ 10.31 (s, 1H), 8.85 (s, 1H), 7.54-7.47 (m, 4H), 7.42-7.37 (m, 1H), 6.48 (s, 1H), 6.28 (s, 1H), 2.21 (s, 3H); HRMS (ESI): m/z calcd for C$_{15}$H$_{12}$Cl$_2$N$_4$OS [M+H]$^+$, 367.0182; found, 367.0181.

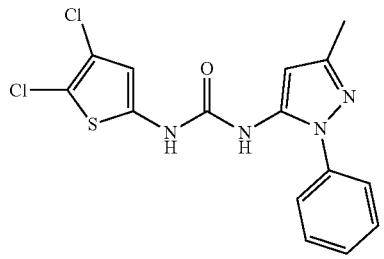

Molecular Weight: 367.25

1-(3-methyl-1-phenyl-1H-pyrazol-5-yl)-3-(5-methyl-isoxazol-3-yl)urea (GAT1513): The compound was synthesized according to the general procedure A using 5-methyl-isoxazole-3-carboxylic acid (219 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 180 mg, 52% yield, of a pale yellowish white solid: $^1$H NMR (500 MHz, DMSO-d$_6$): δ 9.81 (s, 1H), 8.69 (s, 1H), 7.56-7.47 (m, 4H), 7.46-7.37 (m, 1H), 6.46 (s, 1H), 6.29 (s, 1H), 2.34 (s, 3H), 2.19 (s, 3H); HRMS (ESI): m/z calcd for C$_{15}$H$_{15}$N$_5$O$_2$ [M+H]$^+$, 298.1299; found, 298.1276.

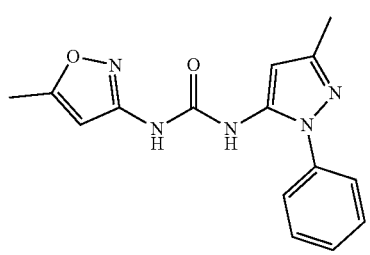

Molecular Weight: 297.32

1-(3,4-difluorophenethyl)-3-(3-methyl-1-phenyl-1H-pyrazol-5-yl)urea (GAT1514): The compound was synthesized according to the general procedure B using 3-4-difluoro-hydrocinnamic acid (322 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 230 mg, 56% yield, of a white solid: $^1$H NMR (500 MHz, DMSO-d$_6$): δ 8.16 (s, 1H), 7.48 (dd as t, J=8.0 Hz, 2H), 7.43-7.38 (m, 2H), 7.37-7.29 (m, 2H), 7.25 (ddd, J=12, 8.0, 2.5 Hz, 1H), 7.03-6.98 (m, 1H), 6.45 (brt, J=5.5 Hz, 1H), 6.10 (s, 1H), 3.25 (q, J=7.0 Hz, 2H), 2.66 (t, J=7.0 Hz, 2H), 2.16 (s, 3H); HRMS (ESI): m/z calcd for C$_{19}$H$_{18}$F$_2$N$_4$O [M+H]$^+$, 357.1521; found, 357.1536.

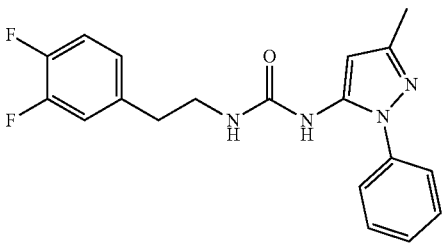

Molecular Weight: 356.38

1-benzyl-3-(3-methyl-1-phenyl-1H-pyrazol-5-yl)urea (GAT1515): The compound was synthesized according to the general procedure B using phenyl acetic acid (236 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 100 mg, 28% yield, of a white solid: $^1$H NMR (500 MHz DMSO-d$_6$): δ 8.25 (s, 1H), 7.52-7.43 (m, 4H), 7.42-7.35 (m, 1H), 7.31 (dd as t, J=7.5 Hz, 2H), 7.28-7.18 (m, 3H), 6.94 (brt, J=6.0 Hz, 1H), 6.18 (s, 1H), 4.23 (d, J=6.0 Hz, 2H), 2.17 (s, 3H); HRMS (ESI): m/z calcd for C$_{18}$H$_{18}$N$_4$O [M+H]$^+$, 307.1553; found, 307.1514.

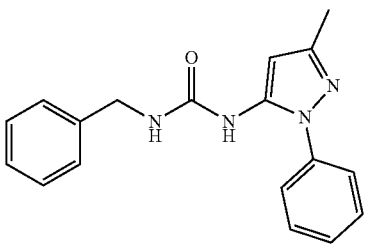

Molecular Weight: 306.37

1-(2,2-difluorobenzo[d][1,3]dioxol-5-yl)-3-(3-methyl-1-phenyl-1H-pyrazol-5-yl)urea (GAT1516): The compound was synthesized according to the general procedure A using 2,2-difluorobenzo [1,3]dioxol-5-amine (100 mg, 0.57 mmol), 3-methyl-1 phenyl-1H-pyrazol-5-carboxylic acid, (1.75 mg, 0.87 mmol), DPPA (238 mg, 0.87 mmol), TEA (175 mg, 1.73 mmol) to yield 115 mg, 53% yield, of a white solid: $^1$H NMR (500 MHz, DMSO-d$_6$): δ 9.18 (s, 1H), 8.48 (s, 1H), 7.59 (d, J=2.0 Hz, 1H), 7.56-7.49 (m, 4H), 7.44-7.38 (m, 1H), 7.29 (d, J=9.0 Hz, 1H), 7.04 (dd, J=9.0, 4.0 Hz, 1H), 6.28 (s, 1H), 2.20 (s, 3H); HRMS (ESI): m/z calcd for C$_{18}$H$_{14}$F$_2$N$_4$O$_3$ [M+H]$^+$, 373.1107; found, 373.1114.

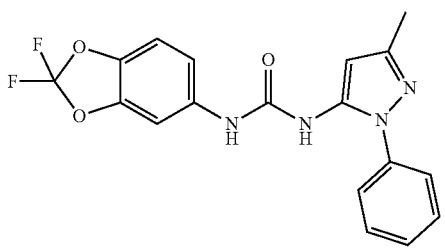

Molecular Weight: 372.33

1-(5-chlorothiophen-3-yl)-3-(3-methyl-1-phenyl-1H-pyrazol-5-yl)urea (GA T1518): The compound was synthesized according to the general procedure A using 5-chlorothiophene-3-carboxylic acid (281 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 123 mg, 32% yield, of a white solid: $^1$H NMR (500 MHz, DMSO-d$_6$): δ 9.24 (s, 1H), 8.49 (s, 1H), 7.58-7.46 (m, 4H), 7.44-7.37 (m, 1H), 7.10 (d, J=2.0 Hz, 1H), 7.04 (d, J=2.0 Hz, 1H), 6.26 (s, 1H), 2.19 (s, 3H); HRMS (ESI): m/z calcd for C$_{15}$H$_{13}$ClN$_4$OS [M+H]$^+$, 333.0571; found, 333.0591.

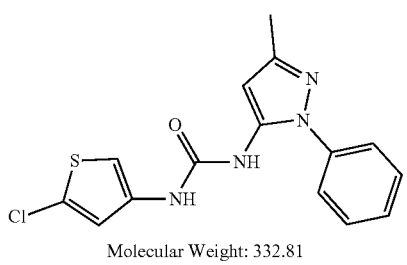 [SMILES: Cc1cc(NC(=O)Nc2csc(Cl)c2)n(-c2ccccc2)n1]

Molecular Weight: 332.81

1-(4,5-dibromothiophen-2-yl)-3-(3-methyl-1-phenyl-1H-pyrazol-5-yl) urea (GA T1519): The compound was synthesized according to the general procedure A using 4,5-dibromothiophene-2-carboxylic acid (490 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 52 mg, 10% yield a orange solid: $^1$H NMR (500 MHz, DMSO-d$_6$): δ 10.3 (s, 1H), 8.85, (s, 1H), 7.59-7.44 (m, 4H), 7.43-7.35 (m, 1H), 6.49 (s, 1H), 6.28 (s, 1H), 2.21 (s, 3H); HRMS (ESI): m/z calcd for C$_{15}$H$_{15}$Br$_2$N$_4$OS [M+H]$^+$, 454.9171; found, 454.9172.

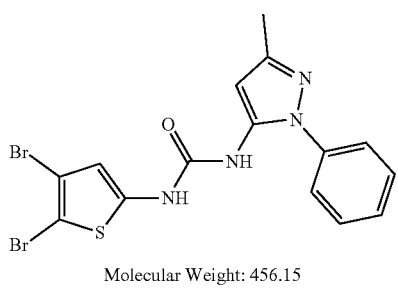 [SMILES: Cc1cc(NC(=O)Nc2cc(Br)c(Br)s2)n(-c2ccccc2)n1]

Molecular Weight: 456.15

1-(benzo[b]thiophen-2-yl)-3-(3-methyl-1-phenyl-1H-pyrazol-5-yl) urea (GAT1522): The compound was synthesized according to the general procedure C using benzo[b]thiophene-2-carboxylic acid (770 mg, 4.33 mmol), 3-methyl-1 phenyl-1H-pyrazol-5-amine (500 mg, 2.89 mmol), DPPA (1.10 g, 4.33 mmol), TEA (877 mg, 8.67 mmol) to yield 120 mg, 30% yield, of a light tan solid: $^1$H NMR (500 MHz, DMSO-d$_6$): δ 10.22 (s, 1H), 8.68 (s, 1H), 7.77 (d, J=8.0 Hz, 1H), 7.58 (d, J=8.0 Hz, 1H) 7.53 (br d, J=5.5 Hz, 4H), 7.42 (sext, J=4.5 Hz, 1H), 7.26 (t, J=7.5 Hz, 1H), 7.15 (t, J=7.5 Hz, 1H), 6.80 (s, 1H), 6.32 (s, 1H), 2.22 (s, 3H); HRMS (ESI): m/z calcd for C$_{19}$H$_{16}$N$_4$OS [M+H]$^+$, 349.1118; found, 349.1117.

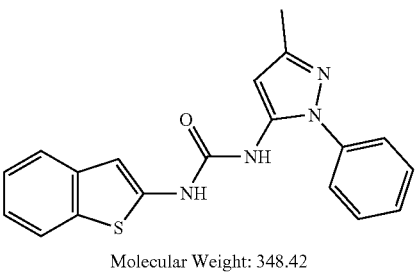 [SMILES: Cc1cc(NC(=O)Nc2cc3ccccc3s2)n(-c2ccccc2)n1]

Molecular Weight: 348.42

1-(3-methyl-1-phenyl-1H-pyrazol-5-yl)-3-(5-phenylthiophen-2-yl)urea (GAT1523): The compound was synthesized according to the general procedure C using 5-phenylthiophene-2-carboxylic acid (352 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 106 mg, 25% yield, of a light tan solid: $^1$H NMR (500 MHz, DMSO-d$_6$): δ 10.04 (s, 1H), 8.62 (s, 1H), 7.58-7.50 (m, 6H), 7.45-7.39 (m, 1H), 7.37 (t, J=7.5 Hz, 2H), 7.24-7.18 (m, 2H), 6.53 (d, J=4.0 Hz, 1H), 6.31 (s, 1H), 2.21 (s, 3H); HRMS (ESI): m/z calcd for C$_{21}$H$_{18}$N$_4$OS [M+H]$^+$, 375.1274; found, 375.1259.

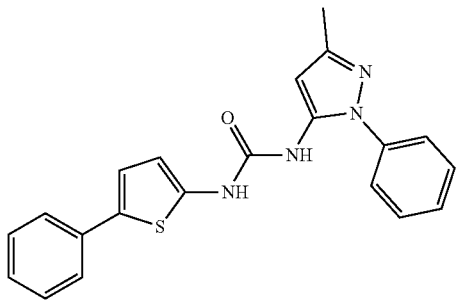

Molecular Weight: 374.46

1-(3-methyl-1-phenyl-1H-pyrazol-5-yl)-3-(thiazol-4-yl)urea (GAT1529): The compound was synthesized according to the general procedure A using thiazole-4-carboxylic acid (223 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 200 mg, 58% yield, of a pale orange solid: $^1$H NMR (500 MHz, DMSO-d$_6$): δ 9.86 (s, 1H), 8.91 (d, J=2.0 Hz, 1H), 8.73 (s, 1H), 7.57-7.47 (m, 4H), 7.46-7.41 (m, 1H), 7.27 (d, J=2.0 Hz, 1H), 6.32 (s, 1H), 2.19 (s, 3H); HRMS (ESI): m/z calcd for C$_{14}$H$_{13}$N$_5$OS [M+H]$^+$, 300.0914; found, 300.0934.

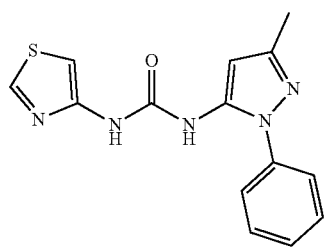

Molecular Weight: 299.35

1-(2-bromothiazol-5-yl)-3-(3-methyl-1-phenyl-1H-pyrazol-5-yl)urea (GAT1530): The compound was synthesized according to the general procedure A using 2-bromothiazole-5-carboxylic acid (360 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 110 mg, 25% yield, of a pale orange solid: $^1$H NMR (400 MHz, DMSO-$d_6$): δ 10.40 (s, 1H), 8.91 (s, 1H), 7.55-7.45 (m, 4H), 7.44-7.35 (m, 1H), 7.23 (s, 1H), 6.28 (s, 1H), 2.21 (s, 3H); HRMS (ESI): m/z calcd for $C_{14}H_{12}BrN_5OS$ [M+H]$^+$, 378.0019; found, 378.0119.

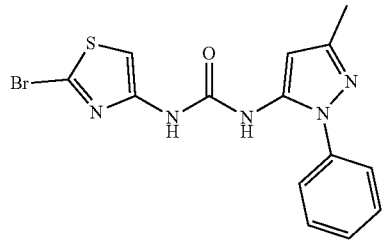

Molecular Weight: 378.25

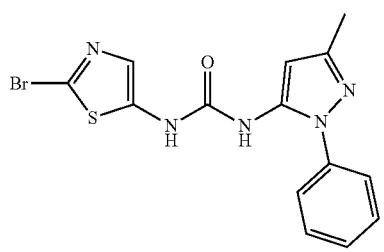

Molecular Weight: 378.25

1-(3-methyl-1-phenyl-1H-pyrazol-5-yl)-3-(thiazol-5-yl)urea (GAT1531): The compound was synthesized according to the general procedure A using thiazole-5-carboxylic acid (223 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 150 mg, 43% yield of a white solid: $^1$H NMR (400 MHz, DMSO-$d_6$): δ 10.12 (s, 1H), 8.72 (s, 1H), 8.49 (s, 1H), 7.56-7.49 (m, 4H), 7.47 (s, 1H), 7.44-7.36 (m, 1H), 6.29 (s, 1H), 2.21 (s, 3H); HRMS (ESI): m/z calcd for $C_{14}H_{13}N_5OS$ [M+H]$^+$, 300.0914; found, 300.0915.

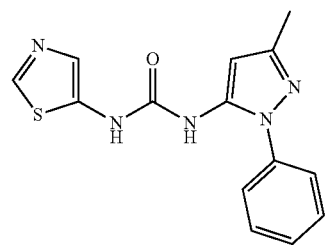

Molecular Weight: 299.35

1-(2-bromothiazol-4-yl)-3-(3-methyl-1-phenyl-1H-pyrazol-5-yl)urea (GAT1532): The compound was synthesized according to the general procedure A using 2-bromothiazole-4-carboxylic acid (360 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 180 mg, 42% yield, of a white solid: $^1$H NMR (500 MHz, DMSO-$d_6$): δ 9.94 (s, 1H), 8.58 (s, 1H), 7.58-7.48 (m, 4H), 7.47-7.39 (m, 1H), 7.26 (s, 1H), 6.30 (s, 1H), 2.19 (s, 3H); HRMS (ESI): m/z calcd for $C_{14}H_{12}BrN_5OS$ [M+H]$^+$, 378.0019; found, 378.0042.

1-(3-methyl-1-phenyl-1H-pyrazol-5-yl)-3-(pyrimidin-5-yl)urea (GAT1535): The compound was synthesized according to the general procedure A using pyrimidine-5-carboxylic acid (107 mg, 0.87 mmol), 3-methyl-1 phenyl-1H-pyrazol-5-amine (100 mg, 0.58 mmol), DPPA (239 mg, 0.87 mmol), TEA (176 mg, 1.75 mmol) to yield 131 mg, 78% yield of a white solid: $^1$H NMR (400 MHz, DMSO-$d_6$): δ 8.93 (s, 1H), 8.79 (s, 1H), 7.55-7.46 (m, 4H), 7.41-7.36 (m, 1H), 7.21 (t, J=8.0 Hz 1H), 7.12 (d, J=8.0 Hz, 1H), 6.95 (t, J=7.2 Hz, 1H), 6.28 (s, 1H), 2.21 (s, 3H); HRMS (ESI): m/z calcd for $C_{14}H_{13}N_5OS$ [M+H]$^+$, 295.1302; found, 295.1323.

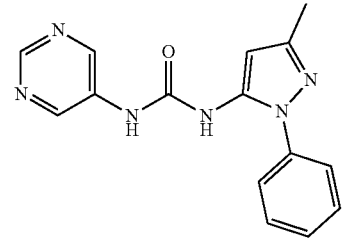

Molecular Weight: 294.32

1-(3-methyl-1-phenyl-1H-pyrazol-5-yl)-3-phenethylurea (GAT1536): The compound was synthesized according to the general procedure B using 3-phenylpropanoic acid (260 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 135 mg, 36.5% yield, of a white solid: $^1$H NMR (400 MHz, DMSO-$d_6$): δ 8.19 (s, 1H), 7.51-7.40 (m, 4H), 7.38-7.36 (m, 1H), 7.31-7.28 (m, 2H), 7.19 (brs, 3H), 6.47 (s, 1H), 6.15 (s, 1H), 3.31-3.26 (m, 2H), 2.71-2.66 (m, 2H), 2.15 (s, 3H); HRMS (ESI): m/z calcd for $C_{19}H_{20}N_4O$ [M+H]$^+$, 321.1710; found, 321.1693.

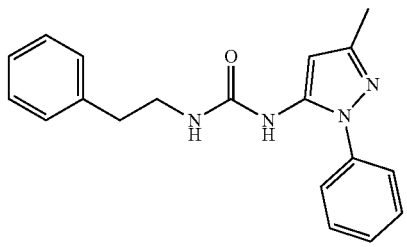

Molecular Weight: 320.40

1-(5-(tert-butyl)thiophen-2-yl)-3-(3-methyl-1-phenyl-1H-pyrazol-5-yl)urea (GAT1551): The compound was synthesized according to the general procedure A using 5-(tert-butyl)thiophene-2-carboxylic acid (318 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 182 mg, 45% yield of a white solid: 1H NMR (400 MHz, DMSO-d$_6$): δ 9.65 (s, 1H), 8.45 (s, 1H), 7.55-7.46 (m, 4H), 7.43 7.36 (m, 1H), 6.50 (d, J=3.6 Hz, 1H), 6.30 (d, J=3.6 Hz, 1H), 6.26 (s, 1H) 2.19 (s, 3H) 1.28 (s, 9H); HRMS (ESI): m/z calcd for C$_{19}$H$_{22}$N$_4$OS [M+H]+, 355.1587; found, 355.1555.

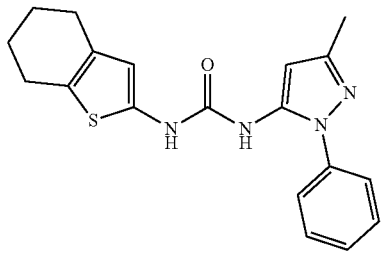

Molecular Weight: 352.46

1-(3-methyl-1-phenyl-1H-pyrazol-5-yl)-3-(5-methylthiazol-2-yl)urea (GAT1561): The compound was synthesized according to the general procedure A using 5-methylthiazole-2-carboxylic acid (164 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 48 mg, 13% yield of a pale yellow solid: $^1$H NMR (400 MHz, DMSO-d$_6$): δ 10.68 (s, 1H), 8.97 (s, 1H), 7.58-7.48 (m, 4H), 7.46-7.38 (m, 1H), 6.98 (s, 1H), 6.32 (s, 1H), 2.29 (s, 3H), 2.20 (s, 3H); HRMS (ESI): m/z calcd for C$_{15}$H$_{15}$N$_5$OS [M+H]$^+$, 314.1070; found, 314.1044.

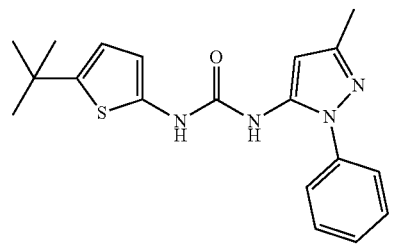

Molecular Weight: 354.47

1-(3-methyl-1-phenyl-1H-pyrazol-5-yl)-3-(4-methylthiophen-2-yl)urea (GAT1552): The compound was synthesized according to the general procedure A using 4-methylthiophene-2-carboxylic acid (245 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 100 mg, 28% yield of a white solid: $^1$H NMR (400 MHz, DMSO-d$_6$): δ 9.78 (s, 1H), 8.47 (s, 1H), 7.55-7.47 (m, 4H), 7.43-7.36 (m, 1H), 6.44 (s, 1H), 6.35 (s, 1H), 6.27 (s, 1H), 2.19 (s, 3H) 2.10 (s, 3H); HRMS (ESI): m/z calcd for C$_{16}$H$_{16}$N$_4$OS [M+H]$^+$, 313.1118; found, 313.1137.

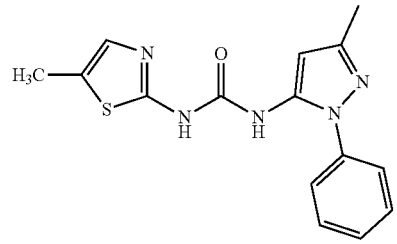

Molecular Weight: 313.38

1-(2,5-dichlorothiophen-3-yl)-3-(3-methyl-1-phenyl-1H-pyrazol-5-yl)urea (GAT1564): The compound was synthesized according to the general procedure A using 2,5-dichlorothiophene-3-carboxylic acid (225 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 118 mg, 28% yield of a amber solid: $^1$H NMR (400 MHz, DMSO-d$_6$): δ 8.99 (s, 1H), 8.90 (s, 1H), 7.60-7.48 (m, 5H), 7.46-7.40 (m, 1H), 6.29 (s, 1H), 2.19 (s, 3H); HRMS (ESI): m/z calcd for C$_{15}$H$_{12}$Cl$_2$N$_4$OS [M+H]$^+$, 367.0182; found, 367.0154.

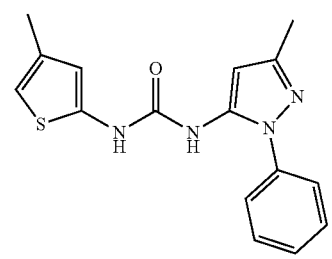

Molecular Weight: 312.39

1-(3-methyl-1-phenyl-1H-pyrazol-5-yl)-3-(4,5,6,7-tetrahydrobenzo[b]thiophen-2-yl)urea (GAT1553): The compound was synthesized according to the general procedure A using 4,5,6,7-tetrahydrobenzo[b]thiophene-2-carboxylic acid (309 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 155 mg, 38% yield of a white solid: $^1$H NMR (400 MHz, DMSO-d$_6$): δ 8.66 (s, 1H), 8.48 (s, 1H), 7.57-7.47 (m, 4H), 7.44-7.35 (m, 1H), 7.16 (s, 1H), 6.28 (s, 1H), 2.66-2.63 (m, 2H), 2.36-2.32 (m, 2H), 2.18 (s, 3H) 1.74 (s, 4H); HRMS (ESI): m/z calcd for C$_{19}$H$_{20}$N$_4$OS [M+H]$^+$, 353.1431; found, 353.1432.

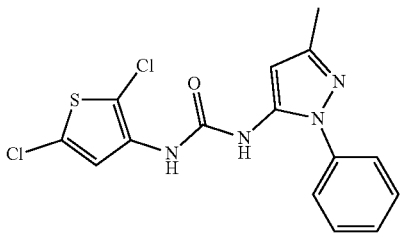

Molecular Weight: 367.25

1-(3-methyl-1-phenyl-1H-pyrazol-5-yl)-3-(pyridin-2-yl)urea (GAT1565): The compound was synthesized according to the general procedure C using picolinic acid (532 mg, 4.33 mmol), 3-methyl-1 phenyl-1H-pyrazol-5-amine (500 mg, 2.89 mmol), DPPA (1.19 g, 4.33 mmol), TEA (870 mg, 8.67 mmol) to yield 78 mg, 9.2% yield of a white solid: $^1$H NMR (400 MHz, DMSO-$d_6$): δ 11.94 (br s, 1H), 9.89 (s, 1H), 7.78 (d, J=4.5 Hz, 1H) 7.73 (t, J=8.0 Hz, 1H), 7.64-7.54 (m, 4H), 7.52-7.46 (m, 1H), 7.12 (d, J=8.0 Hz, 1H) 6.96 (t, J=6.5 Hz, 1H), 6.40 (s, 1H), 2.20 (s, 3H); HRMS (ESI): m/z calcd for $C_{16}H_{15}N_5O$ [M+H]$^+$, 294.1349; found, 294.1363.

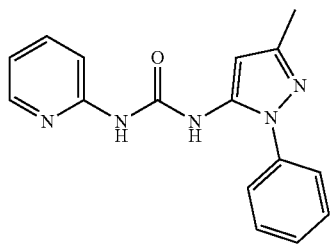

Molecular Weight: 293.33

1-(3-methyl-1-phenyl-1H-pyrazol-5-yl)-3-(6-methylpyridin-3-yl)urea (GAT1566): The compound was synthesized according to the general procedure C using 6-methylnicotinic acid (532 mg, 4.33 mmol), 3-methyl-1 phenyl-1H-pyrazol-5-amine (500 mg, 2.89 mmol), DPPA (1.19 g, 4.33 mmol), TEA (870 mg, 8.67 mmol) to yield 197 mg, 22% yield of a white solid: $^1$H NMR (400 MHz, DMSO-$d_6$): δ 9.06 (s, 1H), 8.53 (s, 1H), 8.41 (s, 1H), 7.77 (d, J=8.0 Hz, 1H), 7.58-7.48 (m, 4H), 7.46-7.36 (m, 1H), 7.15 (d, J=8.8 Hz, 1H), 6.29 (s, 1H), 2.38 (s, 3H), 2.20 (s, 3H); HRMS (ESI): m/z calcd for $C_{17}H_{17}N_5O$ [M+H]$^+$, 308.1506; found, 308.1469.

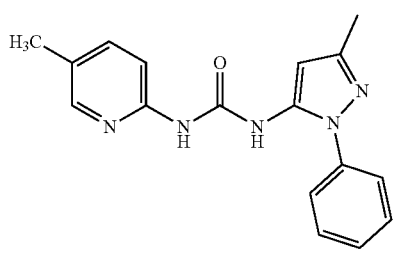

Molecular Weight: 307.36

1-(3-methyl-1-phenyl-1H-pyrazol-5-yl)-3-(pyridin-3-yl)urea (GAT1568): The compound was synthesized according to the general procedure C using nicotinic acid (532 mg, 4.33 mmol), 3-methyl-1 phenyl-1H-pyrazol-5-amine (500 mg, 2.89 mmol), DPPA (1.19 g, 4.33 mmol), TEA (870 mg, 8.67 mmol) to yield 177 mg, 21% yield of a white solid: $^1$H NMR (400 MHz, DMSO-$d_6$): δ 9.17 (s, 1H), 8.59 (s, 1H), 8.54 (s, 1H) 8.18 (d, J=3.6 Hz, 1H), 7.89 (d, J=8.0 Hz, 1H), 7.60-7.48 (m, 4H), 7.46-7.38 (m, 1H), 7.30 (dd, J=8.0, 4.4 Hz, 1H) 6.29 (s, 1H), 2.20 (s, 3H); HRMS (ESI): m/z calcd for $C_{16}H_{15}N_5O$ [M+H]$^+$, 294.1349; found, 294.1318.

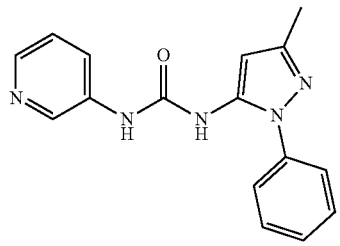

Molecular Weight: 293.33

1-(3-methyl-1-phenyl-1H-pyrazol-5-yl)-3-(pyridin-4-yl)urea (GAT1569): The compound was synthesized according to the general procedure C using isonicotinic acid (532 mg, 4.33 mmol), 3-methyl-1 phenyl-1H-pyrazol-5-amine (500 mg, 2.89 mmol), DPPA (1.19 g, 4.33 mmol), TEA (870 mg, 8.67 mmol) to yield 79 mg, 9.3% yield of a white solid: $^1$H NMR (400 MHz, DMSO-$d_6$): δ 9.41 (s, 1H), 8.65 (s, 1H), 8.35 (brs, 2H) 7.58-7.48 (m, 4H), 7.46-7.32 (m, 3H), 6.31 (s, 1H), 2.20 (s, 3H); HRMS (ESI): m/z calcd for $C_{16}H_{15}N_5O$ [M+H]$^+$, 294.1349; found, 294.1314.

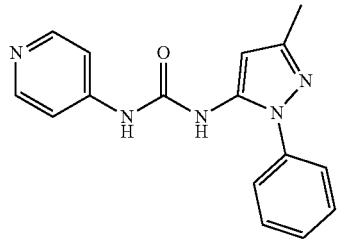

Molecular Weight: 293.33

1-(3-bromothiophen-2-yl)-3-(3-methyl-1-phenyl-1H-pyrazol-5-yl)urea (GAT1570): The compound was synthesized according to the general procedure C using 3-bromothiophene-2-carboxylic acid (238 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 210 mg, 48% yield, of a white solid: $^1$H NMR (400 MHz, DMSO-$d_6$): δ 9.46 (s, 1H), 9.18 (s, 1H), 7.60-7.49 (m, 4H), 7.47-7.40 (m, 1H), 7.07 (d, J=5.8 Hz, 1H), 6.88 (d, J=5.7 Hz, 1H), 6.33 (s, 1H), 2.19 (s, 3H); HRMS (ESI): m/z calcd for $C_{15}H_{13}BrN_4OS$ [M+H]$^+$, 377.0066; found, 377.0086.

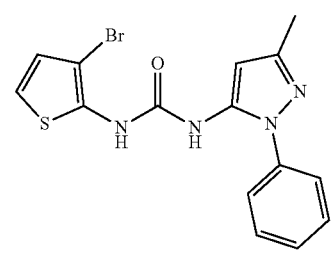

Molecular Weight: 377.26

1-(5-iodothiophen-2-yl)-3-(3-methyl-1-phenyl-1H-pyrazol-5-yl)urea (GAT1574): The compound was synthesized according to the general procedure C using 5-iodothiophene-2-carboxylic acid (550 mg, 2.16 mmol), 3-methyl-1 phenyl- 1H-pyrazol-5-amine (250 mg, 1.44 mmol), DPPA (596 mg, 2.16 mmol), TEA (438 mg, 4.33 mmol) to yield 10 mg, 1.6% yield, of a yellow resin: $^1$H NMR (500 MHz, DMSO-d$_6$): δ 9.29 (s, 1H), 9.17 (s, 1H), 7.60-7.48 (m, 4H), 7.46-7.38 (m, 1H), 7.06 (d, J=5.6 Hz, 1H), 6.89 (d, J=5.9 Hz, 1H), 6.31 (s, 1H), 2.19 (s, 3H); HRMS (ESI): m/z calcd for C$_{15}$H$_{13}$IN$_4$OS [M+H]$^+$, 424.9928; found, 424.9900.

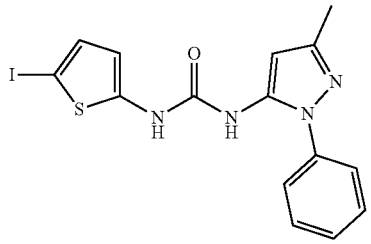

Molecular Weight: 424.26

1-(5-fluorothiophen-2-yl)-3-(3-methyl-1-phenyl-1H-pyrazol-5-yl)urea (GAT1575): The compound was synthesized according to the general procedure C using 5-fluorothiophene-2-carboxylic acid (360 mg, 1.73 mmol), 3-methyl-1 phenyl-1H-pyrazol-5-amine (200 mg, 1.15 mmol), DPPA (476 mg, 1.73 mmol), TEA (349 mg, 3.45 mmol) to yield 16 mg of a white solid: $^1$H NMR (500 MHz, DMSO-d$_6$): δ 9.91 (s, 1H), 8.63 (s, 1H), 7.56-7.46 (m, 4H), 7.44-7.36 (m, 1H), 6.93 (t, J=3.6 Hz, 1H), 6.26 (s, 1H), 6.11 (t, J=3.97 Hz, 1H), 2.20 (s, 3H); HRMS (ESI): m/z calcd for C$_{15}$H$_{13}$FN$_4$OS [M+H]+, 317.0867; found, 317.0687.

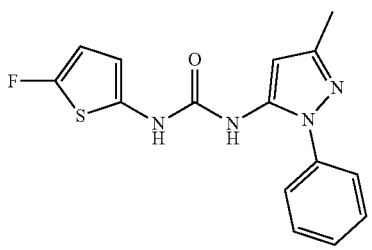

Molecular Weight: 316.35

Example 2. Analysis of Mechanism of Action

Figure 30:
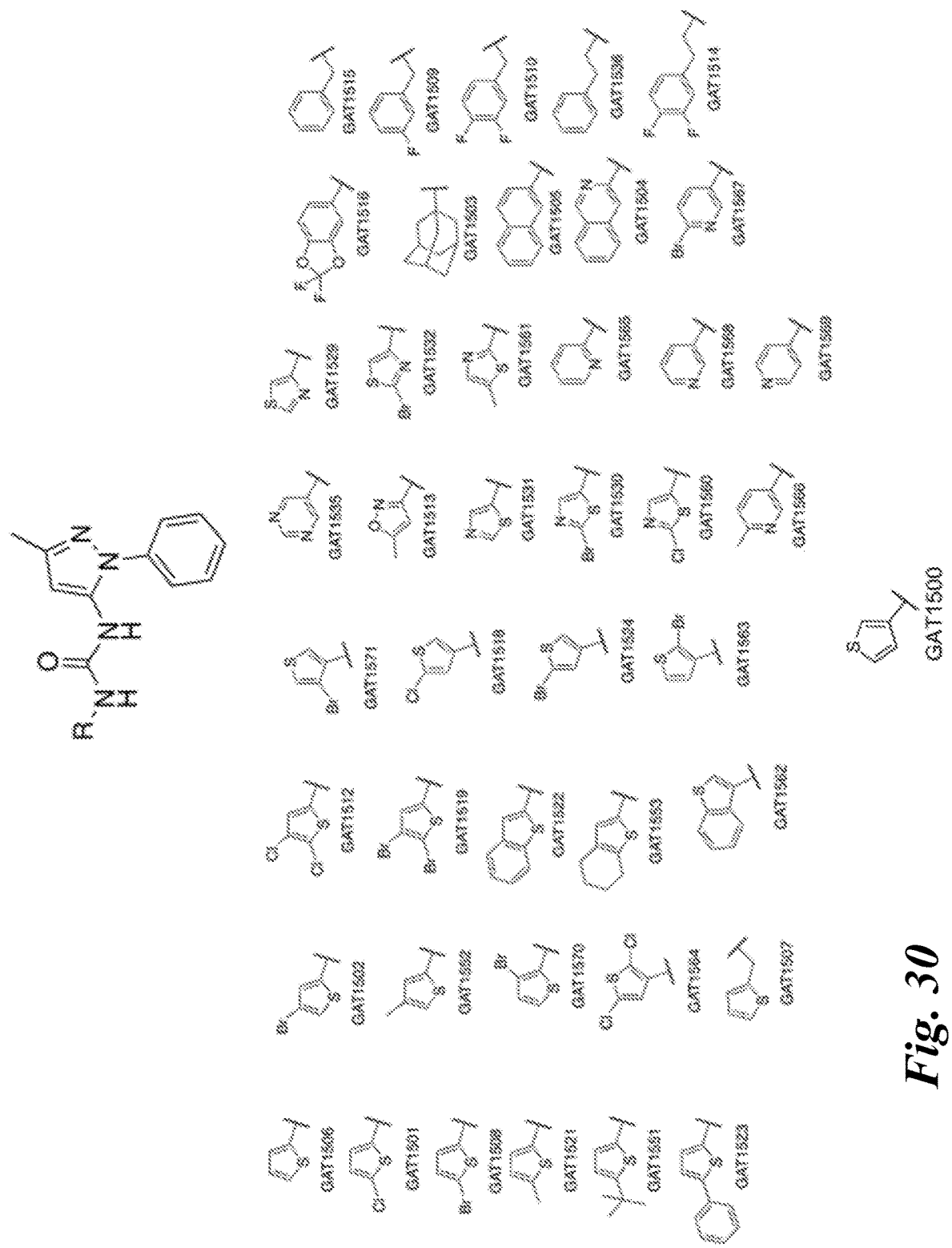
FIG. 30 shows 43 'R' substituents for a molecular scaffold shown representing novel compounds for a focused library, establishing a systematic approach to preliminary SAR studies probing Site I of ML297 for selectivity for GIRK1/2 over GIRK1/4 channels

Chemical optimization focusing on the Site 1 phenyl ring of ML297 resulted in ~40 new analogs that were produced by bioisosteric replacement (FIGS. 2, 30). To explore the selectivity of these compounds, the inventors evaluated their effects using two-electrode voltage-clamp of oocytes from *Xenopus laevis* expressing either brain or cardiac heteromeric GIRK channel isoforms (brain GIRK1/2 versus cardiac GIRK1/4). Current responses to perfusion of 10 μM concentration of each compound were assessed (shown in FIG. 31 summarizing current increases normalized to the responses of the ML297 compound—current level in dashed line at 1 on Y-axis versus current level in compound tested upper dashed lines at ~2.5 and ~1.75). Similar to ML297, most compounds elicited greater current increases in GIRK1/2 compared to GIRK1/4 channels. Among them, two thiophene ring derivatives, one with a bromine and the other with a methyl at the 3' position named GAT1508 and GAT1521 respectively, were the most selective GIRK1/2 activators relative to GIRK1/4 (FIG. 2 and FIG. 31). Concentration-response curves of these two compounds compared to ML297 (FIGS. 5A-5C) further confirmed their selectivity for activation of the brain isoforms and suggested that the GAT1508 possessed the greatest potency.

Figures 34D, 34E, 34F:
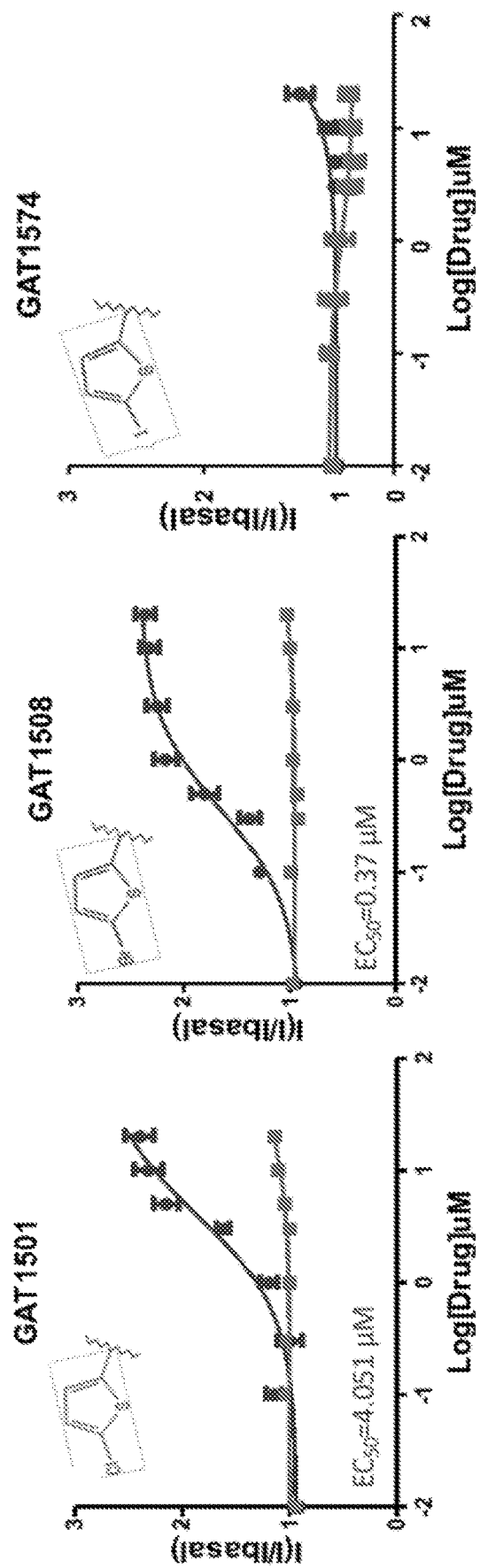

The thiophene ring with no substituents (GAT1506, FIG. 34B) lacked selectivity and was less potent than GAT1508 (FIG. 34E). The inventors then tested different halogens in order of varying size instead of bromine at position 5' of the thiophene ring. A fluorine-substituted thiophene, which occupies a smaller volume than bromine (GAT1575, FIG. 34C), was highly efficacious but much less potent than GAT1508 and less selective between GIRK1/2 and GIRK1/4 than GAT1508. Chlorine (GAT1501, FIG. 34D), still smaller than bromine, retained some selectivity (did not show activation of GIRK1/4 at concentrations less than 20 μM) but was also less potent than GAT1508 for GIRK1/2. Substituting the larger than bromine atom iodine at the 5' position (GAT1574, FIG. 34F), proved a poorer activator than the bromine analog for both GIRK1 heteromeric channels. Modification of the thiophene ring to thiazole (GAT1530) also displayed a lack of specificity. A methyl group substitution rather than a halogen (GAT1521, FIG. 34G), retained the specificity for brain over cardiac currents (perhaps even inhibiting the high basal cardiac currents in oocytes at higher concentrations) but with lower potency than GAT1508 for both GIRK1/2 and GIRK1/4. Substitution of bromine at positions other than the 5' of the thiophene ring (i.e., positions 3' GAT1570 or 4' GAT1502, FIGS. 34H-34I) resulted also in much poorer activators of both GIRK1 heteromeric channels.

Figures 34G, 34H, 34I:
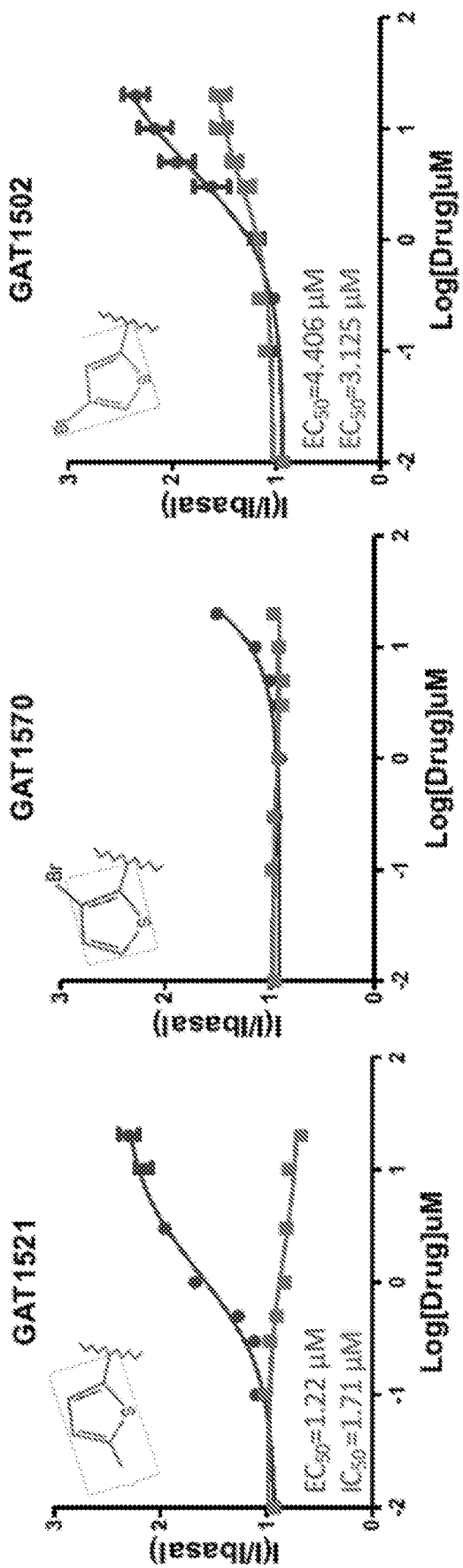
Figure 37A:
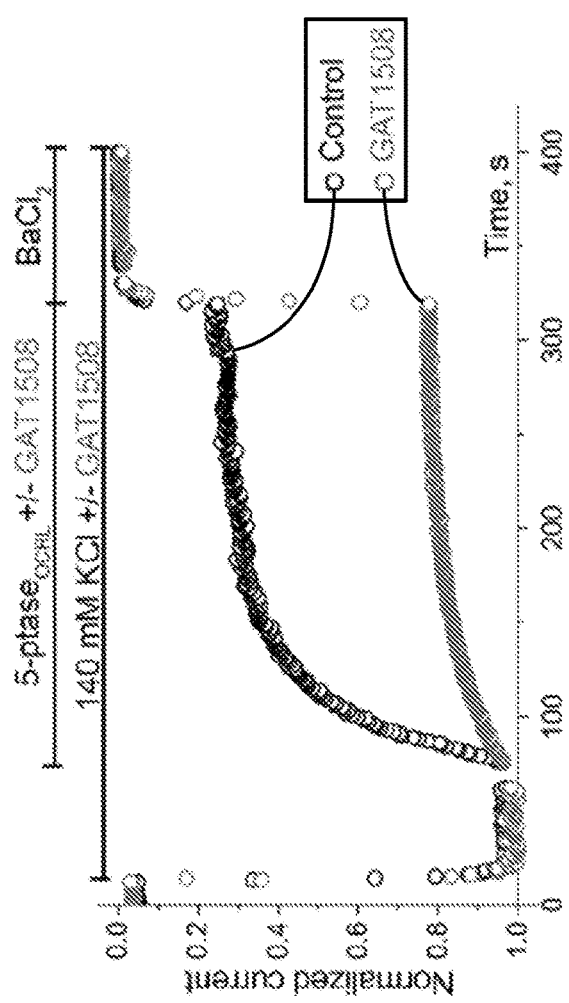
Figure 37B:
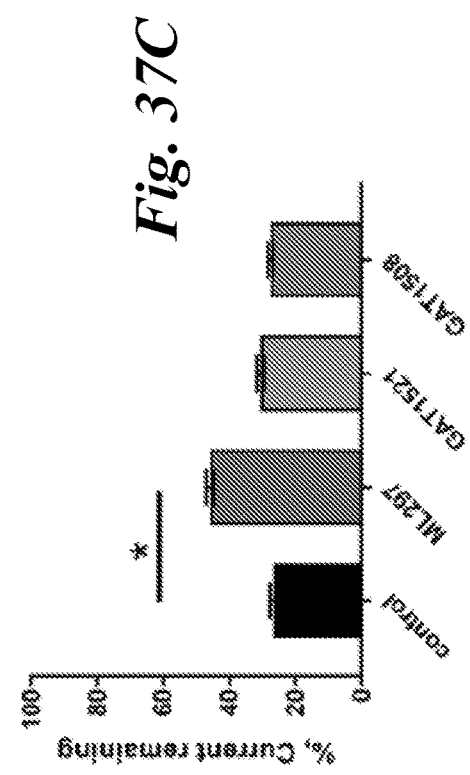
Figure 37C:
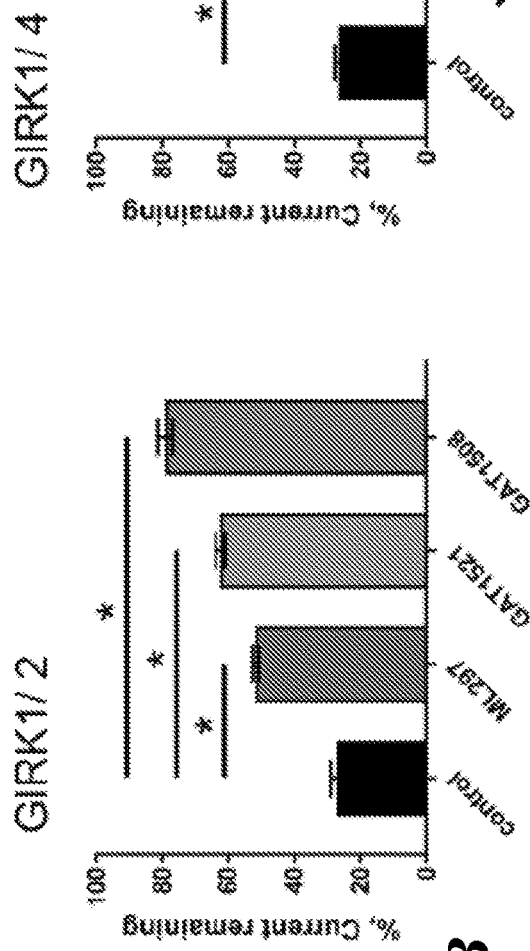

Recordings in FIGS. 34A-34I were conducted in *Xenopus* oocytes expressing GIRK1/2 wild-type (●) and GIRK1/4 wild-type (■). ML297 stimulated both brain and cardiac heteromeric channels, even though it was more effective on the brain channel. In FIG. 34A, the EC$_{50}$ of ML297 at GIRK1/2 was 0.34±0.12 μM and the E$_{MAX}$ was 2.87±0.11 (considered here to be 100%); at GIRK1/4 the EC$_{50}$ was 0.5±0.26 μM and E$_{MAX}$ was 1.60±0.07 (100%). Two selective compounds, GAT1508 and GAT1521, could induce the current increase only in the brain channel (FIGS. 34E, 34G). The EC$_{50}$ of GAT1508 at GIRK1/2 was 0.37±0.11 μM and the E$_{MAX}$ was 2.42±0.07 (76% relative to the ML297). The EC$_{50}$ of GAT1521 at GIRK1/2 was 1.22±0.08 μM and the E$_{MAX}$ was 2.36±0.06 (73% relative to ML297). Concentration-response curves are shown for example, (FIG. 34B) GAT1506 (unsubstituted thiophene ring), where the EC$_{50}$ at GIRK1/2 was 17.07±0.28 μM and the E$_{MAX}$ was 3.9±1.04 (155%); at GIRK1/4 the EC$_{50}$ was 7.02±0.24 μM and E$_{MAX}$ was 1.95±0.21 (157%). GAT1575 (fluoro substitution at position 5'), (FIG. 34C), where the EC$_{50}$ at GIRK1/2 was 9.39±0.12 μM and the E$_{MAX}$ was 4.92±0.49 (210%); at GIRK1/4 the EC$_{50}$ was 11.22±0.25 μM and E$_{MAX}$ was 2.16±0.32 (192%). GAT1501 (chloro substitution at position 5'), (FIG. 34D) where the EC$_{50}$ at GIRK1/2 was 4.05±0.14 μM and the E$_{MAX}$ was 2.79±0.18 (96%); at GIRK1/4 activation was negligible; (FIG. 34F) GAT1574 (iodo substitution at position 5') where activation of GIRK1/2 and GIRK1/4 was negligible; (FIG. 34H) GAT1570 (bromo substitution at position 3'), where activation of GIRK1/2 and GIRK1/4 was negligible; (FIG. 34I), GAT1502 (bromo substitution at position 4'), where the EC$_{50}$ at GIRK1/2 was 4.41±0.15 μM and the E$_{MAX}$ was 2.70±0.20 (91%); at GIRK1/4 the EC$_{50}$ was 3.13±0.24 μM and E$_{MAX}$ was 1.63±0.09 (104%). Data are mean±s.e.m for 24 oocytes (4 oocytes per frog from 6 different frogs).

Thus, highly selective and potent activation of the brain GIRK1/2 over the cardiac GIRK1/4 channels seems to require both substitution of the phenyl ring with a thiophene ring at site 1 of the ML297 compound as well as substitution in its 3' position with a bromine.

Figure 32:
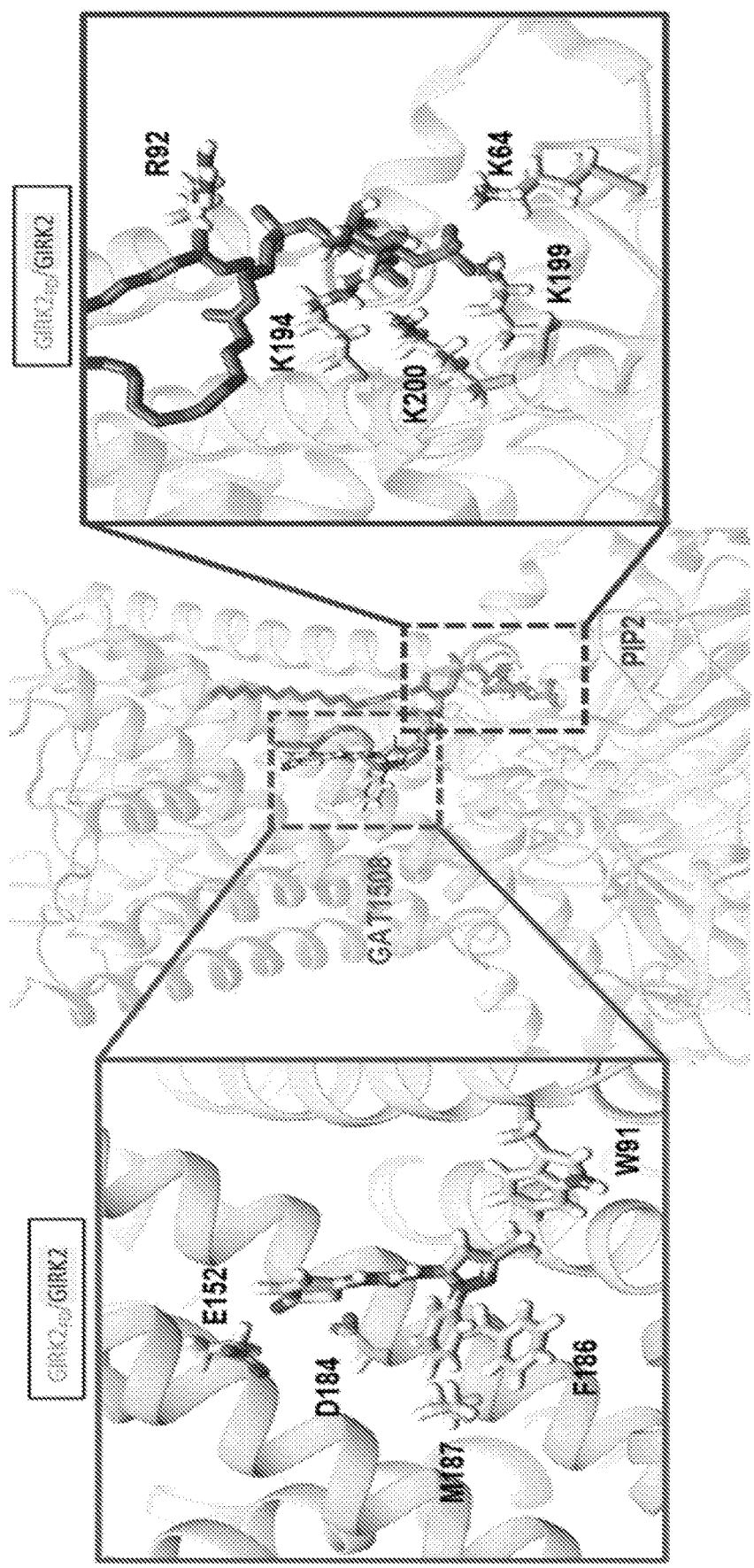
FIG. 32 shows a binding site for specific GAT compounds that opens brain-GIRK1 heteromeric channel gates. In the center of FIG. 32, a binding site of GAT1508 in the $GIRK2^{FD}$ subunit (FD or "GIRK1-like" subunits are shown in darker gray) and phosphatidylinositol-4,5-bisphosphate ($PIP_2$) bound to the adjacent $GIRK2^{WT}$ subunit (WT or nonligand-binding subunits are shown in lighter gray). On the left of FIG. 32, a zoom in on GAT1508 binding site reveals interactions of the compound with residues D184 and M187 in the $M2^{FD}$ helix, with E152 in the $M1^{FD}$ helix and π-π interactions with F186 in the $M2^{FD}$ and W91 in the $M1^{WT}$ helices. On the right of FIG. 32, a zoom in on $PIP_2$ interactions with the wild-type GIRK2 subunits illustrates coordination of Phosphate 1 (P1) of $PIP_2$ with R92, P4 with K64 and K199 and P5 with K194, K199, and K200.

The double GIRK2 mutant S148F, N184D (GIRK2$^{FD}$, also referred to as "GIRK1-like") mimics the contribution of GIRK1(F137, D173) in heteromers with wild-type GIRK2 (GIRK2/GIRK2$^{FD}$ or GIRK2/2$^{FD}$) subunits and endows the channel with sensitivity to ML297 activation. As previously shown both the S148F and N184D mutations in GIRK2 are needed to make it GIRK1-like and sufficient when co-expressed with GIRK2 (GIRK2/2$^{FD}$) to yield sensitivity to ML297 activation (Wydeven et al., 2014). These two residues are distant from each other, with F148 in the pore helix and unlikely to directly interact with ML297. Thus, our docking box for GAT compounds was set around D184 in the doubly mutated GIRK2 subunit (GIRK2$^{FD}$), an excellent template requiring a minor change from the experimentally determined X-ray structure (Whorton and MacKinnon, 2013) for docking studies and Molecular Dynamics (MD) simulations. When GAT compounds and ML297 were docked around N184D of the GIRK2$^{FD}$ in GIRK2/GIRK2$^{FD}$ (FIG. 32, center, left), they bound to a second proximal region next to the PIP$_2$ binding region of the non GIRK1-like subunit (FIG. 32, center, right) consistent with data suggesting ML297 action is dependent on intact PIP$_2$ levels. This region is localized between the M1 and M2 helices, above the slide or interfacial helix region and about 10~16 angstroms away from the PIP$_2$ head group. GAT1508 forms TT-TT interactions with aromatic residues in M1 and M2 as well as H-bonds with D184 (FIG. 32, left). The detailed interactions of the wild-type subunit with PIP$_2$ are shown (FIG. 32, right). GAT1521 (not shown) behaved similarly to GAT1508.

In order to assess whether the binding of GAT1508 at the predicted site has any effect on the conformation of a channel gate, the inventors monitored the distance of the cytosolic G-loop gate (Ca atoms of GIRK2-T317/GIRK4-T312) during a Molecular Dynamics (MD) simulation (FIGS. 33A-33B). At the beginning of either the GIRK2/2$^{FD}$ or GIRK4/4$^{FD}$ heteromeric channel simulation, and in the absence of ligands, the diameter of the G-loop gate was ~15 angstroms. By the end of the simulation it decreased to ~10 angstroms. In contrast, an increase of ~2 angstroms in the G-loop gate opening was observed in both heteromeric channels upon ML297 binding. Consistent with the experimental results, GAT1508 could only selectively keep the G-loop gate open in the GIRK2/2$^{FD}$ but not the GIRK4/4$^{FD}$ heteromeric channel.

Selective Binding of GAT1508 to Cardiac GIRK Channels.

Figure 15:
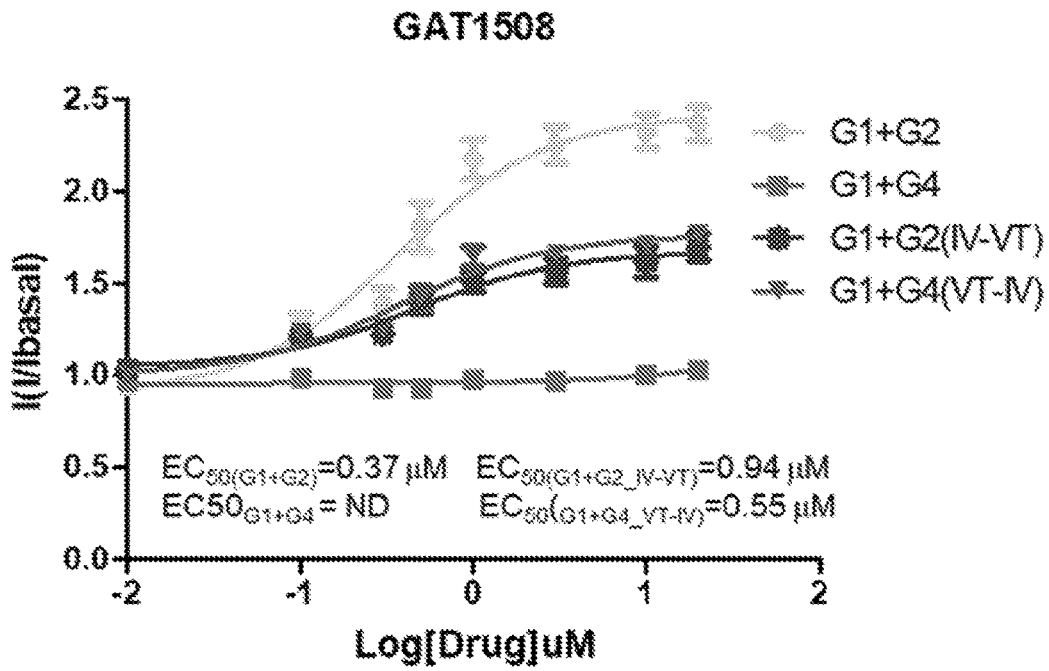
FIG. 15 shows concentration-response curves of GAT1508 in GIRK1/2 (●) and GIRK1/4 (■) wild-type or the double mutant channels GIRK1/2(IV-VT) (▲) or GIRK1/4(VT-IV) (▼). Data are means±s.e.m for 16 cells (4 oocytes×4 frogs) per concentration. GAT1508 stimulated brain (GIRK1/2) heteromeric channel currents with an EC$_{50}$ of 0.37±0.11 μM and an E$_{MAX}$ of 2.42±0.07 (considered here to be 100%). Double mutants in the GIRK2 wild-type subunits to corresponding GIRK4 residues significantly reduced the potency and efficacy of the GAT1508-induced selective currents with an EC$_{50}$ of 0.94±0.15 μM and an E$_{MAX}$ of 1.68±0.04 (72% of the control GIRK1/2). Double mutants in GIRK4 wild-type subunits to corresponding GIRK2 residues conferred stimulation of the heteromeric channel by GAT1508 with an EC$_{50}$ of 0.55±0.11 μM and an E$_{MAX}$ of 1.76±0.03 (75% of the control GIRK1/2).

The inventors next addressed how GAT1508 is able to specifically activate the GIRK2-containing rather than the GIRK4-containing heteromeric channels. To gain insight and answer this question, the inventors compared ML297, GAT1508, and GAT1521 interactions with GIRK2/2$^{FD}$ versus GIRK4/4$^{FD}$ in the course of 35 ns Molecular Dynamics (MD) simulations. Movement in the binding of the ML297 and GAT compounds in the FD subunits of heteromeric GIRK channels showed significant differences during the MD simulation. The contacts between the ML297 or GAT1508 with each of the two transmembrane helices of GIRK2 or GIRK4 heteromeric channels (M1 and M2) were calculated during the 20-35 ns period of the MD run (FIG. 6). For both heteromeric GIRK channels, ML297 induced further channel activation and showed consistent binding modes with greater contacts with the M1 helix than the M2 helix. Although GAT1508 also showed a contact pattern similar to ML297 in the GIRK2/2$^{FD}$ heteromeric channel (FIG. 6, FIG. 7A), in the GIRK4/4$^{FD}$ heteromeric channel, where it lost its stimulatory effect, it made greater contacts with the M2 helix (FIG. 6, FIG. 7B). As shown in the snapshots of GAT1508 binding in the two heteromeric channels, GAT1508 flips in the GIRK4/GIRK4$^{FD}$ channel, such that the thiophene moiety points toward the M2 helix of the GIRK4$^{FD}$ subunit and forms a hydrogen bond with T94 (with the bromine at position 5' of the thiophene ring) as well as hydrophobic interaction with V92 in the M1 helix of GIRK4 wild-type subunit. This re-orientation of GAT1508 anchored the selective compound around the M2 helix of the FD-containing subunit. In contrast in the GIRK2/2$^{FD}$ heteromer, GAT1508 that interacted between the M1-M2 helices and predominantly with the M1-helix of the GIRK2$^{FD}$ subunit, never established the above interactions with the corresponding residues V97/I99 of the wild-type GIRK2 subunits (FIG. 15). Similar results were also obtained from the MD simulation of the GAT1521 compound.

Figure 16:
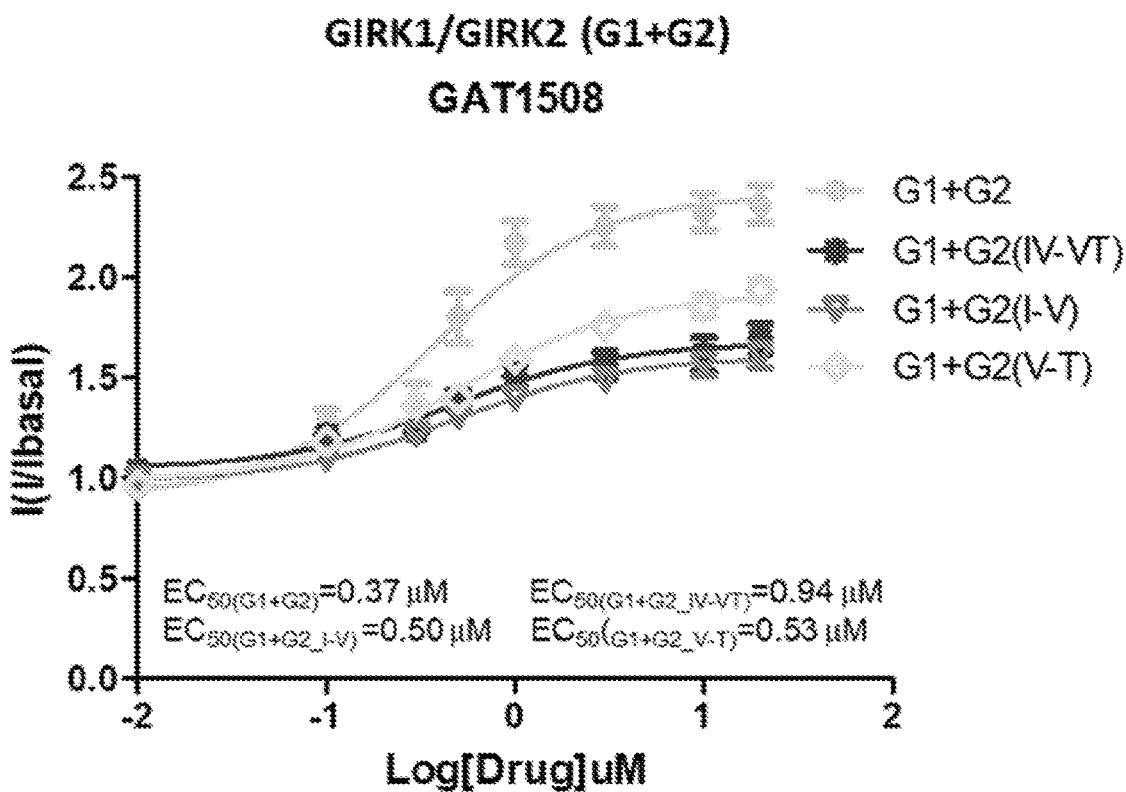
FIG. 16 shows concentration-response experiments for GAT1508 that were performed in GIRK1/2 wild-type, single (GIRK2-I97V, GIRK2-V99T) and double mutants (GIRK1/2-dm) expressing cells, using TEVC recording. In general, mutants decreased the GAT1508 ability to activate GIRK2-containing heteromers, while they increased GAT1508-induced activation for GIRK4-containing heteromers of single and double mutants (FIGS. 15, 17).
Figure 17:
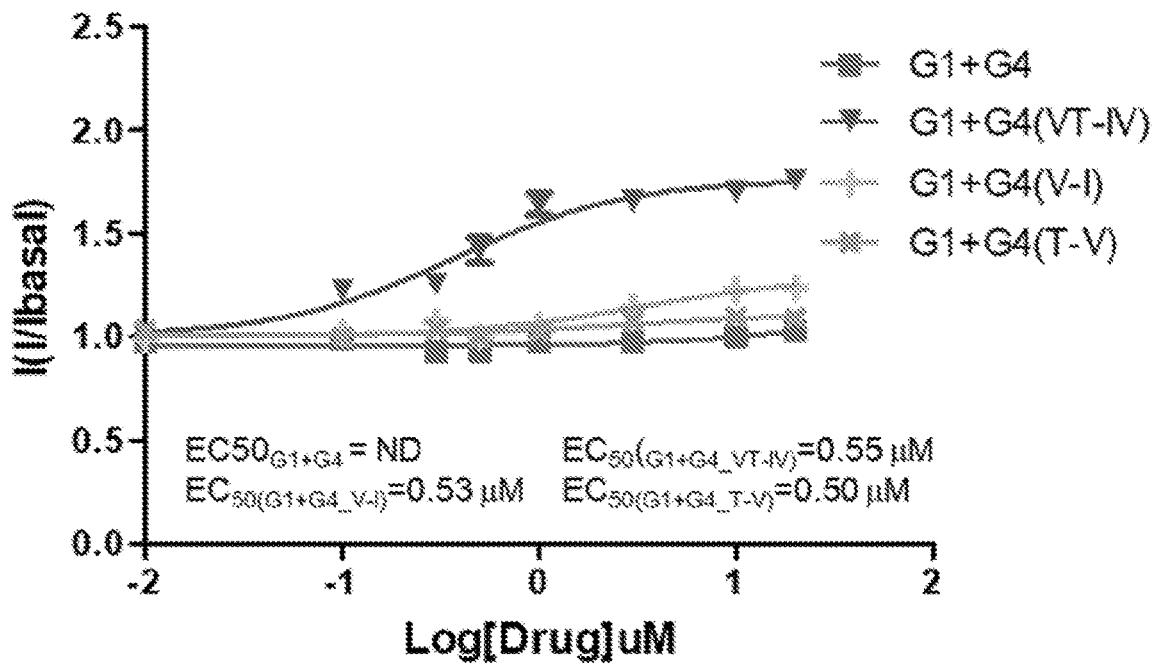
FIG. 17 shows concentration-response experiments for GAT1508 that were performed in GIRK1/4 wild-type, single (GIRK4-V92I, GIRK4-T94V) and double mutants (GIRK1/4-dm) expressing cells, using TEVC recording. In general, mutants decreased the GAT1508 ability to activate GIRK2-containing heteromers, while they increased GAT1508-induced activation for GIRK4-containing heteromers of single and double mutants (FIGS. 15-16).
Figure 18:
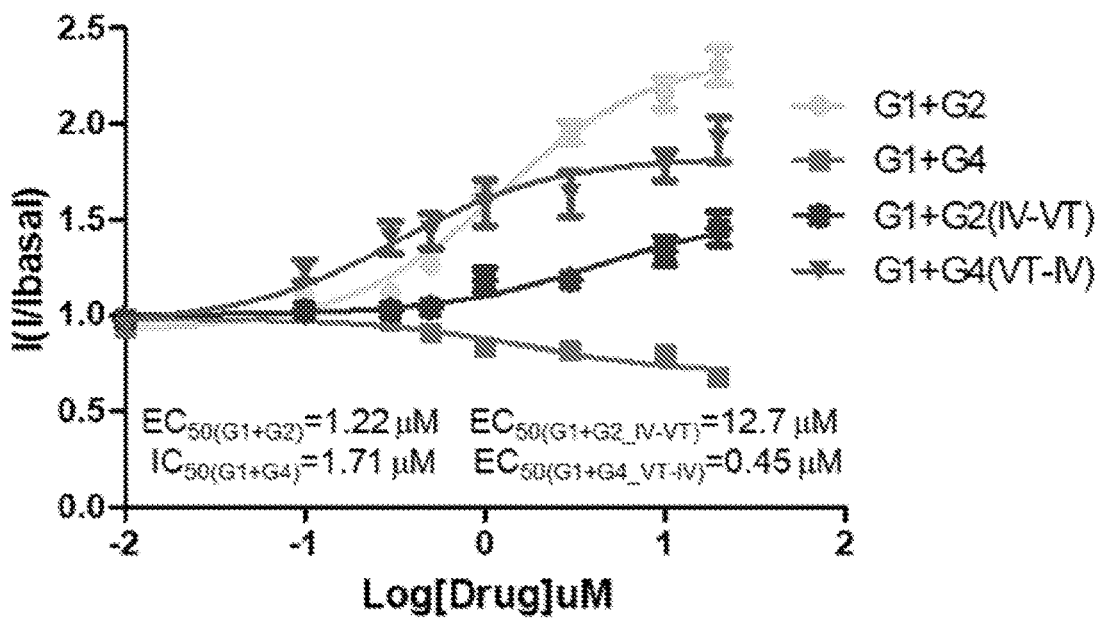
FIG. 18 shows concentration-response experiments for GAT1521 that were performed in GIRK1/2 and GIRK1/4 wild-type and double mutants (GIRK2-I97V-V99T, GIRK4-V92I-T94V) in expressing cells, using TEVC recording.

To test these computational predictions, the inventors mutated each or both of the two M1 key wild-type GIRK4 subunit residues to the corresponding GIRK2 residues (GIRK4-V92I, GIRK4-T94V, GIRK4-V92I/T94V or GIRK4-dm) and vice-versa the GIRK2 residues to the corresponding GIRK4 ones (GIRK2-I97V, GIRK2-V99T, GIRK2-I97VA/99T or GIRK2-dm) (FIG. 35). Concentration-response experiments for GAT1508 and GAT1521 were performed in GIRK1/2 and GIRK1/4 wild-type, single (GIRK2-I97V, GIRK2-V99T, GIRK4-V92I, GIRK4-T94V) and double mutants (GIRK1/2-dm and GIRK1/4-dm) expressing cells, using two-electrode voltage clamp (TEVC) recording. In general, mutants decreased the GAT1508 ability to activate GIRK2-containing heteromers, while they increased GAT1508-induced activation for GIRK4-containing heteromers of single (FIGS. 16-17) and double (FIG. 18) mutants.

Figure 10:
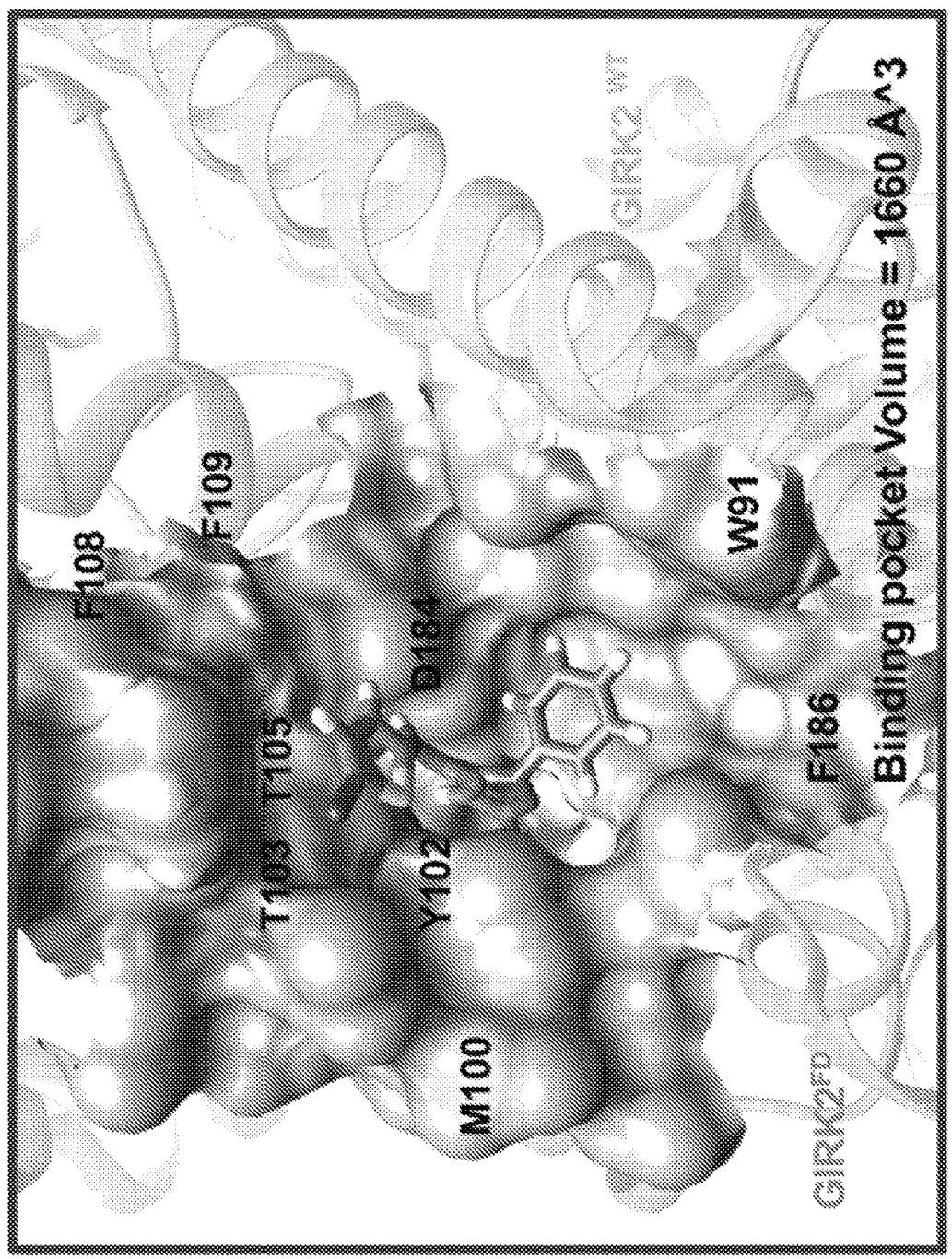
FIG. 10 shows the binding site surface with GAT1508 between the M1 and M2 helical regions in GIRK2/2$^{FD}$. The binding pocket volume=1660 cubic angstroms.
Figure 11:
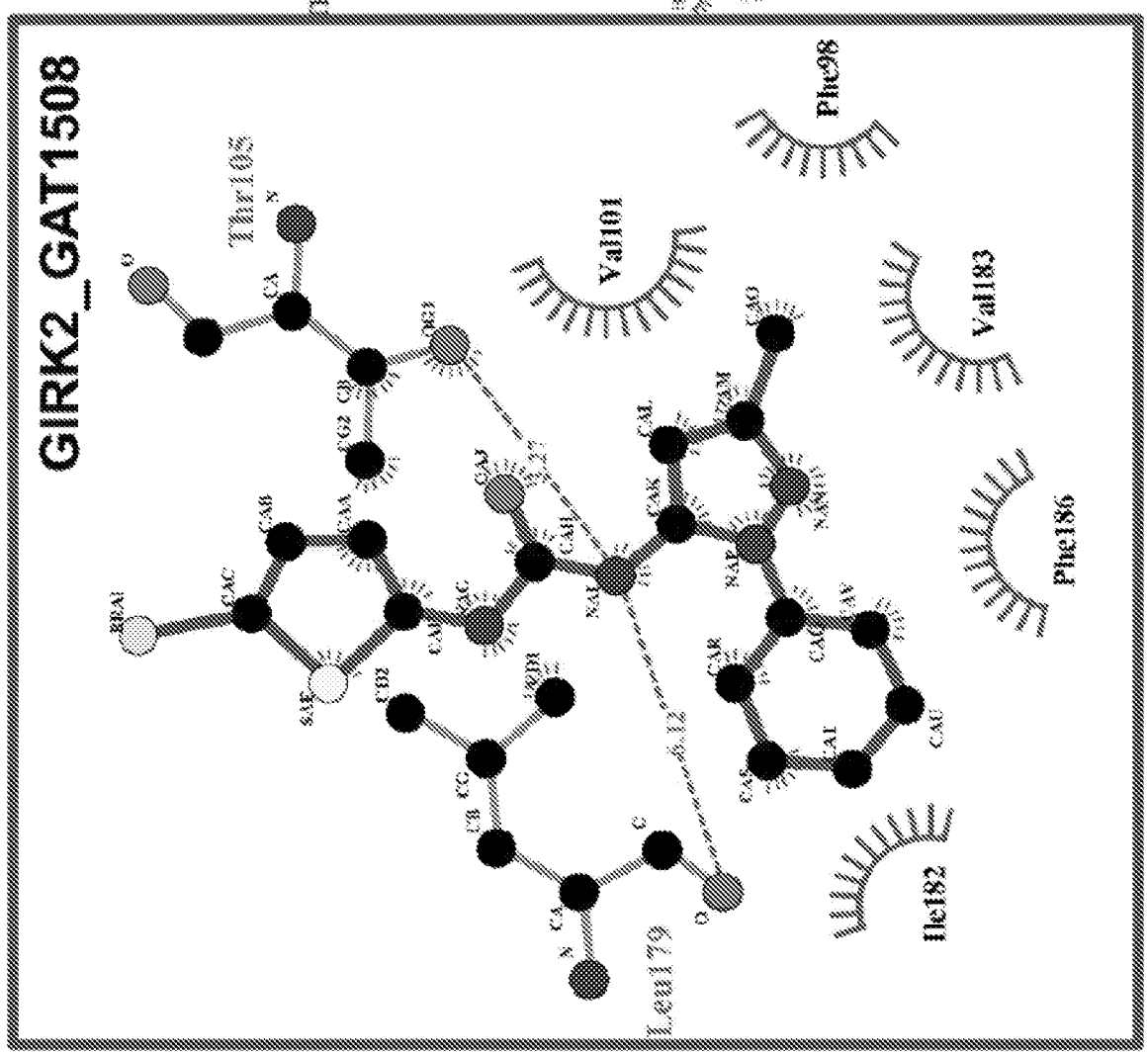
FIG. 11 shows a LIGPLOT diagram of GAT1508 interactions with its immediate environment in GIRK2/2$^{FD}$. LIGPLOT is a software program for generating schematic diagrams of protein-ligand interactions. Hydrogen bonds are dashed lines with indicated distances in angstroms. Residues in hydrophobic contact with GAT1508 are represented by semicircles with radiating spokes.

The volume of the binding pocket for GAT1508 and the interacting residues are shown for GIRK4/4$^{FD}$ (FIG. 8, FIG. 9) and GIRK2/2$^{FD}$ (FIG. 10, FIG. 11). GIRK2 residues I97 and V99 differ from the corresponding GIRK4 residues V92 and T94 in an otherwise highly conserved region between these two channel subunits (FIG. 35). Single (FIGS. 36A-36B) and double (FIG. 15) mutations demonstrated that these residue differences accounted in part for the selectivity of GAT1508 for GIRK1/2 over GIRK1/4, decreasing or increasing the efficacy and potency of the two wild-type heteromers, respectively.

FIGS. 36A-36B show that GAT1508 stimulated brain (GIRK1/2) heteromeric channel currents with an EC$_{50}$ of 0.37±0.11 µM and an E$_{MAX}$ of 2.36±0.23 (considered here to be 100%). Single mutants in the GIRK2 wild-type subunits to corresponding GIRK4 residues significantly reduced the potency and efficacy of the GAT1508-induced selective currents: GIRK1/2(V-T) with an EC$_{50}$ of 0.53±0.07 µM and an E$_{MAX}$ of 1.92±0.03 (65% of the control GIRK1/2); GIRK1/2(I-V) with an EC$_{50}$ of 0.50±0.11 µM and an E$_{MAX}$ of 1.61±0.03 (42% of the control GIRK1/2). Single mutants in GIRK4 wild-type subunits to corresponding GIRK2 residues conferred stimulation of the heteromeric channel by GAT1508: GIRK1/4(T-V) with an EC$_{50}$ of 0.50±0.47 µM and an E$_{MAX}$ of 1.12±0.03 (7% of the control GIRK1/2); GIRK1/4(V-I) with an EC$_{50}$ of 0.53±0.15 µM and an E$_{MAX}$ of 1.29±0.03 (11% of the control GIRK1/2).

These experimental results provide validation for the computational predictions that the selective GAT compounds re-oriented their binding in GIRK4-containing heteromers to interact predominantly with the M2 helix of the GIRK4$^{FD}$ subunit, thus enabling them to form interactions with the adjacent GIRK4 wild-type M1 subunit residues V92 and T94. These interactions that do not take place in GIRK2-containing channels are somehow interfering with stimulation of the activity of the cardiac channels, accounting to a large extent for the specific activation of the brain channel isoform by GAT1508 and GAT1521.

Example 3. Direct or Allosteric Activators of GIRK1/2 in the Basolateral Amygdala (BLA)

Figure 24A:
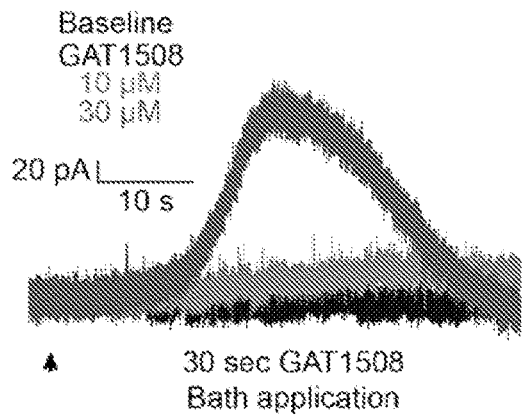
FIGS. 24A-24B show that GAT1508 demonstrates GIRK agonist and GIRK positive allosteric modulator activity in the basolateral amygdala (BLA).
Figure 24B:
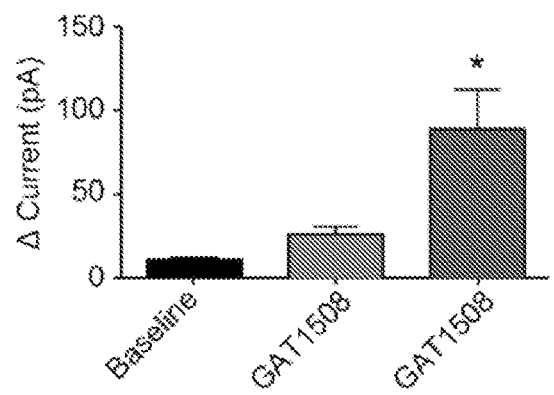
Figure 25A:
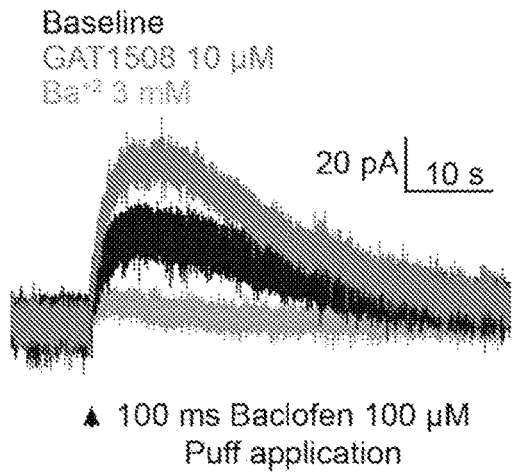
FIG. 25A shows representative current responses from BLA neurons in response to 100 ms, 100 μM, baclofen administered via pressure micropipette, compared with baseline and with 10 μM GAT1508. Responses to each condition were recorded from the same cells.
Figure 25B:
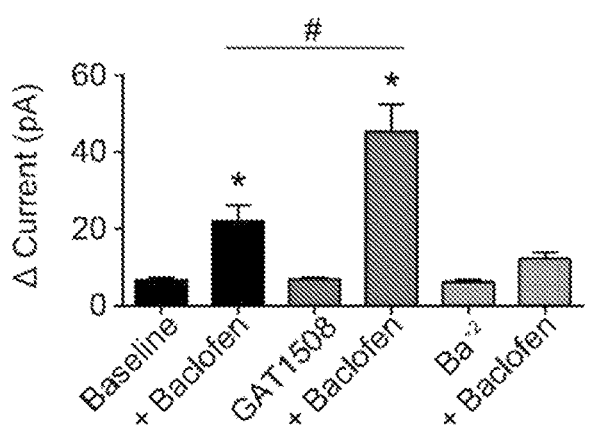
FIG. 25B shows summary data depicting significant current response to baclofen and significant potentiation of baclofen response by GAT1508 that was blocked by $Ba^{2+}$. Symbols denote statistical significance by one-way ANOVA and Tukey's post-hoc, *$p<0.05$ versus all other conditions, #$p<0.05$ compares baclofen responses before and during GAT1508 treatment, n=9 cells.

The inventors employed whole-cell patch-clamp recording in acute brain slices to examine the effect of GAT1508. The inventors utilized brain slices that included the basolateral amygdala (BLA), a limbic structure that has been extensively described to coordinate the acquisition and expression of fear memories. In the rat amygdala, GIRK mRNA expression reveals abundance of GIRK1, GIRK2, and GIRK3, but not GIRK4 transcripts. The inventors observed that perfusion of 10 µM GAT1508 did not produce responses in recordings of BLA neurons at −50 mV, but 30 µM GAT1508 produced significant outward current (ligand effect $F_{2,16}=10.1$, $p=0.0013$, ANOVA, FIGS. 24A-24B). These data further support that GAT1508 functions as a GIRK1/2 activator. Next, the inventors examined the response of BLA neurons to baclofen, a GABA$_B$-receptor agonist that induces GIRK-mediated potassium currents. Compared to baseline, a 100 ms puff of 100 µM baclofen via a glass electrode tip induced a significant outward current (Tukey's posthoc test $p<0.05$, FIGS. 25A-25B, black trace and bars). In the same cells, 10 min perfusion of 10 µM GAT1508 significantly potentiated baclofen-induced current without affecting baseline currents recorded prior to baclofen application (treatment effect $F_{5,40}=25.8$, $p<0.0001$, ANOVA, FIGS. 25A-25B, GAT1508 trace, GAT1508 and +Baclofen bars). Lastly, antagonism of GIRK currents by 3 mM Ba$^{2+}$ blocked significant current-responses (FIGS. 25A-25B, gray trace and bars) suggesting that the baclofen response and the GAT1508 potentiation of the baclofen response are mediated by Ba$^{2+}$-sensitive GIRK activity. GAT1508-mediated enhancement of GIRK currents at 10 µM, a concentration that does not produce agonist activity, suggests that the compound functions synergistically with G protein activation mechanisms, reminiscent of the action of a positive allosteric modulator (PAM). Thus, GAT1508 activates GIRK1/2 channels and at sub-activating concentrations potentiates baclofen-induced GIRK activation in basolateral amygdala brain slices.

Example 4. Efficacy in Facilitating Fear Extinction in a Rodent Conditioned Fear Paradigm Slice electrophysiology data of the inventors suggested that as an agonist and a PAM, GAT1508 increases GIRK-mediated inhibitory tone in the BLA. Because the BLA together with the central nucleus of the amygdala are essential structures in the neurocircuitry underlying fear conditioning, the inventors tested if systemic treatment with different concentrations of GAT1508, GAT1521, and ML297 modulates fear memories in a Pavlovian conditioning fear paradigm.

The acquisition, expression, extinction and recall of fear memories were assessed in a 4-day learning paradigm (modified from Johnson, P. L., et al., Pharmacological depletion of serotonin in the basolateral amygdala complex reduces anxiety and disrupts fear conditioning, Pharmacol Biochem Behav, 2015. 138: p. 174-9). Rats were habituated to the sound attenuating fear conditioning chamber on day 1 (Kinder Scientific, Poway, Calif.) for 10 min. For all experiments, the chamber was cleaned between animals. On day 2 acquisition of fear occurred where the rats were placed back into the chamber and after a 120 s acclimation period received 5 pairings (120 s inter-trial interval) of the conditioned stimulus (CS; 20 s, 80 dB) followed immediately by the unconditioned shock stimulus (US; 500 ms, 0.8 mA foot shock). On day 3 conditioned stimulus (CS) consolidation was assessed by placing the rats back into the chamber with a 120 s acclimation period followed by 5 presentations of the CS only (20 s, 80 dB) separated by 120 s. On day 4 extinction was assessed which consisted of the 120 s acclimation period followed by 20 trials of the CS (20 s, 80 dB) separated by 120 s intervals. On day 5, all animals were assessed for the recall. Animals were placed in the chamber and were presented with 5 tones. The same experimenter handled the rats during all sessions and was blinded to the phenotype. All trials were digitally video-recorded. Freezing behavior (no visible signs of movement) was scored by a blind scorer during the sound presentation and converted to percentage of total time.

The Selective GAT Compounds are Effective in Fear Extinction Paradigms

Figure 62B:
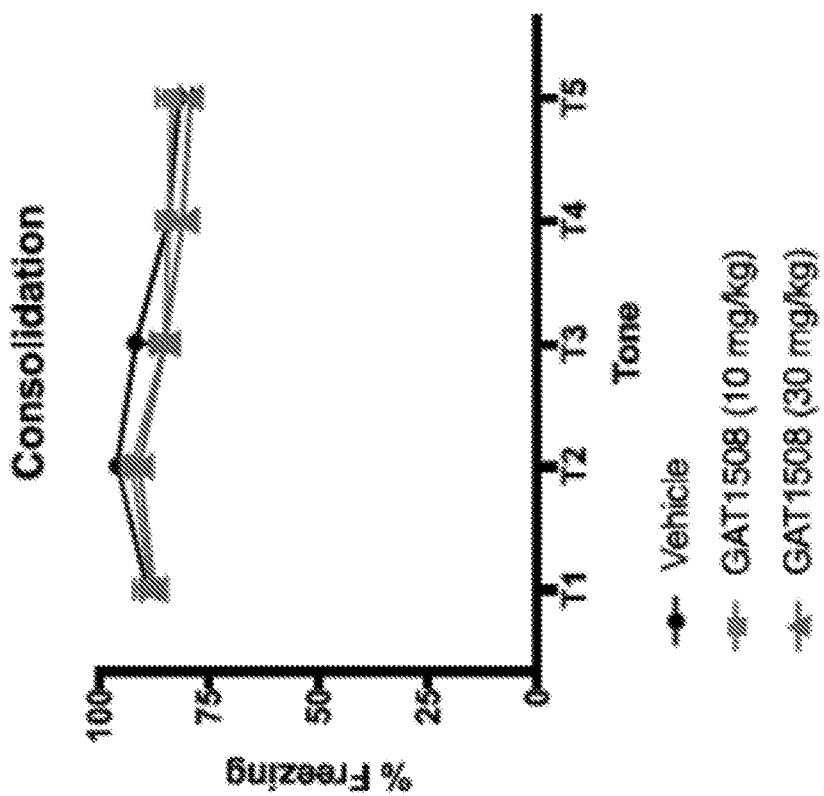
FIGS. 62A-62E show fear acquisition, consolidation, extinction, and recall tests with GAT1508. GAT1508 at 10 mg/kg showed no significant effects on either acquisition or consolidation (FIGS. 62A-62B), while at 30 mg/kg in some of the early pairings significant reductions in fear acquisition could be seen (FIG. 62A). In fear extinction follow-up experiments, GAT1508 gave more efficient extinction of the freezing behavior, particularly when administered at the higher concentrations.
Figure 62A:
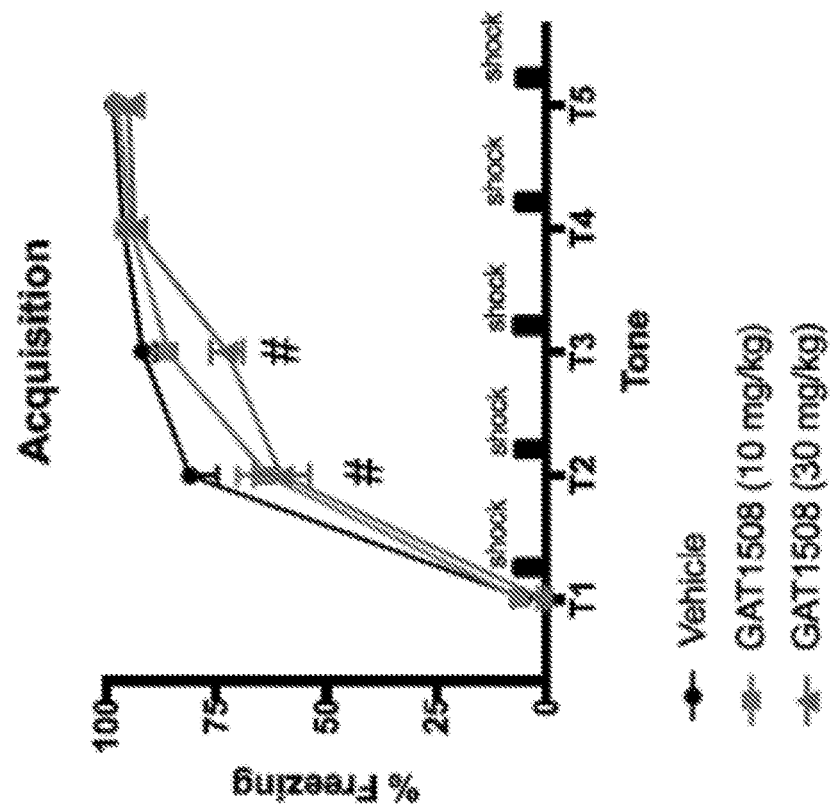
Figure 62D:
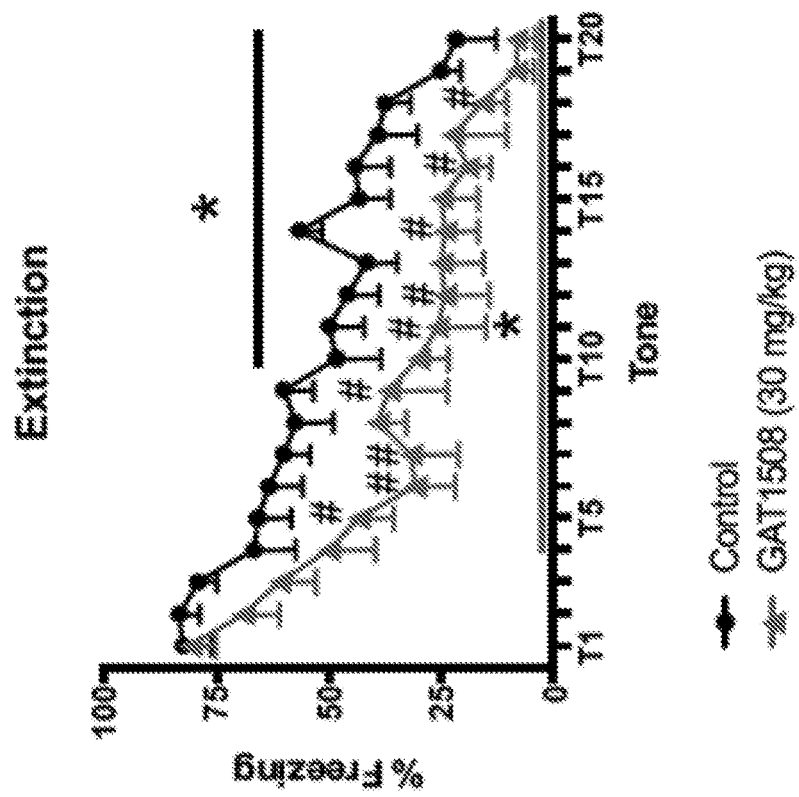
Figure 62C:
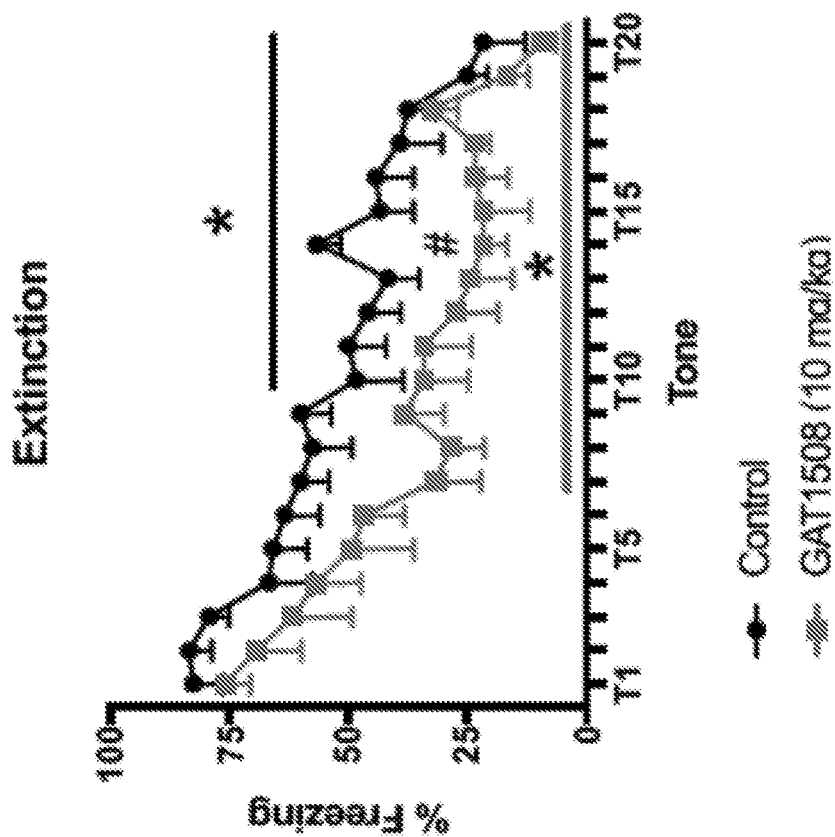
Figure 62E:
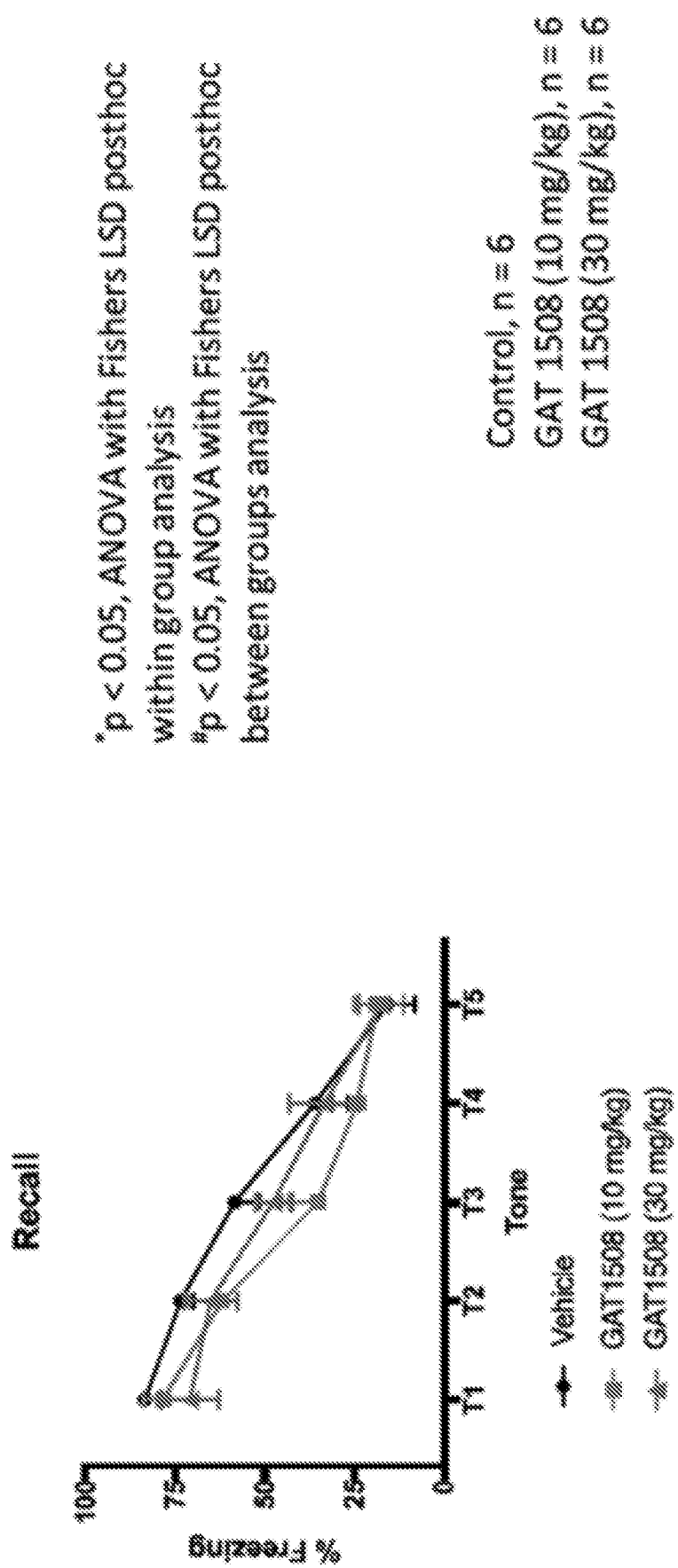
Figure 63B:
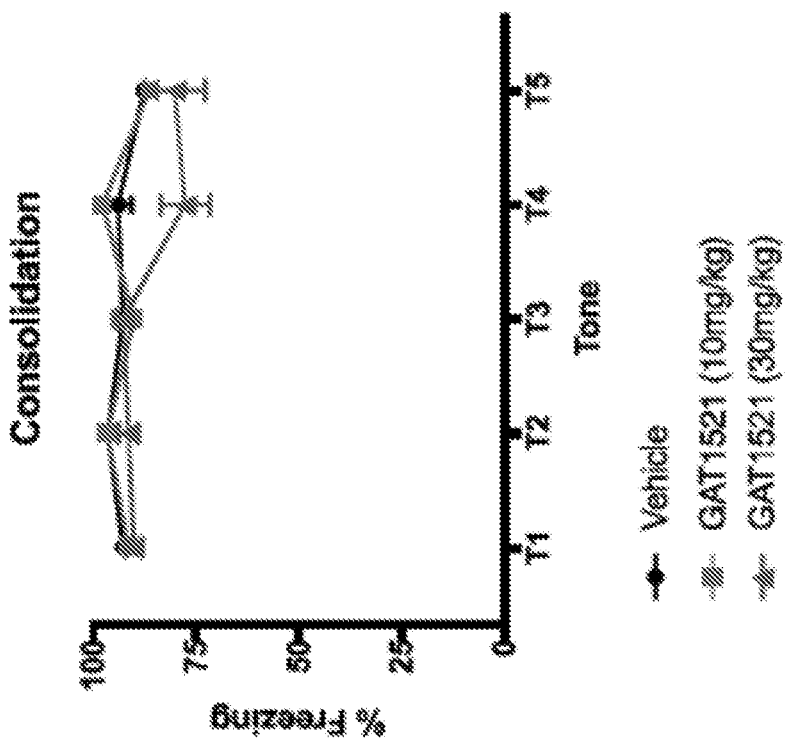
FIGS. 63A-63E show fear acquisition, consolidation, extinction, and recall tests with GAT1521. Results were similar to GAT1508 (FIGS. 62A-62E) although the effects were less significant.
Figure 63A:
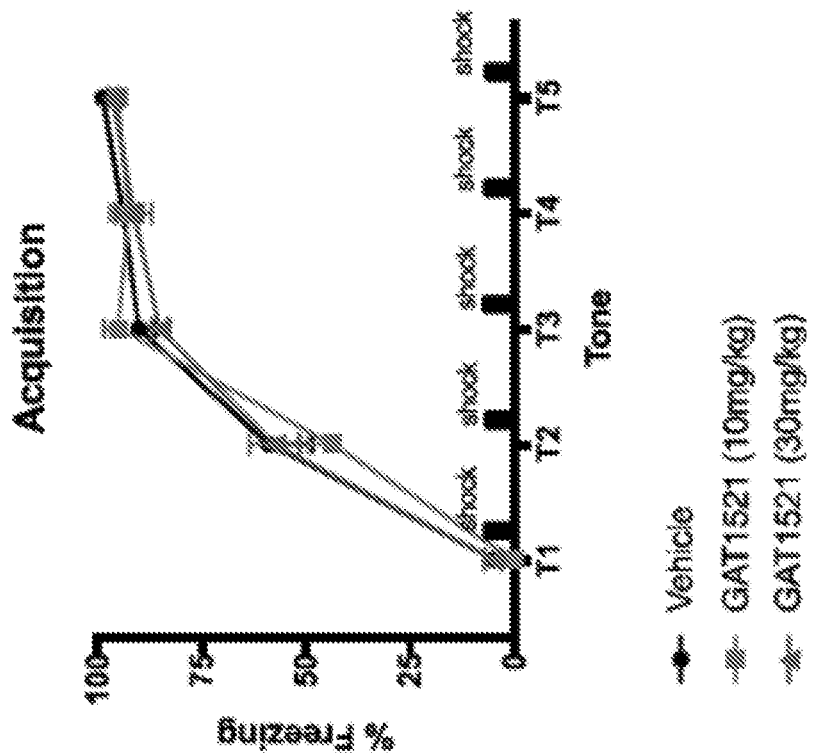
Figure 63D:
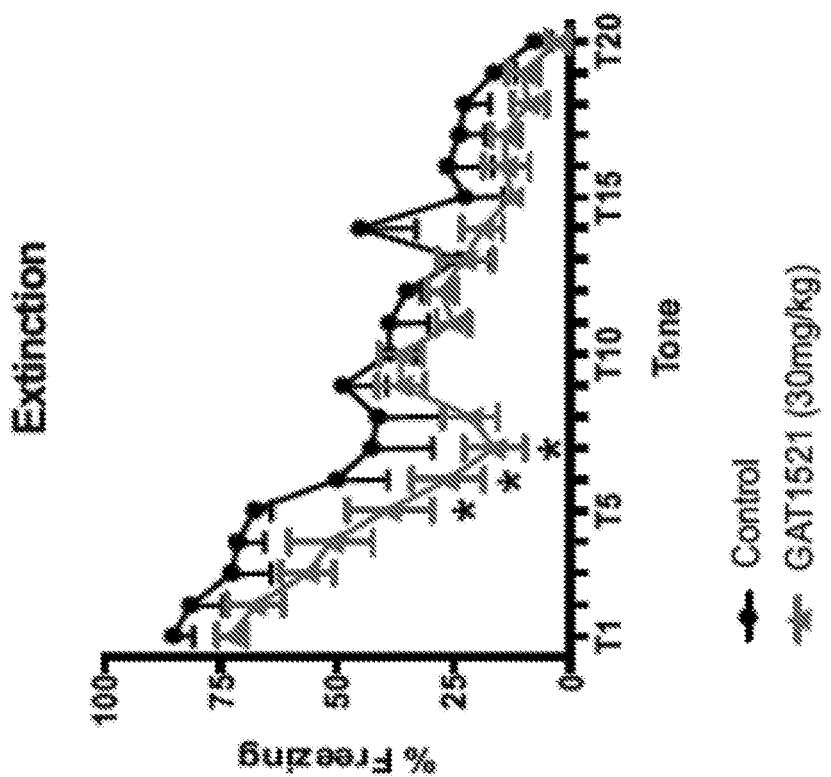
Figure 63C:
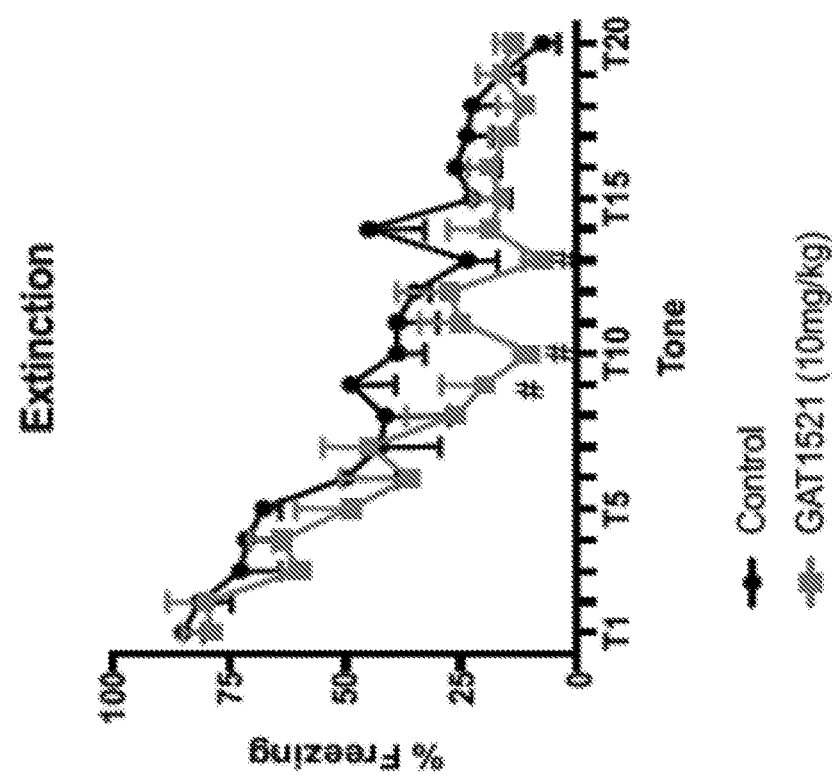
Figure 63E:
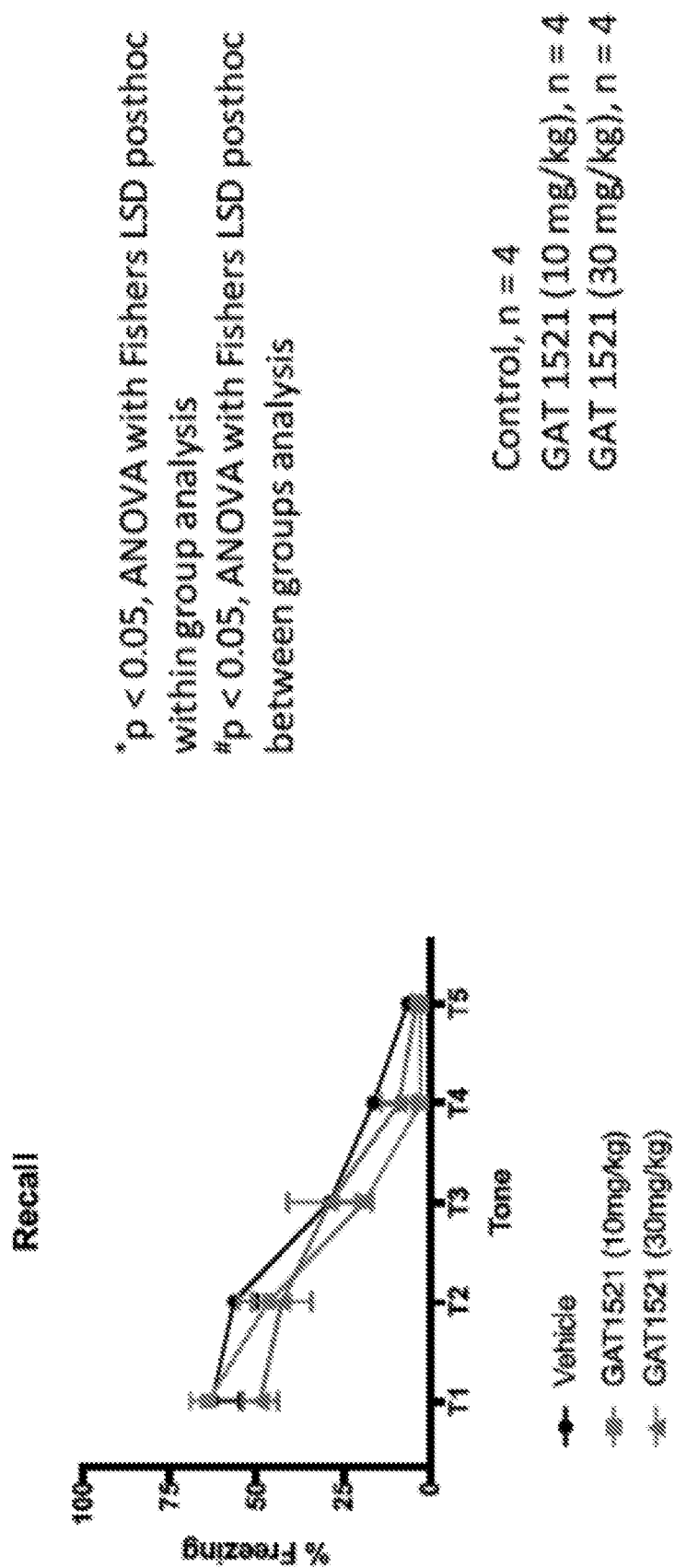

The inventors proceeded to test the two GAT compounds in rodent models of post-traumatic stress disorder (PTSD). Fear was induced by 5 pairings of a foot-shock stimulus with a tone (T1-T5) and was manifested as freezing behavior by rats that acquired the full freezing behavior within 5 paired stimuli (FIG. 62A). 24 hours following fear acquisition, the behavior showed full consolidation upon presentation of 5 unpaired stimuli (tone without shock) (FIG. 62B). GAT1508 at 10 mg/kg showed no significant effects on either acquisition or consolidation, while at 30 mg/kg in some of the early pairings significant reductions in fear acquisition could be seen. In fear extinction follow-up experiments, GAT1508 gave more efficient extinction of the freezing behavior, particularly when administered at the higher concentrations (FIGS. 62C-62D). No significant changes were seen on recall experiments of the freezing behavior upon administration of GAT1508 (FIG. 62E). These results show GAT1508 to be highly effective in extinguishing fear in rodent models of classical fear conditioning. Similar results were obtained with GAT1521 (FIGS. 63A-63E), although the effects were not as significant as those seen with GAT1508.

Figure 26:
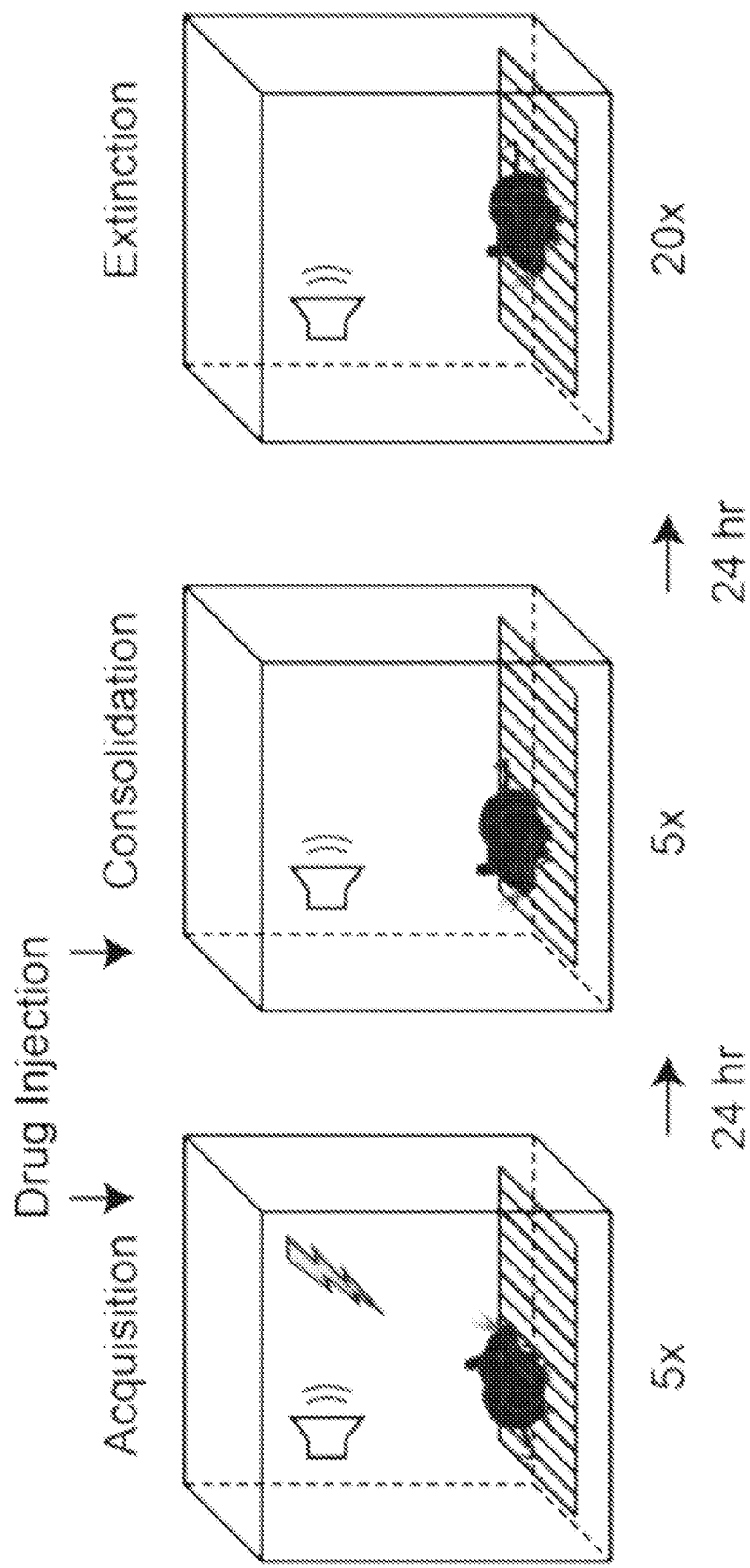
FIG. 26 shows a schematic diagram of the cue-induced fear conditioning procedure.
Figure 27:
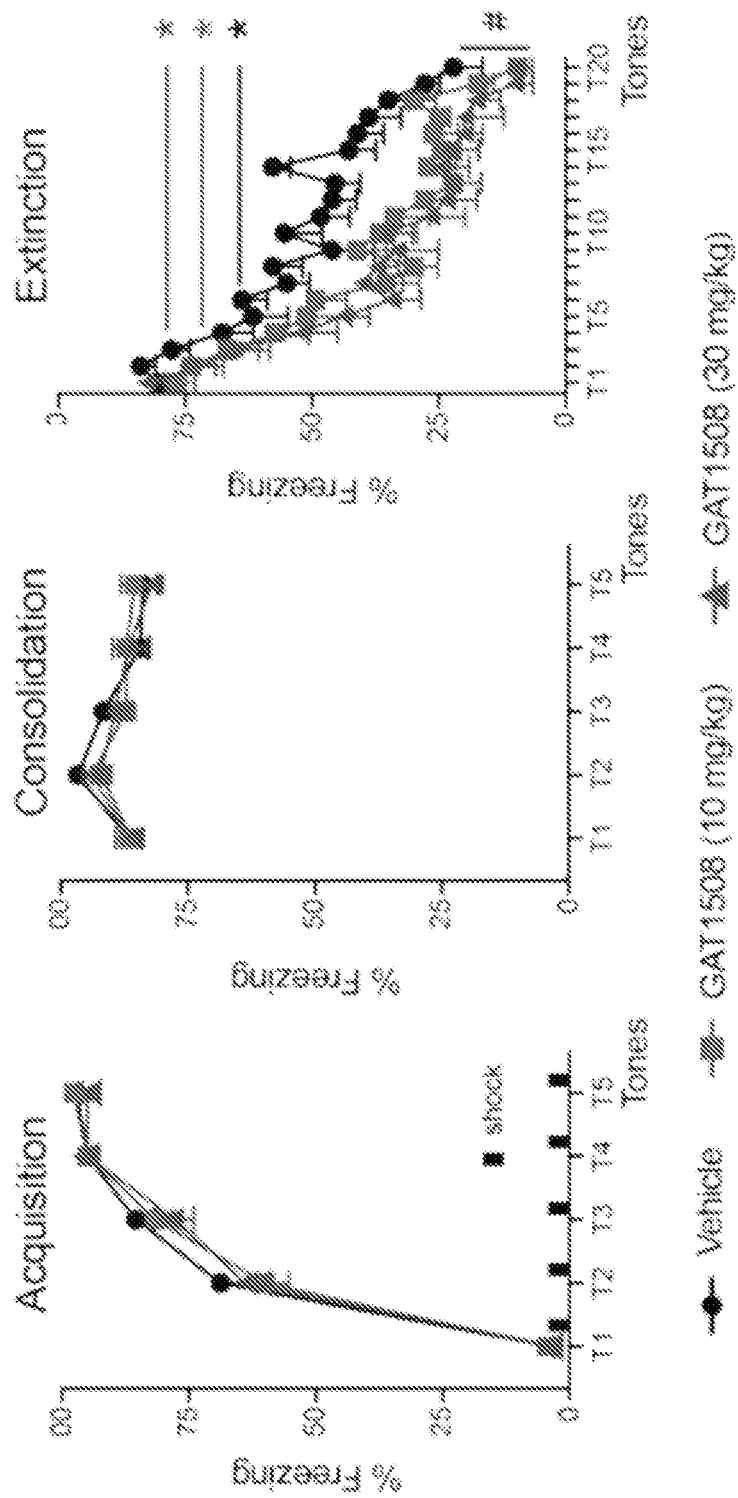
FIG. 27 shows effects of GAT1508 using cue-induced fear conditioning procedure (FIG. 26). All groups of animals that had tone/shock pairings showed normal cue-induced fear acquisition. Animals were injected with vehicle (●), or GAT1508 at 10 mg/kg (■), or 30 mg/kg (▲). Pretreatment with GAT1508 had no effects on consolidation of fear memories. Animals injected with either 10 mg/kg or 30 mg/kg of GAT1508 showed significantly faster fear extinction compared to vehicle control rats. *$p<0.05$, ANOVA with Tukey's posthoc within group analysis. #$p<0.05$, ANOVA with Sidak's posthoc between groups analysis, n=9 in all groups.

Rats treated with either GAT1508 (10 mg/kg or 30 mg/kg) or vehicle immediately after acquisition and 30 min prior to consolidation of fear memories (FIG. 26), showed normal acquisition (tone effect, $F_{4,96}=576.4$, $p<0.0001$, FIG. 27, left) and consolidation of fear memories (tone effect, $F_{4,96}=8.1$, $p<0.0001$, FIG. 27, center). Additionally, all groups demonstrated significant extinction of fear memories, but animals treated with GAT1508 extinguished fear memories much faster than animals from vehicle group (tone effect $F_{19,456}=41.9$, $p<0.0001$, treatment effect $F_{2,24}=9.4$, $p=0.001$, no interaction, FIG. 27, right). Dunnett's posthoc within each group test showed significant reduction of freezing in the GAT1508 group by tone 4, whereas animals from the control group did not show significant reduction of freezing until tone 7 (FIG. 27, right). Moreover, Sidak's between groups posthoc analysis confirmed significant differences between vehicle and GAT1508-treated groups ($p=0.008$ 10 mg/kg GAT1508, $p=0.001$ 30 mg/kg GAT1508, FIG. 27, right). Therefore, the inventors conclude that systemic treatment with GAT1508 enhances extinction of fear memories and selective activation of GIRK1/2 channels facilitates fear extinction.

Figure 28:
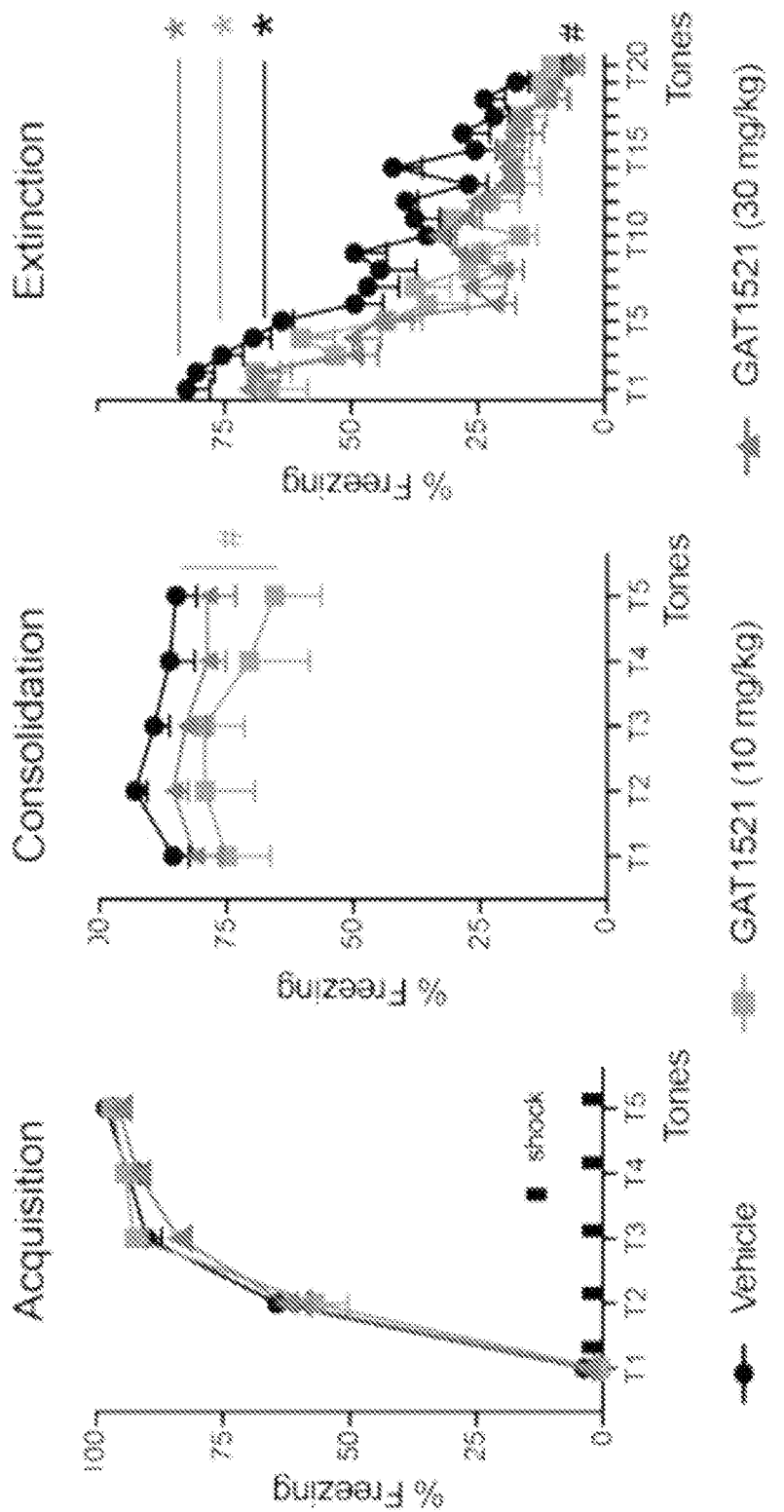
FIG. 28 shows effects of GAT1521 using cue-induced fear conditioning procedure (FIG. 26). All groups of animals that had tone/shock pairings showed normal cue-induced fear acquisition. Animals were injected with vehicle (●), or GAT1521 at 10 mg/kg (■) or 30 mg/kg (▲). Pretreatment with GAT1521 showed significant effects on consolidation of fear memories (treatment effect, $F_{2,105}=5.8$, $p=0.004$). Animals injected with either 10 mg/kg or 30 mg/kg of GAT1521 showed significantly faster fear extinction compared to vehicle control rats. *$p<0.05$, ANOVA with Tukey's posthoc within group analysis. #$p<0.05$, ANOVA with Sidak's posthoc between groups analysis, n=9 in all groups.

Next, the inventors also tested our second selective GIRK agonist GAT1521 in the fear conditioning paradigm. No differences in fear acquisition between GAT1521-treated and vehicle groups were observed (treatment effect, p=0.54, tone effect $F_{4,84}$=513.3, p<0.001, FIG. 28, left). Interestingly, post-training treatment with GAT1521 also affected consolidation of fear memories (treatment effect, $F_{2,105}$=5.8, p=0.004, FIG. 28, center). Similar to GAT1508, i.p. (intraperitoneal) injections of GAT1521 (after acquisition and 30 min prior consolidation), also significantly reduced overall freezing during extinction (tone effect, $F_{19,399}$=52.2, p<0.0001, treatment effect $F_{2,21}$=14.3, p=0.0001, FIG. 28, right) compared to the control group. Dunnett's posthoc within each group test revealed significantly lower freezing time in the 30 mg/kg GAT1521-treated groups by tone 3, whereas rats from the vehicle group showed significantly lower freezing only by tone 5 (FIG. 28, right). Sidak's between groups posthoc analysis also confirmed significant differences between vehicle and GAT1521-treated groups (p=0.006 10 mg/kg GAT1521, p=0.0003 30 mg/kg GAT1521, FIG. 28, right). Overall, these data further suggest that systemic activation of GIRK 1/2 channels enhances fear extinction.

Figure 29:
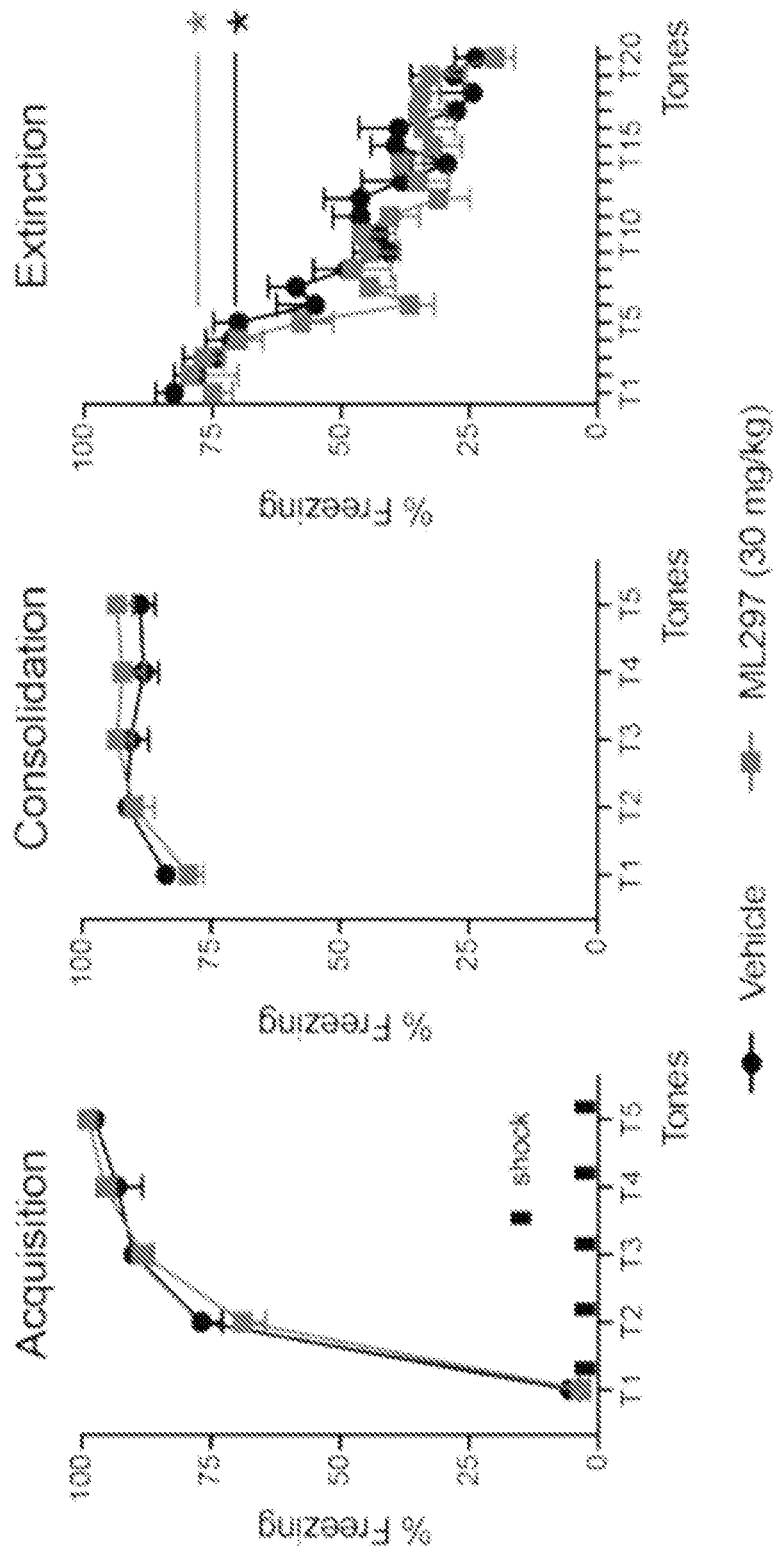
FIG. 29 shows effects of ML297 using cue-induced fear conditioning procedure (FIG. 26). All groups of animals that had tone/shock pairings showed normal cue-induced fear acquisition. Animals were injected with vehicle (●), ML297 (■); 30 mg/kg) (▲). Pretreatment with ML297 had no effects on consolidation of fear memories. Animals injected with vehicle of ML297 had similar rates of extinction. *$p<0.05$, ANOVA with Tukey's posthoc within group analysis. #$p<0.05$, ANOVA with Sidak's posthoc between groups analysis, n=9 in all groups.
Figures 54A, 54B:
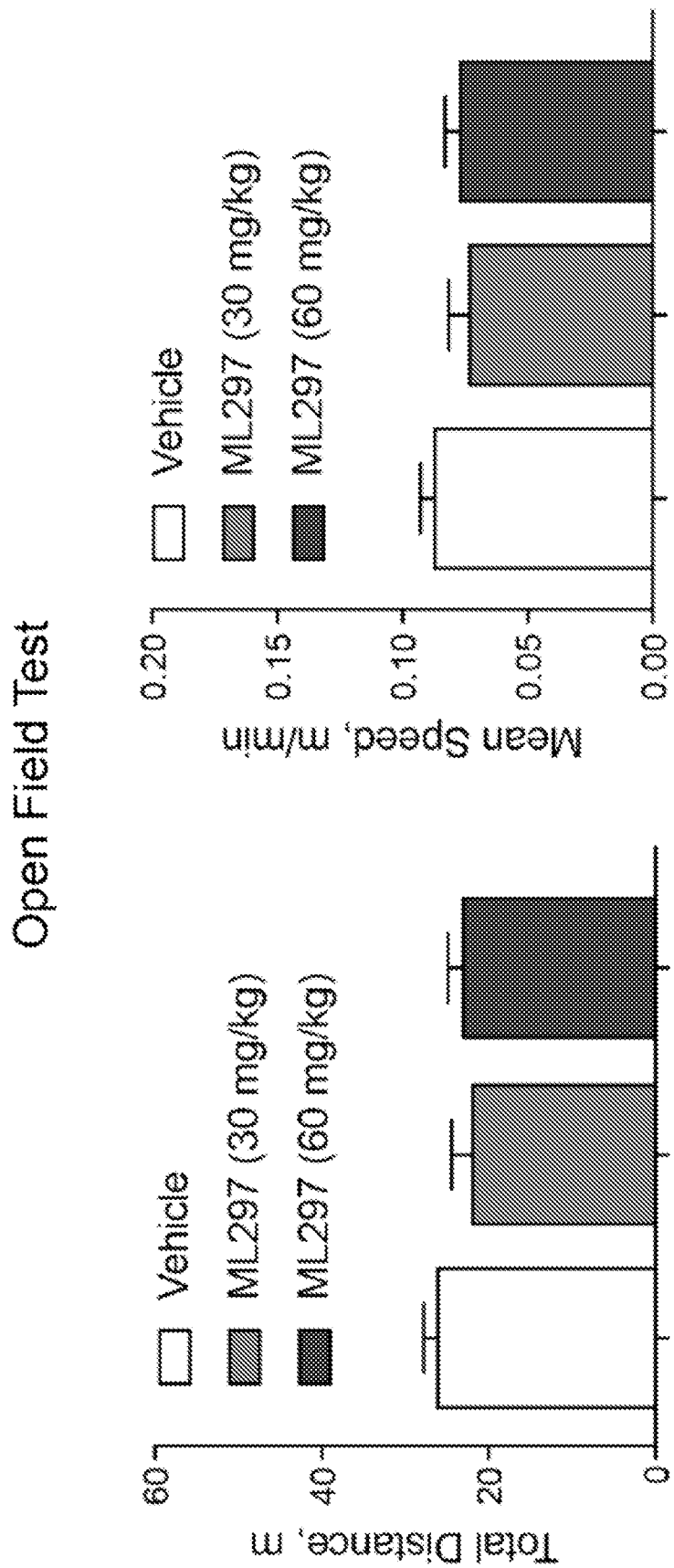
FIGS. 54A-54B show bar charts indicating the impacts of treatment with ML297 on motor function.

Finally, the inventors assessed the effect of treatment with the non-selective compound ML297 on fear memories. Again, all three groups showed normal fear acquisition (treatment effect, p=0.8, tone effect $F_{4,120}$=650.5, p<0.0001, FIG. 29, left). However, systemic pre-treatment with ML297 at 30 mg/kg had no effect on consolidation of fear memories compared to control group (treatment effect $F_{1,15}$=0.09 p=0.77, FIG. 29, center). Moreover, ML297-treated animals also showed no significant differences in extinction of fear memories compared to controls (treatment effect F1,15=0.56, p=0.47, tone effect $F_{19,285}$=19.6, p<0.0001). Dunnett's within group posthoc analysis revealed the reduction of freezing overtime by tone 6 in both groups of animals (p<0.05, FIG. 29, right). Additionally, the inventors also tested the effect of 30 and 60 mg/kg of ML297 on motor activity using the open field (OF) test. The total distance traveled in the open arena and mean speed 30 min after ML297 treatment were comparable to the vehicle group (FIGS. 54A-54B). Thus, the non-selective ML297 did not have the same effects of enhancing fear extinction like the GIRK1/2 GAT-selective compounds at comparable concentrations. In summary, the results of fear conditioning experiments suggest that compounds selective to GIRK1/2 enhance extinction of fear memories.

Figure 55A:
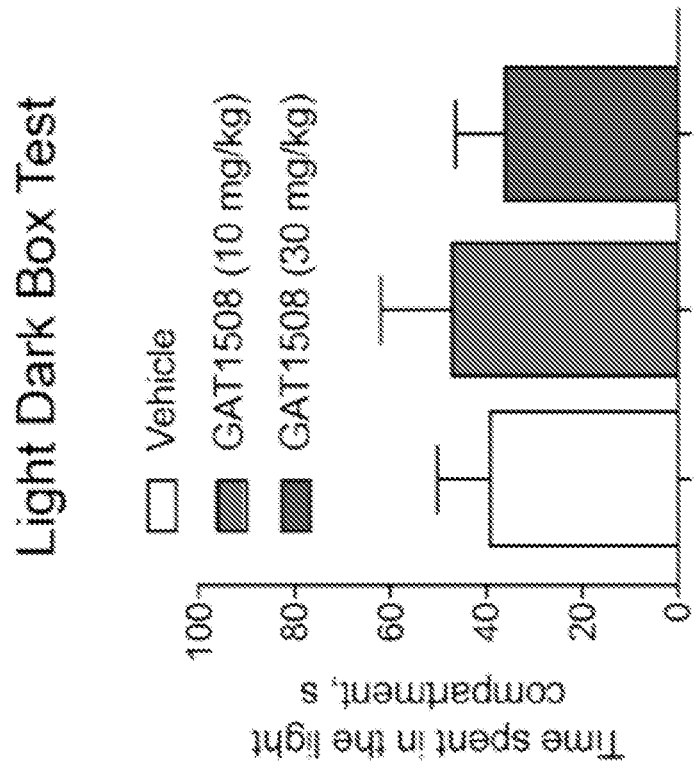
FIGS. 55A-55B, 56A-56B, 57A-57B, and 58A-58B show data indicating treatment with GIRK1/2 positive allosteric modulators (PAMs) does not have non-specific acute behavioral side effects. All bar graphs and the plot in FIG. 57B indicate the effect of intraperitoneal (i.p.) treatment of rats (n=6-9 animals per group) with different doses of GAT1508.
Figure 55B:
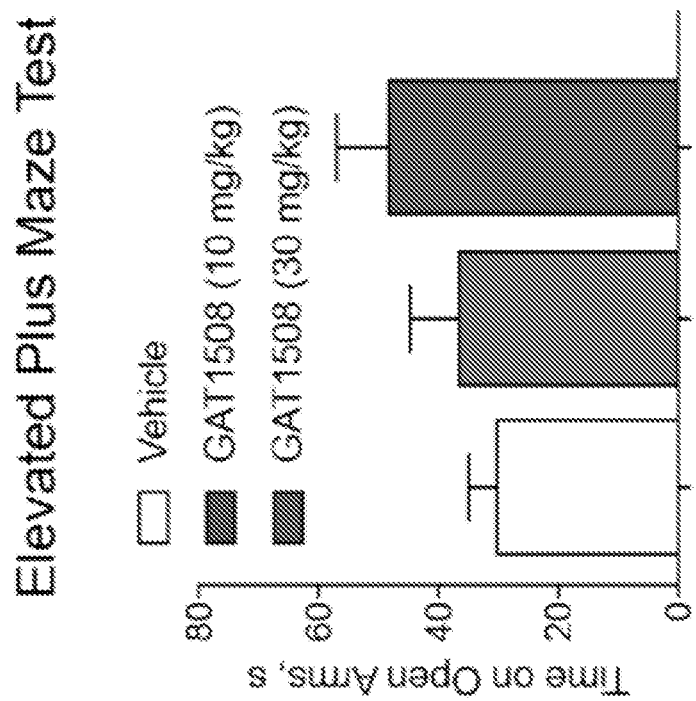
Figure 56B:
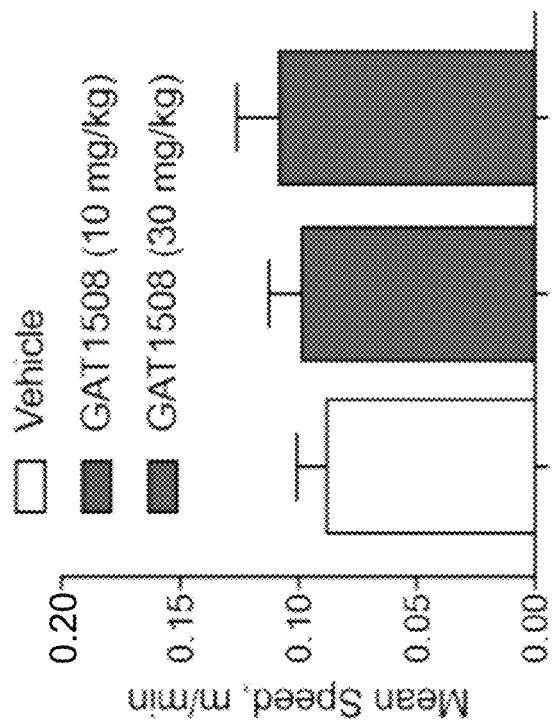
Figure 56A:
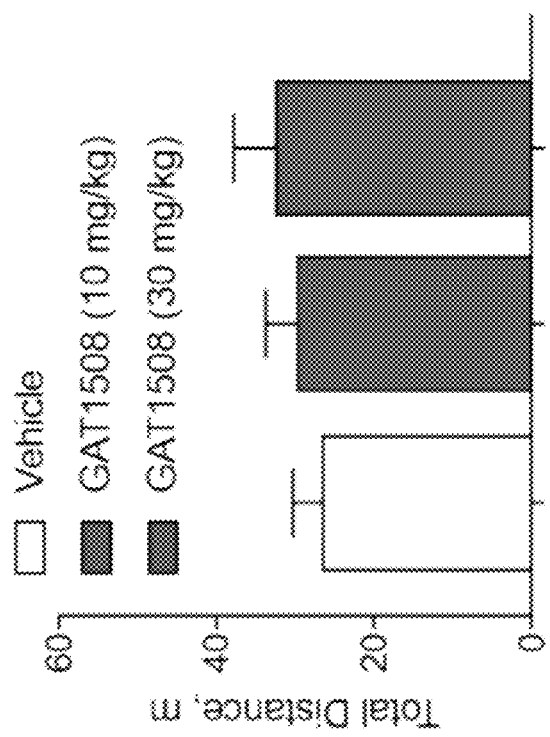
Figure 57B:
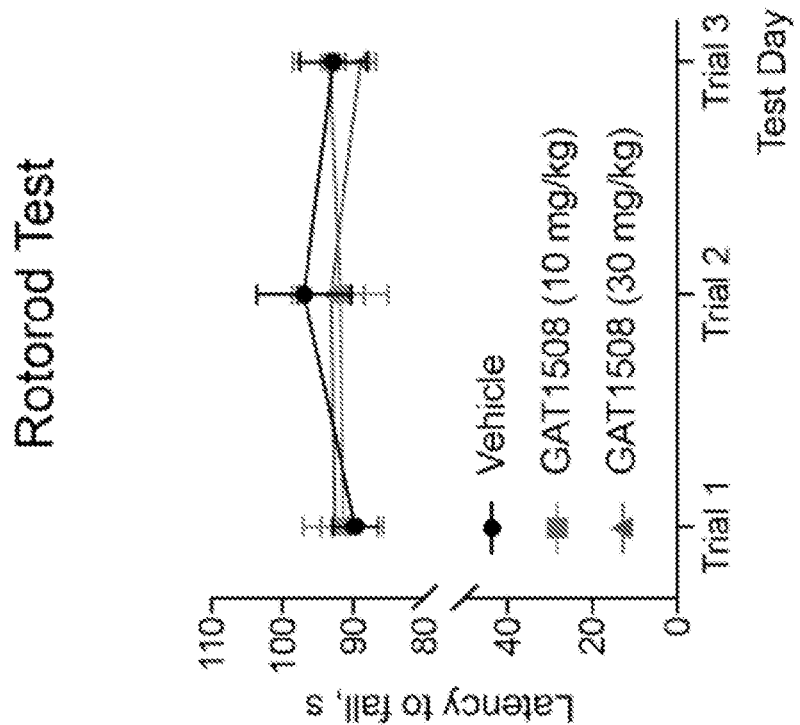
Figure 57A:
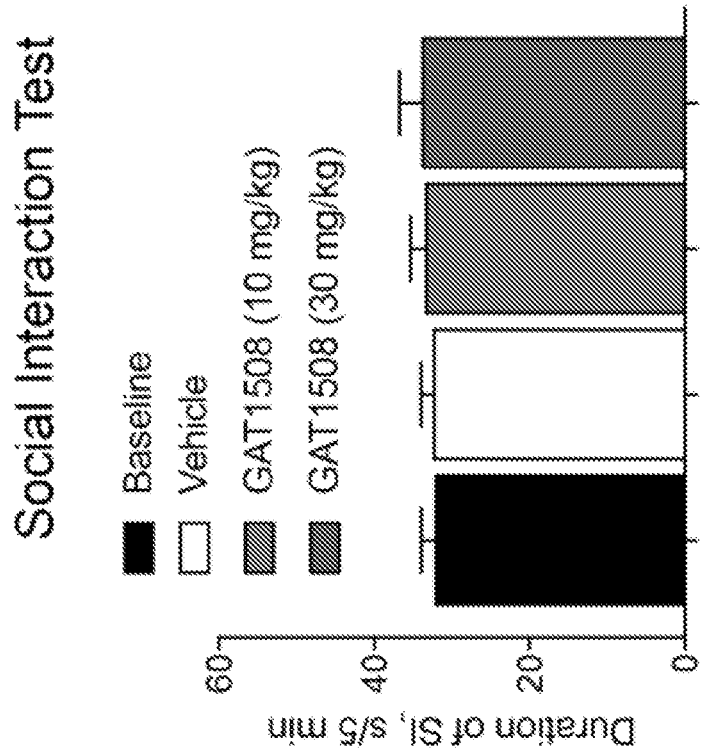
Figure 58A:
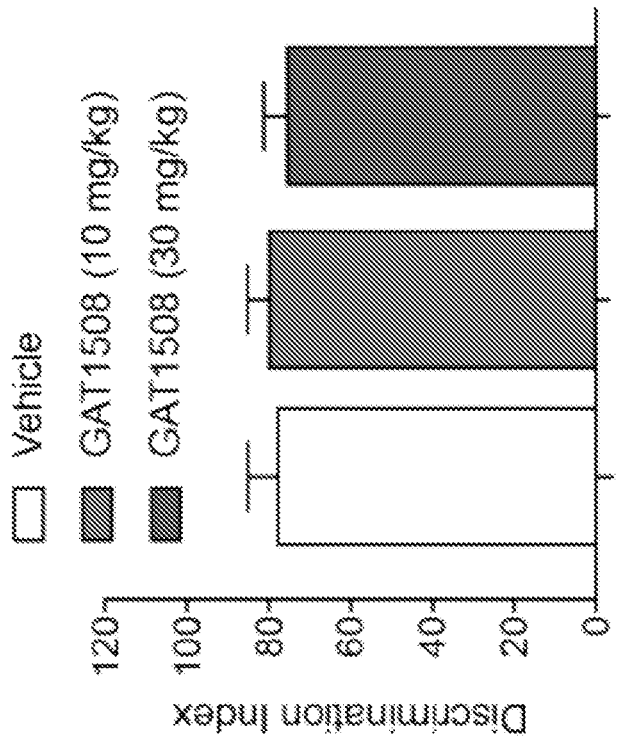
Figure 58B:
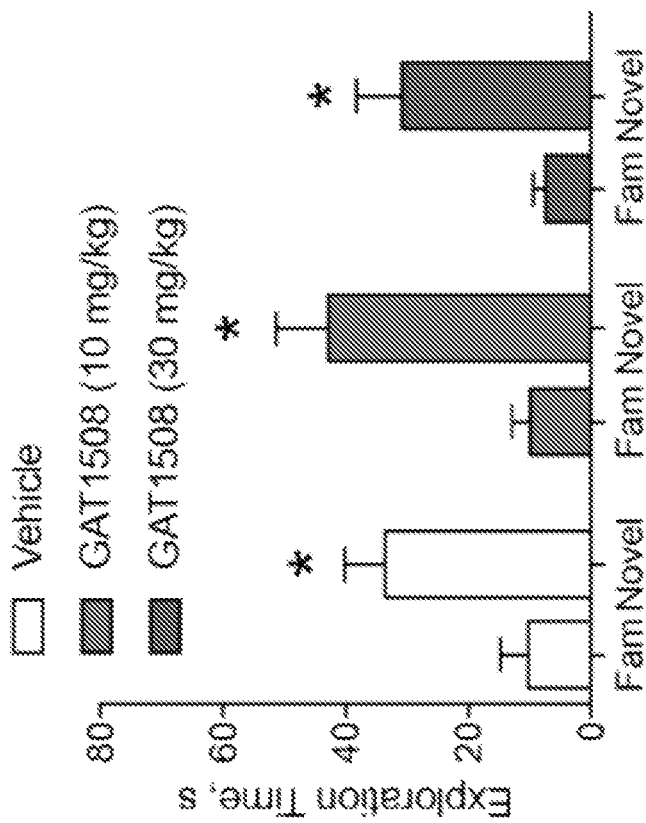

It was shown that selective activation of GIRK1/2 channels does not broadly affect behavioral, cognitive or motor functions. The inventors tested the effects of treatment with various doses of GAT1508 (10 and 30 mg/kg) on cognition, anxiety and motor function using a battery of behavioral tests. First, in the elevated plus maze (EPM), animals treated with GAT1508 demonstrated a trend toward an increase of time spent on the open arm (from 30.6±4.4 in vehicle group to 48.7±8.3 s in 30 mg/kg of GAT1508 group, FIG. 55A). In the light-dark box (LD) test, no difference in time spent in the light compartment was observed between vehicle and GAT1508-treated groups (FIG. 55B). In the open-field (OF) test, the total distance travelled and the mean speed after GAT1508 treatment were comparable to the vehicle group (FIGS. 56A-56B). In the social interaction (SI) test, all groups showed similar interaction time (FIG. 57A). In the rotorod test, the inventors also observed similar latency to fall between the vehicle and GAT1508-treated groups (FIG. 57B). Next, in the novel object recognition (NOR) test, the discrimination index was also similar between three groups, which suggests that GAT1508 treatment did not affect the ability to discriminate between novel and familiar arms (FIGS. 58A-58B). Collectively, the findings of the inventors confirmed that treatment with various doses of GAT1508 had no acute side effects on cognitive and motor functions.

Example 5. Selective Inhibition of GIRK1/4 Channels

Figure 64:
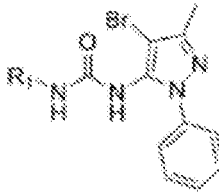
FIG. 64 shows the structures of a series of compounds synthesized for evaluation as selective GIRK1/4 inhibitors.
Figure 65:
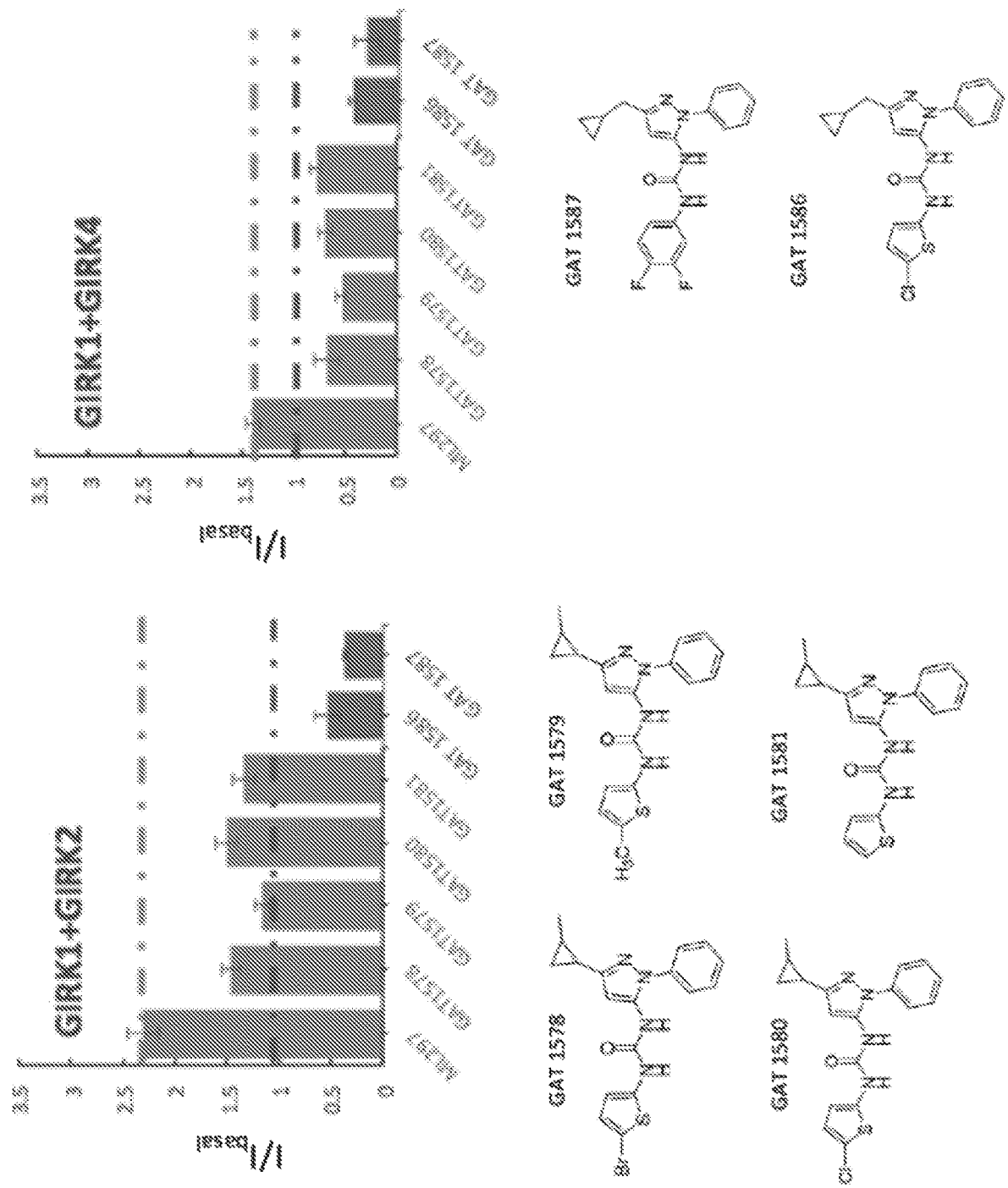
FIG. 65 shows the structures of several compounds (lower portion) synthesized for evaluation of modulation of GIRK currents in *Xenopus* oocytes expressing GIRK1/2 channels (upper left portion) or GIRK1/4 channels (upper right portion).
Figure 66:
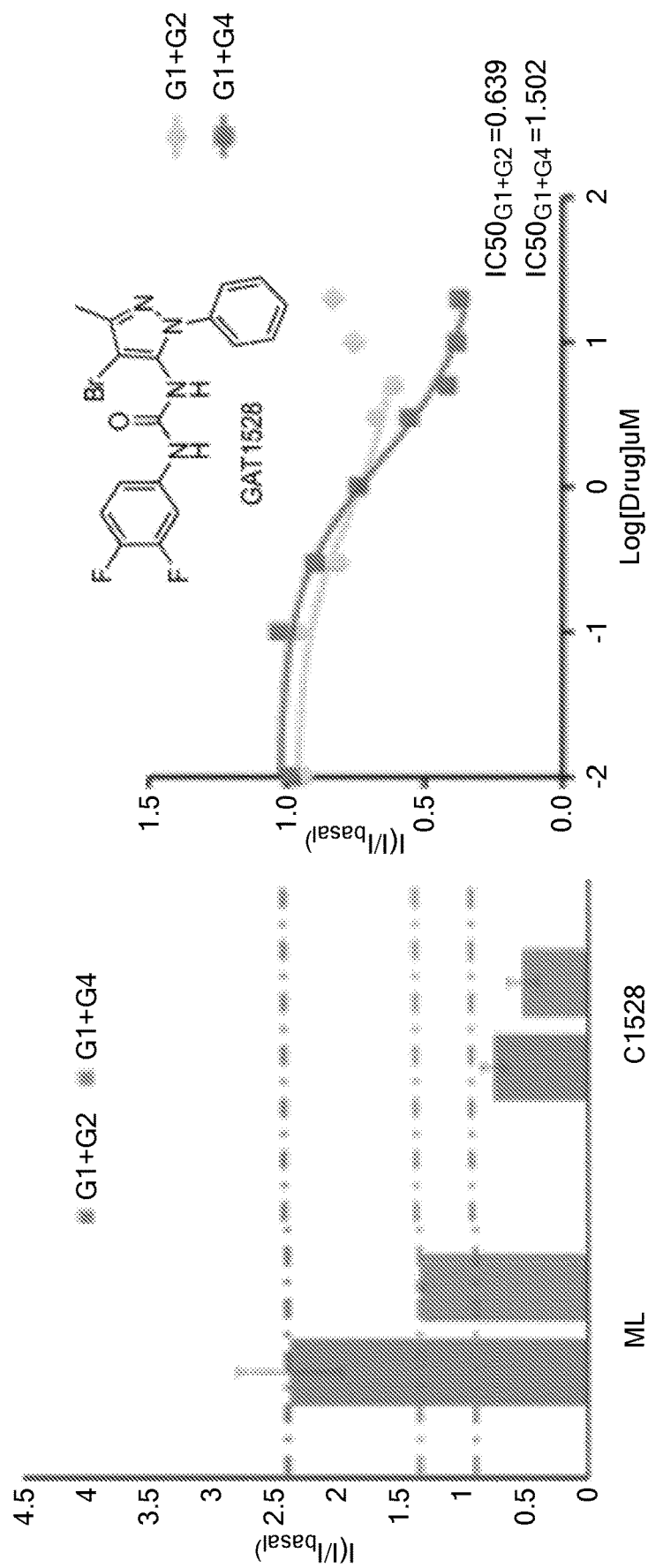
FIG. 66 shows the structures of several compounds synthesized for evaluation of GIRK currents in *Xenopus* oocytes expressing GIRK1/2 channels (left-hand bar of each pair) or GIRK1/4 channels (right-hand bar of each pair).
Figure 66:
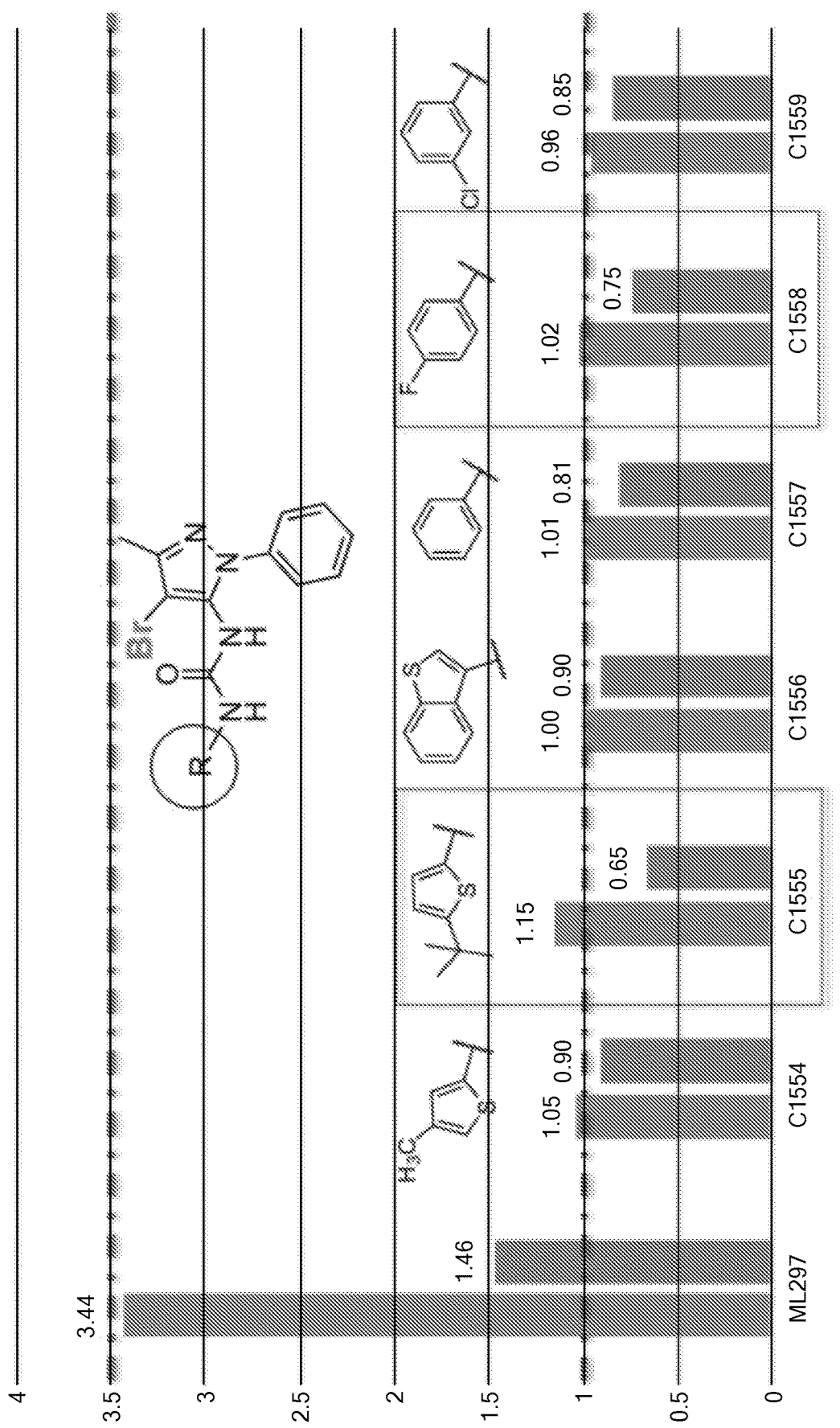

Variants of Formula V having a bromine attached to the thiophene ring and various ring-containing substituents at R3 were synthesized and are shown in FIGS. 64-67. A number of these compounds proved to be selective inhibitors of GIRK1/4 channels, and had little or no effect on GIRK1/2 channels, expressed in *Xenopus* oocytes, as shown in FIGS. 65, 66, and 67. Compounds such as GAT1555, GAT1558, GAT1578, GAT1579, GAT1580, GAT1581, and GAT1528 can be used to treat or prevent cardiac arrhythmias, such as atrial fibrillation, which benefit from inhibition of GIRK1/4 channels.

FIG. 64 shows that a site selective bromination of the pyrazole core imparts selective GIRK1/4 channel inhibition. A small focused library of compounds have laid the ground work for an initial structure activity relationship study (SAR) and has found that substitutions of the phenyl ring can tune the percent inhibition and selectivity of the compound. Emerging from this library are compounds GAT1528, GAT1555, and GAT1558 as lead compounds that are selective for GIRK1/4 inhibition against GIRK1/2 channel activity in which all named compounds had no effect on basal activity.

In FIG. 65 the normalized currents are shown for GIRK1/2 and GIRK1/4 channels tested in *Xenopus* ooctyes. Compounds GAT1578 to GAT1581 where tested at 10 micro molar concentration. These compounds were rationally designed to have a bioisoteric replacement of the phenyl ring of ML297 to a thiophene ring. The addition of a cycloprpopyl methyl group to the pyrazole core imparted a molecular determinant for subtype selectivity leading to favored GIRK1/4 inhibition. GAT1578 and GAT1579 have both emerged as lead compounds.

Example 6. Selective Activation of GIRK1/2 Channels

Figure 68:
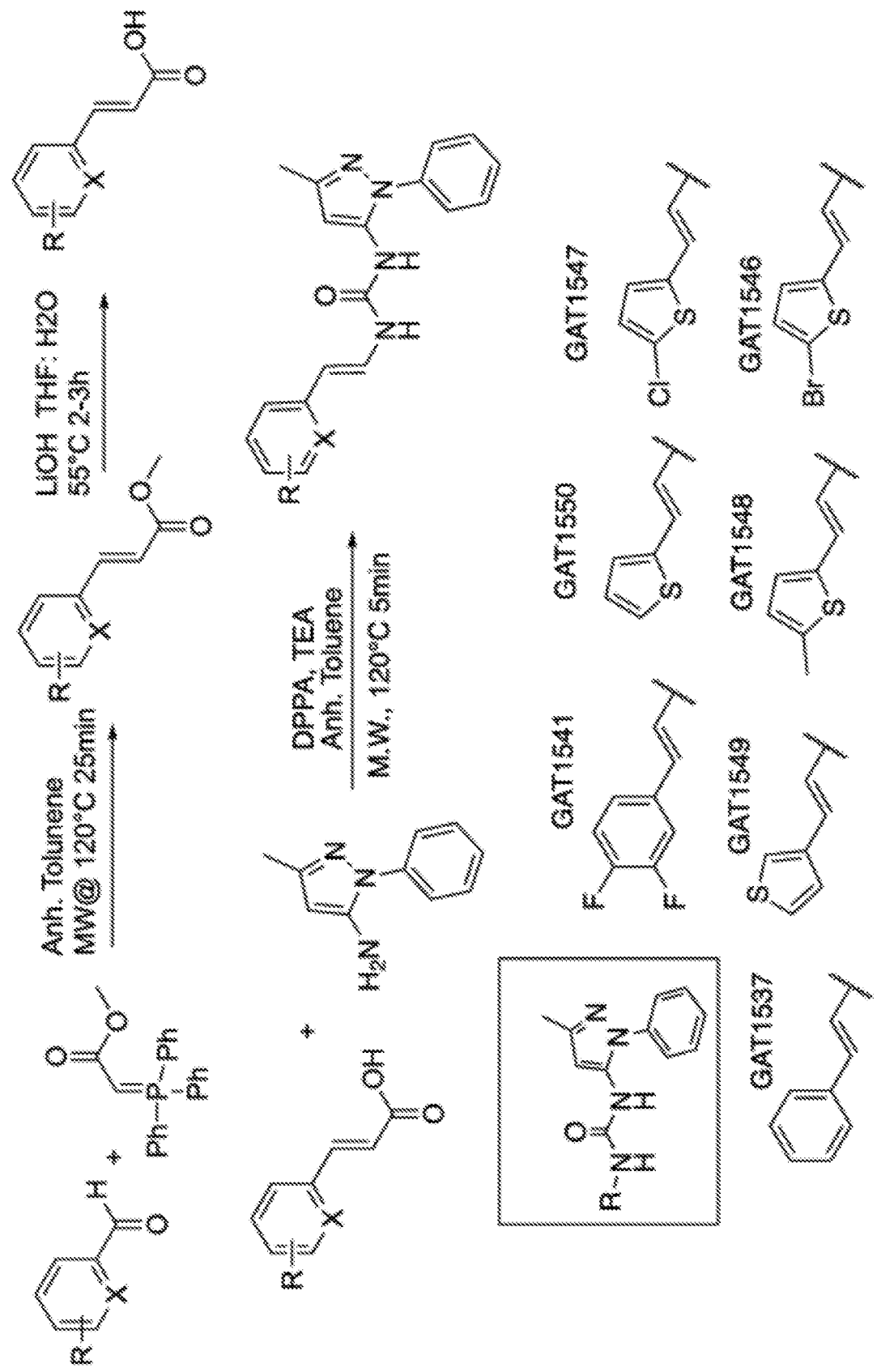
FIG. 68 shows the synthetic scheme for several compounds evaluated as selective GIRK1/2 activators.
Figure 69:
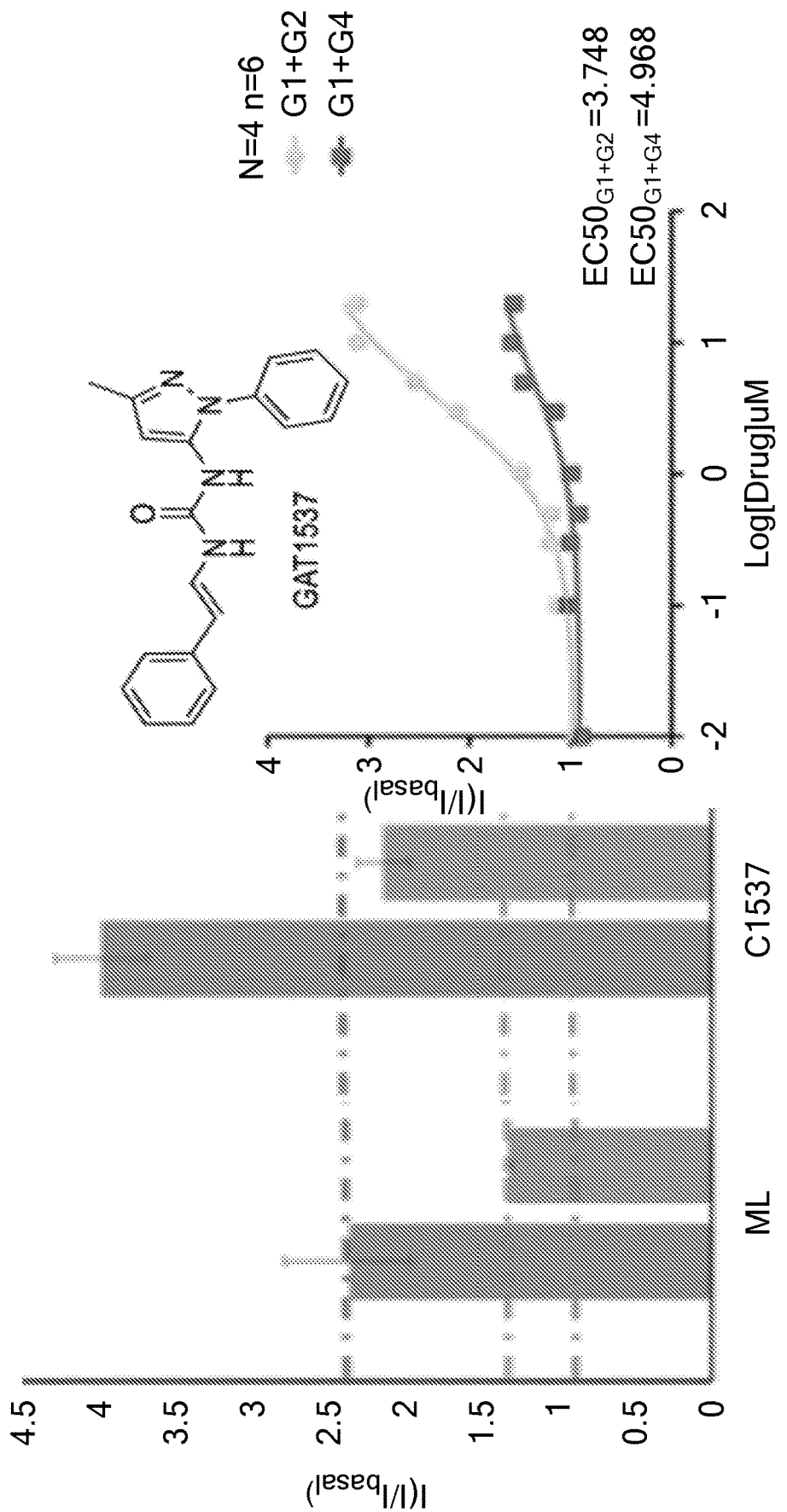
FIG. 69 shows the results of effects of ML297 and GAT1537 on GIRK1/2 (left-hand bar of each pair and circles on graph) and GIRK1/4 (right-hand bar and squares) channels expressed in *Xenopus* oocytes.

Variants of Formula V having various ring-containing substituents at R3 were synthesized and are shown in FIGS. 68-69. A number of these compounds, such as GAT1537, proved to be selective inhibitors of GIRK1/2 channels, and had little or no effect on GIRK1/4 channels, expressed in *Xenopus* oocytes, as shown in FIGS. 65, 66. Such compounds, including GAT1537, can be used to treat neurological and neuropsychiatric conditions such as PTSD, stroke, epilepsy, pain, anxiety, and traumatic brain injury with little or no effect on the heart.

FIG. 65 shows the synthetic route that was utilized to synthesize a library of compounds with a unique pharmacophore that imparts regiospecific interaction with the receptor byway of the introduction of a trans double bound adjacent and connected to the urea moiety. Lead compound GAT1537 has emerged as an effective activator lead compound that induces high GIRK1/2 currents. The figure shows a dose-response curve in *Xenopus* oocytes expressing GIRK1/2 and GIRK1/4 channels, as well as a single 10 micromolar concentration.

REFERENCES

1. Hibino, H. et al. Inwardly rectifying potassium channels: their structure, function, and physiological roles. *Physiol. Rev.* 90, 291-366 (2010).
2. Lüscher, C. & Slesinger, P. A. Emerging roles for G protein-gated inwardly rectifying potassium (GIRK) channels in health and disease. *Nat. Rev. Neurosci.* 11, 301-15 (2010).
3. Logothetis, D. E. et al. Unifying Mechanism of Controlling Kir3 Channel Activity by G Proteins and Phosphoinositides. *Int. Rev. Neurobiol.* 123, 1-26 (2015).
4. Dascal, N. & Kahanovitch, U. The Roles of Gβγ and Gα in Gating and Regulation of GIRK Channels. *Int. Rev. Neurobiol.* 123, 27-85 (2015).
5. Doupnik, C. A. RGS Redundancy and Implications in GPCR-GIRK Signaling. *Int. Rev. Neurobiol.* 123, 87-116 (2015).
6. Glaaser, I. W. & Slesinger, P. A. Structural Insights into GIRK Channel Function. *Int Rev. Neurobiol.* 123, 117-60 (2015).
7. Luján, R., Marron Fernandez de Velasco, E., Aguado, C. & Wickman, K. New insights into the therapeutic potential of Girk channels. *Trends Neurosci.* 37, 20-9 (2014).
8. Marron Fernandez de Velasco, E., McCall, N. & Wickman, K. GIRK Channel Plasticity and Implications for Drug Addiction. *Int. Rev. Neurobiol.* 123, 201-38 (2015).
9. Tipps, M. E. & Buck, K. J. GIRK Channels: A Potential Link Between Learning and Addiction. *Int Rev. Neurobiol.* 123, 239-77 (2015).
10. Mayfield, J., Blednov, Y. A. & Harris, R. A. Behavioral and Genetic Evidence for GIRK Channels in the CNS: Role in Physiology, Pathophysiology, and Drug Addiction. *Int. Rev. Neurobiol.* 123, 279-313 (2015).
11. Logothetis, D. E., Kurachi, Y., Galper, J., Neer, E. J. & Clapham, D. E. The βγ subunits of GTP-binding proteins activate the muscarinic $K^+$ channel in heart. *Nature* 325, 321-6 (1987).
12. Reuveny, E. et al. Activation of the cloned muscarinic potassium channel by G protein beta gamma subunits. *Nature* 370, 143-6 (1994).
13. Clapham, D. E. & Neer, E. J. G protein beta gamma subunits. *Annu. Rev. Pharmacol. Toxicol.* 37, 167-203 (1997).
14. Huang, C. L., Feng, S. & Hilgemann, D. W. Direct activation of inward rectifier potassium channels by $PIP_2$ and its stabilization by Gbetagamma. *Nature* 391, 803-6 (1998).
15. Sui, J. L., Petit-Jacques, J. & Logothetis, D. E. Activation of the atrial $_{KACh}$ channel by the betagamma subunits of G proteins or intracellular $Na^+$ ions depends on the presence of phosphatidylinositol phosphates. *Proc. Natl. Acad. Sci. USA* 95, 1307-12 (1998).
16. Mahajan, R. et al. A computational model predicts that Gl3γ acts at a cleft between channel subunits to activate GIRK1 channels. *Sci. Signal.* 6, ra69 (2013).
17. Logothetis, D. E. et al. Phosphoinositide control of membrane protein function: a frontier led by studies on ion channels. *Annu. Rev. Physiol.* 77, 81-104 (2015b).
18. Meng, X. Y., Zhang, H. X., Logothetis, D. E. & Cui, M. The molecular mechanism by which PIP(2) opens the intracellular G-loop gate of a Kir3.1 channel. *Biophys. J.* 102, 2049-59 (2012).
19. Whorton, M. R. & MacKinnon, R. Crystal structure of the mammalian GIRK2 $K^+$ channel and gating regulation by G proteins, $PIP_2$, and sodium. *Cell* 147, 199-208 (2011).
20. Whorton, M. R. & MacKinnon, R. X-ray structure of the mammalian GIRK2-I3γ G-protein complex. *Nature* 498, 190-7 (2013).
21. Sui, J. L., Chan, K. W. & Logothetis, D. E. $Na^+$ activation of the muscarinic $K^+$ channel by a G-protein-independent mechanism. *J. Gen. Physiol.* 108, 381-91 (1996).
22. Ho, I. H. & Murrell-Lagnado, R. D. Molecular determinants for sodium-dependent activation of G protein-gated $K^+$ channels. *J. Biol. Chem.* 274, 8639-48 (1999).
23. Ho, I. H. & Murrell-Lagnado, R. D. Molecular mechanism for sodium-dependent activation of G protein-gated $K^+$ channels. *J. Physiol.* 520, 645-51 (1999).
24. Zhang, H., He, C., Yan, X., Mirshahi, T. & Logothetis, D. E. Activation of inwardly rectifying K+ channels by distinct PtdIns (4,5)P2 interactions. *Nat. Cell Biol.* 1, 183-8 (1999).
25. Kobayashi, T. et al. Ethanol opens G-protein-activated inwardly rectifying $K^+$ channels. *Nat. Neurosci.* 2, 1091-7 (1999).
26. Lewohl, J. M. et al. G-protein-coupled inwardly rectifying potassium channels are targets of alcohol action. *Nat. Neurosci.* 2, 1084-90 (1999).
27. Weigl, L. G. & Schreibmayer, W. G protein-gated inwardly rectifying potassium channels are targets for volatile anesthetics. *Mol. Pharmacol.* 60, 282-9 (2001).
28. Yamakura, T., Lewohl, J. M. & Harris, R. A. Differential effects of general anesthetics on G protein-coupled inwardly rectifying and other potassium channels. *Anesthesiology* 95, 144-53 (2001).
29. Yow, T. T. et al. Naringin directly activates inwardly rectifying potassium channels at an overlapping binding site to tertiapin-Q. *Br. J. Pharmacol.* 163, 1017-33 (2011).
30. Kobayashi, T. & Ikeda, K. G protein-activated inwardly rectifying potassium channels as potential therapeutic targets. *Curr. Pharm. Des.* 12, 4513-23 (2006).
31. Krapivinsky, G. et al. The G-protein-gated atrial $K^+$ channel $_{IKACh}$ is a heteromultimer of two inwardly rectifying $K^+$-channel proteins. *Nature* 374, 135-41 (1995).
32. Liao, Y. J., Jan, Y. N. & Jan, L. Y. Heteromultimerization of G-protein-gated inwardly rectifying K+ channel proteins GIRK1 and GIRK2 and their altered expression in weaver brain. *J. Neurosci.* 16, 7137-50 (1996).
33. Jelacic, T. M., Kennedy, M. E., Wickman, K. & Clapham, D. E. Functional and biochemical evidence for G-protein-gated inwardly rectifying $K^+$ (GIRK) channels composed of GIRK2 and GIRK3. *J. Biol. Chem.* 275, 6211-6 (2000).
34. Luján, R. & Aguado, C. Localization and Targeting of GIRK Channels in Mammalian Central Neurons. *Int. Rev. Neurobiol.* 123, 161-200 (2015).
35. Ma, D. et al. Diverse trafficking patterns due to multiple traffic motifs in G protein-activated inwardly rectifying potassium channels from brain and heart. *Neuron* 33, 715-29 (2002).
36. Mirshahi, T. & Logothetis, D. E. GIRK channel trafficking: different paths for different family members. *Mol. Interv.* 2, 289-91 (2002).
37. Chan, K. W. et al. A recombinant inwardly rectifying potassium channel coupled to GTP-binding proteins. *J. Gen. Physiol.* 107, 381-97 (1996).

38. Slesinger, P. A., Reuveny, E., Jan, Y. N. & Jan, L. Y. Identification of structural elements involved in G protein gating of the GIRK1 potassium channel. *Neuron* 15, 1145-56 (1995).
39. Chan, K. W., Sui, J. L., Vivaudou, M. & Logothetis, D. E. Control of channel activity through a unique amino acid residue of a G protein-gated inwardly rectifying $K^+$ channel subunit. *Proc. Natl. Acad. Sci. USA* 93, 14193-8 (1996).
40. Wydeven, N., Young, D., Mirkovic, K. & Wickman, K. Structural elements in the Girk1 subunit that potentiate G protein-gated potassium channel activity. *Proc. Natl. Acad. Sci. USA* 109, 21492-7 (2012).
41. Chan, K. W., Sui, J. L., Vivaudou, M. & Logothetis, D. E. Specific regions of heteromeric subunits involved in enhancement of G protein-gated $K^+$ channel activity. *J. Biol. Chem.* 272, 6548-55 (1997).
42. Mase, Y., Yokogawa, M., Osawa, M. & Shimada, I. Structural basis for modulation of gating property of G protein-gated inwardly rectifying potassium ion channel (GIRK) by i/o-family G protein a subunit (Gαi/o). *J. Biol. Chem.* 287, 19537-49 (2012).
43. Days, E. et al. Discovery and Characterization of a Selective Activator of the G-Protein Activated Inward-Rectifying Potassium (GIRK) Channel. Probe Reports from the NIH Molecular Libraries Program [Internet], Bethesda (Md.): National Center for Biotechnology Information (US); (2010-2012) [updated Mar. 14, 2013],
44. Kaufmann, K. et al. ML297 (VU0456810), the first potent and selective activator of the GIRK potassium channel, displays antiepileptic properties in mice. *ACS Chem. Neurosci.* 4, 1278-86 (2013).
45. Wen, W., Wu, W., Weaver, C. D. & Lindsley, C. W. Discovery of potent and selective GIRK1/2 modulators via 'molecular switches' within a series of 1-(3-cyclopropyl-1-phenyl-1H-pyrazol-5-yl)ureas. *Bioorg. Med. Chem. Lett.* 24, 5102-6 (2014).
46. Wydeven, N. et al. Mechanisms underlying the activation of G-protein-gated inwardly rectifying $K^+$ (GIRK) channels by the novel anxiolytic drug, ML297. *Proc. Natl. Acad. Sci. USA.* 111, 10755-60 (2014).
47. Wieting, J. M. et al. Discovery and Characterization of 1H-Pyrazol-5-yl-2-phenylacetamides as Novel, Non-Urea-Containing GIRK1/2 Potassium Channel Activators. *ACS Chem. Neurosci.* 8, 1873-1879 (2017).
48. Zarzoso, M. et al. Nerves projecting from the intrinsic cardiac ganglia of the pulmonary veins modulate sinoatrial node pacemaker function. *Cardiovascular research* 99, 566-575 (2013).
49. Takemoto, Y. et al. Structural basis for the antiarrhythmic blockade of a potassium channel with a small molecule. *FASEB J.* 32, 1778-1793 (2018).
50. Johnson P. L. et al. Pharmacological depletion of serotonin in the basolateral amygdala complex reduces anxiety and disrupts fear conditioning. *Pharmacol. Biochem. Behav.* 138, 174-9 (2015).
51. Mahan A. L. & Ressler K. J. Fear conditioning, synaptic plasticity and the amygdala: implications for posttraumatic stress disorder. *Trends Neurosci.* 35, 24-35 (2012).
52. Karschin C., Dissmann E., Stühmer W. & Karschin A. IRK(1-3) and GIRK(1-4) inwardly rectifying $K^+$ channel mRNAs are differentially expressed in the adult rat brain. *J. Neurosci.* 16, 3559-70 (1996).
53. Petit-Jacques, J., Sui, J. L. & Logothetis, D. E. Synergistic activation of G protein-gated inwardly rectifying potassium channels by the betagamma subunits of G proteins and $Na^+$ and $Mg^{2+}$ ions. *J. Gen. Physiol.* 114, 673-84 (1999).
54. Davis, M. & Whalen, P. J. The amygdala: vigilance and emotion. *Mol. Psychiatry* 6, 13-34 (2001).
55. Fanselow, M. S. & LeDoux, J. E. Why the inventors think plasticity underlying Pavlovian fear conditioning occurs in the basolateral amygdala. *Neuron* 23, 229-232 (1999).
56. LeDoux, J. E. Emotion circuits in the brain. *Annu. Rev. Neurosci.* 23, 155-184 (2000).
57. Maren, S. Neurobiology of Pavlovian fear conditioning. *Annu. Rev. Neurosci.* 24, 897-931 (2001).
58. Quirk, G. J. & Mueller, D. Neural mechanisms of extinction learning and retrieval. *Neuropsychopharmacology* 33, 56-72 (2008).
59. Rogan, M. T., Staubli, U. V. & LeDoux, J. E. Fear conditioning induces associative long-term potentiation in the amygdala. *Nature* 390, 604-607 (1997).
60. Sosulina, L., Schwesig, G., Seifert, G. & Pape, H. C. Neuropeptide Y activates a G-protein-coupled inwardly rectifying potassium current and dampens excitability in the lateral amygdala. *Mol. Cell. Neurosci.* 39, 491-8 (2008).
61. Manteghi, A. A., Hebrani, P., Mortezania, M., Haghighi, M. B. & Javanbakht, A. Baclofen add-on to citalopram in treatment of posttraumatic stress disorder. *J. Clin. Psychopharmacol.* 34, 240-3 (2014).
62. Liman, E. R., Tytgat, J. & Hess, P. Subunit stoichiometry of a mammalian K+ channel determined by construction of multimeric cDNAs. *Neuron* 9, 861-71 (1992).
63. Jespersen, T., Grunnet, M., Angelo, K., Klaerke, D. A. & Olesen, S. P. Dual-function vector for protein expression in both mammalian cells and *Xenopus laevis* oocytes. Biotechniques 32, 536-8, 540 (2002).
64. Idevall-Hagren, O., Dickson, E. J., Hille, B., Toomre, D. K. & De Camilli, P. Optogenetic control of phosphoinositide metabolism. *Proc. Natl. Acad. Sci. USA* 109, E2316-E2323 (2012).
65. Molosh, A. I. et al. A. Social learning and amygdala disruptions in Nf1 mice are rescued by blocking p21-activated kinase. *Nat. Neurosci.* 17, 1583-90 (2014).
66. Li, L. P. et al. PSD95 and nNOS interaction as a novel molecular target to modulate conditioned fear: relevance to PTSD. *Transl. Psychiatry* 8, 155 (2018).
67. Lee, Y., Fitz, S., Johnson, P. L., Shekhar, A. Repeated stimulation of CRF receptors in the BNST of rats selectively induces social but not panic-like anxiety. *Neuropsychopharmacology.* 33, 2586-94 (2008).
68. Ha J, Xu Y, Kawano T, Hendon T, Baki L, Garai S, Papapetropoulos A, Thakur G, Plant LD, and Logothetis DE. Sulfhydration of cytoplasmic cysteines in Kir3 channels inhibits channel activity by decreasing sensitivity to the phospholipid $PIP_2$. J Biol Chem. Mar. 9, 2018; 293 (10):3546-3561.

The invention claimed is:

1. A compound for modulation of GIRK channels, the compound having a structure according to Formula I:

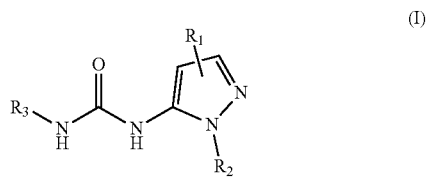

(I)

wherein R₁ is chosen from hydrogen, halo, methyl, halomethyl, deuteromethyl, cyclopropyl, and cyclopropylmethyl;

wherein R₂ is —(CH₂)—R_C or —R_C; R_C can be piperidine, thiane, tetrahydropyran, cyclohexyl, or phenyl optionally substituted with one R_D, one carbon atom of the phenyl optionally replaced with N, S, or O, wherein R_D can be C1-C6 alkyl, halogen, or CF₃;

wherein R₃ is chosen from —R_E—R_G, —R_F—R_G, —R_H, and —R_I; R_E is C2 alkene with trans configuration; R_F is cyclopropyl or oxirane; R_G is a 5 or 6 membered aromatic ring optionally comprising one or two N, S, or O in place of one or two carbon atoms, the 5 or 6 membered aromatic ring can be optionally substituted with R_H; R_H can be halogen, CF₃, or CD₃; R_I is a substituted or unsubstituted ring or ring system chosen from thiophene, benzo[b]thiophene, 4,5,6,7-tetrahydrobenzo[b]thiophene, pyrimidine, isoxazole, thiazole, adamantane, benzo[d][1,3]dioxole, and isoquinoline; and wherein R_I is optionally substituted with one or more functional groups chosen from halo, and C1-C6 branched or unbranched alkyl optionally substituted with one or more halogens;

or a pharmaceutically-acceptable salt thereof.

2. The compound of claim 1 which has a structure according to Formula V:

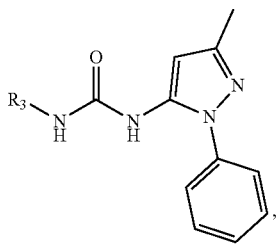

(V)

wherein R₃ is chosen from —R_E—R_G, —R_F—R_G, —R_H, and —R_I; R_E is C2 alkene with trans configuration; R_F is cyclopropyl or oxirane; R_G is a 5 or 6 membered aromatic ring optionally having one or two carbon atoms replaced with N, S, or O, the 5 or 6 membered aromatic ring can be optionally substituted with R_H; R_H can be halogen, CF₃, or CD3; R_I is a substituted or unsubstituted ring or ring system chosen from thiophene, benzo[b]thiophene, 4,5,6,7-tetrahydrobenzo[b]thiophene, pyrimidine, isoxazole, thiazole, adamantane, benzo[d][1,3]dioxole, and isoquinoline; and wherein R_I is optionally substituted with one or more functional groups chosen from halo, and C1-C6 branched or unbranched alkyl optionally substituted with one or more halogens;

or a pharmaceutically-acceptable salt thereof.

3. The compound of claim 2, wherein the compound is selected from the group consisting of:

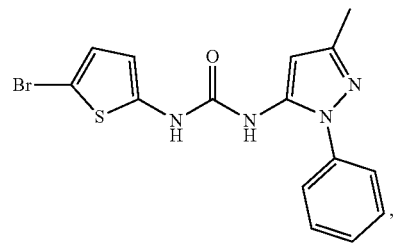

GAT1508

Molecular Weight: 377.26

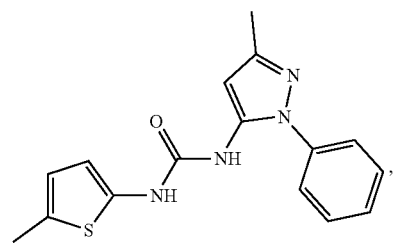

GAT1521

Molecular Weight: 312.39

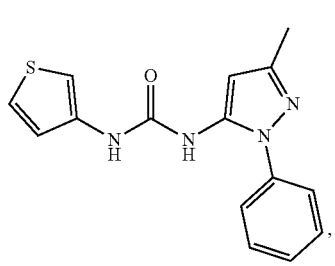

GAT1500

Molecular Weight: 298.36

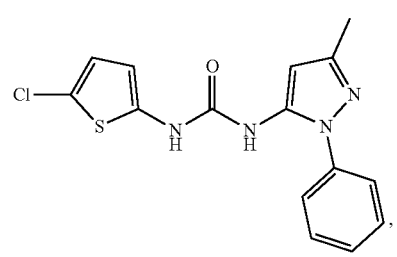

GAT1501

Molecular Weight: 332.81

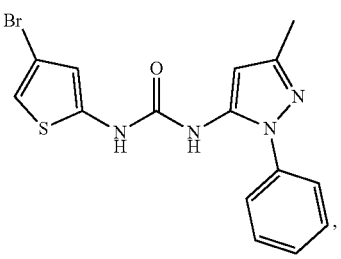

GAT1502

Molecular Weight: 377.26

-continued
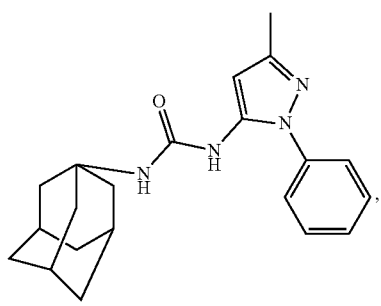
GAT1503
Molecular Weight: 350.47
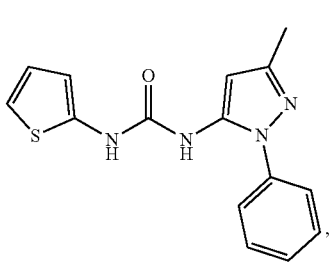
GAT1506
Molecular Weight: 298.36
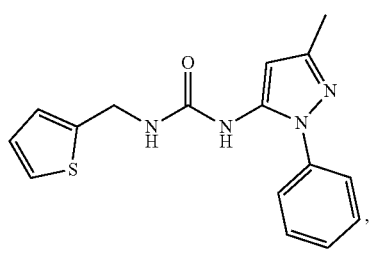
GAT1507
Molecular Weight: 312.39
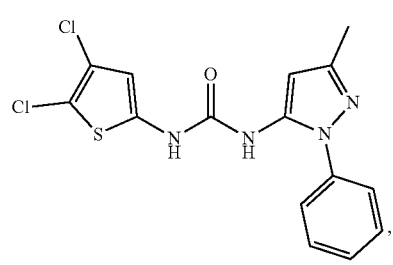
GAT1512
Molecular Weight: 367.25
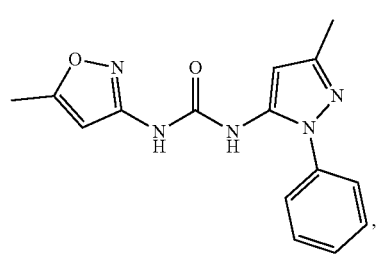
GAT1513
Molecular Weight: 297.32
-continued
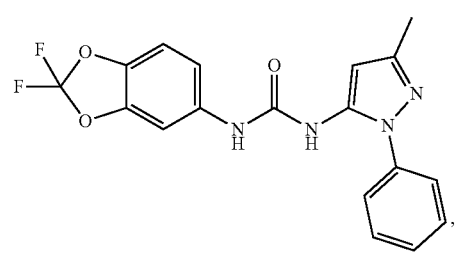
GAT1516
Molecular Weight: 372.33
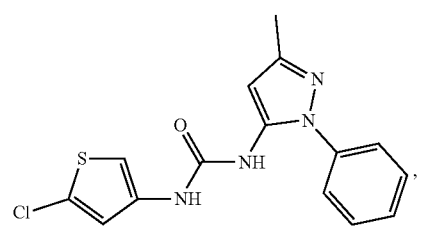
GAT1518
Molecular Weight: 332.81
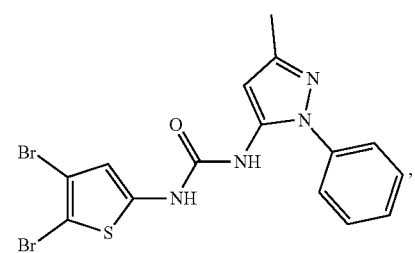
GAT1519
Molecular Weight: 456.15
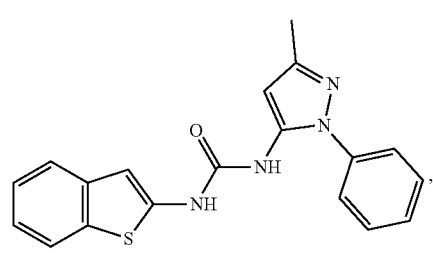
GAT1522
Molecular Weight: 348.42
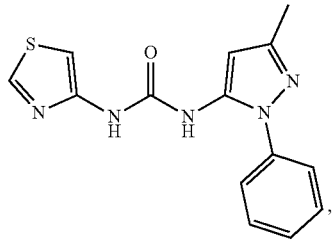
GAT1529
Molecular Weight: 299.35

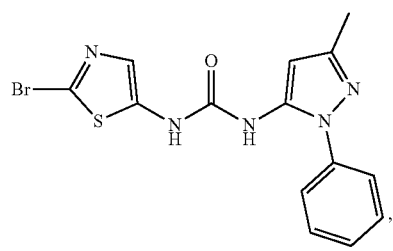
GAT1530
Molecular Weight: 378.25
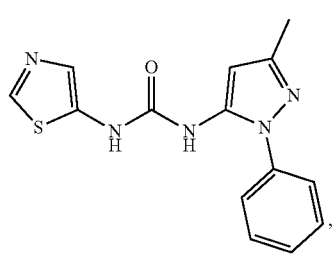
GAT1531
Molecular Weight: 299.35
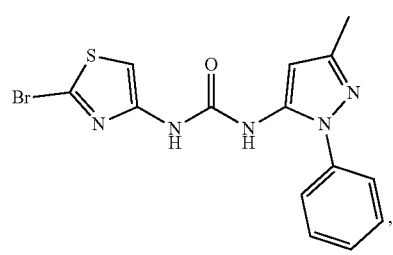
GAT1532
Molecular Weight: 378.25
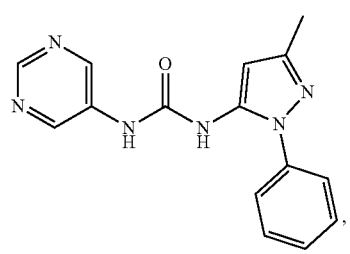
GAT1535
Molecular Weight: 294.32
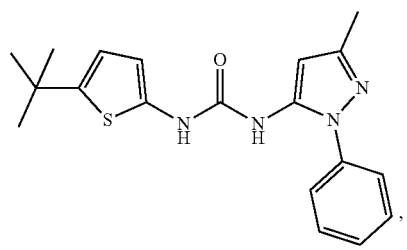
GAT1551
Molecular Weight: 254.47
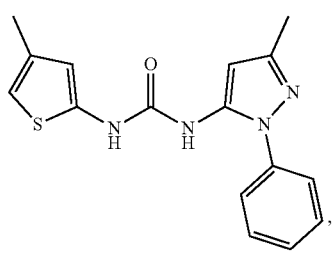
GAT1552
Molecular Weight: 312.39
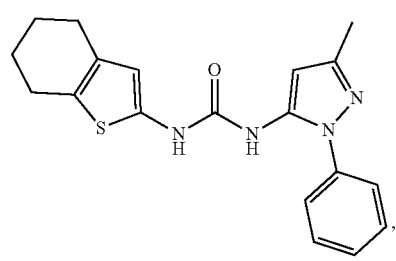
GAT1553
Molecular Weight: 352.46
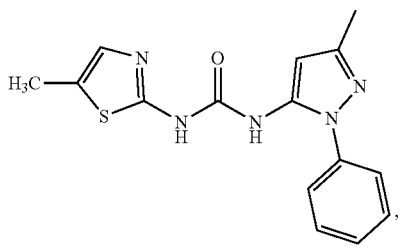
GAT1561
Molecular Weight: 313.38
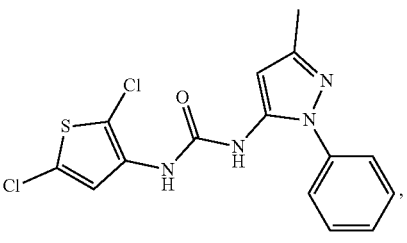
GAT1564
Molecular Weight: 367.25
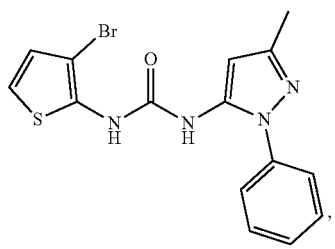
GAT1570
Molecular Weight: 377.26

GAT1574

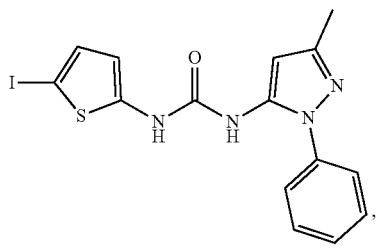

Molecular Weight: 424.26

GAT1575

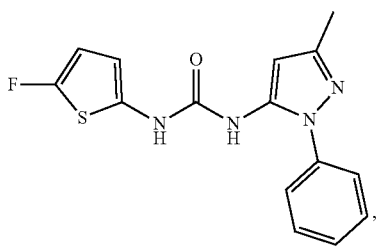

Molecular Weight: 316.35 and pharmaceutically-acceptable salts thereof.

4. The compound of claim 1, wherein the compound comprises one or more of $^{18}$F, $^{19}$F, $^{75}$Br, $^{78}$Br, $^{123}$I, $^{124}$I, $^{125}$I, $^{131}$I, $^{11}$O, $^{13}$O, $^{13}$N, $^{15}$O, or $^{3}$H.

5. The compound of claim 1, wherein the compound is a modulator of a GIRK channel.

6. The compound of claim 5, wherein the compound activates GIRK1/2 channels.

7. The compound of claim 5, wherein the compound activates GIRK1/4 channels.

8. The compound of claim 5, wherein the compound does not activate GIRK1/4 channels at physiologically-relevant levels.

9. A pharmaceutical composition comprising a therapeutically effective amount of a compound of claim 1, or a pharmaceutically acceptable salt thereof, and an excipient.

10. The pharmaceutical composition of claim 9, wherein the composition activates GIRK1/2 channels.

11. The compound of claim 3 which is GAT1508.

12. The pharmaceutical composition of claim 9, wherein the compound is

GAT1508

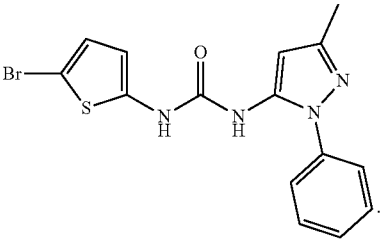

Molecular Weight: 377.26

13. A compound for modulation of GIRK channels, the compound having a structure selected from the group consisting of:

GAT1509

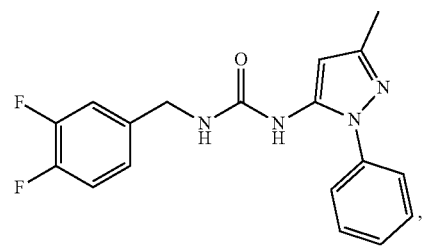

Molecular Weight: 342.35

GAT1514

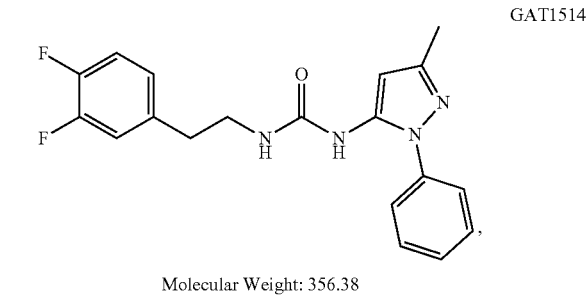

Molecular Weight: 356.38

GAT1536

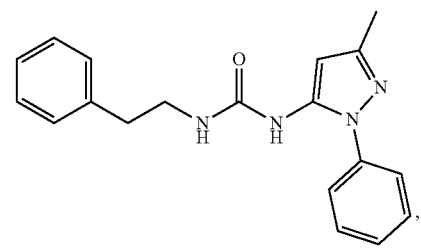

Molecular Weight: 320.40

GAT1566

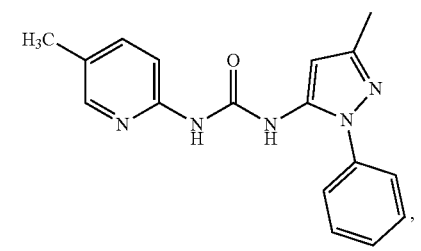

Molecular Weight: 307.36 and pharmaceutically-acceptable salts thereof.

* * * * *